US010041117B2

(12) United States Patent
Nazarenko et al.

(10) Patent No.: US 10,041,117 B2
(45) Date of Patent: Aug. 7, 2018

(54) PRIMERS AND METHODS FOR THE DETECTION AND DISCRIMINATION OF NUCLEIC ACIDS

(71) Applicant: LIFE TECHNOLOGIES CORPORATION, Carlsbad, CA (US)

(72) Inventors: Irina Nazarenko, Gaithersburg, MD (US); Ayoub Rashtchian, Gaithersburg, MD (US); Joseph Solus, Gaithersburg, MD (US); Richard M. Pires, Mount Airy, MD (US); Marlene Darfler, Derwood, MD (US); Gulilat Gebeyehu, Potomac, MD (US); Mekbib Astatke, Germantown, MD (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 810 days.

(21) Appl. No.: 14/329,773

(22) Filed: Jul. 11, 2014

(65) Prior Publication Data
US 2015/0037792 A1 Feb. 5, 2015

Related U.S. Application Data

(63) Continuation of application No. 13/751,615, filed on Jan. 28, 2013, now abandoned, which is a continuation of application No. 12/629,045, filed on Dec. 1, 2009, now Pat. No. 8,394,609, which is a continuation of application No. 12/251,378, filed on Oct. 14, 2008, now abandoned, which is a continuation of application No. 10/932,045, filed on Sep. 2, 2004, now abandoned, which is a continuation of application No. 10/026,952, filed on Dec. 27, 2001, now abandoned.

(60) Provisional application No. 60/330,468, filed on Oct. 23, 2001.

(51) Int. Cl.
| C12Q 1/68 | (2018.01) |
| C12Q 1/6876 | (2018.01) |
| C12P 19/34 | (2006.01) |
| C12Q 1/6816 | (2018.01) |
| C12Q 1/6827 | (2018.01) |
| C12Q 1/686 | (2018.01) |
| C12Q 1/6869 | (2018.01) |
| G01N 21/64 | (2006.01) |

(52) U.S. Cl.
CPC .......... *C12Q 1/6876* (2013.01); *C12P 19/34* (2013.01); *C12Q 1/686* (2013.01); *C12Q 1/6816* (2013.01); *C12Q 1/6827* (2013.01); *C12Q 1/6869* (2013.01); *G01N 21/6486* (2013.01)

(58) Field of Classification Search
None
See application file for complete search history.

(56) References Cited

U.S. PATENT DOCUMENTS

| 4,358,535 A | 11/1982 | Falkow et al. |
| 4,446,237 A | 5/1984 | Berninger |
| 4,563,417 A | 1/1986 | Albarella et al. |
| 4,581,333 A | 4/1986 | Kourilsky |
| 4,582,788 A | 4/1986 | Erlich |
| 4,582,789 A | 4/1986 | Sheldon, III et al. |
| 4,683,194 A | 7/1987 | Saiki et al. |
| 4,683,202 A | 7/1987 | Mullis |
| 4,889,818 A | 12/1989 | Gelfand et al. |
| 4,965,188 A | 10/1990 | Mullis et al. |
| 5,047,342 A | 9/1991 | Chatterjee |
| 5,079,352 A | 1/1992 | Gelfand et al. |
| 5,118,801 A | 6/1992 | Lizardi et al. |
| 5,137,814 A | 8/1992 | Rashtchian et al. |
| 5,143,854 A | 9/1992 | Pirrung et al. |
| 5,194,370 A | 3/1993 | Berninger et al. |
| 5,200,314 A | 4/1993 | Urdea |
| 5,244,797 A | 9/1993 | Kotewicz et al. |
| 5,252,743 A | 10/1993 | Barrett et al. |
| 5,270,179 A | 12/1993 | Chatterjee |
| 5,312,728 A | 5/1994 | Lizardi et al. |
| 5,334,515 A | 8/1994 | Rashtchian et al. |
| 5,338,671 A | 8/1994 | Scalice et al. |
| 5,348,853 A | 9/1994 | Wang et al. |
| 5,374,553 A | 12/1994 | Gelfand et al. |
| 5,436,149 A | 7/1995 | Barnes |
| 5,436,327 A | 7/1995 | Southern et al. |
| 5,445,934 A | 8/1995 | Fodor et al. |
| 5,449,603 A | 9/1995 | Nielson et al. |
| 5,455,166 A | 10/1995 | Walker |
| 5,487,972 A | 1/1996 | Gelfand et al. |
| 5,491,063 A | 2/1996 | Fisher et al. |
| 5,503,979 A | 4/1996 | Kramer et al. |

(Continued)

FOREIGN PATENT DOCUMENTS

| EP | 0 050 424 | 9/1981 |
| EP | 0084796 A2 | 8/1983 |

(Continued)

OTHER PUBLICATIONS

"Amplifuor™ Universal Amplification & Detection System", *Intergen Company Catalog*, Purchase, NY, 1999, 1-4.

Abe, Takayuki et al., "Specific Inhibition of Influenza Virus RNA Polymerase and Nucleoprotein Gene Expression by Circular Dumbbell RNA/DNA Chimeric Oligonucleotides Containing Antisense Phosphodiester Oligonucleotides", *FEBS Letters,*, vol. 425, Elsevier Science, Publishers B.V.,, 1998, pp. 91-96.

Ailenberg, M. et al., "Controlled Hot Start and Improved Specificity in Carrying Out PCR Utilizing Touch Up and Loop Incorporated Primers (TULIPS)", *BioTechniques 29,*, Eaton Publishing Co., Nov. 2000, pp. 1018-1024.

Austermann, Sabine et al., "Inhibition of Human Immunodeficiency Virus Type 1 Reserve Transcriptase by 3'-Blocked Oligonucleotide Primers", *Bicohemical Pharmacology,*, vol. 43, No. 12, Elsevier Science, 1992, pp. 2581-2589.

(Continued)

Primary Examiner — David C Thomas

(57) ABSTRACT

The present invention provides novel primers and methods for the detection of specific nucleic acid sequences. The primers and methods of the invention are useful in a wide variety of molecular biology applications and are particularly useful in allele specific PCR.

16 Claims, 60 Drawing Sheets

(56) References Cited

U.S. PATENT DOCUMENTS

| | | |
|---|---|---|
| 5,512,462 A | 4/1996 | Cheng |
| 5,538,848 A | 7/1996 | Livak et al. |
| 5,563,253 A | 10/1996 | Agrawal et al. |
| 5,565,322 A | 10/1996 | Heller |
| 5,571,674 A | 11/1996 | Hoshina et al. |
| 5,578,467 A | 11/1996 | Schuster et al. |
| 5,587,287 A | 12/1996 | Scalice et al. |
| 5,591,721 A | 1/1997 | Agrawal et al. |
| 5,593,840 A | 1/1997 | Bhatnagar et al. |
| 5,594,138 A | 1/1997 | Dykstra et al. |
| 5,594,183 A | 1/1997 | Colin |
| 5,595,890 A | 1/1997 | Newton et al. |
| 5,599,695 A | 2/1997 | Pease et al. |
| 5,605,824 A | 2/1997 | Nielson et al. |
| 5,614,365 A | 3/1997 | Tabor et al. |
| 5,639,611 A | 6/1997 | Wallace et al. |
| 5,646,019 A | 7/1997 | Nielson et al. |
| 5,668,005 A | 9/1997 | Kotewicz et al. |
| 5,714,331 A | 2/1998 | Buchardt et al. |
| 5,728,526 A | 3/1998 | George, Jr. et al. |
| 5,736,336 A | 4/1998 | Buchardt et al. |
| 5,763,170 A | 6/1998 | Raybuck |
| 5,773,257 A | 6/1998 | Nielson et al. |
| 5,800,992 A | 9/1998 | Fodor et al. |
| 5,837,832 A | 11/1998 | Chee et al. |
| 5,846,729 A | 12/1998 | Wu et al. |
| 5,866,336 A | 2/1999 | Nazarenko et al. |
| 5,869,251 A | 2/1999 | Schuster et al. |
| 5,876,930 A | 3/1999 | Livak et al. |
| 5,876,936 A | 3/1999 | Ju |
| 5,912,148 A | 6/1999 | Eggerding |
| 5,925,517 A | 7/1999 | Tyagi et al. |
| 5,945,526 A | 8/1999 | Lee et al. |
| 5,948,614 A | 9/1999 | Chatterjee |
| 5,948,899 A | 9/1999 | Arnold, Jr. et al. |
| 5,952,172 A | 9/1999 | Meade et al. |
| 6,015,668 A | 1/2000 | Hughes et al. |
| 6,037,130 A | 3/2000 | Tyagi et al. |
| 6,048,690 A | 4/2000 | Heller et al. |
| 6,090,552 A | 7/2000 | Nazarenko et al. |
| 6,117,635 A | 9/2000 | Nazarenko et al. |
| 6,117,986 A | 9/2000 | Nardone et al. |
| 6,130,038 A * | 10/2000 | Becker .................. C07H 21/00 435/6.1 |
| 6,150,097 A | 11/2000 | Tyagi et al. |
| 6,174,670 B1 | 1/2001 | Wittwer et al. |
| 6,207,425 B1 | 3/2001 | Liu et al. |
| 6,232,130 B1 | 5/2001 | Wolf |
| 6,248,526 B1 | 6/2001 | Weimer |
| 6,265,163 B1 | 7/2001 | Albrecht et al. |
| 6,277,607 B1 | 8/2001 | Tyagi et al. |
| 6,316,200 B1 | 11/2001 | Nadeau et al. |
| 6,316,230 B1 | 11/2001 | Egholm et al. |
| 6,342,376 B1 | 1/2002 | Kozian et al. |
| 6,440,723 B1 | 8/2002 | Dale |
| 6,465,175 B2 | 10/2002 | Horn et al. |
| 7,537,886 B1 | 5/2009 | Nazarenko et al. |
| 7,803,528 B1 | 9/2010 | Chiang et al. |
| 2003/0165865 A1 | 9/2003 | Hinkel et al. |
| 2009/0092990 A1 | 4/2009 | Nazarenko et al. |
| 2010/0233699 A1 | 9/2010 | Nazarenko et al. |
| 2011/0143350 A1 | 6/2011 | Nazarenko et al. |

FOREIGN PATENT DOCUMENTS

| | | |
|---|---|---|
| EP | 0119448 A1 | 9/1984 |
| EP | 0144914 A2 | 6/1985 |
| EP | 0201184 A2 | 12/1986 |
| EP | 0237362 A1 | 9/1987 |
| EP | 0329822 B1 | 8/1989 |
| EP | 0436644 B1 | 4/1996 |
| EP | 0709466 | 5/1996 |
| EP | 0774516 A2 | 5/1997 |
| EP | 0258017 B1 | 6/1997 |
| EP | 0795612 A2 | 9/1997 |
| EP | 0881302 | 12/1998 |
| EP | 1087020 | 3/2001 |
| EP | 0684315 B1 | 6/2002 |
| WO | WO-1988/010315 | 12/1988 |
| WO | WO-1989/006700 | 7/1989 |
| WO | WO-1990/003446 | 4/1990 |
| WO | WO-1992/006188 | 4/1992 |
| WO | WO-1992/006200 | 4/1992 |
| WO | WO-1992/014845 | 9/1992 |
| WO | WO-1996/010640 | 4/1996 |
| WO | WO-1996/15270 | 5/1996 |
| WO | WO-97/39008 | 10/1997 |
| WO | WO-1997/39008 | 10/1997 |
| WO | WO-98/02449 | 1/1998 |
| WO | WO-1998/02449 | 1/1998 |
| WO | WO-1998/035060 | 8/1998 |
| WO | WO-1998/047921 | 10/1998 |
| WO | WO1999/010366 | 3/1999 |
| WO | WO-00/56916 | 9/2000 |
| WO | WO-2000/56916 | 9/2000 |

OTHER PUBLICATIONS

Barnes, "The Fidelity of Taq Polymerase Catalyzing PCR is Improved by an N-Terminal Deletion", *Gene*, vol. 112, No. 1, Mar. 1, 1992, 29-35.

Blok, H. J. et al., "Amplifiable hybridization probes containing a molecular switch", *Mol. Cell. Probes* 11, Academic Press, Ltd., 1997, 187-194.

Bonnet, Gregoire et al., "Thermodynamic Basis of the Enhanced Specificity of Structured DNA Probes", *Proceedings of the National Academy of Sciences (PNAS), Biophysics*, vol. 96,, May 1999, pp. 6171-6176.

Cardullo, et al., "Detection of Nucleic Acid Hybridization by Non Radiative Fluorescence Resonance Energy Transfer", *Proceedings of the National Academy of Sciences*, vol. 85, 1988, 8790-8794.

Chedin, Frederic et al., "Novel Homologs of Replication Protein A in Archaea: Implications for the Evolution of ssDNA-Binding Proteins", *Trends in Biochemical Science (TIBS)*,, vol. 23, No. 8, Elsevier Science, Ltd.,, Aug. 1998, pp. 273-277.

Clegg, "Fluorescence Resonance Energy Transfer and Nucleic Acids", *Methods in Enzymology*, vol. 211, 1992, 353-388.

Clegg, Robert M. et al., "Fluorescence Resonance Energy Transfer Analysis of the Structure of the Four-Way DNA Junction", *Biochemistry,*, vol. 31, No. 20, American Chemical Society,, 1992, pp. 4846-4856.

Clegg, Robert M. et al., "Observing the Helical Geometry of Double-Stranded DNA in Solution by Fluorescence Resonance Energy Transfer", *Proceedings of the National Academy of Sciences (PNAS)*, vol. 90, 1993, pp. 2994-2998.

Ehlen, T. et al., "Detection of Ras Point Mutations by Polymerase Chain Reaction Using Mutation Specific, Inosine Containing Oligonucleotide Primers", *Biochem. Biophys. Res. Commun.*, Academic Press, Inc., 1989, 160: 441-447.

EP01997138, "Supplementary Partial European Search Report dated Jan. 5, 2005".

Flaman, et al., "A Rapid PCR Fidelity Assay", *Nucleic Acids Research*, vol. 22, No. 15, Aug. 11, 1994, 3259-3260.

Forster, "Experimentelle und theoretische Untersuchung des zwischenmolekularen Ubergangs von Elektronenanregungsenergie", *Z. Naturforsch, 4A*, Verlag der Zeitschrift fur Naturforschung, 1949, 323-327.

Gerard, et al., "cDNA Synthesis by Moloney Murine Leukemia Virus RNase H-Minus Reverse Transcriptase Possessing Full DNA Polymerase Activity", *Focus*, vol. 14, No. 3,, 1992, 91-93.

Giesendorf, B. A. et al., "Molecular beacons: a new approach for semiautomated mutation analysis", *Clin. Chem.* 44, American Association for Clinical Chemistry, 1998, 482-486.

Haas, S. et al., "Primer design for large scale sequencing", *Nucl. Acids Res.*, 26:, Oxford University Press, 1998, 3006-3012.

Holland, et al., "Detection of Specific Polymerase Chain Reaction Product by Utilizing the 5'->3' Exonuclease Activity of Thermus Aquaticus DNA Polymerase", *Proceedings of the National Academy of Sciences*, vol. 88, Issue 16, Aug. 15, 1991, 7276-7280.

(56) References Cited

OTHER PUBLICATIONS

Houts, et al., "Reverse Transcriptase from Avian Myeloblastosis Virus", *Journal of Virology*, vol. 29, No. 2, Feb. 1979, 517-522.
Hu, X. et al., "Fluorescence Based Single Tube Assays to Rapidly Detect Human MutationsGene", *Strategies*, vol. 13, 2000, 71-73.
Idriss, Haitham et al., "Inhibition of HIV-1 Reverse Transcriptase by Defined Template/Primer DNA Oligonucleotides: Effect of Template Length and Binding Characteristics", *Journal of Enzyme Inhibition*, vol. 8, Harwood Academic Publishers GmbH, 1994, 97-112.
Jendis, Jorg et al., "Inhibition of Replication of Fresh HIV Type 1 Patient Isolates by a Polypurine Tract-Specific Self-Complementary Oligodeoxynucleotide", *AIDS Research and Human Retroviruses*, vol. 12, No. 12: Mary Ann Leibert, Inc., Publishers, 1996, 1161-1168.
Ju, Jingyue et al., "Fluorescence Energy Transfer Dye-Labeled Primers for DNA Sequencing and Analysis", *Proceedings of the National Academy of Sciences (PNAS)*, vol. 92: National Academy of Sciences of the USA, May 1995, 4347-4351.
Kaboev, O. K. et al., "PCR Hot Start Using Primers With the Structure of Molecular Beacons (Hairpin-Like Structures)", *Nucleic Acids Research* vol. 28, No. 21, Oxford University Press, 2000, pp. 1-2.
Kainz, Peter et al., "Specificity-Enhanced Hot-Start PCR: Addition of Double-Stranded DNA Fragments Adapted to the Annealing Temperature", *BioTechniques*, vol. 28, No. 2: BPA International, 2000, 278-282.
Kelly, Thomas J. et al., "Identification and Characterization of a Single-Stranded DNA-Binding Protein From the Archaeon Methanococcus Jannaschii", *Proceedings of the National Academy of Sciences (PNAS)*, vol. 95, National Academy of Sciences of the USA, Dec. 1998, 14634-14639.
Kleppe, K et al., "Studies on Polynucleotides. XCVI. Repair Replications of Short Synthetic DNA's as Catalyzed by DNA Polymerases", *Journal of Molecular Biology*, vol. 56, Academic Press, Inc., 1971, 341-361.
Kolocheva, T. I. et al., "Recognition of the primers containing different modified nucleotide units by the Klenow fragment of DNA polymerase I from *E. coli*", *Biochimie*, vol. 78, Issue 3, 1996, 201-203.
Kostrikis, L. G. et al., "Spectral Genotyping of Human Alleles", *Science*, 279:, American Association for the Advancement of Science, 1998, 1228-1229.
Kotewicz, et al., "Isolation of cloned Moloney murine leukemia virus reverse transcriptase lacking ribonuclease H activity", *Nucleic Acids Research*, vol. 16, No. 1, IRL Press Limited, Oxford, England, Jan. 11, 1988, 265-277.
Kramer, F. R. et al., "Replicatable RNA reporters", *Nature*, vol. 339, Macmillan Journals Ltd., Jun. 1, 1989, 401-402.
Kricka, Larry J., "Chemiluminescent and Bioluminescent Techniques", *Clin. Chem.* 37 (9), Sensitive Detection Systems, 1991, 1472-1481.
Kumke, Michael et al., "Hybirdization of Fluorescein-Labeled DNA Oligomers Detected by Fluorescence Anisotropy with Protein Binding Enchancement", *Anal. Chem.*, vol. 67, 1995, 3945-3951.
Kuwasaki, Tomoyuki et al., "Hairpin Antisense Oligonucleotides Containing 2'-Methoxynucleosides With Base-Pairing in the Stem Region at the 3'-End: Penetration, Localization, and Anti-HIV Activity", *Biochemical and Biophysical Research Communications*, vol. 228, Article #1707, Academic Press, Inc., 1996, 623-631.
Kwoh, et al., "Transcription-Based Amplification System and Detection of Amplified Human Immunodeficiency Virus Type 1 With a Bead-Based Sandwich Hybridization Format", *Proceedings of the National Academy of Sciences*, vol. 86, Issue 4, Feb. 15, 1989, 1173-1177.
Lawyer, et al., "High-level Expression, Purification, and Enzymatic characterization of Full-length Thermus aquaticus DNA polymerase and a Truncated Form Deficient in 5' to 3' Exonuclease activity", *PCR Methods and Applications*, vol. 2, No. 4, May 1993, 275-287.
Lee et al., "Allelic Discrimination by Nick-Translation PCR With Fluorogenic Probes", *Nucleic Acids Research*, vol. 21, No. 16, Aug. 11, 1993, 3761-3766.
Lengauer, Christoph et al., "Genetic instabilities in human cancers", *Nature*, vol. 396, Macmillan Journals Ltd., Dec. 17, 1998, 643-649.
Leone, G. et al., "Molecular beacon probes combined with amplification by NASBA enable homogeneous,real time detection of RNA", *Nucleic Acids Research*, vol. 26, Oxford University Press, 1998, 2150-2155.
Luo, Guangxiang et al., "Inhibition of Influenza Viral Polymerases by Minimal Viral RNA Decoys", *Journal of General Virology*, vol. 78, Society for General Microbiology, 1997, 2329-2333.
Lyamichev, Victor et al., "Structure-Specific Endonucleolytic Cleavage of Nucleic Acids by Eubacterial DNA Polymerases", *Science*, vol. 260, Association for the Advancement of Science, May 7, 1993, 778-783.
Marras, S. E. et al., "Multiplex detection of single nucleotide variations using molecular beacons", *Genet. Anal.: Biomol. Eng.*, 14:, Elsevier Science B.V., 1999, 151-156.
Maury, Georges et al., "Template. Phosphorothioate Oligonucleotides Duplexes as Inhibitors of HIV-1 Reverese Transcriptase", *Biochemical and Biophysical Research Communications*, vol. 186, Academic Press, Inc., Aug. 14, 1992, 1249-1256.
Monia, B. P. et al., "Selective Inhibition of Mutant Ha ras mRNA Expression by Antisense Oligonucleotides", *J. Biol. Chem.*, 267:, American Society for Biochemistry and Molecular Biology, Inc., 1992, 19954-19962.
Moran, S. et al., "Non hydrogen bonding 'terminator' nucleosides increase the 3' end homogeneity of enzymatic RNA and DNA synthesis", *Nucl. Acids Res.*, 24:, Oxford University Press, 1996, 2044-2052.
Mullis, et al., "Specific Enzymatic Amplification of DNA In Vitro: The Polymerase Chain Reaction", *Cold Spring Harbor Symposia on Quantitative Biology*, vol. 51, Part 1, 1986, 263-273.
Myakishev, Maxim et al., "High-Throughput SNP Genotyping by Allele-Specific PCR with Universal Energy-Transfer-Labeled Primers", *Genome Research*, vol. 11, 2001, 163-169.
Nakaya, Takaaki et al., "Decoy Approach Using RNA-DNA Chimera Oligonucleotides to Inhibit the Regulatory Function of Human Immunodeficiency Virus Type 1 Rev Protein", *Antimicrobial Agents Chemotherapy*, vol. 41, No. 2, American Society for Microbiology, Feb. 1997, 319-325.
Nazarenko, Irina et al., "Effect of primary and secondary structure of oligodeoxyribonucleotides on the fluorescent properties of conjugated dyes", *Nucleic Acids Research*, vol. 30, No. 9, 2002, 2089-2095.
Nazarenko, Irina et al., "Multiplex quantitative PCR using self quenched primers labeled with a single fluorophore", *Nucleic Acids Research*, vol. 30, No. 9, e37, 2002, 1-7.
Nazarenko, Irina A. et al., "A Closed Tube Format for Amplification and Detection of DNA Based on Energy Transfer", *Nucleic Acids Research*, vol. 25, No. 12, 1997, 2516-2521.
Newton, C. R. et al., "Analysis of any point mutation in DNA. The amplification refractory mutation system (ARMS)", *Nucl. Acids Res.*, IRL Press, 17:, 1989, 2503-2516.
Nuovo, G. J. et al., "In Situ Amplification Using Universal Energy Transfer-labeled Primers", *The Journal of Histochemistry and Cytochemistry* vol. 47(3), 1999, 273-279.
Ozaki, Hiroaki et al., "The Estimation of Distances Between Specific Backbone-Labeled Sites in DNA Using Fluorescence Resonance Energy Transfer", *Nucleic Acids Research*, vol. 20, No. 19, 1992, 5205-5214.
Panet, Amos et al., "Studies on Polynucletoides. The Linkage of Deoxyribopolynucleotide Templates to Cellulose and its Use in Their Replication", *The Journal of Biological Chemistry*, vol. 249, No. 16, American Society of Biological Chemists, Aug. 25, 1974, 5213-5221.
Paris, Pamela L. et al., "Probing DNA Sequences in Solution With a Monomer-Excimer Fluorescence Color Change", *Nucleic Acids Research*, vol. 26, No. 16: Oxford University Press, 1998, 3789-3793.
PCT/US00/17085, "International Search Report, dated May 23, 2001".

(56) References Cited

OTHER PUBLICATIONS

PCT/US01/050460, "PCT International Search Report, dated May 30, 2003".
PCT/US01/50460, "International Preliminary Examination Report, dated Feb. 17, 2004".
Rye, H. S. et al., "Stable Fluorescent Complexes of Double-Stranded DNA With Bis-Intercalating Asymmetric Cyanine Dyes: Properties and Applications", *Nucleic Acids Research*, vol. 20(11), 1992, pp. 2803-2812.
Saiki, Randall K. et al., "Primer-Directed Enzymatic Amplification of DNA with a Thermostable DNA Polymerase", *Science*, Reports, vol. 239,, Jan. 29, 1988, 487-491.
Sarin, et al., "Inhibition of Acquired Immunodeficiency Syndrome Virus by Oligodeoxynucleoside Methylphosphonates", *Proceedings of the National Academy of Sciences*, vol. 85, No. 20, Oct. 15, 1988, 7448-7451.
Schneider, Daniel J. et al., "High Affinity ssDNA Inhibitors of the Reverse Transcriptase of Type 1 Human Immunodeficiency Virus", *Biochemistry*, vol. 34 , American Chemical Society, 1995, 9599-9610.
Selvin, "Fluorescence Resonance Energy Transfer", *Methods in Enzymology*, vol. 246, 1995, 300-334.
Selvin, Paul R. et al., "Luminescence Energy Transfer Using a Terbium Chelate: Improvements on Fluorescence Energy Transfer", *Proceedings of the National Academy of Sciences (PNAS)*, vol. 91, National Academy of Sciences of the USA, Oct. 1994, 10024-10028.
Serra, M. J. et al., "Predicting Thermodynamic Properties of RNA", *Meth.Enzymol.*, 259:, Academic Press, Inc., 1995, 242-261.
Smith, N. R. et al., "Automated Differential Display Using a Fluorescently Labeled Universal Primer", *BioTechniques*, vol. 23, 1997, 274-279.
Smith, N. R. et al., "Automated Differential Display Using a Fluorescently Labeled Universal Primer", *BioTechniques*, vol. 23, No. 2, 1997, 274-279.
Soltis, et al., "The α and β Chains of Avian Retrovirus Reverse Transcriptase Independently Expressed in *Escherichia coli*: Characterization of Enzymatic Activities", *Proceedings of the National Academy of Sciences*, vol. 85, No. 10, May 1988, 3372-3376.
Stein, et al., "Physicochemical Properties of Phosphorothioate Oligodeozynucleotides", *Nucleic Acids Research*, vol. 16, No. 8, 1988, 3209-3221.
Tyagi, et al., "Molecular Beacons: Probes that Fluoresce upon Hybridization", *Nature Biotechnology*, vol. 14, No. 3, Mar. 1996, 303-308.
Tyagi, Sanjay et al., "Extremely sensitive, background free gene detection using binary probes and beta replicase", *Proceedings of the National Academy of Sciences (PNAS)*, vol. 93, No. 11, National Academy of Sciences, May 28, 1996, 5395-5400.
Tyagi, Sanjay et al., "Multicolor molecular beacons for allele discrimination", *Nature Biotechnology*, vol. 16, 1998, 49-53.
Varani, G., "Exceptionally Stable Nucleic Acid Hairpins", *Annu. Rev. Biophys. Biomol. Struct.*, 24 :, Annual Reviews Inc., 1995, 379-404.
Vet, et al., "Multiplex detection of four pathogenic retroviruses using molecular beacons", *Proceedings of the National Academy of Sciences (PNAS)*, vol. 96, Issue 11,, May 25, 1999, 6394-6399.
Walder, R Y. et al., "Use of PCR primers containing a 3' terminal ribose residue to prevent cross contamination of amplified sequences", *Nucl. Acids Res.*, 21, Oxford University Press, 1993, 4339-4343.
Wang, et al., "Design and Synthesis of New Fluorogenic HIV Protease Substrates Based on Resonance Energy Transfer", *Tetrahedron Letters*, vol. 31, No. 45, 1990, 6493-6496.
Wang, et al., "Rapid Sizing of Short Tandem Repeat Alleles Using Capillary Array Electrophoresis and Energy-Transfer Fluorescent Primers", *Analytical Chemistry*, vol. 67, No. 7, Apr. 1, 1995, 1197-1203.
Whitcombe, D et al., "Detection of PCR products using self probing amplicons and fluorescence", *Nature Biotechnology*, vol. 17, No. 8, Nature Publishing Group, Aug. 1999, 804-807.
Wittwer, C. T. et al., "Continous Fluorescence Monitoring of Rapid Cycle DNA Amplification", *Biotechniques, Informa Life Sciences Publishing*, Westborough, MA, vol. 22, No. 1, Jan. 1, 1997, 130-138.
Wu, Dan Y. et al., "Allele-Specific Enzymatic Amplification of a Beta-Globin Genomic DNA for Diagnosis of Sickle Cell Anemia", *Proceedings of the National Academy of Sciences (PNAS)*, vol. 86, National Academy of Sciences of the USA, Apr. 1989, 2757-2760.
Wu, Dan Y. et al., "The Ligation Amplification Reaction (LAR)—Amplification of Specific DNA Sequences Using Sequential Rounds of Template-Dependent Ligation", *Genomics*, vol. 4, 1989, 560-569.
Xu, Daguang et al., "Melting and Premelting Transitions of an Oligomer Measured by DNA Base Fluorescence and Absorption", *Biochemistry*, vol. 33: American Chemical Society, 1994, 9592-9599.
Yamamoto, N. et al., "A rapid detection of PCR amplification product using a new fluorescent intercalator; the pyrylium dye, P2", *Nucl. Acids Res.*, 23:, Oxford University Press, 1995, 1445-1446.
Yamana, Kazushige et al., "Fluorescent-Labeled Oligonucleotide That Exhibit a Measurable Signal in the Presence of Complementary DNA", *Nineteenth Symposium on Nucleic Acids Chemistry*, vol. 27, Nucleic Acids Symposium Series, IRL Press Ltd., Nov. 1992, 135-136.
Zubritsky, E., "Pinning Down PCR", *Analytical Chemistry News & Features*, vol. 71, American Chemical Society, 1999, 191A-195A.
Kleparnik, K. et al., "DNA cycle sequencing of a common restriction fragment of *Staphylococcus aureus* bacteriophages by capillary electrophoresis using replaceable linear polyacrylamide", *Electrophoresis*, vol. 19 (5), 1998, 695-700.

\* cited by examiner

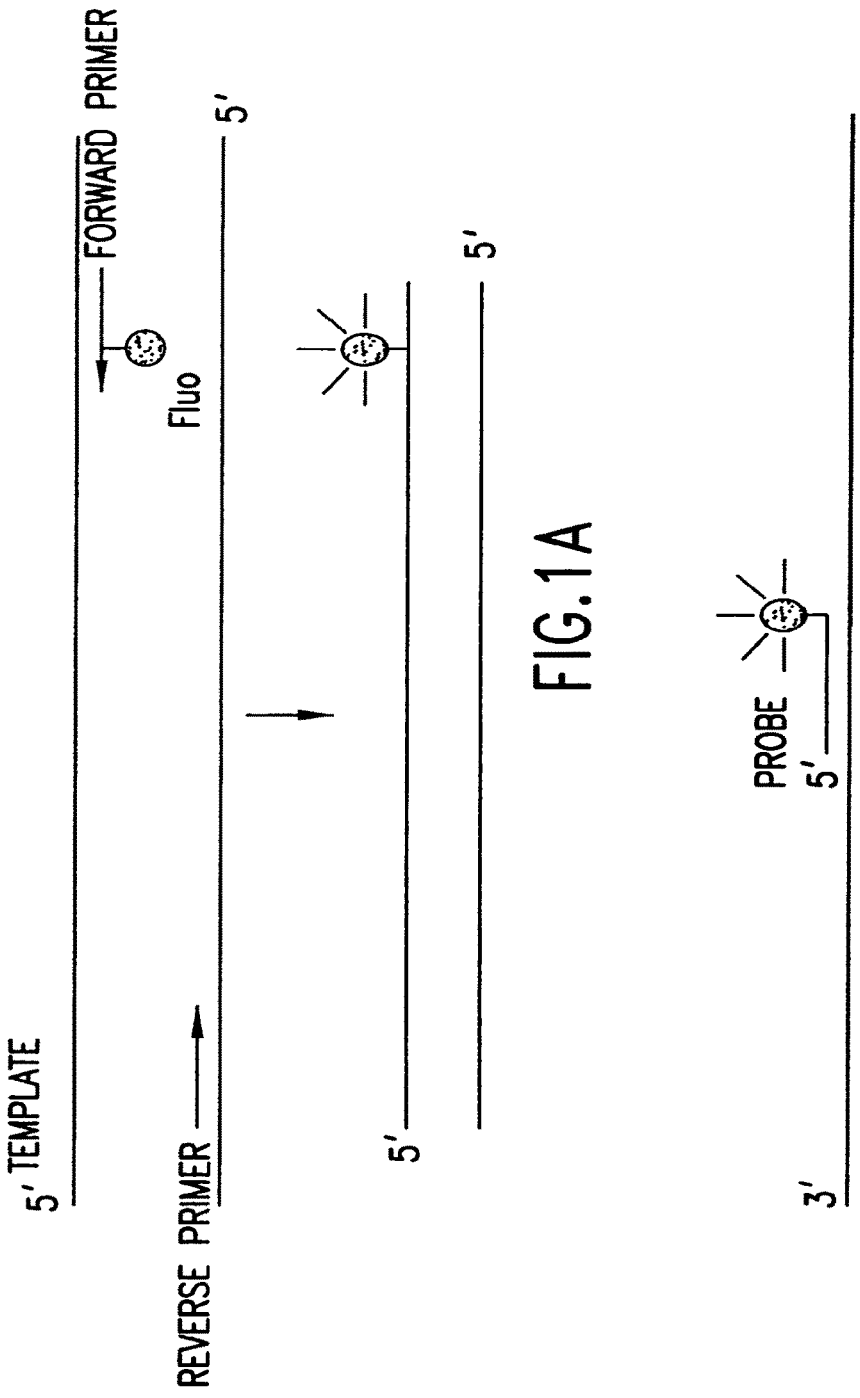

THRESHOLD CYCLE CALCULATION

THRESHOLD

USE THRESHOLD: 505.0　[SUGGEST]

MULT. * STDDEV: 10.0 * 14.012

OMIT THRESHOLD: 2.0

BASELINE

START: 4　　STOP: 12

[UPDATE CALCULATIONS]

| | CT | STD DEV |
|---|---|---|
| FAM-G1 | 45.000 | 13.424 |
| FAM-H1 | 30.459 | 23.908 |
| FAM-H2 | 26.266 | 18.654 |
| FAM-H3 | 22.661 | 14.066 |
| FAM-H4 | 18.267 | 18.699 |

FIG.5B

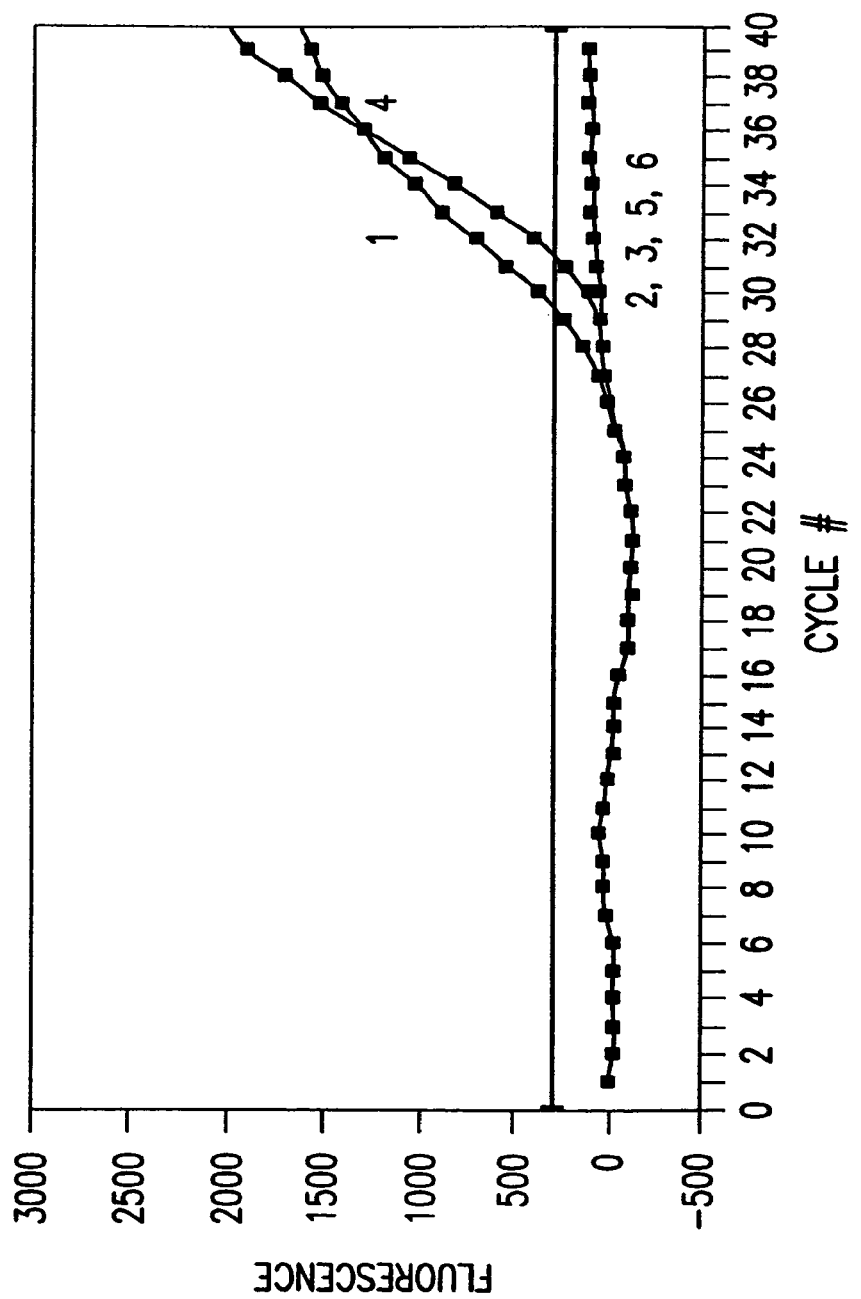

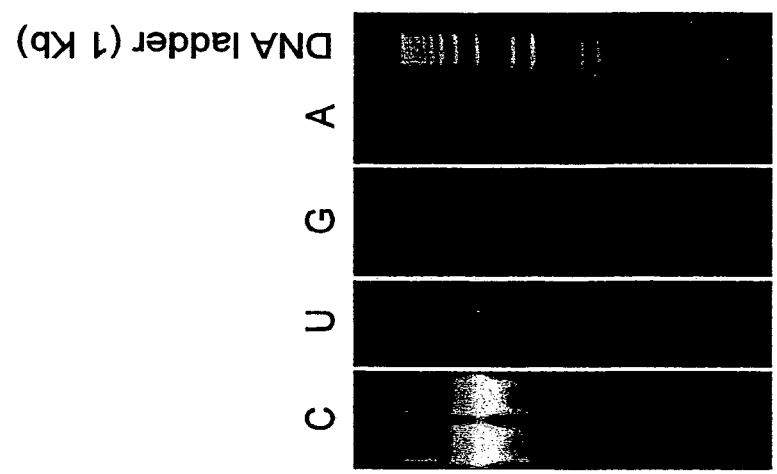
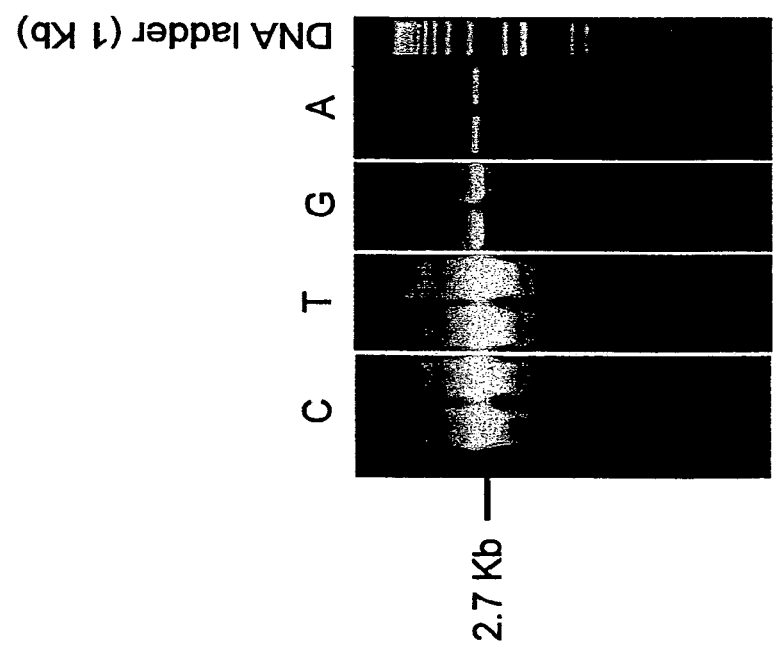

PRIMERS AND METHODS FOR THE DETECTION AND DISCRIMINATION OF NUCLEIC ACIDS

CROSS-REFERENCE TO RELATED APPLICATIONS

The present application is a continuation of U.S. patent application Ser. No. 13/751,615, filed Jan. 28, 2013, which is a continuation of U.S. patent application Ser. No. 12/629,045, filed Dec. 1, 2009, now U.S. Pat. No. 8,394,609, which is a continuation of U.S. patent application Ser. No. 12/251,378, filed Oct. 14, 2008 (now abandoned), which is a continuation of U.S. patent application Ser. No. 10/932,045, filed Sep. 2, 2004 (now abandoned), which is a continuation of U.S. patent application Ser. No. 10/026,952, filed Dec. 27, 2001 (now abandoned), which claims the benefit of priority to U.S. Provisional Application No. 60/330,468, filed Oct. 23, 2001.

BACKGROUND OF THE INVENTION

Field of the Invention

The present invention relates to the field of molecular biology. In particular, the present invention relates to novel primers for use in the detection and discrimination of nucleic acids. The novel primers of the present invention will find broad applicability in the field of molecular biology and, in particular, in increasing specificity (e.g., reducing mis-priming) during nucleic acid synthesis or amplification, in the detection of products in nucleic acid amplification and synthesis reactions and in the discrimination between alleles of a given target gene.

Related Art

Assays capable of detecting and quantifying the presence of a particular nucleic acid molecule in a sample are of substantial importance in forensics, medicine, epidemiology and public health, and in the prediction and diagnosis of disease. Such assays can be used, for example, to identify the causal agent of an infectious disease, to predict the likelihood that an individual will suffer from a genetic disease, to determine the purity of drinking water or milk, or to identify tissue samples. The desire to increase the utility and applicability of such assays is often frustrated by assay sensitivity. Hence, it would be highly desirable to develop more sensitive detection assays.

Nucleic acid detection assays can be predicated on any characteristic of the nucleic acid molecule, such as its size, sequence and, if DNA, susceptibility to digestion by restriction endonucleases. The sensitivity of such assays may be increased by altering the manner in which detection is reported or signaled to the observer. Thus, for example, assay sensitivity can be increased through the use of detectably labeled reagents. A wide variety of such labels have been used for this purpose. Detectable labels include, for example, radioactive isotopes, fluorescent labels, chemiluminescent labels, bioluminescent labels and enzyme labels. U.S. Pat. No. 4,581,333 describes the use of enzyme labels to increase sensitivity in a detection assay. Radioisotopic labels are disclosed in U.S. Pat. Nos. 4,358,535, and 4,446,237. Fluorescent labels (EP 144,914), chemical labels (U.S. Pat. Nos. 4,582,789 and 4,563,417) and modified bases (EP 119,448) have also been used in an effort to improve the efficiency with which detection can be observed.

Although the use of highly detectable labeled reagents can improve the sensitivity of nucleic acid detection assays, the sensitivity of such assays remains limited by practical problems which are largely related to non-specific reactions which increase the background signal produced in the absence of the nucleic acid the assay is designed to detect. In response to these problems, a variety of detection and quantification methods using DNA amplification have been developed.

Many current methods of identification and quantification of nucleic acids rely on amplification and/or hybridization techniques. While many of these involve a separation step, several that allow detection of nucleic acids without separating the labeled primer or probe from the reaction have been developed. These methods have numerous advantages compared to gel-based methods, such as gel electrophoresis, and dot-blot analysis, for example, and require less time, permit high throughput, prevent carryover contamination and permit quantification through real time detection. Most of these current methods are solution-based fluorescence methods that utilize two chromophores. These methods utilize the phenomena of fluorescence resonance energy transfer (FRET) in which the energy from an excited fluorescent moiety is transferred to an acceptor molecule when the two molecules are in close proximity to each other. This transfer prevents the excited fluorescent moiety from releasing the energy in the form of a photon of light thus quenching the fluorescence of the fluorescent moiety. When the acceptor molecule is not sufficiently close, the transfer does not occur and the excited fluorescent moiety may then fluoresce. The major disadvantages of systems based on FRET are the cost of requiring the presence of two modified nucleotides in a detection oligonucleotide and the possibility that the efficiency of the quenching may not be sufficient to provide a usable difference in signal under a given set of assay conditions. Other known methods which permit detection without separation are: luminescence resonance energy transfer (LRET) where energy transfer occurs between sensitized lanthanide metals and acceptor dyes (Selvin, P. R., and Hearst, J. D., *Proc. Natl. Acad. Sci. USA* 91:10024-10028 (1994)); and color change from excimer-forming dyes where two adjacent pyrenes can form an excimer (fluorescent dimer) in the presence of the complementary target, resulting in a detectably shifted fluorescence peak (Paris, P. L. et al., *Nucleic Acids Research* 26:3789-3793 (1998)).

Various methods are known to those skilled in the art for the amplification of nucleic acid molecules. In general, a nucleic acid target molecule is used as a template for extension of an oligonucleotide primer in a reaction catalyzed by polymerase. For example, Panet and Khorana (*J. Biol. Chem.* 249:5213-5221 (1974)) demonstrate the replication of deoxyribopolynucleotide templates bound to cellulose. Kleppe et al., (*J. Mol. Biol.* 56:341-361 (1971)) disclose the use of double- and single-stranded DNA molecules as templates for the synthesis of complementary DNA.

Other known nucleic acid amplification procedures include transcription based amplification systems (Kwoh, D. et al., *Proc. Natl. Acad. Sci. USA* 86:1173 (1989); PCT appl. WO 88/10315). Schemes based on ligation ("Ligation Chain Reaction" ("LCR")) of two or more oligonucleotides in the presence of a target nucleic acid having a sequence complementary to the sequence of the product of the ligation reaction have also been used (Wu, D. Y. et al., *Genomics* 4:560 (1989)). Other suitable methods for amplifying nucleic acid based on ligation of two oligonucleotides after annealing to complementary nucleic acids are known in the art.

PCT appl. WO 89/06700 discloses a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts.

EP 329,822 discloses an alternative amplification procedure termed Nucleic Acid Sequence-Based Amplification (NASBA). NASBA is a nucleic acid amplification process comprising cyclically synthesizing single-stranded RNA ("ssRNA"), ssDNA, and double-stranded DNA (dsDNA). The ssRNA is a first template for a first primer oligonucleotide, which is elongated by reverse transcriptase (RNA dependent DNA polymerase). The RNA is then removed from the resulting DNA:RNA duplex by the action of ribonuclease H (RNase H, an RNase specific for RNA in a duplex with either DNA or RNA). The resultant ssDNA is a second template for a second primer. The second primer includes the sequences of an RNA polymerase promoter (exemplified by T7 RNA polymerase) located 5' to the primer sequence which hybridizes to the ssDNA template. This primer is then extended by a DNA polymerase (exemplified by the large "Klenow" fragment of *E. coli* DNA polymerase I), resulting in the production of a dsDNA molecule, having a sequence identical to that of the portion of the original RNA located between the primers and having, additionally, at one end, a promoter sequence. This promoter sequence can be used by the appropriate RNA polymerase to make many RNA copies of the DNA. These copies can then re-enter the cycle leading to very swift amplification. With the proper choice of enzymes, this amplification can be done isothermally without the addition of enzymes at each cycle. Because of the cyclical nature of this process, the starting sequence can be chosen to be in the form of either DNA or RNA.

U.S. Pat. No. 5,455,166 and EP 684 315 disclose a method called Strand Displacement Amplification (SDA). This method is performed at a single temperature and uses a combination of a polymerase, an endonuclease and a modified nucleoside triphosphate to amplify single-stranded fragments of the target DNA sequence. A target sequence is fragmented, made single-stranded and hybridized to a primer that contains a recognition site for an endonuclease. The primer:target complex is then extended with a polymerase enzyme using a mixture of nucleoside triphosphates, one of which is modified. The result is a duplex molecule containing the original target sequence and an endonuclease recognition sequence. One of the strands making up the recognition sequence is derived from the primer and the other is a result of the extension reaction. Since the extension reaction is performed using a modified nucleotide, one strand of the recognition site is modified and resistant to endonuclease digestion. The resultant duplex molecule is then contacted with an endonuclease which cleaves the unmodified strand causing a nick. The nicked strand is extended by a polymerase enzyme lacking 5'-3' exonuclease activity resulting in the displacement of the nicked strand and the production of a new duplex molecule. The new duplex molecule can then go through multiple rounds of nicking and extending to produce multiple copies of the target sequence.

The most widely used method of nucleic acid amplification is the polymerase chain reaction (PCR). A detailed description of PCR is provided in the following references: Mullis, K. et al., *Cold Spring Harbor Symp. Quant. Biol.* 51:263-273 (1986); EP 50,424; EP 84,796; EP 258,017; EP 237,362; EP 201,184; U.S. Pat. No. 4,683,202; U.S. Pat. No. 4,582,788; and U.S. Pat. No. 4,683,194. In its simplest form, PCR involves the amplification of a target double-stranded nucleic acid sequence. The double-stranded sequence is denatured and an oligonucleotide primer is annealed to each of the resultant single strands. The sequences of the primers are selected so that they will hybridize in positions flanking the portion of the double-stranded nucleic acid sequence to be amplified. The oligonucleotides are extended in a reaction with a polymerase enzyme, nucleotide triphosphates and the appropriate cofactors resulting in the formation of two double-stranded molecules each containing the target sequence. Each subsequent round of denaturation, annealing and extension reactions results in a doubling of the number of copies of the target sequence as extension products from earlier rounds serve as templates for subsequent replication steps. Thus, PCR provides a method for selectively increasing the concentration of a nucleic acid molecule having a particular sequence even when that molecule has not been previously purified and is present only in a single copy in a particular sample. The method can be used to amplify either single- or double-stranded nucleic acids. The essence of the method involves the use of two oligonucleotides to serve as primers for the template dependent, polymerase-mediated replication of the desired nucleic acid molecule.

PCR has found numerous applications in the fields of research and diagnostics. One area in which PCR has proven useful is the detection of single nucleotide mutations by allele specific PCR (ASPCR) (see, for example, U.S. Pat. Nos. 5,639,611 and 5,595,890). As originally described by Wu, et al. (*Proceedings of the National Academy of Sciences, USA,* 86:2757-2760 (1989)), ASPCR involves the detection of a single nucleotide variation at a specific location in a nucleic acid molecule by comparing the amplification of the target using a primer sequence whose 3'-termini nucleotide is complementary to a suspected variant nucleotide to the amplification of the target using a primer in which the 3'-termini nucleotide is complementary to the normal nucleotide. In the case where the variant nucleotide is present in the target, amplification occurs more efficiently with the primer containing the 3'-nucleotide complementary to the variant nucleotide while in the case where the normal nucleotide is present in the target, amplification is more efficient with the primer containing 3'-nucleotide complementary to the normal nucleotide.

While this technology can be used to identify single nucleotide substitutions in a nucleic acid, it nonetheless suffers from some drawbacks in practical applications. The difference in efficiency of amplification between the primers may not be sufficiently large to permit easily distinguishing between the normal nucleotide and the mutant nucleotide. When the mismatched primer is extended with a significant frequency in the earlier rounds of the amplification, there may not be a large difference in the amount of product present in the later rounds. To avoid this problem requires careful selection of the number of amplification cycles and reaction conditions. An additional problem with this methodology is presented by the detection step after the amplification. In general, this is accomplished by separating the reaction products by electrophoresis and then visualizing the products. The imposition of a separation step dramatically increases the time and expense required for conducting this type of analysis. In order to obviate the need for a separation step, various FRET-based solution phase methods of detection have been used. These methods suffer from the drawbacks discussed above.

Methods for detecting nucleic acid amplification products commonly use gel electrophoresis, which separates the amplification product from the primers on the basis of a size differential. Alternatively, amplification products can be detected by immobilization of the product, which allows one to wash away free primer (for example, in dot-blot analysis), and hybridization of specific probes by traditional solid phase hybridization methods. Several methods for monitoring the amplification process without prior separation of primer or probes have been described. All of these methods are based on FRET.

One method, described in U.S. Pat. No. 5,348,853 and Wang et al., *Anal. Chem.* 67:1197-1203 (1995), uses an energy transfer system in which energy transfer occurs between two fluorophores on the probe. In this method, detection of the amplified molecule takes place in the amplification reaction vessel, without the need for a separation step. The Wang et al. method uses an "energy-sink" oligonucleotide complementary to the reverse primer. The "energy-sink" and reverse primer oligonucleotides have donor and acceptor labels, respectively. Prior to amplification, the labeled oligonucleotides form a primer duplex in which energy transfer occurs freely. Then, asymmetric PCR is carried out to its late-log phase before one of the target strands is significantly overproduced.

A second method for detection of an amplification product without prior separation of primer and product is the 5' nuclease PCR assay (also referred to as the TAQMAN® assay) (Holland et al., *Proc. Natl. Acad. Sci. USA* 88:7276-7280 (1991); Lee et al., *Nucleic Acids Res.* 21:3761-3766 (1993)). This assay detects the accumulation of a specific PCR product by hybridization and cleavage of a doubly labeled fluorogenic probe (the "TAQMAN®" probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if it hybridizes to the segment being amplified. Cleavage of the probe generates an increase in the fluorescence intensity of the reporter dye. In the TAQMAN® assay, the donor and quencher are preferably located on the 3'- and 5'-ends of the probe, because the requirement that 5'-3' hydrolysis be performed between the fluorophore and quencher may be met only when these two moieties are not too close to each other (Lyamichev et al., *Science* 260:778-783 (1993)).

Another method of detecting amplification products (namely MOLECULAR BEACONS) relies on the use of energy transfer using a "beacon probe" described by Tyagi and Kramer (*Nature Biotech.* 14:303-309 (1996)). This method employs oligonucleotide hybridization probes that can form hairpin structures. On one end of the hybridization probe (either the 5'- or 3'-end), there is a donor fluorophore, and on the other end, an acceptor moiety. In the case of the Tyagi and Kramer method, the acceptor moiety is a quencher, that is, the acceptor absorbs energy released by the donor, but then does not itself fluoresce. Thus, when the beacon is in the open conformation, the fluorescence of the donor fluorophore is detectable, whereas when the beacon is in hairpin (closed) conformation, the fluorescence of the donor fluorophore is quenched. When employed in PCR, the beacon probe, which hybridizes to one of the strands of the PCR product, is in "open conformation," and fluorescence is detected, while those that remain unhybridized will not fluoresce. As a result, the amount of fluorescence will increase as the amount of PCR product increases, and thus may be used as a measure of the progress of the PCR.

Another method of detecting amplification products which relies on the use of energy transfer is the SUNRISE PRIMER method of Nazarenko et al. (*Nucleic Acids Research* 25:2516-2521 (1997); U.S. Pat. No. 5,866,336). SUNRISE PRIMERS are based on FRET and other mechanisms of non-fluorescent quenching. SUNRISE PRIMERS consist of a single-stranded primer with a hairpin structure at its 5'-end. The hairpin stem is labeled with a donor/quencher pair. The signal is generated upon the unfolding and replication of the hairpin sequence by polymerase.

While there is a body of literature on the use of fluorescently labeled nucleic acids in a variety of applications involving nucleic acid hybridization or nucleic acid amplification, the majority of applications involve the separation of unhybridized probes or unincorporated primers, followed by detection. None of these methodologies describe or discuss real time detection of probes or primers, or changes in the fluorescence properties of a fluorescently labeled oligonucleotide upon hybridization or incorporation into an amplified product. Thus, whether detection of a given nucleic acid target sequence is to be done with or without amplification of the nucleic acid sample containing the target sequence, there remains a need in the art for more sensitive and more discriminating methods of detecting a target nucleic acid sequence.

The surprising and novel finding of the present invention is based, in part, on the measurement of a change in one or more of the fluorescent properties of labeled probes or primers upon becoming double-stranded. The present invention thus solves the problem of detecting nucleic acids, in particular amplification and/or synthesis products, by providing methods for detecting such products that are adaptable to many methods for amplification or synthesis of nucleic acid sequences and that greatly decrease the possibility of carryover contamination. The compounds and methods of the invention provide substantial improvements over those of the prior art. First, they permit detection of the amplification or synthesis products without prior separation of unincorporated fluorescent labeled oligonucleotides. Second, they allow detection of the amplification or synthesis product directly, by incorporating the labeled oligonucleotide into the product. Third, they do not require labeling of oligonucleotides with two different compounds (like FRET-based methods), and thus, simplify the production of the labeled oligonucleotides.

SUMMARY OF THE INVENTION

The present invention provides oligonucleotides that may comprise one or more modifications internally, and/or, at or near the 3'- and/or 5'-termini. Suitable modifications include, but are not limited to, the inclusion of labels, the inclusion of specificity enhancing groups, the inclusion of modified groups (e.g., modified or derivative nucleotide), the inclusion of quenching moieties, the inclusion of nucleotide analogues and the like. The oligonucleotides of the present invention may also comprise one or more sequences complementary to all or a portion of a target or template sequence of interest. In some embodiments, the oligonucleotides of the present invention may be in the form of a hairpin. Hairpin oligonucleotides may be modified or unmodified. Hairpin oligonucleotides of the present invention may contain one or more single-stranded regions at or near the stem of the hairpin and may be blunt ended or comprise overhanging sequences on the 3'- and/or 5'-end. The hairpin oligonucleotides of the present invention may also contain any number of stem and loop structures at any location in the oligonucleotide. In some preferred embodiments, the oligonucleotides of the present invention may be used for the detection and/or discrimination of target or template nucleic acid molecules by methods involving primer extension including, but not limited to, nucleic acid synthesis and amplification (e.g. PCR) as well as by other methods involving hybridization of a probe and/or primer. The oligonucleotides of the present invention may be used with any extension reaction known to those skilled in the art. Such extension reactions include, but are not limited to, extension of a primer on a DNA template using a DNA polymerase to produce a complementary DNA strand and extension of a primer on an RNA template using a reverse transcriptase to produce a complementary DNA strand. The oligonucleotides of the present invention may also be used in detection/discrimination of target or template nucleic acid molecules using methods involving hybridization of one or more of the oligonucleotides of the invention to one or more target nucleic acid molecules of interest.

In one aspect, oligonucleotides of the invention may comprise one or multiple labels (e.g. detectable labels), which may be the same or different. In some preferred embodiments, the labels may be fluorescent moieties. Labeled oligonucleotides of the invention may be used to detect the presence or absence of or to quantify the amount of nucleic acid molecules in a sample by, for example, hybridization of such oligonucleotides to such nucleic acid molecules. Optionally, such oligonucleotides may be extended in a synthesis and/or amplification reaction and detection/quantification may be accomplished during or after such reactions. In accordance with one aspect of the invention, such detection/quantification is based on the observation that the labeled oligonucleotides in double-stranded form have a detectable change in one or more properties (preferably a fluorescent property) compared to the oligonucleotides in single-stranded form. In another aspect of the invention, a change in a detectable property (preferably a fluorescent property) upon extension of the oligonucleotide of the invention is used to detect/quantify a target/template nucleic acid. Fluorescent properties in which a change may be detected include, but are not limited to, fluorescent intensity (increase or decrease), fluorescent polarization, fluorescence lifetime and quantum yield of fluorescence. Thus, hybridization and/or extension of the labeled oligonucleotides of the invention to a nucleic acid molecule to be detected/quantified results in a detectable change in one or more of the labels used and, in particular, when using fluorescent labels, a detectable change in one or more fluorescent properties. In this aspect of the invention, multiple different oligonucleotides may be used to detect multiple different target sequences in the same sample (e.g. multiplexing) and such different oligonucleotides may be differentially labeled to allow simultaneous and/or sequential detection of the multiple target sequences.

In another aspect, the present invention provides oligonucleotides comprising one or more specificity enhancing groups. In some preferred embodiments, oligonucleotides of the present invention may be provided with one or more specificity enhancing groups that render such oligonucleotides substantially less extendable, for example, in a synthesis or amplification reaction, for example, when the 3'-most nucleotide of the oligonucleotide is not base paired with a target or template nucleic acid sequence. In some embodiments, the specificity enhancing group may be placed at or near the 3'-most nucleotide of the oligonucleotide.

The specificity enhancing group may be attached to the oligonucleotide using any methodology known to those of skill in the art and may be attached to the oligonucleotide via a linker group. Such linker groups may be of varying length and chemical composition, i.e., hydrophobicity, charge, etc.

The specificity enhancing groups of the present invention may be attached to any part of the nucleotide to be modified, i.e., base, sugar or phosphate group. Specificity enhancing groups of the present invention may be or include detectable groups, including, but not limited to, fluorescent groups, chemiluminescent groups, radiolabeled groups and the like. In another aspect, the specificity enhancing groups may be modified or may be derivative nucleotides which are incorporated at one or a number of positions within the oligonucleotides of the invention. In some embodiments, the specificity enhancing groups of the present invention may be fluorescent groups which undergo a detectable change in one or more fluorescent properties upon extension of the oligonucleotide or may be any other detectable label allowing detection of the nucleic acid of interest. Preferably, the label exhibits a detectable change when the oligonucleotide of the invention is extended in a synthesis or amplification reaction.

Oligonucleotides of the present invention may be in the form of a hairpin. The hairpins of the present invention preferably comprise at least one stem structure and at least one loop structure. The sequences which form the stem structure by base pairing may be of any length and preferably contain at least a portion of a sequence complementary to a target or template sequence. For example, the sequence of an oligonucleotide may be selected so as to form a hairpin structure at a temperature below the temperatures used in a synthesis or amplification reaction by first selecting a sequence at least partially complementary to a portion of a nucleic acid target or template sequence and then adding one or more nucleotides to the 5'-end of the oligonucleotide that are complementary to the nucleotides at the 3'-end of the oligonucleotide. At a reduced temperature, the complementary nucleotides at the 3'- and 5'-ends can base pair forming a stem structure. The number of complementary nucleotides to be added may be selected by determining the desired melting temperature of the stem structure. The melting temperature preferably is high enough that the oligonucleotide is in the hairpin structure when the reaction mixture is being prepared thereby preventing the oligonucleotide from mis-annealing or mis-priming to the target or template nucleic acid molecule, but low enough such that all or a portion of the oligonucleotides are capable of assuming a linear structure and annealing to the target or template at the appropriate point in the synthesis or amplification reaction. The selection of an appropriate melting temperature for the stem structure is routine for those of ordinary skill in the art.

The oligonucleotides of the present invention may incorporate more than one of the characteristics described above or combinations thereof. For example, an oligonucleotide may comprise one or more labels and/or one or more specificity enhancing groups and/or one or more hairpin structures.

In another aspect, one or more of the oligonucleotides of the present invention may be covalently or non-covalently attached to a support by any means known to those skilled in the art. Such support bound oligonucleotides may be used to carry out the methods of the present invention. For example, the detection or quantification of nucleic acid molecules may be accomplished on a support and/or the synthesis or amplification of nucleic acids may be accomplished on a support. Such a support may be solid or semi-solid and may be made of any material known to those skilled in the art. Some examples of supports, without limitation, include polyolefin, scintered polyethylene, nitrocellulose, polypropylene, polycarbonate, cellulose acetate, silica and the like.

In one aspect, the present invention provides for reaction mixtures or compositions for use in a process for the synthesis and/or amplification of one or more nucleic acid molecules complementary to all or a portion of one or more nucleic acid target or template molecules of interest or the hybridization of one or more oligonucleotides of the invention to such targets. In some preferred embodiments, the reaction mixture may comprise at least a first and preferably a first and a second oligonucleotide primer of the invention which primers may be the same or different and may contain the same or different labels and/or specificity enhancing groups. Such first primer preferably comprises at least one sequence which is at least partially complementary to said target or template nucleic acid and which primes synthesis of a first extension product that is complementary to all or a portion of said target or template nucleic acid. Such second oligonucleotide primer preferably comprises a sequence which is at least partially complementary to all or a portion of said first extension product and primes the synthesis of a second extension product which is at least partially complementary to all or a portion of said first extension product. In some embodiments, the reaction mixture may comprise one or more oligonucleotide primers of the invention, which may be the same or different, and which may contain one or more of the same or different labels and/or specificity enhancing groups. For example, the reaction mixture or composition may comprise more than one oligonucleotide primer, wherein at least one of said primers is in the form of a hairpin and the other is not (preferably, such other primer is in linear form). In another aspect, one primer may be provided with at least one label that undergoes a detectable change in one or more properties upon hybridization and/or amplification/extension while a second primer may be in the form of a hairpin and/or comprise at least one specificity enhancing group. In another aspect, both the first and the second primer may be in the form of a hairpin and may also comprise labels and/or specificity enhancing groups as described above. Such reaction mixtures or compositions of the present invention may further comprise one or more components selected from a group consisting of one or more nucleotides, one or more DNA polymerases, one or more reverse transcriptases, one or more buffers or buffering salts, one or more target or template molecules and one or more products produced by a hybridization or synthesis/amplification reaction of the present invention. Thus, the invention relates generally to compositions/reaction mixtures produced to carry out the invention and/or to composition/reaction mixtures resulting from carrying out the invention.

The present invention relates to a method for detecting the presence or absence of a nucleic acid molecule or for quantifying the amount of a nucleic acid molecule in a sample comprising:

(a) contacting a sample thought to contain one or more nucleic acid molecules with one or more oligonucleotides of the invention; and (b) detecting the presence or absence or quantifying the amount of nucleic acid molecules in said sample.

In some embodiments, the oligonucleotide may be labeled and the detecting step may involve the detection of a change in one or more fluorescent or other detectable properties of the labeled oligonucleotide of the present invention. In some embodiments, the fluorescent property which undergoes a change is the intensity of fluorescence. In some embodiments, an increase in fluorescence intensity is detected.

Preferably, the oligonucleotides of the invention are incubated under conditions sufficient to allow hybridization of such oligonucleotides to the nucleic acid molecules in the sample. In a preferred aspect, the detection or quantification step includes a comparison of a control sample (without nucleic acid molecules present) to the sample containing nucleic acid molecules. Additional control samples containing known amounts of nucleic acid molecules may be used in accordance with the invention as a positive control for comparison purposes to determine the exact or approximate amount of the nucleic acid molecules present in the unknown sample.

In a related aspect, the invention relates to detection or quantification of nucleic acid molecules in a sample during or after nucleic acid synthesis or amplification. Thus, the invention relates to a method for the detection or quantification of one or more nucleic acid molecules in a sample comprising:

(a) mixing one or more nucleic acid templates or target nucleic acid molecules of the sample with one or more oligonucleotides for the invention;

(b) incubating said mixture under conditions sufficient to synthesize or amplify one or more nucleic acid molecules complementary to all or a portion of said templates or target molecules, wherein said synthesized or amplified nucleic acid molecules comprise said oligonucleotide; and (c) detecting or quantifying said synthesized or amplified nucleic acid molecules.

In some embodiments, the oligonucleotide may be labeled and the detecting step may involve the detection of a change in one or more fluorescent or other detectable properties of the labeled oligonucleotide of the present invention. In some embodiments, the fluorescent property which undergoes a change is the intensity of fluorescence. In some embodiments, an increase in fluorescence intensity is detected.

Conditions sufficient to synthesize or amplify one or more nucleic acid molecules complementary to all or a portion of said templates or target molecules preferably comprise incubating the template/oligonucleotide mixture in the presence of one or more nucleotides and one or more polymerases and/or reverse transcriptases (preferably, DNA polymerases and most preferably, thermostable DNA polymerases). In a most preferred aspect, the amplification process used is polymerase chain reaction (PCR) or RT PCR, although other amplification methods may be used in accordance with the invention. In this aspect of the invention, the detection/quantification step may be accomplished during amplification or synthesis or after synthesis or amplification is complete. For detection during an amplification reaction, a thermocycler capable of real time fluorescence detection may be used. Further, the nucleic acid synthesis or amplification method preferably produces double-stranded nucleic acid molecules (preferably, double-stranded DNA/DNA or DNA/RNA molecules) and the presence or absence or amount of such double-stranded molecules may be determined by this method of the invention. In a preferred aspect, using the labeled oligonucleotides of the invention as a primer during synthesis or amplification, the labeled oligonucleotide primer is incorporated into the synthesized or amplified molecule thereby creating a labeled product molecule (which may be single-stranded or double-stranded). In another aspect, the synthesized or amplified nucleic acid molecules produced in accordance with the invention may contain one or more labels, which may be the same or different. In a preferred aspect, the detection or quantification step includes a comparison of a control sample to the sample containing the target/template nucleic acid molecules of interest. Additional control samples containing known amounts of target/template may be used as a positive control for comparison purposes and/or to determine the exact or approximate amount of target/template in an unknown sample.

More specifically, the invention is directed to a method for amplifying a double-stranded nucleic acid target molecule (e.g., DNA/DNA; RNA/RNA; or RNA/DNA), comprising:

(a) providing at least a first and a second primer, wherein said first primer is complementary to a sequence within or at or near the 3'-termini of a first strand of said nucleic acid molecule and said second primer is complementary to a sequence within or at or near the 3'-termini of the second strand of said nucleic acid molecule;

(b) hybridizing said first primer to said first strand and said second primer to said second strand in the presence of one or more polymerases or reverse transcriptases, under conditions such that a third nucleic acid molecule complementary to all or a portion of said first strand and a fourth nucleic acid molecule complementary to all or a portion of said second strand are synthesized;

(c) denaturing said first and third strand, and said second and fourth strands; and (d) repeating steps (a) to (c) one or more times, wherein one or more of said primers are oligonucleotides of the present invention.

In some embodiments, at least one of the primers comprises at least one label that undergoes a detectable change in one or more fluorescent or other detectable properties upon hybridization and/or amplification/extension. In some embodiments, at least one of the primers comprises at least one specificity enhancing group that renders the primer substantially less extendable when the 3'-nucleotide of the primer is not base paired with the target molecule. In some embodiments, one or more of the primers is in the form of a hairpin. In some embodiments, at least one of the primers is in the form of a hairpin and further comprises a detectable label and/or a specificity enhancing group.

In a further aspect, the present invention provides a method for the direct detection of amplification or synthesis products in which the detection may be performed without opening the reaction tube. This embodiment, the "closed-tube" format, reduces greatly the possibility of carryover contamination with amplification or synthesis products. The closed-tube method also provides for high throughput analysis of samples and may be automated. The closed-tube format significantly simplifies the detection process, eliminating the need for post-amplification or post-synthesis analysis such as gel electrophoresis or dot-blot analysis.

In another aspect, the invention relates to a method for hybridizing or binding one or more of the oligonucleotides of the invention with one or more nucleic acid molecules of interest comprising:

(a) mixing one or more of said oligonucleotides with one or more of said nucleic acid molecules; and (b) incubating said mixture under conditions sufficient to hybridize or bind one or more of said oligonucleotides with one or more of said nucleic acid molecules.

In a preferred aspect, at least one or more of the oligonucleotides used in this method are hairpins and more preferably, the one or more oligonucleotides are hairpin molecules comprising one or more specificity enhancing groups and/or one or more labels.

The invention also relates to methods of synthesis or amplification of one or more nucleic acid molecules comprising:

(a) mixing one or more templates or target nucleic acid molecules with one or more oligonucleotides of the invention; and (b) incubating said mixture under conditions sufficient to synthesize or amplify one or more nucleic acid molecules complementary to all or a portion of said templates or target molecules.

In a preferred aspect, the oligonucleotides are hairpins and more preferably, are hairpin molecules comprising one or more specificity enhancing groups and/or one or more labels. Conditions sufficient to synthesize or amplify one or more nucleic acid molecules complementary to all or a portion of said templates or target molecules preferably comprise incubating the template/oligonucleotide mixture (e.g., the template-oligonucleotide complex) in the presence of one or more nucleotides and one or more polymerases and/or one or more reverse transcriptases (preferably, DNA polymerases and most preferably, thermostable DNA polymerases). In a most preferred aspect, the amplification process used is polymerase chain reaction (PCR) or RT PCR, although other amplification methods may be used in accordance with the invention. Further, the nucleic acid synthesis or amplification methods preferably produce double-stranded nucleic acid molecules (preferably, double-stranded DNA/DNA or DNA/RNA molecules). Use of the oligonucleotides of the invention allows for more efficient synthesis and/or amplification of nucleic acid molecules.

More specifically, the invention is directed to a method for amplifying a double-stranded nucleic acid target molecule comprising:

(a) providing a first and second primer, wherein said first primer is complementary to a sequence within or at or near the 3'-termini of the first strand of said nucleic acid molecule and said second primer is complementary to a sequence within or at or near the 3'-termini of the second strand of said nucleic acid molecule;

(b) hybriding said first primer to said first strand and said second primer to said second strand in the presence of one or more polymerases or reverse transcriptases, under conditions such that a third nucleic acid molecule complementary to all or a portion of said first strand and a fourth nucleic acid molecule complementary to all or a portion of said second strand are synthesized;

(c) denaturing said first and third strands, and said second and first strands; and (d) repeating steps (a) to (c) one or more times, wherein one or more of said primers are oligonucleotides of the present invention.

In one embodiment, the oligonucleotides of the invention used are hairpins, and preferably, are hairpins comprising one or more specificity enhancing groups and/or one or more labels.

The invention also provides the embodiments of the above methods wherein the nucleic acid molecule to be detected/quantified/amplified/synthesized is an RNA or a DNA molecule, and wherein such molecule is either single-stranded or double-stranded.

The invention also provides the embodiment of the above methods wherein the nucleic acid target or template molecule is polyadenylated at its 3'-end (e.g., poly(A) RNA or mRNA), and/or at least one of the primers or oligonucleotides of the invention contains a poly(T) sequence, and/or at least one of the other of the primers or oligonucleotides of the invention contains at least one deoxyinosine residue. In a related aspect, the template or target nucleic acid is an mRNA molecule, at least one primer/oligonucleotide is labeled and comprises a poly(T) sequence and at least one primer/oligonucleotide comprises at least one deoxyinosine residue.

As will be further appreciated, the oligonucleotides of the invention may be employed in other amplification methods, such as those involving the application of PCR to the amplification of cDNA-ends derived from mRNAs using a single gene specific primer. Thus, oligonucleotides of the invention can be used in methods such as "RT-PCR," "5'-RACE," "anchor PCR" and "one-sided PCR" which facilitate the capture of a sequence from the 5'-ends of mRNA. The methods of the invention are adaptable to many methods for amplification of nucleic acid sequences, including, without limitation, PCR, LCR, SDA and NASBA, and other amplification systems known to those of ordinary skill in the art.

In other embodiments, the inventive oligonucleotides can be specific sequences not initially present in the target nucleic acid sequences or gene target of interest (e.g. allele specific PCR). In such aspect, an adaptor or tail sequence is first introduced to the target or template molecules. Such adaptor molecules can be attached by a variety of methods. Such as ligation to the target or template or may be added through a synthesis reaction (such as PCR) in which the adaptor or tail sequence is part of one or more primers used to synthesize one or more nucleic acid molecules complementary to the target or template. Such tailed or adaptor containing templates or target sequences may than be detected through the use of one or more oligonucleotides of the invention according to the methods described herein. Thus, the invention also provides universal detection oligonucleotides for detecting a variety of sequences. In this way, a particular universal oligonucleotide of the invention may be used to detect any number of target or template molecules simply by adding by a number of methods one or a number of adaptor sequences all of or particular of which are complementary to the universal oligonucleotides of the invention. See Example 20. In one aspect, an universal oligonucleotide will anneal to any nucleic acid sequence to which a complementary (to the primer) adaptor terminal sequence has been added or attached. With a universal oligonucleotide, care must be taken to isolate the nucleic acid of interest, or otherwise direct the ligation procedure only to the sequence of interest, to avoid randomly attaching the "adaptor" to all nucleic acid sequences present (U.S. Pat. No. 6,174,709). In another aspect, a universal oligonucleotide may be employed which anneals or is complementary to a known vector sequence flanking the target sequence. Such vector sequences which may be used as adaptor molecules are known in the art and commercially available include pUC/M13, pBR322, lambdagt10, lambdagt11 and the like (U.S. Pat. No. 5,876,936). The adaptor may be derived from a universal primer, such as pUC/M13, lambdagt10, lambdagt11, and the like, (See Sambrook et al., Molecular Cloning: A Laboratory Manual, 2nd ed., CSHL, 1989, Section 13) and one or more primers containing such adaptor sequences may be added to the target or template molecules by a nucleic acid synthesis reaction (such as PCR).

In another aspect of the invention, the invention is directed to a method for determining the activity or amount of a polymerase in a sample, comprising amplifying a nucleic acid molecule, comprising:

(a) providing a first and second primer, wherein said first primer is complementary to a sequence within or at or near the 3'-termini of the first strand of said nucleic acid molecule and said second primer is complementary to a sequence within or at or near the 3'-termini of the second strand of said nucleic acid molecule;

(b) hybridizing said first primer to said first strand and said second primer to said second strand in the presence of said polymerase, under conditions such that a third nucleic acid molecule complementary to all or a portion of said first strand and a fourth nucleic acid molecule complementary to all or a portion of said second strand are synthesized;

(c) denaturing said first and third strands, and said second and fourth strands;

(d) repeating steps (a) to (c) one or more times; and (e) detecting the amplification product, wherein at least one of the primers is an oligonucleotide of the present invention, and wherein the amount of the amplification product produced is indicative of the activity or amount of the polymerase.

In some embodiments, the amount of the amplification product produced is determined by detecting a change in one or more fluorescent or other detectable properties of an incorporated detectable label.

Generally, the invention thus relates to a method for determining the activity or the amount of a polymerase or reverse transcriptase in a sample comprising:

(a) mixing a sample thought to contain a polymerase or reverse transcriptase with one or more nucleic acid templates and one or more labeled oligonucleotides of the invention;

(b) incubating said mixture under conditions sufficient to allow synthesis or amplification of one or more nucleic acid molecules complementary to all or a portion of said templates, wherein said synthesized or amplified nucleic acid molecules comprise said oligonucleotides; and (c) determining the activity or amount of said polymerase or reverse transcriptase in said sample based on detection of one or more detectable labels.

In another aspect, the invention relates to quenching background fluorescence or other detectable properties during detection of nucleic acid molecules or polymerases in accordance with the methods of the invention. In this aspect of the invention, one or more quenching agents which bind one or more labeled single-stranded nucleic acid molecules are used to quench the fluorescence or other detectable properties produced by such single-stranded molecules. In a preferred aspect, the quenching agent is specific for single-stranded molecules and will not substantially interact with double-stranded labeled nucleic acid molecules. Thus, labeled oligonucleotides of the invention (fluorescent or other detectable labels) will be quenched or substantially quenched in the presence of such agents. Upon interaction with the target molecule (e.g. hybridization) or during amplification or synthesis reactions, the double-stranded nucleic acid molecule formed which comprises the labeled oligonucleotides of the invention (fluorescent or other detectable label) will not substantially interact with such agents and thus will not be substantially quenched by such agents. This aspect of the invention thus allows for reduced background fluorescence (or reduced background of the detectable properties) and enhanced detection of target nucleic acid molecules in the methods of the invention. Preferred quenchers for use in the invention include one or more single-stranded binding proteins (SSB). Such SSB are known in the art (U.S. Pat. No. 5,449,603 and U.S. Pat. No. 5,605,824). In another aspect, such quenching agents may include blocking oligonucleotides which contain one or more quenchers, for example, DABCYL. In another aspect, the quenching moiety may be part of the oligonucleotide of the invention. For example, one or more quenching moieties may be incorporated into one or more stem structures of the hairpin of the invention. Such stem structures may also incorporate one or more labels and, in the hairpin configuration, the quenching moieties reduce the level of background activity of the label. Upon denaturation (unfolding) of the stem structure, the quenching of the label is reduced or prevented.

In another embodiment, the invention relates to a composition comprising one or more labeled oligonucleotides of the invention, wherein the label is a detectable label, and wherein the oligonucleotide is selected from the group consisting of DNA and RNA. The labeled oligonucleotides of the invention may be primers and/or probes, depending on the use. The compositions of the invention may further comprise one or more components selected from the group consisting of one or more polymerases, one or more quenching agents, one or more nucleotides, one or more nucleic acid molecules (which may be templates or nucleic acid molecules which may comprise one or more oligonucleotides of the invention), and one or more buffering salts.

In another embodiment of the invention, the oligonucleotide label is a member of a FRET pair. In this embodiment, one or more labeled oligonucleotides of the invention containing single or multiple members of a FRET pair internally, and/or, at or near the 3'- and/or 5'-end. In a preferred aspect, the labeled moiety is one or more fluorescent moieties whose emission may then be measured to assess the progress of the reaction.

The present invention also relates to kits for the detection or measurement of nucleic acid synthesis or amplification products or for the measurement or detection of nucleic acid molecules. Such kits may be diagnostic kits wherein the presence of the nucleic acid being hybridized, amplified or synthesized is correlated with the presence or absence of a disease or disorder. Kits of the invention may also be used to detect or determine activity or amount of a polymerase in a sample. In addition, kits of the invention may be used to carry out hybridization, synthesis, amplification or other extension reactions using the oligonucleotides of the invention. Preferred kits of the invention may comprise one or more containers (such as vials, tubes, and the like) configured to contain the reagents used in the methods of the invention and optionally may contain instructions or protocols for using such reagents. The kits of the invention may comprise one or more components selected from the group consisting of one or more oligonucleotides of the invention (including, but not limited to, probes and/or primers), one or more DNA polymerases, such as a thermostable polymerase, one or more reverse transcriptases, or any other DNA or RNA polymerase, one or more agents capable of quenching one or more of the labels, one or more buffers or buffering salts, one or more nucleotides, one or more target/template molecules (which may used for determining reaction performance, i.e., control reactions) and other reagents for analysis or further manipulation of the products or intermediates produced by the methods of the invention. Such additional components may include components used for cloning and/or sequencing and components or equipment needed for the detection or quantification of the nucleic acid molecule of interest.

The invention also relates to any of the products or intermediates (e.g, nucleic acid molecules) produced by carrying out the methods of the invention. The invention also relates to vectors or host cells containing such products or intermediates produced by the methods of the invention.

Introduction of such vectors into host cells may be accomplished using any of the cloning and transformation techniques known to those skilled in the art.

The invention further relates to a method for synthesizing or amplifying one or more nucleic acid molecules comprising:

mixing one or more nucleic acid templates or targets with one or more oligonucleotides, wherein said one or more of said oligonucleotides comprises at least one modified oligonucleotide; and incubating said mixture under conditions sufficient to synthesize or amplify one or more nucleic acid molecules complementary to all or a portion of said templates or targets.

The invention further relates to a method for synthesizing or amplifying one or more nucleic acid molecules, wherein the specificity of the nucleic acid synthesis or amplification is increased, comprising:

mixing one or more nucleic acid templates or targets with one or more oligonucleotides, wherein said one or more of said oligonucleotides comprises at least one hairpin structure; and incubating said mixture under conditions sufficient to synthesize or amplify one or more nucleic acid molecules complementary to all or a portion of said templates or targets, wherein the synthesis or amplification has increased specificity when compared to amplification or synthesis conducted with an oligonucleotide not in a hairpin conformation.

The invention further relates to a method for synthesizing or amplifying one or more nucleic acid molecules, wherein the specificity of the nucleic acid synthesis or amplification is increased, comprising:

mixing one or more nucleic acid templates or targets with one or more oligonucleotides, wherein said one or more of said oligonucleotides comprises at least one modified oligonucleotide; and incubating said mixture under conditions sufficient to synthesize or amplify one or more nucleic acid molecules complementary to all or a portion of said templates or targets, wherein the synthesis or amplification has increased specificity when compared to amplification or synthesis conducted with an unmodified oligonucleotide.

The invention further relates to a method for synthesizing or amplifying one or more nucleic acid molecules, wherein the synthesis or amplification inhibits or reduces mis-priming, comprising:

mixing one or more nucleic acid templates or targets with one or more oligonucleotides, wherein said one or more of said oligonucleotides comprises at least one hairpin structure; and incubating said mixture under conditions sufficient to synthesize or amplify one or more nucleic acid molecules complementary to all or a portion of said templates or targets, wherein the synthesis or amplification inhibits or reduces mis-priming when compared to amplification or synthesis conducted with an oligonucleotide not in a hairpin conformation.

The invention further relates to a method for synthesizing or amplifying one or more nucleic acid molecules, wherein the synthesis or amplification inhibits or reduces mis-priming, comprising:

mixing one or more nucleic acid templates or targets with one or more oligonucleotides, wherein said one or more of said oligonucleotides comprises at least one modified oligonucleotide; and incubating said mixture under conditions sufficient to synthesize or amplify one or more nucleic acid molecules complementary to all or a portion of said templates or targets, wherein the synthesis or amplification inhibits or reduces mis-priming when compared to amplification or synthesis conducted with an unmodified oligonucleotide.

Oligonucleotides of the present invention may be in the form of a modified nucleotide, such as a deoxynucleotide or ribonucleotide modification or a 2'- or 3'-substituted modification, for example, without limitation, a 2'- or 3'-alkyl, alkyloxy, alkylamino, alkylthio, aryl, or aryloxy modification, or a 2'- or 3'-O-alkyl or 2'- or 3'-O-aryl modification, preferably, a 2'-O-methyl modification of the nucleotide residue at or near the 3'-termini. Methods of preparing 2'-O-alkyl modifications are shown according to U.S. Pat. No. 6,090,932. Such oligonucleotides may incorporate more than one of the characteristics described above or combinations thereof. For example, an oligonucleotide may comprise one or more labels and/or one or more specificity enhancing groups and/or one or more hairpins and/or one or more nucleotide modifications, preferably, a 2'-O-methyl modification of the nucleotide residue at or near the 3'-termini. As will be further appreciated, the modified oligonucleotide sequences of the invention may be employed in other amplification methods, such as those involving the application of PCR to the amplification of cDNA-ends derived from mRNAs using a single gene specific primer. Thus, modified oligonucleotides of the invention can be used in methods such as "RT-PCR," "5'-RACE," "anchor PCR" and "one-sided PCR." The methods of the invention are adaptable to many methods for amplification of nucleic acid sequences, including PCR, LCR, SDA and NASBA, and other amplification systems known to those of ordinary skill in the art.

The invention further relates to a composition comprising one or more nucleic acid molecules and at least one oligonucleotide, wherein at least a portion of said oligonucleotide is capable of hybridizing with at least a portion of said nucleic acid molecule and wherein said oligonucleotide comprises a modified nucleotide or a 2'-substituted nucleotide modification, preferably, a 2'-O-methyl ribonucleotide modification at or near the 3'-terminal nucleotide. Such reaction mixtures or compositions of the present invention may further comprise one or more components selected from the group consisting of one or more nucleotides, one or more DNA polymerases, one or more reverse transcriptases, one or more buffers or buffering salts, one or more target or template molecules and one or more products produced by a hybridization or synthesis/amplification reaction of the present invention.

The invention further relates to a method for amplifying a double-stranded nucleic acid molecule, comprising:

(a) providing a first and second primer, wherein said first primer is complementary to a sequence within or at or near the 3'-termini of the first strand of said nucleic molecule and said second primer is complementary to a sequence within or at or near the 3'-termini of the second strand of said nucleic acid molecule;

(b) hybridizing said first primer to said first strand and said second primer to said second strand in the presence of one or more of the polymerases, under conditions such that a third nucleic acid molecule complementary to all or a portion of said first strand and a fourth nucleic acid molecule complementary to all or a portion said second strand are synthesized;

(c) denaturing said first and third strand, and said second and fourth strands; and repeating the above steps one or more times, wherein one or more of the primers comprise a nucleotide modification at or near the 3'-terminal nucleotide.

The invention further relates to a method of determining the presence of at least one nucleotide of interest at a specific position in a target nucleic acid molecule, comprising:

(a) contacting at least one target nucleic acid molecule having said nucleotide of interest at a specific position on a target nucleic acid molecule with at least one oligonucleotide, wherein at least a portion of the oligonucleotide is capable of forming base pairs or hybridizing with at least a portion of the target nucleic acid molecule and wherein the oligonucleotide comprises a nucleotide modification at or near the 3'-terminal nucleotide; and (b) incubating the oligonucleotide and the target nucleic acid molecule under conditions sufficient to cause extension of the oligonucleotide when the 3'-most nucleotide of the oligonucleotide base pair with the nucleotide at the specific position of the target nucleic acid molecule, wherein the presence of or increased production of an extension product indicates the presence of the particular nucleotide at the specific position.

The invention further relates to a method of determining the absence of at least one nucleotide at a specific position in a target nucleic acid molecule, comprising:

(a) contacting at least one target nucleic acid molecule having said nucleotide of interest at a specific position on the target nucleic acid molecule with at least one oligonucleotide, wherein at least one portion of the oligonucleotide is capable of forming base pairs or hybridizing with at least a portion of the target nucleic acid molecule and wherein the oligonucleotide comprises a nucleotide modification at or near the 3'-terminal nucleotide; and (b) incubating the oligonucleotide and target nucleic acid molecule under conditions sufficient to inhibit or prevent extension of the oligonucleotide when the 3'-most nucleotide of the oligonucleotide does not substantially base pair with the nucleotide of the specific position of the target nucleic acid molecule, wherein the lack of or reduced production of an extension product indicates the absence of the particular nucleotide at the specific position.

The invention further relates to a method of determining the presence or absence of a nucleotide at a specific position in a target nucleic acid molecule, comprising:

(a) contacting at least first oligonucleotide with at least one target nucleic acid molecule under conditions sufficient to cause extension of the first oligonucleotide when the 3'-most nucleotide of the oligonucleotide base pairs with the nucleotide at the specific position of the target nucleic acid molecule, wherein said first oligonucleotide comprises a nucleotide modification at or near the 3'-terminal nucleotide;

(b) contacting at least a second oligonucleotide with at least one target nucleic acid molecule under conditions sufficient to inhibit or prevent extension of the oligonucleotide when the 3'-most nucleotide of the oligonucleotide do not substantially base pair with the nucleotide at the specific position of the target nucleic acid molecule, wherein said second oligonucleotide comprises a nucleotide modification at or near the 3'-terminal nucleotide; and (c) comparing the level of extension or the amount of extension product accomplished with the first oligonucleotide compared to the second oligonucleotide.

The invention further relates to a method for synthesizing or amplifying one or more nucleic acid molecules comprising:

(a) mixing one or more nucleic acid templates or targets with one or more oligonucleotides, wherein said one or more of said oligonucleotides comprise a nucleotide modification at or near the 3'-terminal nucleotide; and (b) incubating said mixture under conditions sufficient to synthesize or amplify one or more nucleic acid molecules complementary to all or a portion of said templates or targets.

The invention further relates to a method for synthesizing or amplifying one or more nucleic acid molecules, wherein the specificity of the nucleic acid synthesis or amplification is increased, comprising:

(a) mixing one or more nucleic acid templates or targets with one or more oligonucleotides, wherein said one or more of said oligonucleotides comprises a nucleotide modification at or near the 3'-terminal nucleotide; and (b) incubating said mixture under conditions sufficient to synthesize or amplify one or more nucleic acid molecules complementary to all or a portion of said templates or targets, wherein the synthesis or amplification has increased specificity when compared to amplification or synthesis conducted with an oligonucleotide not modified with a nucleotide modification at or near the 3'-terminal nucleotide.

This invention further relates to a nucleotide analogue having the formula:

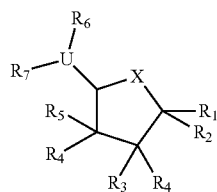

where,

X is selected from the group consisting of —O—, —S—, —SO—, —SO$_2$—, —Se—, C(R$_8$R$_9$), —N(R$_{10}$R$_{11}$), NR$_{10}$, P(O$_2$), and P(O)—O—R$_{12}$;

R$_1$ is selected from the group consisting of nucleobases, heteroaromatic groups, heterocyclic group and aryl;

R$_2$ is selected from the group consisting of H, alkyl, alkyloxy, alkylamino, alkylmercapto, aryl, aryloxy, carboxylic acid, carboxamide, aminoacid, hydroxyacid, peptide, sugar, hydroxy, amino and thio;

R$_3$ is selected from the group consisting of H, alkyl, alkyloxy, alkylamino, alkylmercapto, aryl, aryloxy, carboxylic acid, carboxamide, aminoacid, hydroxyacid, peptide, sugar, hydroxy, amino and thio;

each R$_4$ is independently selected from the group consisting of hydroxy, alkoxy, amino and thio;

R$_5$ is selected from the group consisting of H, alkyl, alkyloxy, alkylamino, alkylmercapto, aryl, aryloxy, carboxylic acid, carboxamide, aminoacid, hydroxyacid, peptide, sugar, hydroxy, amino and thio;

U is selected from the group consisting of nucleobases, hetroaromatic groups, hetrocyclic group and aryl;

R$_6$ is R$_2$ when U=CR$_8$, NR$_{10}$, N or R$_6$ is absent when U=—O—, —S—, —SO—, —SO$_2$—, —Se—;

R$_7$ is selected from the group consisting of triphosphate, diphosphate, monophosphate, phosphorotioate, oligonucleotide, nucleic acid, DNA, RNA, LNA and PNA;

R$_8$ is selected from the group consisting of H, alkyl, alkyloxy, alkylamino, alkylmercapto, aryl, aryloxy, carboxylic acid, carboxamide, aminoacid, hydroxyacid, peptide, sugar, hydroxy, amino and thio;

R$_9$ is selected from the group consisting of H, alkyl, alkyloxy, alkylamino, alkylmercapto, aryl, aryloxy, carboxylic acid, carboxamide, aminoacid, hydroxyacid, peptide, sugar, hydroxy, amino and thio; and R$_{10}$, R$_{11}$, and R$_{12}$ are the same or different and are selected from the group consisting of alkyl, alkyloxy, alkylamino, alkylmercapto, aryl, aryloxy, carboxylic acid, carboxamide, aminoacid, hydroxyacid, peptide and sugar.

In another aspect, this present invention provides oligonucleotides comprising one or more of nucleotide analogues. The oligonucleotides of the invention may comprise one or more of such nucleotides at any one or a number of positions within or at or near the 5'- and/or 3'-termini of the oligonucleotide. Moreover, the oligonucleotides may incorporate more than one of the characteristics described above or combinations thereof. For example, an oligonucleotide may comprise one or more labels and/or one or more specificity enhancing groups and/or one or more hairpins and/or one or more nucleotide analogues.

This invention further relates to a composition comprising one or more nucleic acid molecules and at least one oligonucleotide, wherein at least a portion of said oligonucleotide is capable of hybridizing with at least a portion of said nucleic acid molecule and wherein said oligonucleotide is an oligonucleotide of the invention or is an oligonucleotide which comprises one or more nucleotide analogues.

The invention further relates to a method of making a composition, comprising the steps of:

(a) providing at least one oligonucleotide; and (b) contacting said oligonucleotide with at least one nucleic acid molecule, wherein at least a portion of said oligonucleotide is capable of hybridizing with at least a portion of said nucleic acid molecule and wherein said oligonucleotide is an oligonucleotide of the invention or is an oligonucleotide which comprises one or more nucleotide analogues.

The invention further relates to a composition for quantifying or detecting one or more target nucleic acid molecules in a sample comprising one or more oligonucleotides and one or more target nucleic acid molecules to be detected or quantified, wherein said oligonucleotides is an oligonucleotide of the invention or is an oligonucleotide which contains one or more nucleotide analogues.

The invention further relates to a method for the quantification or detection of one or more target nucleic acid molecules in a sample comprising hybridizing one or more oligonucleotides with one or more molecules to be detected or quantified, and detecting the presence or absence and/or quantifying the amount of said target nucleic acid molecules, wherein said oligonucleotides is an oligonucleotide of the invention or is an oligonucleotide which contains one or more nucleotide analogues.

The invention further relates to a method for the quantitation or detection of one or more nucleic acid molecules in a sample during nucleic acid synthesis comprising:

(a) mixing one or more nucleic acid templates with one or more oligonucleotides, wherein said oligonucleotides are oligonucleotides of the invention or are oligonucleotides that contain one or more nucleotide analogues;

(b) incubating said mixture under conditions sufficient to synthesize one or more nucleic acid molecules complementary to all or a portion of said templates, said synthesized nucleic acid molecule comprising said oligonucleotides; and (c) detecting the presence or absence or quantifying the amount of said synthesized nucleic acid molecules by measuring the amount of nucleic acid molecules synthesized in said sample.

The invention further relates to a method for quantitation or detection of one or more nucleic acid molecules in a sample during nucleic acid amplification comprising:

(a) mixing one or more nucleic acid templates with one or more oligonucleotides, wherein said oligonucleotides are oligonucleotides of the invention or are oligonucleotides that contain one or more nucleotide analogues; and (b) incubating said mixture under conditions sufficient to amplify one or more nucleic acid molecules complementary to all or a portion of said templates, said amplified nucleic acid molecule comprising said oligonucleotides; and (c) detecting the presence or absence or quantifying the amount of said nucleic acid molecules by measuring the amount or the presence or absence of nucleic acid molecules amplified in said sample.

The invention further relates to the method for amplifying a double stranded nucleic acid molecule, comprising:

(a) providing a first and second primer, wherein said first primer is complementary to a sequence within or at or near the 3'-termini of the first strand of said nucleic molecule and said second primer is complementary to a sequence within or at or near the 3'-termini of the second strand of said nucleic acid molecule;

(b) hybridizing said first primer to said first strand and said second primer to said second strand in the presence of one or more of polymerases, under conditions such that a third nucleic acid molecule complementary to all or a portion of said first strand and a fourth nucleic acid molecule complementary to all or a portion said second strand are synthesized;

(c) denaturing said first and third strand, and said second and fourth strands; and (d) repeating the above steps one or more times, wherein one or more of the primers are oligonucleotides of the invention or are oligonucleotides that comprise one or more of the nucleotide analogues.

The invention further relates to a method of determining the presence of one or more particular nucleotides at a specific position or positions in a target nucleic acid molecule, comprising:

(a) contacting at least one target nucleic acid molecule having one or more nucleotides of interest at a specific position or positions on a target nucleic acid molecule with at least one oligonucleotide, wherein at least a portion of the oligonucleotide is capable of forming base pairs or hybridizing with at least a portion of the target nucleic acid molecule and wherein the oligonucleotide is an oligonucleotide of the invention or is an oligonucleotide which comprises one or more nucleotide analogues; and (b) incubating the oligonucleotide and the target nucleic acid molecule under conditions sufficient to cause extension of the oligonucleotide when the 3'-most nucleotide or nucleotides of the oligonucleotide base pair with the nucleotide or nucleotides at the specific position or positions of the target nucleic acid molecule, wherein the production of an extension product indicates the presence of the particular nucleotide at the specific position.

The invention further relates to a method of determining the absence of one or more particular nucleotides at a specific position or positions in a target nucleic acid molecule, comprising:

(a) contacting at least one target nucleic acid molecule having one or more nucleotides of interest at a specific position or positions on the target nucleic acid molecule with at least one oligonucleotide, wherein at least one portion of the oligonucleotide is capable of forming base pairs or hybridizing with at least a portion of the target nucleic acid molecule and wherein the oligonucleotide comprises one or more nucleotide analogues; and (b) incubating the oligonucleotide and target nucleic acid molecule under conditions sufficient to inhibit or prevent extension of the oligonucleotide when the 3'-most nucleotide or nucleotides of the oligonucleotide does not substantially base pair with the nucleotide or nucleotides of the specific position or positions of the target nucleic acid molecule, wherein the lack of or reduced production of an extension product indicates the absence of the particular nucleotide at the specific position.

The invention further relates to a method of determining the presence or absence of one or more particular nucleotides at a specific position or positions in a target nucleic acid molecule, comprising:

(a) contacting at least a first oligonucleotide with at least one target nucleic acid molecule under conditions sufficient to cause extension of the first oligonucleotide when the 3'-most nucleotide or nucleotides of the oligonucleotide base pairs with the nucleotide or nucleotides at the specific position or positions of the target nucleic acid molecule;

(b) contacting at least a second oligonucleotide with at least one target nucleic acid molecule under conditions sufficient to inhibit or prevent extension of the oligonucleotide when the 3'-most nucleotide or nucleotides of the oligonucleotide do not substantially base pair with the nucleotide or nucleotides at the specific position or positions of the target nucleic acid molecule; and (c) comparing the level of extension or the amount of extension product or the presence or absence of extension product accomplished with the first oligonucleotide compared to the second oligonucleotide, wherein said first and/or second oligonucleotide is an oligonucleotide of the invention or is an oligonucleotide which comprises one or more nucleotide analogues.

The invention further relates to a method of determining the presence or absence of at least one particular nucleotide of interest at a specific position in a target nucleic acid molecule, comprising:

(a) providing at least one target nucleic acid molecule having said nucleotide of interest at a specific position;

(b) contacting said target nucleic acid molecule with at least one oligonucleotide, wherein at least a portion of the oligonucleotide is capable of forming base pairs or hybridizing with at least a portion of the nucleic acid molecule and wherein the oligonucleotide is an oligonucleotide of the invention or is an oligonucleotide which comprises at least one nucleotide analogue; and (c) contacting the oligonucleotide and the target nucleic acid molecule with a polymerase less able to extend the oligonucleotide when the 3'-most nucleotide of the oligonucleotide does not base pair with the target nucleic acid and more able to extend the oligonucleotide when the 3'-most nucleotide of the oligonucleotide base pairs with the target nucleic acid molecule; and optimally measuring the level of extension or amount of extension or presence or absence of extension of the oligonucleotide.

The invention further relates to a method for synthesizing or amplifying one or more nucleic acid molecules comprising:

(a) mixing one or more nucleic acid templates or targets with one or more oligonucleotides, wherein said oligonucleotides is an oligonucleotide of the invention or is an oligonucleotide which comprises one or more nucleotide analogues; and (b) incubating said mixture under conditions sufficient to synthesize or amplify one or more nucleic acid molecules complementary to all or a portion of said templates or targets.

In addition, kits of the invention may be used to carry out hybridization, synthesis, amplification or other extension reactions using the oligonucleotides of the invention. Preferred kits of the invention may comprise one or more containers (such as vials, tubes, and the like) configured to contain the reagents used in the methods of the invention and optionally may contain instructions or protocols for using such reagents. The kits of the invention may comprise one or more components selected from the group consisting of one or more oligonucleotides of the invention (including, but not limited to, probes and/or primers), one or more DNA polymerases, such as a thermostable polymerase, one or more reverse transcriptases, or any other DNA or RNA polymerase, one or more agents capable of quenching one or more of the labels, one or more buffers or buffering salts, one or more nucleotides, one or more target/template molecules (which may used for determining reaction performance, i.e., control reactions) and other reagents for analysis or further manipulation of the products or intermediates produced by the methods of the invention. Such additional components may include components used for cloning and/or sequencing and components or equipment needed for the detection or quantification of the nucleic acid molecule of interest.

The invention further relates to a kit for use in synthesis of a nucleic acid molecule, said kit comprising one or more oligonucleotides that are oligonucleotides of the invention or are oligonucleotide comprising nucleotide analogues of the invention.

The invention further relates to a kit for use in amplification of a nucleic acid molecule, said kit comprising one or more oligonucleotides that are oligonucleotides of the invention or are oligonucleotides comprising nucleotide analogues of the invention.

The invention further relates to a kit for the detection or measurement of nucleic acid synthesis or amplification products comprising one or more oligonucleotides that are oligonucleotides of the invention or are oligonucleotides comprising nucleotide analogues of the invention.

The invention further relates to a method of detecting a single nucleotide polymorphism comprising the steps of:

(a) contacting at least a first oligonucleotide with at least one target nucleic acid molecule under conditions sufficient to cause extension of the first oligonucleotide when the 3'-most nucleotide or nucleotides of the oligonucleotide base pairs with the nucleotide or nucleotides at the specific position or positions of the target nucleic acid molecule;

(b) contacting at least a second oligonucleotide with at least one target nucleic acid molecule under conditions sufficient to inhibit or prevent extension of the oligonucleotide when the 3'-most nucleotide or nucleotides of the oligonucleotide do not substantially base pair with the nucleotide or nucleotides at the specific position or positions of the target nucleic acid molecule; and (c) comparing the level of extension or the amount of extension product or the presence of absence of extension product accomplished with the first oligonucleotide compared to the second oligonucleotide, wherein said first and/or second oligonucleotide is an oligonucleotide of the invention or is an oligonucleotide which comprises one or more nucleotide analogues.

The invention further relates to an oligonucleotide comprising: a cytosine or guanine or analog of the cytosine or guanine at the 3'-termini, and one or more detectable labels on at least the second, third, fourth, fifth or sixth base from the 3'-termini.

The invention further relates to an oligonucleotide comprising: an adenine or thymidine at the 3'-termini, an overhanging guanine at the 5'-termini, and one or more detectable labels located internally.

BRIEF DESCRIPTION OF THE FIGURES

FIGS. 1A-B are schematic representations of the homogeneous/real-time detection system of the invention. A change in one or more fluorescent or other detectable properties can be detected either through the incorporation of the labeled primer into the double-stranded amplification product (1A), or through the direct hybridization of the labeled probe to the nucleic acid target (1B). In accordance with the invention, the nucleic acid molecules detected or quantified can be a synthesized or amplified product or a nucleic acid molecule found in nature. Such nucleic acid molecules may be single- or double-stranded and can be RNA, DNA or RNA/DNA hybrids. In accordance with the invention, any one or more labels (which may be the same or different) may be used.

FIG. 12 is a plot of fluorescence as a function of the number of cycles of PCR performed in an allele specific PCR reaction comparing the hairpin primers of the present invention to standard linear primers using a two-step PCR reaction format.

FIG. 16A shows the amplification of a 3.6 kb fragment of the human beta-globin gene using a first primer set. FIG. 16B shows the amplification of a 3.6 kb fragment of the human beta-globin gene using a second primer set.

FIG. 17A shows the amplification of a 1.3 kb fragment of the NF2 gene. FIG. 17B shows the amplification of a 1.6 kb fragment of the NF2 gene.

(FIG. 24A) shows detection using regular PCR primers. (FIG. 24B) shows detection using PCR primers modified with 2'-O methyl at the 3'-ends. See Example 22.

FIGS. 25A-B are photographs of an agarose gel stained with ethidium bromide showing amplification of a 2.7 Kb target DNA sequence (pUC19). Amplification cycle was repeated for 40-times.

FIG. 42A shows IL-4 cDNA (grey) from 303,030 to 22 copies. FIG. 42B shows c-myc cDNA (grey) from 1,000,000 to 22 copies; each dilution had 1,000,000 copies of cloned GAPDH cDNA (black). FAM-labeled fluorogenic primers were used to detect IL-4 (see Example 31, primer set 2, Table 8) and c-myc (see Example 31, primer set 5, Table 8) and a JOE-labeled primer was used to detect GAPDH (see Example 31, primer set 12, Table 8).

DETAILED DESCRIPTION OF THE INVENTION

Definitions and Abbreviations

Figure 2A:
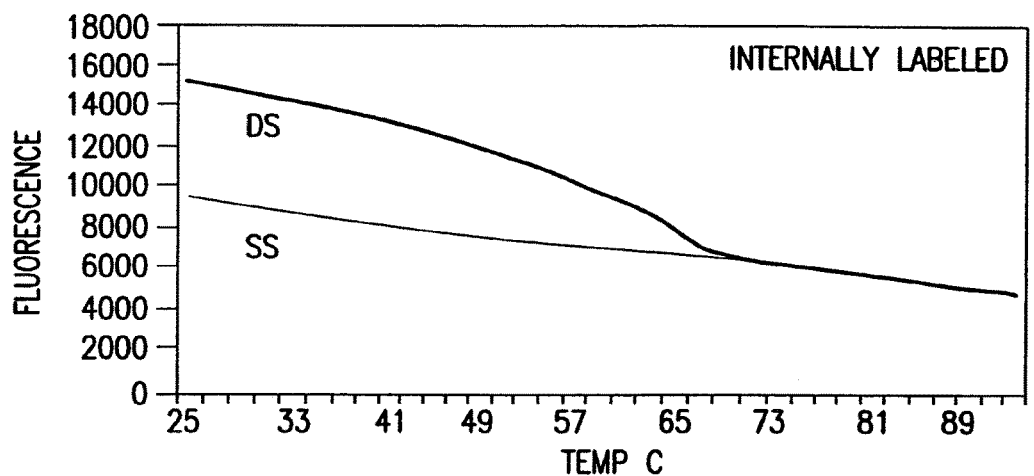
FIGS. 2A-B are line graphs of fluorescent intensity as a function of temperature which show the effect of hybridization on the fluorescence of internally (2A) and 5'-fluorescein labeled (2B) oligonucleotides. Labeled oligonucleotides were tested for fluorescence under different temperatures. Single-stranded (SS) or double-stranded (DS) oligonucleotides were melted as described in Example 4. For 5'-labeled oligonucleotides, conversion from SS oligonucleotides to DS oligonucleotides caused a decrease in fluorescence, while for internally labeled oligonucleotides, conversion from SS oligonucleotides to DS oligonucleotides caused an increase in fluorescence.

In the description that follows, a number of terms used in recombinant DNA technology are extensively utilized. As used herein, the following terms shall have the abbreviations indicated:

ASP, allele-specific polymerase chain reaction
bp, base pairs
DAB or DABCYL, 4-(4'-dimethylaminophenylazo)benzoic acid
EDANS, 5-(2'-aminoethyl)aminonapthalene-1-sulfonic acid
FAM or Flu, 5-carboxyfluorescein
JOE, 2'7'-dimethoxy-4'5'-dichloro-6-carboxyfluorescein
HPLC, high-performance liquid chromatography
NASBA, nucleic acid sequence-based amplification
Rhod, rhodamine
ROX, 6-carboxy-X-rhodamine
R6G, 6-carboxyrhodamine
TAMRA, N,N,N',N'-tetramethyl-6-carboxyrhodamine Amplification. As used herein, "amplification" refers to any in vitro method for increasing the number of copies of a nucleotide sequence with the use of a polymerase. Nucleic acid amplification results in the incorporation of nucleotides into a nucleic acid molecule (e.g., DNA) or primer thereby forming a new nucleic acid molecule complementary to the nucleic acid template. The formed nucleic acid molecule and its template can be used as templates to synthesize additional nucleic acid molecules. As used herein, one amplification reaction may consist of many rounds of nucleic acid synthesis. Amplification reactions include, for example, polymerase chain reactions (PCR). One PCR reaction may consist of 5 to 100 "cycles" of denaturation and synthesis of a nucleic acid molecule.

Specificity enhancing group. As used herein "specificity enhancing group" refers to any molecule or group of molecules that causes an oligonucleotide of the present invention to be less and preferably substantially less extendable when the 3'-most nucleotide of the oligonucleotide is substantially not base paired with a nucleotide on the nucleic acid target/template molecule. Any type of group may be used. Preferred examples include, but are not limited to, fluorescent groups, modified nucleotides, nucleotide analogues, small molecules, haptens and the like. Specificity enhancing groups may be attached at any position of the oligonucleotide or be a part of the oligonucleotide at any position (for example, when the specificity enhancing group is a modified nucleotide or nucleotide analogue) so long as they make the oligonucleotide less and preferably substantially less extendable when the 3'-termini nucleotide of the oligonucleotide is substantially not base paired with the corresponding nucleotide of the target/template nucleic acid. Such groups are preferably attached to the primer or oligonucleotide or part of the primer or oligonucleotide at or near the 3'-end of the primer or oligonucleotide, but may be attached or placed at other positions as well. Preferably, they are attached to or located to one or more of the 25 bases adjacent to the 3'-end of the primer or oligonucleotide. In some preferred embodiments, such groups may be attached to or located to one or more of the 20 bases adjacent to the 3'-end of the oligonucleotide, or to or part of the 15 bases adjacent to the 3'-end or to or part of the 10 bases adjacent to the 3'-end or, most preferably to or part of one or more of the five bases adjacent to the 3'-end of the oligonucleotide. In addition, specificity enhancing groups may be attached to or a part of the 3'-most nucleotide so long as the presence of the group does not prevent or inhibit the extension of the primer when the 3'-most nucleotide of the primer is complementary to the corresponding nucleotide on the target/template molecule more than the extension is inhibited when the 3'-most nucleotide is substantially not base paired to the target/template. Any group that can decrease the stability of the duplex (double-stranded complex) formed by the primer and template when the 3'-most nucleotide of the primer or oligonucleotide is not complementary to the corresponding nucleotide of the target/template and/or any group that can make a polymerase less efficient at extending the 3'-end of the oligonucleotide when the 3'-most nucleotide is not complementary to the corresponding nucleotide of the template/target may be used to practice the present invention. In some embodiments, the specificity enhancing groups of the invention may be modified nucleotides or nucleotide analogues incorporated into the sequence of the primer or oligonucleotide. Such modifications may be made at the base, sugar or phosphate portion of the nucleotide and include, but are not limited to, phosphothioate nucleotides, phosphonate nucleotides, peptide nucleic acids and the like. A specificity enhancing group is used, for example, in allele-specific PCR to enhance discrimination.

Polymerase. As used herein "polymerase" refers to any enzyme having a nucleotide polymerizing activity. Polymerases (including DNA polymerases and RNA polymerases) useful in accordance with the present invention include, but are not limited to, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT®) DNA polymerase, *Pyrococcus furiosus* (Pfu) DNA polymerase, DEEPVENT® DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME®) DNA polymerase, *Methanobacterium thermoautotrophicum* (Mth) DNA polymerase, mycobacterium DNA polymerase (Mtb, Mlep), and mutants, variants and derivatives thereof. RNA polymerases such as T3, T5 and SP6 and mutants, variants and derivatives thereof may also be used in accordance with the invention. Generally, any type I DNA polymerase may be used in accordance with the invention although other DNA polymerases may be used including, but not limited to, type III or family A, B, C, etc. DNA polymerases.

Polymerases used in accordance with the invention may be any enzyme that can synthesize a nucleic acid molecule from a nucleic acid template, typically in the 5' to 3' direction. "3' to 5' exonuclease activity" is an enzymatic activity well known to the art. This activity is often associated with DNA polymerases, and is thought to be involved in a DNA replication "editing" or correction mechanism. A "polymerase substantially reduced in 3' to 5' exonuclease activity" is defined herein as either (1) a mutated or modified polymerase that has about or less than 10%, or preferably about or less than 1%, of the 3' to 5' exonuclease activity of the corresponding unmutated, wild-type enzyme, or (2) a polymerase having a 3' to 5' exonuclease specific activity which is less than about 1 unit/mg protein, or preferably about or less than 0.1 units/mg protein. A unit of activity of 3' to 5' exonuclease is defined as the amount of activity that solubilizes 10 nmoles of substrate ends in 60 min. at 37° C., assayed as described in the "BRL 1989 Catalogue & Reference Guide," page 5, with HhaI fragments of lambda DNA 3'-end labeled with [$^3$H]dTTP by terminal deoxynucleotidyl transferase (TdT). Protein is measured by the method of Bradford, *Anal. Biochem.* 72:248 (1976). As a means of comparison, natural, wild-type T5-DNA polymerase (DNAP) or T5-DNAP encoded by pTTQ19-T5-2 has a specific activity of about 10 units/mg protein while the DNA polymerase encoded by pTTQ19-T5-2(Exo-) (U.S. Pat. No. 5,270,179) has a specific activity of about 0.0001 units/mg protein, or 0.001% of the specific activity of the unmodified enzyme, a 105-fold reduction. "5' to 3' exonuclease activity" is also an enzymatic activity well known in the art. This activity is often associated with DNA polymerases, such as E. coli PolI and Taq DNA polymerase. A "polymerase substantially reduced in 5' to 3' exonuclease activity" is defined herein as either (1) a mutated or modified polymerase that has about or less than 10%, or preferably about or less than 1%, of the 5' to 3' exonuclease activity of the corresponding unmutated, wild-type enzyme, or (2) a polymerase having 5' to 3' exonuclease specific activity which is less than about 1 unit mg protein, or preferably about or less than 0.1 units/mg protein. Both of the 3' to 5' and 5' to 3' exonuclease activities can be observed on sequencing gels. Active 5' to 3' exonuclease activity will produce nonspecific ladders in a sequencing gel by removing nucleotides from the 5'-end of the growing primers. 3' to 5' exonuclease activity can be measured by following the degradation of radiolabeled primers in a sequencing gel. Thus, the relative amounts of these activities, e.g., by comparing wild-type and mutant or modified polymerases, can be determined with no more than routine experimentation.

The nucleic acid polymerases used in the present invention may be mesophilic or thermophilic, and are preferably thermophilic. Preferred mesophilic DNA polymerases include T7 DNA polymerase, T5 DNA polymerase, Klenow fragment DNA polymerase, DNA polymerase III and the like. Preferred thermostable DNA polymerases that may be used in the invention include Taq, Tne, Tma, Pfu, Tfl, Tth, Stoffel fragment, VENT® and DEEPVENT® DNA polymerases, and mutants, variants and derivatives thereof (U.S. Pat. No. 5,436,149; U.S. Pat. No. 4,889,818; U.S. Pat. No. 4,965,188; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; U.S. Pat. No. 6,015,668; U.S. Pat. No. 5,939,301; U.S. Pat. No. 5,948,614; U.S. Pat. No. 5,912,155; WO 97/09451; WO 98/35060; WO 92/06188; WO 92/06200; WO 96/10640; Barnes, W. M., Gene 112:29-35 (1992); Lawyer, F. C., et al., PCR Meth. Appl. 2:275-287 (1993); Flaman, J.-M, et al., Nucl. Acids Res. 22(15):3259-3260 (1994)). For amplification of long nucleic acid molecules (e.g., nucleic acid molecules longer than about 3-5 Kb in length), at least two DNA polymerases (one substantially lacking 3' exonuclease activity and the other having 3' exonuclease activity) are typically used. See U.S. Pat. No. 5,436,149; U.S. Pat. No. 5,512,462; Barnes, W. M., Gene 112:29-35 (1992), the disclosures of which are incorporated herein in their entireties. Examples of DNA polymerases substantially lacking in 3' exonuclease activity include, but are not limited to, Taq, Tne(exo$^-$), Tma(exo$^-$), Pfu(exo$^-$), Pwo(exo$^-$) and Tth DNA polymerases, and mutants, variants and derivatives thereof.

DNA polymerases for use in the present invention may be obtained commercially, for example, from Invitrogen Corporation (Life Technologies Division) (Rockville, Md.), Pharmacia (Piscataway, N.J.), Sigma (St. Louis, Mo.) and Boehringer Mannheim Biochemicals. Preferred DNA polymerases for use in the present invention include Tsp DNA polymerase from Invitrogen Corporation (Life Technologies Division).

Enzymes for use in the compositions, methods and kits of the invention include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, R. K., et al., Science 239:487-491 (1988); U.S. Pat. Nos. 4,889,818 and 4,965,188), Tne DNA polymerase (WO 96/10640), Tma DNA polymerase (U.S. Pat. No. 5,374,553) and mutants, fragments, variants or derivatives thereof (see, e.g., U.S. Pat. Nos. 5,948,614 and 6,015,668, which are incorporated by reference herein in their entireties). As will be understood by one of ordinary skill in the art, modified reverse transcriptases and DNA polymerases having RT activity may be obtained by recombinant or genetic engineering techniques that are well-known in the art. Mutant reverse transcriptases or polymerases can, for example, be obtained by mutating the gene or genes encoding the reverse transcriptase or polymerase of interest by site-directed or random mutagenesis. Such mutations may include point mutations, deletion mutations and insertional mutations. Preferably, one or more point mutations (e.g., substitution of one or more amino acids with one or more different amino acids) are used to construct mutant reverse transcriptases or polymerases for use in the invention. Fragments of reverse transcriptases or polymerases may also be obtained by deletion mutation by recombinant techniques that are well-known in the art, or by enzymatic digestion of the reverse transcriptase(s) or polymerase(s) of interest using any of a number of well-known proteolytic enzymes.

Preferred enzymes for use in the invention include those that are reduced or substantially reduced in RNase H activity. Such enzymes that are reduced or substantially reduced in RNase H activity may be obtained by mutating the RNase H domain within the reverse transcriptase of interest, preferably by one or more point mutations, one or more deletion mutations, and/or one or more insertion mutations as described above. By an enzyme "substantially reduced in RNase H activity" is meant that the enzyme has less than about 30%, less than about 25%, less than about 20%, more preferably, less than about 15%, less than about 10%, less than about 7.5%, or less than about 5%, and most preferably, less than about 5% or less than about 2%, of the RNase H activity of the corresponding wildtype or RNase H$^+$ enzyme such as wildtype Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for example, in U.S. Pat. No. 5,244,797, Kotewicz, M. L., et al., Nucl. Acids Res. 16:265 (1988), Gerard, G. F., et al., FOCUS 14(5):91 (1992), and U.S. Pat. Nos. 5,668,005 and 6,063,608, the disclosures of all of which are fully incorporated herein by reference.

Polypeptides having reverse transcriptase activity for use in the invention may be obtained commercially, for example from Invitrogen Corporation (Life Technologies Division) (Rockville, Md.), Pharmacia (Piscataway, N.J.), Sigma (Saint Louis, Mo.) or Boehringer Mannheim Biochemicals (Indianapolis, Ind.). Alternatively, polypeptides having reverse transcriptase activity may be isolated from their natural viral or bacterial sources according to standard procedures for isolating and purifying natural proteins that are well-known to one of ordinary skill in the art (see, e.g., Houts, G. E., et al., J. Virol. 29:517 (1979)). In addition, the polypeptides having reverse transcriptase activity may be prepared by recombinant DNA techniques that are familiar to one of ordinary skill in the art (see, e.g., Kotewicz, M. L., et al., Nucl. Acids Res. 16:265 (1988); Soltis, D. A., and Skalka, A. M., Proc. Natl. Acad. Sci. USA 85:3372-3376 (1988)).

Preferred polypeptides having reverse transcriptase activity for use in the invention include M-MLV reverse transcriptase, RSV reverse transcriptase, AMV reverse transcriptase, Rous Associated Virus (RAV) reverse transcriptase, Myeloblastosis Associated Virus (MAV) reverse transcriptase and Human Immunodeficiency Virus (HIV) reverse transcriptase, and others described in WO 98/47921 and derivatives, variants, fragments or mutants thereof, and combinations thereof. In a further preferred embodiment, the reverse transcriptases are reduced or substantially reduced in RNase H activity, and are most preferably selected from the group consisting of M-MLV H$^-$ reverse transcriptase, RSV H$^-$ reverse transcriptase, AMV H$^-$ reverse transcriptase, RAV H$^-$ reverse transcriptase, MAV H$^-$ reverse transcriptase and HIV H$^-$ reverse transcriptase, and derivatives, variants, fragments and mutants thereof, and combinations thereof. Reverse transcriptases of particular interest include AMV RT and M-MLV RT, and more preferably, AMV RT and M-MLV RT having reduced or substantially reduced RNase H activity (preferably, AMV RT $\alpha$H$^-$/BH$^+$ and M-MLV RT H$^-$). The most preferred reverse transcriptases for use in the invention include SuperScript™, SuperScript™ II, ThermoScript™ and ThermoScript™ II available from Invitrogen Corporation (Life Technologies Division) See, generally, WO 98/47921 and U.S. Pat. Nos. 5,244,797, 5,668,005 and 6,063,608, the entire contents of each of which are herein incorporated by reference.

Hairpin. As used herein, the term "hairpin" is used to indicate the structure of an oligonucleotide in which one or more portions of the oligonucleotide form base pairs with one or more other portions of the oligonucleotide. When the two portions are base paired to form a double-stranded portion of the oligonucleotide, the double-stranded portion may be referred to as a stem. Thus, depending on the number of complementary portions used, a number of stems (preferably about 1 to about 10) may be formed.

In some preferred embodiments, the primers of the present invention may be modified such that they assume a hairpin structure. This may be accomplished by adding one or more bases to the 5'-termini of the oligonucleotide wherein the bases are selected to be complementary to the bases at the 3'-termini of the oligonucleotide. In some preferred embodiments, at least one to about 20 contiguous nucleotides are added to the 5'-end of the oligonucleotide that are complementary to the at least one to 20 contiguous nucleotides present in the 3'-end of the oligonucleotide. In a preferred embodiment, from one to about 10 nucleotides are added to the 5'-end of the oligonucleotide, the nucleotides selected such that they are complementary to the at least one to about 10 contiguous nucleotides present in the 3'-end of the oligonucleotide. In another preferred embodiment, from one to about 5 nucleotides are added to the 5'-end of the oligonucleotide, the nucleotides selected such that they are complementary to the at least one to about 5 contiguous nucleotides present in the 3'-end of the oligonucleotide.

Additionally, formation of the one or more stems preferably allows formation of one or more loop structures in the hairpin molecule. In one aspect, any one or more of the loop structures may be cut or nicked at one or more sites within the loop or loops but, preferably, at least one loop is not so cut or nicked. The sequence of the oligonucleotide may be selected so as to vary the number of nucleotides which base pair to form the stem from about 3 nucleotides to about 100 or more nucleotides, from about 3 nucleotides to about 50 nucleotides, from about 3 nucleotides to about 25 nucleotides, and from about 3 to about 10 nucleotides. In addition, the sequence of the oligonucleotide may be varied so as to vary the number of nucleotides which do not form base pairs from 0 nucleotides to about 100 or more nucleotides, from 0 nucleotides to about 50 nucleotides, from 0 nucleotides to about 25 nucleotides or from 0 to about 10 nucleotides. The two portions of the oligonucleotide which base pair may be located anywhere or at any number of locations in the sequence of the oligonucleotide. In some embodiments, one base pairing portion of the oligonucleotide may include the 3'-termini of the oligonucleotide. In some embodiments, one base pairing-portion may include the 5'-termini of the oligonucleotide. In some embodiments, one base pairing portion of the oligonucleotide may include the 3'-termini while the other base pairing portion may include the 5'-termini and, when base paired, the stem of the oligonucleotide is blunt ended. In other embodiments, the location of the base pairing portions of the oligonucleotide may be selected so as to form a 3'-overhang and/or a 5'-overhang and/or may be selected so that neither the 3'-nor the 5'-most nucleotides are involved in base pairing.

The hairpin version of the oligonucleotide primers can be constructed by adding bases to the 5'-end of the primer sequence that are complementary to the 3'-end of the oligonucleotide, for example. Typically, the number of bases added to the 5'-end is selected such that the oligonucleotide forms a hairpin at temperatures below the annealing temperature and assumes a linear form at or near the annealing temperature. Those skilled in the art can readily determine the number of nucleotides to be added to the 5'-end of the primer so as to control the temperature at which the primer assumes a linear form. It is not necessary that the oligonucleotides of the invention be entirely converted to linear form at the annealing temperature; those skilled in the art will appreciate that the oligonucleotides of the present invention may be capable of reversibly melting and self-reannealing (i.e., breathing). So long as the sequences of the oligonucleotides of the invention are selected such that a sufficient number of oligonucleotides are available to prime the extension, amplification, etc. at the annealing temperature, the sequences are suitable for use in the present invention whether or not some of the oligonucleotides remain in a hairpin form at the annealing temperature. The number of nucleotides that may be added may be from about 3 nucleotides to about 25 nucleotides, or from about 3 nucleotides to about 20 nucleotides, or from about 3 nucleotides to about 15 nucleotides, or from about 3 nucleotides to about 10 nucleotides, or from about 3 nucleotides to about 7 nucleotides. In some preferred embodiments, from about 5 to about 8 nucleotides may be added to the 5'-end of the primer oligonucleotide in order to form the hairpin oligonucleotides of the present invention.

Hybridization. As used herein, the terms "hybridization" and "hybridizing" refer to the pairing of two complementary single-stranded nucleic acid molecules (RNA and/or DNA) to give a double-stranded molecule. As used herein, two nucleic acid molecules may be hybridized, although the base pairing is not completely complementary. Accordingly, mismatched bases do not prevent hybridization of two nucleic acid molecules provided that appropriate conditions, well-known in the art, are used.

Incorporating. The term "incorporating" as used herein means becoming a part of a DNA or RNA molecule or primer.

Nucleotide. As used herein "nucleotide" refers to a base-sugar-phosphate combination. Nucleotides are monomeric units of a nucleic acid sequence (DNA and RNA). The term nucleotide includes mono-, di- and triphosphate forms of deoxyribonucleosides and ribonucleosides and their derivatives. The term nucleotide particularly includes deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well-known techniques. Detectable labels include, for example, radioactive isotopes, fluorescent labels, chemiluminescent labels, bioluminescent labels and enzyme labels.

Oligonucleotide. As used herein, "oligonucleotide" refers to a synthetic or biologically produced molecule comprising a covalently linked sequence of nucleotides or derivatives thereof. Such nucleotides may be joined by a phosphodiester bond between the 3' or 5' position of the pentose of one nucleotide, for example, and the 5' or 3' position of the pentose of the adjacent nucleotide, for example. Bonds can also occur between 3' positions and 5' positions and between any other at least two positions.

Oligonucleotide, as used herein, includes natural nucleic acid molecules (i.e., DNA and RNA) as well as non-natural or derivative molecules such as peptide nucleic acids, phosphothioate containing nucleic acids, phosphonate containing nucleic acids and the like. In one embodiment, oligonucleotides of the invention may comprise 5-100 nucleotides (e.g. 5-10, 15-20, 25-30, 35-40, 45-50, 55-60, 65-70, 75-80, 85-90, 95-100 etc. nucleotides), preferably, 6 nucleotides. In addition, oligonucleotides of the present invention may contain modified or non-naturally occurring sugar residues (i.e., arabainose) and/or modified base residues as described below. Oligonucleotide encompasses derivative molecules such as nucleic acid molecules comprising various natural nucleotides, derivative nucleotides, nucleotide analogues, modified nucleotides or combinations thereof. Such modifications include, but are not limited to, adding a 2'-O-alkyl group to the oligonucleotide or specifically, a 2'-O-methyl group, creating a 5'-5' phosphodiester bond between oligonucleotides, and adding a C3-amino, a C6-amino or biotin to the oligonucleotide. Thus, any oligonucleotide or other molecule useful in the methods of the invention, e.g., primer or oligonucleotide primer, are contemplated by this definition. Oligonucleotides of the present invention may also comprise blocking groups which prevent the interaction of the molecule with particular proteins, enzymes or substrates.

Primer. As used herein, "primer" refers to a synthetic or biologically produced single-stranded oligonucleotide that is extended by covalent bonding of nucleotide monomers during amplification or polymerization of a nucleic acid molecule. Nucleic acid amplification often is based on nucleic acid synthesis by a nucleic acid polymerase or reverse transcriptase. Many such polymerases or reverse transcriptases require the presence of a primer that can be extended to initiate such nucleic acid synthesis. A primer is typically 11 bases or longer; most preferably, a primer is 17 bases or longer, although shorter or longer primers may be used depending on the need. As will be appreciated by those skilled in the art, the oligonucleotides of the invention may be used as one or more primers in various extension, synthesis or amplification reactions.

Probe. As used herein, "probe" refers to synthetic or biologically produced nucleic acids (DNA or RNA) which, by design or selection, contain specific nucleotide sequences that allow them to hybridize, under defined stringencies, specifically (i.e., preferentially) to target nucleic acid sequences. As will be appreciated by those skilled in the art, the oligonucleotides of the present invention may be used as one or more probes and preferably may be used as probes for the detection or quantification of nucleic acid molecules.

Substantially less extendable. As used herein, "substantially less extendable" is used to characterize an oligonucleotide that is inefficiently extended or not extended in an extension and/or amplification reaction when the 3'-most nucleotide of the oligonucleotide is not complementary to the corresponding base of a target/template nucleic acid. Preferably, an oligonucleotide is substantially less extendable as a result of the presence of a specificity enhancing group on the oligonucleotide. In this event, an oligonucleotide is substantially less extendable when the oligonucleotide is not extended or is extended by a lesser amount and/or at a slower rate than an oligonucleotide lacking the specificity enhancing group, but having an otherwise identical structure. Those skilled in the art can readily determine if an oligonucleotide is substantially less extendable by conducting an extension reaction using an oligonucleotide containing a specificity enhancing group and comparing the extension to the extension of an oligonucleotide of the same structure, but lacking the specificity enhancing group. Under identical extension conditions, (e.g., melting temperature and time, annealing temperature and time, extension temperature and time, reactant concentrations and the like), a substantially less extendable oligonucleotide will produce less extension product when the 3'-most nucleotide of the oligonucleotide is not complementary to the corresponding nucleotide on a target/template nucleic acid than will be produced by an oligonucleotide lacking a specificity enhancing group, but having an otherwise identical structure. Alternatively, one skilled in the art can determine if an oligonucleotide is substantially less extendable by conducting allele specific PCR with a first set of oligonucleotides at least one of which comprises one or more specificity enhancing groups and with a second set of oligonucleotides lacking specificity enhancing groups, but otherwise of identical structure to those of the first set. Then, a determination is separately made for each set of primers of the difference in the amount of product made and/or the rate at which the product is made with the oligonucleotide having the 3'-nucleotide complementary to the corresponding nucleotide on a target/template nucleic acid to the amount of product made and/or the rate at which the product is made with an oligonucleotide having the 3'-nucleotide not complementary to the corresponding nucleotide on a target/template nucleic acid. Substantially less extendable oligonucleotides will produce a larger difference in amount of product made and/or rate at which product is made between 3'-complementary and 3'-not-complementary oligonucleotides. Preferably, the difference in the amount of product made and/or rate at which product is made using oligonucleotides containing specificity enhancing groups will be between from about 1.1 fold to about 1000 fold larger than the difference obtained using primers lacking specificity enhancing groups, or from about 1.1 fold to about 500 fold larger, or from about 1.1 fold to about 250 fold larger, or from about 1.1 fold to about 100 fold larger, or from about 1.1 fold to about 50 fold larger, or from about 1.1 to about 25 fold larger, or from about 1.1 to about 10 fold larger, or from about 1.1 fold to about 5 fold or from about 1.1 fold to about 2 fold larger. The amount of product can be determined using any methodology known to those of skill in the art, for example, by running the product on an agarose gel and staining with ethidium bromide and comparing to known amounts of similarly treated nucleic acid standards. The amount of product may be determined at any convenient time point in allele specific PCR. One convenient way to compare the rate of formation of product is to compare the number of cycles required to form a specified amount of product in PCR. A determination is separately made for each set of primers of the difference between the number of cycles required to make a given amount of product with the oligonucleotide having the 3'-nucleotide complementary to the corresponding nucleotide on a target/template nucleic acid and the number of cycles required to make the same amount of product with an oligonucleotide having the 3'-nucleotide not complementary to the corresponding nucleotide on a target/template nucleic acid. Substantially less extendable oligonucleotides will produce a larger difference in the number of cycles required to produce a specified amount of product between 3'-complementary and 3'-not-complementary oligonucleotides. The amount of product made can be determined using any means known to those skilled in the art, for example, by determining the fluorescence intensity of a labeled product using a thermocycler adapted to perform real time fluorescence detection. Preferably the difference between the number of cycles required to make a specified amount of product using oligonucleotides containing specificity enhancing groups will be between from about 1.05 fold to about 100 fold larger than the difference obtained using primers lacking specificity enhancing groups, or from about 1.05 fold to about 50 fold larger, or from about 1.05 fold to about 25 fold larger, or from about 1.05 fold to about 10 fold larger, or from about 1.05 fold to about 5 fold larger, or from about 1.05 to about 2.5 fold larger, or from about 1.05 to about 1.5 fold larger, or from about 1.05 fold to about 1.2 fold larger.

Support. As used herein a "support" may be any material or matrix suitable for attaching the oligonucleotides of the present invention or target/template nucleic acid sequences. Such oligonucleotides and/or sequences may be added or bound (covalently or non-covalently) to the supports of the invention by any technique or any combination of techniques well-known in the art. Supports of the invention may comprise nitrocellulose, diazocellulose, glass, silicon, polystyrene (including microtitre plates), polyvinylchloride, polypropylene, polyethylene, dextran, Sepharose®, agar, starch, nylon or any other material that allows for the immobilization of nucleic acids. Supports of the invention may be in any form or configuration including, but not limited to, a flat surface, beads, filters, membranes, sheets, fits, plugs, columns, microspheres, fibers (e.g., optical fibers) and the like. Solid supports may also include multi-well tubes (such as microtitre plates) such as 12-well plates, 24-well plates, 48-well plates, 96-well plates, and 384-well plates. Preferred beads are made of glass, latex or a magnetic material (magnetic, paramagnetic or superparamagnetic beads). When using solid a support, labeled oligonucleotide may be immobilized or added in solution (in the latter case, other components of the detection mixture will be immobilized).

Any number of different sequences can be immobilized onto a support into any number of distinct regions to detect one or more sequences, including, but not limited to, nucleic acid target sequences.

In a preferred aspect, methods of the invention may be used in conjunction with arrays of nucleic acid molecules (RNA or DNA). Arrays of nucleic acid template/target or arrays of oligonucleotides of the invention are both contemplated in the methods of the invention. Such arrays may be formed on microplates, glass slides or standard blotting membranes and may be referred to as microarrays or genechips depending on the format and design of the array. Uses for such arrays include gene discovery, gene expression profiling and genotyping (SNP analysis, pharmacogenomics and toxicogenetics).

Synthesis and use of nucleic acid arrays and, generally, attachment of nucleic acids to supports have been described (see, for example, U.S. Pat. No. 5,436,327, U.S. Pat. No. 5,800,992, U.S. Pat. No. 5,445,934, U.S. Pat. No. 5,763,170, U.S. Pat. No. 5,599,695 and U.S. Pat. No. 5,837,832). An automated process for attaching various reagents to positionally defined sites on a substrate is provided in U.S. Pat. No. 5,143,854 and U.S. Pat. No. 5,252,743.

Essentially, any conceivable support may be employed in the invention. The support may be biological, nonbiological, organic, inorganic, or a combination of any of these, existing as particles, strands, precipitates, gels, sheets, tubing, spheres, containers, capillaries, pads, slices, films, plates, slides, etc. The support may have any convenient shape, such as a disc, square, sphere, circle, etc. The support is preferably flat, but may take on a variety of alternative surface configurations. For example, the support may contain raised or depressed regions on which one or more methods of the invention may take place. The support and its surface preferably form a rigid support on which to carry out the reactions described herein. The support and its surface are also chosen to provide appropriate light-absorbing characteristics. For instance, the support may be a polymerized Langmuir Blodgett film, functionalized glass, Si, Ge, GaAs, GaP, $SiO_2$, $SIN_4$, modified silicon, or any one of a wide variety of gels or polymers such as (poly)tetrafluoroethylene, (poly)vinylidenedifluoride, polystyrene, polycarbonate, or combinations thereof. Other support materials will be readily apparent to those of skill in the art upon review of this disclosure. In a preferred embodiment, the support is flat glass or single-crystal silicon.

Target molecule. As used herein, "target molecule" refers to a nucleic acid molecule to which a particular primer or probe is capable of preferentially hybridizing.

Target sequence. As used herein, "target sequence" refers to a nucleic acid sequence within the target molecules to which a particular primer or probe is capable of preferentially hybridizing.

Template. The term "template" as used herein refers to a double-stranded or single-stranded molecule which is to be amplified, synthesized or sequenced. In the case of a double-stranded DNA molecule, denaturation of its strands to form a first and a second strand is preferably performed to amplify, sequence or synthesize these molecules. A primer, complementary to a portion of a template is hybridized under appropriate conditions and the polymerase (DNA polymerase or reverse transcriptase) may then synthesize a nucleic acid molecule complementary to said template or a portion thereof. The newly synthesized molecule, according to the invention, may be equal or shorter in length than the original template. Mismatch incorporation during the synthesis or extension of the newly synthesized molecule may result in one or a number of mismatched base pairs. Thus, the synthesized molecule need not be exactly complementary to the template. The template can be an RNA molecule, a DNA molecule or an RNA/DNA hybrid molecule. A newly synthesized molecule may serve as a template for subsequent nucleic acid synthesis or amplification.

Thermostable. As used herein, "thermostable" refers to a polymerase (RNA, DNA or RT) which is resistant to inactivation by heat. DNA polymerases synthesize the formation of a DNA molecule complementary to a single-stranded DNA template by extending a primer in the 5'-to-3' direction. This activity for mesophilic DNA polymerases may be inactivated by heat treatment. For example, T5 DNA polymerase activity is totally inactivated by exposing the enzyme to a temperature of 90° C. for 30 seconds. As used herein, a thermostable DNA polymerase activity is more resistant to heat inactivation than a mesophilic DNA polymerase. However, a thermostable DNA polymerase does not mean to refer to an enzyme which is totally resistant to heat inactivation and thus, heat treatment may reduce the DNA polymerase activity to some extent. A thermostable DNA polymerase typically will also have a higher optimum temperature than mesophilic DNA polymerases.

Vector. As used herein, is a DNA that is able to replicate or be replicated in vitro or in a host cell or that provides a useful biological or biochemical property to an inserted gene. Examples include plasmids, phages, and other DNA sequences. A Vector can have one or more restriction endonuclease recognition sites at which the DNA sequences can be cut in a determinable fashion without loss of an essential biological function of the vector, and into which a DNA fragment can be spliced in order to bring about its replication and cloning. Vectors can further provide primer sites, e.g., for PCR, transcriptional and/or translational initiation and/or regulation sites, recombinational signals, replicons, Selectable markers, etc. The cloning vector can further contain a Selectable marker suitable for use in the identification of cells transformed with the cloning vector. Any number of hosts may be used to express the present invention; including prokaryotic and eukaryotic cells. Host cells that may be used are those well known in the art.

Other terms used in the fields of recombinant DNA technology and molecular and cell biology as used herein will be generally understood by one of ordinary skill in the applicable arts.

Oligonucleotides

The oligonucleotides of the invention can be DNA or RNA or chimeric mixtures or derivatives or modified versions thereof. In addition to being labeled with a detectable moiety, the oligonucleotide can be modified at the base moiety, sugar moiety, or phosphate backbone, and may include other appending groups or labels. Further, the oligonucleotides for use in the invention can be any suitable size, and are preferably in the range of 10-100 or 10-80 nucleotides, more preferably, 11-40 nucleotides and most preferably, in the range of 17-25 nucleotides although oligonucleotides may be longer or shorter depending upon the need.

The oligonucleotides of the invention may comprise at least one or more modified base moieties which are selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylamino-methyl-2-thiouridine, 5-carboxymethylaminomethyl-uracil, dihydrouracil, beta-D-galactosylqueosine, inosine, $N^6$-isopentenyladenine, 1-methylguanine, 1-methy-linosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxy-methyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouridine, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the oligonucleotides of the invention comprises at least one modified or unmodified sugar moiety selected from the group including, but not limited to, arabinose, 2-fluoroarabinose, xylulose, hexose, and glycopyranosyl groups including, but not limited to, those of glucose, mannose, galactose, gulose, allose, altrose, idose, and talose. Among the furanosyl structures, examples include, but are not limited to, those derived from fructose, arabinose or xylose.

In yet another embodiment, the oligonucleotides of the invention comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

Additionally, one or a number of the oligonucleotides of the present invention comprise at least one nucleotide derivative or nucleotide analogue. Examples of such derivatives include, but are not limited to, a deoxyinosine residue, a thionucleotide, a peptide nucleic acid and the like.

Further examples of modified oligonucleotides or nucleotide analogues that can be used in the practice of the invention are represented by the following formula:

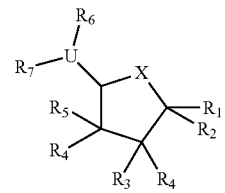

wherein,

X is —O—, —S—, —SO—, —SO$_2$—, —Se—, C(R$_8$R$_9$), —N(R$_{10}$R$_{11}$), NR$_{10}$, P(O$_2$), or P(O)—O—R$_{12}$;

U is —O—, —S—, —SO—, —SO$_2$—, —Se—, C(R$_8$), or NR$_{10}$;

R$_1$ is heteroaryl, heterocyclic, or aryl; preferably, R$_1$ is a heteroaryl group, e.g., a nucleobase such as adenine, guanine, cytosine, uracil and thymine and analogs and derivatives thereof;

R$_2$, R$_3$, R$_5$, R$_8$, R$_9$, independently are hydrogen, alkyl, alkyloxy, alkylamino, alkylthio, aryl, aryloxy, carboxylic acid, carboxamide, aminoacid ester, hydroxyacid ester, peptide, sugar residue, hydroxy, amino, or thio;

each R$_4$ is hydroxy, alkoxy, amino, thio, a nucleic acid molecule or a modified nucleic acid molecule;

R$_6$ is R$_2$ (when U is CR$_8$) or any one of hydrogen, alkyl, aryl, carboxamide, amino acid amide, hydroxy acid amide, peptide, or sugar residue (when U is NR$_{10}$) or R$_6$ is absent when U is —O—, —S', —SO—, —SO$_2$—, or —Se—;

R$_7$ is hydrogen, triphosphate, diphosphate, monophosphate, a nucleic acid molecule or a modified nucleic acid molecule;

R$_{10}$ and R$_{12}$ independently are alkyl, aryl, carboxamide, amino acid ester or amide, hydroxy acid ester or amide, peptide, or a sugar residue; and R$_{11}$ is alkyl, alkyloxy, alkylamino, alkylthio, aryl, aryloxy, carboxylic acid, carboxamide, amino acid, hydroxyacid, peptide, or sugar residue;

wherein at least one of $R_4$ and $R_7$ is a nucleic acid molecule or a modified nucleic acid molecule and wherein the above structure is attached to the sugar moiety, for example, of the nucleic acid molecule or modified nucleic acid molecule.

Such nucleotide analogues may be prepared according to methods well known to those of ordinary skill in the art. For example, a synthetic oligodeoxynucleotide containing 5-[6-aminohexyl)-3-acrylimido]-2'-deoxyuridine is prepared using phosphoramidite chemistry and the appropriate phosphoramidites. This oligodexoynucleotide is dissolved in 0.1 M sodium borate buffer at pH 8.5. A solution containing a 30 fold excess of the N-hydroxysuccinimide ester of a fluorescent dye is dissolved in dimethyl sulfoxide and this solution is added to the oligodeoxynucleotide. The reaction is allowed to proceed for 1 hour. The excess dye is removed by precipitation, and the modified oligodeoxynucleotide is purified by gel filtration, polystyrene cartridge, or HPLC. The list of dyes used in this procedure include, without limitation, the following: 5-ROX, 6-ROX, Fluorescein (5+6 mixture of isomers as well as pure 5 and pure 6 isomer), TAMRA, Texas Red, Tet, Hex, Alexa Fluor 350, Alexa Fluor 430, Alexa Fluor 532, Alexa Fluor 546, Alexa Fluor 568, Alexa Fluor 594, BODIPY 650, LaJolla Blue, and JOE.

Useful alkyl groups include, but are not limited to, straight-chained and branched $C_{1-18}$ alkyl groups, preferably $C_{1-10}$ alkyl groups, more preferably $C_{1-5}$ alkyl groups. Typical $C_{1-18}$ alkyl groups include, but are not limited to, methyl, ethyl, propyl, isopropyl, butyl, sec-butyl, tert-butyl, 3-pentyl, hexyl, octyl, decyl, dodecyl, tetradecyl, hexadecyl and octadecyl groups.

Useful aryl groups include, but are not limited to, $C_{6-14}$ aryl, especially $C_{6-10}$ aryl. Typical $C_{6-14}$ aryl groups include, but are not limited to, phenyl, naphthyl, phenanthryl, anthracyl, indenyl, azulenyl, biphenyl, biphenylenyl and fluorenyl groups.

Useful alkoxy groups include, but are not limited to, oxygen substituted by one of the $C_{1-10}$ alkyl groups mentioned above.

Useful alkylthio groups include, but are not limited to, sulfur substituted by one of the $C_{1-10}$ alkyl groups mentioned above.

Useful alkylamino and dialkylamino groups include, but are not limited to, —$NHR_{13}$ and —$NR_{14}R_{15}$, wherein $R_{13}$-$R_{15}$ are independently $C_{1-10}$ alkyl groups.

Useful saturated or partially saturated heterocyclic groups include, but are not limited to, tetrahydrofuranyl, pyranyl, piperidinyl, piperizinyl, pyrrolidinyl, imidazolidinyl, imidazolinyl, indolinyl, isoindolinyl, quinuclidinyl, morpholinyl, isochromanyl, chromanyl, pyrazolidinyl pyrazolinyl, tetronoyl and tetramoyl groups.

Useful heteroaryl groups include, but are not limited to, any one of the following: thienyl, benzo[b]thienyl, naphtho[2,3-b]thienyl, thianthrenyl, furyl, pyranyl, isobenzofuranyl, chromenyl, xanthenyl, phenoxanthiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide, pyrimidinyl N-oxide and the like.

Amino acids include, but are not limited to, any of the naturally occurring amino acids as well as non-naturally occurring amino acids. Examples of amino acids include, but are not limited to, tyrosine, glycine, phenylalanine, methionine, alanine, serine, isoleucine, leucine, threonine, valine, proline, lysine, histidine, glutamine, glutamic acid, tryptophan, arginine, aspartic acid, asparagine and cysteine.

Examples of peptides include, but are not limited to, those having about 2 to about 50 amino acids.

Hydroxy acids include, but are not limited to, any alkylcarboxylic acid substituted on the alkyl group with a hydroxy group. Such hydroxy acids may contain from about 2 to about 50 carbon atoms, preferably, about 2 to about 6 carbon atoms, and include, without limitation, glycolic acid, lactic acid, 2-hydroxybutyric acid, 3-hydroxybutyric acid, 4-hydroxybutyric acid, 2-hydroxyisobutryic acid, 2-hydroxy-2-methylbutyric acid, 2-hydroxy-3-methylbutyric acid, 2-hydroxyvaleric acid, 2-hydroxycaproic acid, 2-hydroxyisocaproic acid and the like.

Such nucleic acid molecules may be DNA, RNA, and modified nucleic acid molecules such as phosphorothioates, protein nucleic acids (PNA) and locked nucleoside analogs (LNA). Such modifications may be at or near the 3'- and/or 5'-termini of the nucleic acid molecules and/or within the nucleic acid molecule.

There are many known modifications of nucleic acid molecules. See, for example, U.S. Pat. Nos. 6,160,109, 6,153,737, 6,153,599, 5,147,200, 6,146,829, 6,133,444, 6,133,438, 6,127,533, 6,114,519, 6,114,513, 6,111,085, 6,093,807, 6,063,569, 6,043,352, 6,025,482, 6,005,087, 6,001,841, 5,998,603, 5,998,419, 5,969,118, 5,965,721, 5,955,600, 5,914,396, 5,866,691, 5,859,232, 5,859,221, 5,856,466, 5,808,023, 5,736,336, 5,717,083, 5,714,331, 5,705,621, 5,700,922, 5,654,284, 5,646,265, 5,644,048, 5,637,684, 5,602,240, 5,596,091, 5,506,212, 5,521,302, 5,541,307, 5,543,507, 5,519,134, and 5,554,746, as well as WO 99/14226 (LNAs), WO 96/35706, WO 96/32474, WO 96/29337 (thiono triester modified antisense oligodeoxynucleotide phosphorothioates), WO 94/17093 (oligonucleotide alkylphosphonates and alkylphosphothioates), WO 94/08004 (oligonucleotide phosphothioates, methyl phosphates, phosphoramidates, dithioates, bridged phosphorothioates, bridge phosphoramidates, sulfones, sulfates, ketos, phosphate esters and phosphorobutylamines (van der Krol et al., *Biotech.* 6:958-976 (1988); Uhlmann et al., *Chem. Rev.* 90:542-585 (1990)), WO 94/02499 (oligonucleotide alkylphosphonothioates and arylphosphonothioates), and WO 92/20697 (3'-end capped oligonucleotides).

Modified oligonucleotides of the invention may have one or more modifications at one or more positions within the oligonucleotide(s) and/or at or near the 3'- and/or 5'-termini. In one embodiment, the oligonucleotide(s) may be modified on one of the two 3'- or 5'-most terminal nucleotides, one of the five 3'- or 5'-most terminal nucleotides, one of the ten 3'- or 5'-most terminal nucleotides, one of the fifteen 3'- or 5'-most terminal nucleotides, or one of the twenty 3'- or 5'-most terminal nucleotides. In a specific embodiment, the oligonucleotide(s) may be modified at the second base from the 3'- or 5'-termini, at the third base from the 3'- or 5'-termini, at the fourth base from the 3'- or 5'-termini, at the sixth base from the 3'- or 5'-termini, or up to the twentieth base from the 3'- or 5'-termini.

The oligonucleotides of the invention may be immobilized on a solid support. The methods of immobilizing labeled oligonucleotides which are quenched (by the methods of the invention) provide a homogenous method for detection of various nucleic acids. In a preferred embodiment, target DNA or RNA from a sample can be hybridized to an immobilized oligonucleotide and the change in the detectable label on the immobilized oligonucleotide used as an indication of the presence or absence of a particular gene or sequence in the sample. Thus, the immobilized oligonucleotide can function as a probe. By immobilizing the oligonucleotide, the target nucleic acid does not need to be copied (which can result in missed sequences due to inefficient copying) or labeled. The change in the oligonucleotide detectable label can be due to hybridization or hybridization followed by enzymatic extension of the immobilized oligonucleotide. In other embodiments, the enzymatic extension may result in the amplification of the nucleic acid target locally at the position of the immobilized oligonucleotide.

Labeling

The present invention provides oligonucleotides, which may be labeled internally, and/or, at or near the 3'- and/or 5'-termini or may be unlabeled. In one embodiment, the oligonucleotide(s) may be labeled on one of the two 3'- or 5'-most terminal nucleotides, one of the five 3'- or 5'-most terminal nucleotides, one of the ten 3'- or 5'-most terminal nucleotides, one of the fifteen 3'- or 5'-most terminal nucleotides, or one of the twenty 3'- or 5'-most terminal nucleotide. In a specific embodiment, the oligonucleotide(s) may be labeled at the second base from the 3'- or 5'-termini, at the third base from the 3'- or 5'-termini, at the fourth base from the 3'- or 5'-termini, at the sixth base from the 3'- or 5'-termini, or up to the twentieth base from the 3'- or 5'-termini.

In another aspect, the oligonucleotides of the present invention may be provided with a specificity enhancing group. Such a group may be located internally and/or at or near the 3'- and/or the 5'-termini of the oligonucleotide. In another aspect, the oligonucleotides of the present invention may be in the form of a hairpin. In some preferred embodiments, the oligonucleotides may be provided with more than one of these characteristics, i.e., they may comprise a label and/or a specificity enhancing group and/or may be in the form of a hairpin.

When labeled, oligonucleotides of the invention may contain one or multiple labels (which may be the same or different). The oligonucleotides of the invention may be used as primers and/or probes. In a preferred aspect, the oligonucleotides are labeled and the label is any moiety which undergoes a detectable change in any observable property upon hybridization and/or extension. In a preferred embodiment, the label is a fluorescent moiety and the label undergoes a detectable change in one or more fluorescent properties. Such properties include, but are not limited to, fluorescent intensity, fluorescent polarization, fluorescent lifetime and quantum yield of fluorescence.

The oligonucleotides of the invention can be labeled (as described above) using any known labeling method. As an example, the oligonucleotides may be labeled by: (1) attachment at the sulfur of a phosphorothioate linkage; (2) attachment at a 2'-amino group; (3) attachment at the 1' position using an appropriately modified sugar containing an alkylamine substituted carboxamide, for example; (4) attachment at the 1' position using an abasic site, for example, and an alkyl diamine as a linker, for example; (5) creation of a structure by reductive alkylation of the adduct formed between an alkyl diamine and an abasic site; (6) incorporation using 4'-thio-2'-deoxyuridine or 4'-thiothymidine; (7) attachment at the 2'-position of 4-thiothymidine or 4-thio-2'-deoxyuridine; (8) attachment at the 4-amino position of deoxycytidine, if the 4-amino group is derivatized with an alkylamine; (9) attachment through the 6' position of adenine, if the 6-amino group is derivatized with an alkylamino moiety; (10) incorporation using the 8' position of adenine if this position is substituted with an alkyl thioamine; (11) attachment at the $N^2$ of guanine, if the $N^2$ amino is derivatized with an alkylamino group; or (12) attachment at the $N^2$ position of aminoadenine if the 2-amino group is derivatized with an alkylamine.

Modifications to Enhance Specificity and to Reduce Primer-Dimer Formation

It has been unexpectedly found that the oligonucleotides of the present invention may be used to enhance the specificity of amplification and/or synthesis (e.g., reduce mis-priming) and/or hybridization reactions. Without wishing to be bound by theory, it is believed that the ability of the oligonucleotides as primers that form hairpin structures at temperatures around the annealing temperature of the PCR reaction or sequestration of the 3'-end of the primer makes the primers less capable of mis-priming to the target nucleic acid molecule. This increase in specificity is not dependent upon the particular target nucleic acid template and has been observed with a variety of templates. The increase in specificity is particularly important for the amplification of templates that are difficult to amplify and that produce low amounts or none of the desired amplification product in PCR reactions. See, e.g., Examples 14 and 15.

In addition to hairpin structures, any structure that sequesters the 3'-end of the oligonucleotide primer may be used to practice the present invention. For example, the 5'-portion of the oligonucleotide primers of the present invention may be provided with a sequence that is capable of forming a duplex such that the 3'-end interacts with the duplex to form a triplex. In general, any primer sequence that reversibly involves the 3'-portion of the primer in a stable structure that is not capable of annealing to the template DNA while in that structure may be used to practice the present invention. In some embodiments, an oligonucleotide complementary to the primer may be provided so as to sequester the 3'-end of the primer. Complementary oligonucleotides may be provided with a 5'-overhanging region which may be designed to include self-complementary regions capable of forming hairpins. It is not necessary that the entire 3'-portion of the primer be sequestered, so long as the portion not sequestered is not capable of mis-priming the nucleic acid template, it is sufficient to practice the present invention.

Regarding the hairpin structure, when a primer is in hairpin conformation, the 3'-end of the primer is base paired with the 5'-segment and thus, is less available for mispriming or primer-dimer formation. However, when the hairpin has a blunt end, there is another pathway for primer-dimer formation. Specifically, two blunt ends can be taken into close proximity by the polymerase and, as a result, the 3'-ends of the forward primer, for example, can displace the 5'-ends of the reverse primer, for example, or the reverse, and create a complement sequence. The proposed mechanism was confirmed by sequencing primer-dimers obtained with hairpin primers. The understanding of this mechanism enabled the suggestion of a solution for the problem. It was discovered that modification at or near the 5'-termini of a hairpin primer prevents primer-dimer formation. This may be due to inhibition of the displacement of the 5'-end of the hairpin. See Examples 15 and 16. Such modifications include adding 2'-O-alkyl or 2'-O-methyl, creating a 5'-5' phosphodiester bond, and adding C3-amino, C6-amino or biotin.

An alternative method of minimizing primer-dimer formation while using hairpin primers is to make oligonucleotides with the 3'-end extended by 1 or 2 nucleotides that are not complementary to each other. See Example 17.

Another alternative to primer-dimer reduction does not prevent primer-dimer formation, but makes them invisible. Since with hairpin primers, primer-dimers are formed very uniformly (as described in Example 15), the 3'-ends of two primers in double-stranded structure are in immediate proximity. Therefore, by labeling one primer with a reporter and another with a quencher close to their 3'-ends, one causes quenching of fluorescence to occur. The fluorescence of the real amplicon will not be effected as soon as a nucleotide sequence longer than about 20 nucleotides separates the primers. See Example 18.

Thus, for an increase in specificity for nucleic acid amplification or synthesis and/or for decreased or reduced mis-annealing of primers (mis-priming) during nucleic acid synthesis or amplification, the oligonucleotides of the invention may be: (1) in hairpin conformation or otherwise configured so as to sequester or block the 3'-end of the oligonucleotide primer (for example by hybridizing a sequence at or near such 3'-termini); (2) modified at or near the 5'-termini; and/or (3) combinations of (1) and (2).

Exemplary Uses of the Inventive Oligonucleotides

The oligonucleotides of the invention (labeled, unlabeled, hairpin, modified, or unmodified or any combination thereof) have use in nucleic acid amplification, synthesis or hybridization reactions (e.g., as primers) to detect or measure a nucleic acid product of the amplification or synthesis or hybridization reaction, thereby detecting or measuring a target nucleic acid in a sample that is complementary to all or a portion of a primer sequence. The oligonucleotides of the invention may be used in any amplification reaction including PCR, 5-RACE, Anchor PCR, "one-sided PCR," LCR, NASBA, SDA, RT-PCR, real-time PCR, quantitative PCR, quantitative RT-PCR, and other amplification systems known in the art including in a universal primer format.

Thus, the invention generally relates to methods of synthesizing or amplifying one or more nucleic acid molecules comprising:

(a) mixing one or more templates or target nucleic acid molecules with one or more oligonucleotides of the invention; and (b) incubating said mixture under conditions sufficient to synthesize or amplify one or more nucleic acid molecules complementary to all or a portion of said templates or target molecules.

Preferably, the synthesized or amplified nucleic acid molecules comprise one or more oligonucleotides of the invention or portions thereof. In one aspect, the oligonucleotides of the invention are incorporated at or near one or both termini of the synthesized or amplified nucleic acid molecules produced by the methods of the invention. The invention also relates to one or more nucleic acid molecules produced by such amplification or synthesis reactions.

In another aspect, the invention relates to methods of synthesizing one or more nucleic acid molecules, comprising:

(a) mixing one or more nucleic acid templates (which may be DNA molecules such as a cDNA molecules, RNA molecules such as mRNA molecules, or populations of such molecules) with one or more oligonucleotides of the invention and one or more polymerases; and (b) incubating the mixture under conditions sufficient to synthesize one or more first nucleic acid molecules complementary to all or a portion of the templates.

Such incubation conditions may involve the use of one or more nucleotides and one or more nucleic acid synthesis buffers. Such methods of the invention may optionally comprise one or more additional steps, such as incubating the synthesized first nucleic acid molecules under conditions sufficient to make one or more second nucleic acid molecules complementary to all or a portion of the first nucleic acid molecules. Such additional steps may also be accomplished in the presence of one or more primers of the invention and one or more polymerases as described herein. The invention also relates to nucleic acid molecules synthesized by these methods.

The invention also relates to methods for sequencing nucleic acid molecules comprising:

(a) mixing a nucleic acid molecule to be sequenced with one or more primers of the invention, one or more nucleotides and one or more terminating agents to form a mixture;

(b) incubating the mixture under conditions sufficient to synthesize the population of molecules complementary to all or a portion of the molecule to be sequence; and (c) separating the population to determining the nucleotide sequence of all or a portion of the molecule to be sequenced.

The invention more specifically relates to a method of sequencing a nucleic acid molecule, comprising:

(a) mixing one or more of the oligonucleotides of the invention, one or more nucleotides, and one or more terminating agents;

(b) hybridizing said oligonucleotides to a first nucleic acid molecule;

(c) incubating the mixture of step (b) under conditions sufficient to synthesize a random population of nucleic acid molecules complementary to said first nucleic acid molecule, wherein the synthesized molecules are shorter in length than said first molecule and wherein said synthesized molecules comprise a terminator nucleotide at their 3'-termini; and (d) separating said synthesized molecules by size so that at least a part of the nucleotide sequence of said first nucleic acid molecule can be determined. Such terminator nucleotides include ddTTP, ddATP, ddGTP, ddITP or ddCTP. Such incubation conditions may include incubation in the presence of one or more polymerases and/or buffering salts.

In a related aspect, the oligonucleotides of the invention are useful in detecting the presence or absence of or quantifying the amount of nucleic acid molecules in a sample without the need for performing amplification or synthesis reactions. In accordance with the invention, an oligonucleotide may be provided with one or more labels which undergo a detectable change in at least one observable property when the oligonucleotide comprising the label is converted to a double-stranded molecule (e.g., by hybridizing the oligonucleotide to a target molecule). Thus, a change in an observable property indicates the presence of the target molecule in the sample when compared to a control sample not containing the nucleic acid molecule of interest. Quantification of the nucleic acid target molecule in the sample may also be determined by comparing changes in the observable property in an unknown sample to the changes in the observable property in samples containing known amounts of the nucleic acid target molecule of interest. Any samples thought to contain the nucleic acid molecule of interest may be used including, but not limited to, biological samples such as blood, urine, tissue, cells, feces, serum, plasma, or any other samples derived from animals (including humans), plants, bacteria, viruses and the like. Environmental samples such as soil samples, water samples, air samples and the like may also be used in accordance with the invention.

The oligonucleotides of the invention can be used in methods of diagnosis, wherein the oligonucleotide is complementary to a sequence (e.g., genomic or cDNA) of an infectious disease agent or is capable of initiating synthesis or amplification of a sequence of an infectious disease agent, e.g., of human disease including, but not limited to, viruses (e.g, HIV, HPV, etc.), bacteria, parasites, and fungi, thereby diagnosing the presence of the infectious agent in a sample from a patient. The type of target nucleic acid can be genomic, cDNA, mRNA, or synthetic, or the source may be human, animal, or bacterial. In another embodiment that can be used in the diagnosis or prognosis of a disease or disorder, the target sequence is a wild type human genomic or RNA or cDNA sequence, mutation of which is implicated in the presence of a human disease or disorder, or alternatively, can be the mutated sequence. In such an embodiment, the hybridization, amplification or synthesis reaction of the invention can be repeated for the same sample with different sets of oligonucleotides of the invention (for example, with differently labeled oligonucleotides) which selectively identify the wild type sequence or the mutated version. By way of example, the mutation can be an insertion, substitution, and/or deletion of one or more nucleotides, or a translocation. In another embodiment, the oligonucleotides can be used in SNP analysis, pharmacogenomics and toxicogenetics.

In a specific embodiment, the invention provides a method for detecting or measuring a product of a nucleic acid amplification or synthesis reaction comprising: (a) contacting a sample comprising one or more target nucleic acid molecules with one or more primers (such primers may comprise one or multiple labels, which may be the same or different and may be labeled internally, and/or, at or near the 3'- and/or 5'-end), said primers being adapted for use in said amplification or synthesis reaction such that said primers are incorporated into an amplified or synthesized product of said amplification or synthesis reaction when a target sequence or nucleic acid molecule is present in the sample; (b) conducting the amplification or synthesis reaction; and (c) detecting or measuring one or more synthesis or amplification product molecules (preferably by detecting a change in one or more observable properties of one or more labels).

In another specific embodiment, the invention provides for a method of detecting or measuring the presence or absence of or the amount of a target nucleic acid molecule within a sample comprising: (a) contacting a sample comprising one or more target nucleic acid molecules with one or more oligonucleotides of the invention (such oligonucleotides may comprise one or multiple labels, which may be the same or different and may be labeled internally and/or at or near the 3'- and/or 5'-end); (b) incubating said mixture under conditions sufficient to allow said oligonucleotides to interact with said target molecules sufficient to form double-stranded molecules (preferably through hybridization); and (c) detecting one or more of said target nucleic acid molecules (preferably by detecting a change in one or more observable properties of one or more labels).

The present invention provides a method for detecting a target nucleic acid sequence, comprising contacting a sample containing a mixture of nucleic acids with at least one oligonucleotide of the present invention, the oligonucleotide being capable of hybridizing a target nucleic acid sequence and comprising at least one detectable moiety, wherein the detectable moiety undergoes a change in one or more observable properties upon hybridization to the target nucleic acid sequence and observing the observable property, wherein a change in the observable property indicates the presence of the target nucleic acid sequence. In some embodiments, the target nucleic acid sequence is not separated from the mixture. In some embodiments, the observable property is fluorescence. In some embodiments, the change is an increase in fluorescence. In some embodiments, the change is a decrease in fluorescence. In some embodiments, the oligonucleotide comprises a specificity enhancing group. In some embodiments, the oligonucleotide is in the form of a hairpin.

The present invention provides a method for quantifying a target nucleic acid molecule, comprising contacting a sample containing a mixture of nucleic acids comprising the target nucleic acid molecule with at least one oligonucleotide of the present invention, the oligonucleotide being capable of hybridizing to the target nucleic acid molecule and comprising at least one detectable moiety, wherein the detectable moiety undergoes a change in one or more observable properties upon hybridization to the target nucleic acid sequence, and observing the observable property, wherein a change in the observable property is proportional to the amount of the target nucleic acid molecule in the sample.

In a further aspect, the invention relates to the use of one or more treatments to lower or decrease the energy emitted by the labels of the oligonucleotides of the invention. Such treatments may be used in accordance with the invention to lower the background in the hybridization, synthesis or amplification methods of the invention. In one aspect, single-stranded nucleic acid binding protein (*E. coli*, T4 bacteriophage or Archaea (see Kelly, et al. *Proceedings of the National Academy of Sciences, USA* 95:14634-14639 (1998), Chedin, et al., *TIBS* 23:273-277 (1998), U.S. Pat. Nos. 5,449,603, 5,605,824, 5,646,019, and 5,773,257)) may be used to interact with single-stranded labeled oligonucleotides of the invention to reduce or quench energy emitted or other detectable properties from the labels. Such single-stranded binding proteins may be native or modified. During the detection or quantitation process (hybridization, synthesis or amplification reactions) double-stranded nucleic acid molecules formed do not substantially interact with single-stranded binding protein or interact minimally with such double-stranded molecules. Accordingly, in the unreacted state (single-stranded form of the oligonucleotides of the invention), energy emitted or other detectable properties (e.g., fluorescence) is reduced or quenched while in the reactive form (double-stranded molecules) energy emitted or other detectable properties is enhanced. In another aspect, blocking oligonucleotides which contain quencher molecules may be used to competitively bind the labeled oligonucleotides in the invention in the unreacted state thereby reducing energy emitted or other detectable properties of the labeled oligonucleotide. In another aspect, one or more additional fluorescent moieties may be incorporated into the blocking molecule such that the fluorescent moiety on the oligonucleotide of the invention is in proximity to the one or more additional fluorescent moieties when the oligonucleotide of the invention is in the unreacted state. The presence of an additional fluorescent molecule can reduce the background fluorescence level even though there is little or no overlap between the emission spectrum of the fluorescent moiety on the oligonucleotide of the invention and the absorption spectrum of the one or more additional fluorescent moieties on the blocking oligonucleotide. A possible reason for this background reduction is the involvement of the additional mechanism of the fluroescent quencher, for example, collisional. When a fluorophore is used as a quencher in addition to being used as the detectable label, the mechanism of quenching will be collisional.

When the oligonucleotide of the invention has the capability of forming a hairpin structure, those skilled in the art will appreciate that the one or more additional fluorescent moieties can be brought into proximity with the label on the oligonucleotide of the invention by attaching the one or more additional fluorescent moieties to nucleotides in one strand of the stem structure of the hairpin while attaching one or more labels to nucleotides in the other strand. During detection or quantitation, target nucleic acid molecules interact with labeled oligonucleotides of the invention thereby enhancing energy emitted or other detectable properties by the labels. Such interaction may separate the blocking oligonucleotide (e.g., quencher/additional fluorescent moiety-containing molecule) from the label containing oligonucleotide of the invention.

In another aspect of the present invention, the sequence of the oligonucleotide and/or a blocking oligonucleotide may be selected so as to reduce the background fluorescence of the oligonucleotides of the invention. It has been unexpectedly found that the base sequence in the vicinity of the label can have a dramatic effect on the background fluorescence level. The background fluorescence of a single-stranded oligonucleotide of the present invention can be decreased about 5 fold if the sequence of the oligonucleotide is selected so as to form a blunt end double-stranded structure with one or more fluorophores located on one or more bases close to the 3'-end and G-C or C-G base pair being the last base pair of the double-stranded structure. In some preferred embodiments, the double-stranded structure may be a stem of a hairpin structure. In some preferred embodiments, the 3'-end of the oligonucleotides of the invention may be provided with one or more of the following sequences: 5'- . . . T(Fluo)C-3', 5'- . . . T(Fluo)G-3', 5'- . . . T(Fluo)AG-3', 5'- . . . T(Fluo)AC-3', 5'- . . . T(Fluo)TC-3' and 5'- . . . T(Fluo)TG-3' where the attachment of a fluorophore is indicated by (Fluo) and the 3'-sequence is as shown while the blocking oligonucleotide (or 5'-end of a hairpin oligonucleotide) is provided with the complementary sequence (preferably at the 5'-end of the blocking oligonucleotide/hairpin molecule). To achieve a quenching effect, the labeled base should be within 10 nucleotides from the 3'-end, preferably, within 6 nucleotides and most preferably, at position 2-, 3-, 4-, 5-, or 6- from the 3'-end. A specific example of oligonucleotides of this type is provided by Oligo 10 (SEQ ID NO:22) in Table 2.

In a related embodiment, when using an oligonucleotide that does not have G or C for its 3'-most nucleotide and hence cannot form a G-C base pair at the 3'-end, the addition of a 5'-overhanging G residue to the oligonucleotide can reduce the background fluorescence. In this embodiment, the invention relates to an oligonucleotide comprising: a cytosine or guanine or analog of the cytosine or guanine at the 3'-termini, and one or more detectable labels on at least the second, third, fourth, fifth or sixth base from the 3'-termini.

In another embodiment, the method of quenching described above can be combined with another mechanism of quenching like fluorescence resonance energy transfer or static quenching. In some embodiments of the present invention, combinations of quenching techniques may be employed to reduce the background fluorescence. For example, an oligonucleotide of the present invention may have a detectable moiety located near the 3'-end of the oligonucleotide while the sequence of the oligonucleotide may be selected so as to have a G-C base pair at a blunt end of a hairpin structure and one or more additional fluorescent moieties may be attached to nucleotides at or near the 5'-end of the oligonucleotide. A similar structure could be employed utilizing a blocking oligonucleotide instead of a hairpin.

Figure 34:
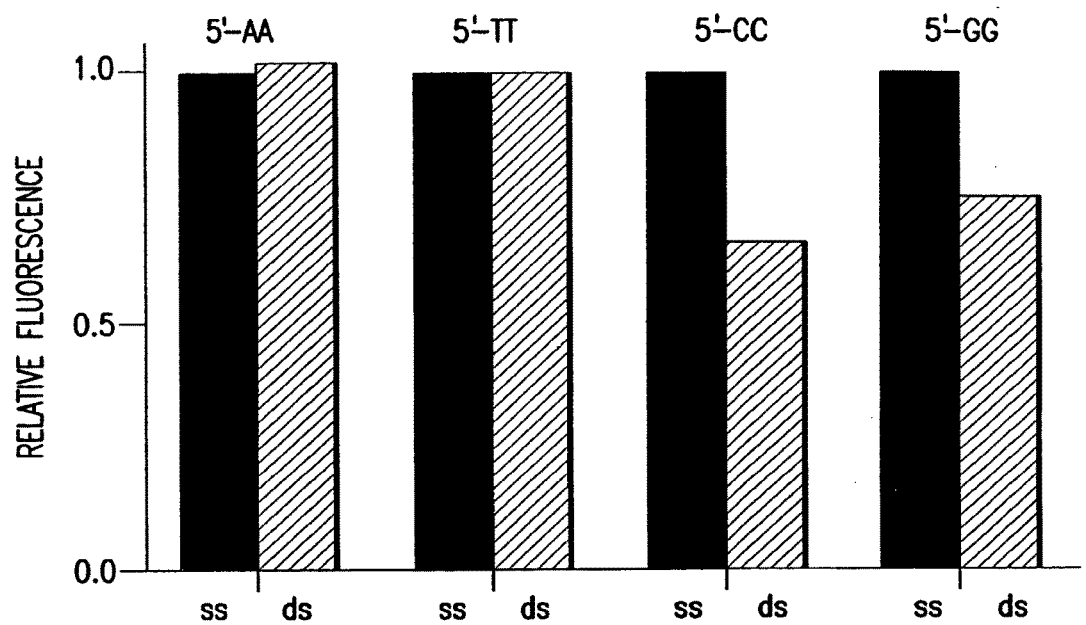
FIG. 34 is a bar graph of relative fluorescence showing the effect of 5'-nucleobases on the fluorescence intensity of oligonucleotides labeled with fluorescein at the 5'-end. 10 pmoles of FAM-d(NNTTCTCATGGTGGCTGTAGAAC) (SEQ ID NO:131) were hybridized to a 5-fold excess of the complementary oligonucleotide of the same size. NN-variable nucleotides as specified on the graph. Melting curves were detected and normalized as described in Example 27. Fluorescence of double-stranded structures is presented relative to the corresponding single-stranded oligonucleotides that are shown as (1.0).

In another related embodiment, fluorescence intensity may decrease or increase upon duplex formation depending on the sequence of the oligonucleotide(s) or template and the position of the fluorophore or other detectable property of the oligonucleotide(s) or template. Oligodeoxynucleotides containing fluorescein at the 5'-terminus showed that in systems with a C or a G at the 5'-end, the fluorescence of the duplex is quenched by approximately 40%, while no quenching is observed when the oligodeoxynucleotide ends in an A or a T. The quenching properties of guanosine have been attributed to its electron donating ability, which permits the charge transfer between the nucleobase and a nearby dye (Seidel, C. A. M. et al., *J. Phys. Chem.* 100:5541-5553 (1996); Steenken, S. and Jovanovic, V., *J. Am. Chem. Soc.* 119:617-618 (1997)). However, fluorescence was also quenched when the fluorescent oligonucleotide containing G at its 5'-end was hybridized to its C containing complement (see FIG. 34). The terminal G/C and C/G base pair may be responsible for the fluorescence quenching In yet another related embodiment, modified oligonucleotides of the invention (e.g. single or multiply labeled oligonucleotides, label(s) located internally or at the 3'- or 5'-most terminal nucleotide, oligonucleotides having a G or C as its 3'- or 5'-most terminal nucleotide etc.) may be used in detection or amplification of target templates that have been modified with a single or multiple label(s) or contain a G or C complement to the oligonucleotide. Fluorescence intensity may decrease or increase upon duplex formation.

In a further related embodiment, terminal G/C and C/G base pair may also quench the fluorophore or other detectable property when located internally close to the 3'-end of oligonucleotide. More than 10 fold fluorescence quenching in duplex was demonstrated when the fluorescein was located on the C-5 position of thymidine two or three nucleotides away from the 3'-end. This effect was absolutely dependent on the presence of C or G residues on the very 3'-end of the labeled strand. As in the case of 5'-labeled oligonucleotides, the G/C base pair not G alone, is an effective quencher. G/T mismatches at the terminus or 5'-G overhangs result in less pronounced quenching than the blunt-end G/C base pair. Only a terminal G/C pair affects the fluorescence of duplex; when flanked with an A/T pair, no quenching occurs. The data is consistent with the proposed formation of the charge transfer complexes between some fluorophores and nucleic bases (Seidel, C. A. M. et al., *J. Phys. Chem.* 100:5541-5553 (1996); Lewis, F. D. et al., *Acc. Chem. Res.* 34:159-170 (2001); Steenken, S. and Jovanovic, V., *J. Am. Chem. Soc.* 119:617-618 (1997)). Guanosine which has the highest electron donating ability of all the bases plays a critical role in this process. However, the ability of guanosine to quench the fluorescence dramatically depends on whether it is involved in hydrogen bond and where it is located—at the end of the chain or internally (see Examples 27-30).

In another aspect of the present invention, oligonucleotides labeled with a single reporter or detectable label but no specific quencher may be used to efficiently detect nucleic acids by PCR or other related methods in real-time, or at end-point, without opening the reaction vessel. The labeled PCR primers may be chemically synthesized oligodeoxynucleotides (Lee, S. P. et al., *Anal. Biochem.* 220: 377-383 (1994); Knemeyer, J. P. et al., *Anal. Chem.* 72: 3717-3724 (2000); Crockett, A. O. et al., *Anal. Biochem.* 290:89-97 (2001); Kurata, S. et al., *Nucleic Acids Res.* 29: E34 (2001); Lakowicz, J. R., Principles of fluorescence spectroscopy, Kluver Academic/Plenum Publishers, New York, 2nd ed., pp. 185-210 (1999); Cianferoni, A. et al., *Blood* 97: 1742-1749 (2001); Farrar, G. J. et al., *Nucleic Acids Res.* 19:6982 (1991)) with a fluorophore attached to the C-5 position of thymidine that increase their fluorescence when incorporated into a double-stranded PCR product. This results from having the fluorophore close to the 3'-end of an oligonucleotide terminated with G or C, the existence of a G within a few bases around the label, and the ability of the oligonucleotide to form a blunt-end hairpin at temperatures close to the annealing temperature of the primer. The mechanism for this change of the fluorescence intensity may be due to charge separation between the nucleobases, specifically guanosines, and the fluorophore (Seidel, C. A. M. et al., *J. Phys. Chem.* 100: 5541-5553 (1996); Walter, N. G. and Burke, J. M. *RNA* 3:392-404 (1997); Sauer, M. et al., *Chem. Physical Letters* 284:153-163 (1998); Lewis, F. D. et al., *Acc. Chem. Res.* 34:159-170 (2001)), which decreases the fluorescence of unincorporated hairpin primers. Thus, the invention further relates to an oligonucleotide comprising: an adenine or thymidine at the 3'-termini, an overhanging guanine at the 5'-termini, and one or more detectable labels located internally. The increase of fluorescence upon primer extension may be as high as 10-fold for various dye-primer combinations; thus, the design of labeled primers is an active area of research supported by proprietary software (Example 31).

Because of several important features, PCR using labeled primers may have great value as a tool in DNA detection, including quantitative, real-time PCR and SNP detection. The synthesis of mono-labeled oligonucleotides is less expensive and the purification requirement is less rigorous compared to dual-labeled probes and primers. Labeled primers may more easily detect targets with high frequency of mutations, such as HIV, or targets with alternate spliceforms, which are problematic using hybridization probes. The incorporation of fluorecence or a label into the PCR product allows the separation of nucleic acids by size using electrophoresis techniques. Finally, labeled primers allow a "universal format" of detection. The same universal, labeled, primer can incorporate into different amplicons through the use of unlabled primer pairs, where one unlabeled primer has an adaptor-tail. The universal format was successfully used with dual-labeled primers (Nuovo, G. J. et al., *J. Histochem. & Cytochem.* 47:273-279 (1999); Myakishev, M. V., *Genome Res.* 11:163-169 (2001)). In addition to the applications mentioned, the ability of labeled oligonucleotides to generate a strong signal in response to the changes in their primary and secondary structure may be useful to study enzymatic reactions as well as other interactions between proteins and nucleic acids.

The present invention provides a method of quenching fluorescence from a fluorescent moiety, comprising attaching the fluorescent moiety to an oligonucleotide, wherein the oligonucleotide is capable of assuming a conformation in which the oligonucleotide quenches the fluorescence of the fluorescent moiety. In some embodiments, the conformation is a hairpin.

Other means for quenching or reducing nonreacted labeled oligonucleotides may be used or any combination of such treatments may be used in accordance with the invention. When a fluorophore is used as a quencher in addition to being used as the detectable label, the mechanism of quenching will be collisional. When a separate quencher (fluorescent or non-fluorescent) is used, the mechanism will be collisional or FRET (fluorescent resonance energy transfer), respectively.

The present invention provides a composition comprising one or more oligonucleotides of the invention and one or more target or template nucleic acid molecules, wherein at least a portion of the oligonucleotide is capable of hybridizing to at least a portion of the target or template nucleic acid molecule (preferably the oligonucleotide comprises one or more detectable moieties that undergo a change in one or more observable properties upon hybridization to the target nucleic acid molecule). In some embodiments, the detectable moiety is a fluorescent moiety and the fluorescent moiety undergoes a change in fluorescence upon hybridizing to the target nucleic acid molecule. In some embodiments, the oligonucleotide is a hairpin when not hybridized to the target nucleic acid molecule.

In some preferred embodiments, the present invention provides a composition comprising at least one nucleic acid molecule and at least one oligonucleotide of the invention, wherein at least a portion of said oligonucleotide is capable of hybridizing with at least a portion of said nucleic acid molecule and wherein said oligonucleotide comprises one or more specificity enhancing groups. In some embodiments, one or more of the specificity enhancing groups may be a fluorescent moiety. A specificity enhancing group may be attached at any position of the oligonucleotide that results in the oligonucleotide being substantially less extendable when the 3'-most nucleotide of the oligonucleotide is not complementary to the corresponding nucleotide of a target/template nucleic acid. In some embodiments, at least one of the one or more groups is attached to a nucleotide at or near the 3'-nucleotide. In some embodiments, at least one of the one or more groups is attached to one of the ten 3'-most nucleotides. In other words, in embodiments of this type, at least one of the one or more specificity enhancing groups may be attached to the 3'-most nucleotide or any of the next nine contiguous nucleotides in the 5'-direction. In some embodiments, at least one of the one or more groups is attached to one of the five 3'-most nucleotides. In some embodiments, the group may be a label, preferably a label which undergoes a detectable change in an observable property upon becoming part of a double-stranded molecule (e.g. by hybridizing to another nucleic acid molecule or by nucleic acid synthesis or amplification). In some embodiments, at least a portion of said oligonucleotide is hybridized to at least a portion of said nucleic acid molecule. In some embodiments, the oligonucleotide is capable of forming a hairpin. In some embodiments, the oligonucleotide is in the form of a hairpin.

In another embodiment, the present invention provides a method of amplification comprising oligonucleotide(s) capable of forming a hairpin with a single label. No quencher molecule or moiety is needed. The label or detectable moiety may be located internally, or at the 3'- or 5'-termini. Incorporation into the PCR product results in an increase in fluorescent signal that may be directly proportional to the amount of product synthesized. Oligonucleotides of the present invention may be used, without limitation, in the following: sequencing, genotyping, SNP, end-point detection, quantitative PCR, quantitative RT-PCR, mutation detection, amplified gene expression and in situ hybridization. The oligonucleotides of the present invention may also be used in multiplexing—used with different amplicons or used with different probes.

The present invention provides a method of making a composition, comprising providing one or more oligonucleotides and contacting the one or more oligonucleotides with at least one nucleic acid molecule, wherein at least a portion of at least one of the oligonucleotides is capable of hybridizing with at least a portion of said at least one nucleic acid molecule. Preferably, the oligonucleotide comprises one or more specificity enhancing groups and/or at least one detectable label. In some embodiments, the group is a fluorescent moiety. A specificity enhancing group may be attached at any position of the oligonucleotide that results in the oligonucleotide being substantially less extendable when the 3'-most nucleotide of the oligonucleotide is not complementary to the corresponding nucleotide of a target/template nucleic acid. In some embodiments, at least one of the one or more groups is attached to a nucleotide at or near the 3'-nucleotide. In some embodiments, at least one of the one or more groups is attached to one of the ten 3'-most nucleotides. In other words, in embodiments of this type, at least one of the one or more specificity enhancing groups may be attached to the 3'-most nucleotide or any of the next nine contiguous nucleotides in the 5'-direction. In some embodiments, at least one of the one or more groups is attached to one of the five 3'-most nucleotides. In some embodiments, the group may be a label, preferably a label which undergoes a detectable change in an observable property upon becoming part of a double-stranded molecule, (e.g. by hybridizing to another nucleic acid molecule). In some embodiments, at least a portion of said oligonucleotide is hybridized to at least a portion of said nucleic acid molecule. In some embodiments, the oligonucleotide is capable of forming a hairpin. In some embodiments, the oligonucleotide is in the form of a hairpin.

The present invention provides a method of determining the presence of a particular nucleotide or nucleotides at a specific position or positions in a target or template nucleic acid molecule, comprising: (a) contacting at least one target or template nucleic acid molecule having a nucleotide or nucleotides at a specific position or positions with one or more oligonucleotides of the invention, wherein at least a portion of the oligonucleotide is capable of forming base pairs (e.g., hybridizing) with at least a portion of the target or template nucleic acid molecule, said oligonucleotide preferably comprises at least one specificity enhancing group and/or label; and (b) incubating the oligonucleotide and the nucleic acid molecule mixture under conditions sufficient to cause extension of the oligonucleotide when the 3'-most nucleotide or nucleotides of the oligonucleotide base pair with the nucleotide or nucleotides at the specific position or positions of the nucleic acid target molecule. Under such conditions, the production of an extension product indicates the presence of the particular nucleotide or nucleotides at the specific position or positions. Presence of or increased production of an extension product, as used herein, refers to the difference in the amount of amplified DNA made using the modified oligonucleotides will be between 1 fold to about 1000 fold larger than the difference obtained using oligonucleotides lacking the modification, or from about 1 fold to about 500 fold larger, or from about 1 fold to about 250 fold larger, or from about 1 fold to about 100 fold larger, or from about 1 fold to about 50 fold larger, or from about 1 to about 25 fold larger, or from about 1 to about 10 fold larger, or from about 1 fold to about 5 fold or from about 1 fold to about 2 fold larger. The amount of product can be determined using any methodology known to those of skill in the art, for example, by running the product on an agarose gel and staining with ethidium bromide and comparing to known amounts of similarly treated nucleic acid standards.

In another aspect, the invention provides a method for determining the absence of at least one particular nucleotide at a specific position or positions in a target or template nucleic acid molecule, comprising: (a) contacting at least one target nucleic acid molecule having a nucleotide or nucleotides at a specific position with an oligonucleotide of the invention, wherein at least a portion of the oligonucleotide is capable of forming base pairs (e.g., hybridizing) with at least a portion of the target nucleic acid molecule (said oligonucleotide preferably comprising at least one specificity enhancing group or label); and (b) incubating the oligonucleotide and the nucleic acid molecule mixture under conditions sufficient to prevent or inhibit extension of the oligonucleotide when the 3'-most nucleotide or nucleotides of the oligonucleotide does not base pair (e.g., does not hybridize) with the nucleotide at the specific position or positions of the target nucleic acid molecule. Under such conditions, the lack of production or reduced production of an extension product indicates the absence of the particular nucleotide or nucleotides at the specific position. Lack of or reduced production of an extension product, as used herein, refers to the difference in the amount of amplified DNA made using oligonucleotides lacking modifications, or from about 1 fold to about 500 fold larger than the difference obtained using modified oligonucleotides, or from about 1 fold to about 250 fold larger, or from about 1 fold to about 100 fold larger, or from about 1 fold to about 50 fold larger, or from about 1 to about 25 fold larger, or from about 1 to about 10 fold larger, or from about 1 fold to about 5 fold larger or from about 1 fold to about 2 fold larger. In a preferred aspect, the results of the extension of the oligonucleotide in the above first method is compared to the lack or reduced level of extension of the oligonucleotide in the above second method. In a preferred aspect, the conditions in the first method are conducted such that all or a portion of the target nucleic acid molecule is amplified, while the conditions in the second method are conducted such that the target nucleic acid molecule is not amplified or amplified at a reduced level or slower rate compared to the amplified target nucleic acid molecule produced by the first method. In some embodiments, the specificity enhancing group is a fluorescent moiety. A specificity enhancing group may be attached at any position of the oligonucleotide that results in the oligonucleotide being less, preferably, substantially less extendable when the 3'-most nucleotide of the oligonucleotide is not complementary to the corresponding nucleotide of a target/template nucleic acid. In some embodiments, at least one of the one or more groups is attached to a nucleotide at or near the 3'-most nucleotide. In some embodiments, at least one of the one or more groups is attached to one of the ten 3'-most nucleotides. In other words, in embodiments of this type, at least one of the one or more specificity enhancing groups may be attached to the 3'-most nucleotide or any of the next nine contiguous nucleotides in the 5'-direction. In some embodiments, at least one of the one or more groups is attached to one of the five 3'-most nucleotides. In some embodiments, the group may be a label, preferably a label which undergoes a detectable change in an observable property upon becoming part of a double-stranded molecule (e.g., by hybridizing to another nucleic acid molecule). In some embodiments, at least a portion of said oligonucleotide is hybridized to at least a portion of said nucleic acid molecule. In some embodiments, the oligonucleotide is capable of forming a hairpin. In some embodiments, the oligonucleotide is in the form of a hairpin. The conditions of incubation preferably include the presence of one or more polymerase enzymes such as Tsp DNA polymerase (available from Invitrogen Corporation (Life Technologies Division), Rockville, Md.).

The present invention provides a method of synthesizing one or more nucleic acid molecules, comprising: (a) contacting at least one target or template nucleic acid molecule with at least one oligonucleotide of the invention, wherein at least a portion of said oligonucleotide is capable of hybridizing with at least a portion of said target/template nucleic acid molecule (said oligonucleotide preferably comprises at least one specificity enhancing group and/or label); and (b) incubating the target nucleic acid and oligonucleotide mixture under conditions sufficient to cause the extension of the oligonucleotide when the 3'-most nucleotide or nucleotides of the oligonucleotide are base paired (e.g. hybridized) to said target nucleic acid molecule.

In another aspect, the invention provides a method for reduced synthesis of one or more nucleic acid molecules, comprising: (a) contacting at least one target or template nucleic acid molecule with at least one oligonucleotide of the invention, wherein at least a portion of said oligonucleotide is capable of hybridizing with at least a portion of said target/template nucleic acid molecule (said oligonucleotide preferably comprises at least one specificity enhancing group and/or label); and (b) incubating the target/template nucleic acid molecule and oligonucleotide mixture under conditions sufficient to prevent or inhibit extension of the oligonucleotide when the 3'-most nucleotide or nucleotides of the oligonucleotide does not base pair (e.g., does not hybridize) with the nucleotide at the specific position or positions of the target/template nucleic acid molecule. In a preferred aspect, the results of the synthesis of the above first method is compared to the lack or reduced level of synthesis in the above second method. In a preferred aspect, the conditions of the first method are conducted such that all or a portion of the target nucleic acid molecule is amplified, while the conditions in the second method are conducted such that a target nucleic acid molecule is not amplified or amplified at a reduced level and/or a slower rate compared to the amplified target nucleic acid molecule produced by the first method. In some embodiments, the specificity enhancing group is a fluorescent moiety. In some embodiments, the group is attached to a nucleotide at or near the 3'-most nucleotide. In some embodiments, the group is attached to one of the ten 3'-most nucleotides. In other words, in embodiments of this type, the group may be attached to the 3'-most nucleotide or any of the next nine contiguous nucleotides in the 5'-direction. In some embodiments, the group may be a label, preferably a label which undergoes a detectable change in an observable property upon becoming part of a double-stranded molecule (e.g., by hybridizing to another nucleic acid molecule). In some embodiments, at least a portion of said oligonucleotide is hybridized to at least a portion of said nucleic acid molecule. In some embodiments, the oligonucleotide is capable of forming a hairpin. In some embodiments, the oligonucleotide is in the form of a hairpin. The incubation conditions preferably include the presence of one or more polymerase enzymes such as Tsp DNA polymerase available from Invitrogen Corporation (Life Technologies Division), Rockville, Md.

This invention provides a method for single nucleotide polymorphism (SNP) detection by using a modified nucleotide, such as a deoxynucleotide or ribonucleotide modification or a 2'- or 3'-substituted modification, for example, without limitation, a 2'- or 3'-alkyl, alkyloxy, alkylamino, alkylthio, aryl, or aryloxy modification, or a 2'- or 3'-O-alkyl or 2'- or 3'-O-aryl modification or preferably, a 2'-O-methyl ribonucleotide modification at or near the 3'-terminal nucleotide of primers in a PCR set-up. This methodology can easily be adapted for high through-put screening set-up using existing technologies. The nucleotide incorporation efficiency by polymerases into a 3'-terminus of a primer strand that is totally complimentary to the template sequence (though the only requirement is no frayed 3'-termini) is significantly higher compared to the incorporation efficiency into a 3'-end that forms a single nucleotide mis-pair at the 3'-terminal nucleotide position. Quantitative comparison between the kinetics of primer extension of fully annealed primer/template substrate compared to that with a frayed-end 3'-termini has been utilized so as to screen for the identification of SNP containing DNA samples. However, polymerases extend mismatch primer termini with significant efficiencies (though the rate of extension of mismatch termini varies due to the specific primer/template sequence) rendering this approach for SNP identification less reliable. An improvement on this basic technique is described herein, employing modified oligonucleotide to enhancing the resolution of the assay hence enabling the reliable detection of single nucleotide variations in target template sequences. This type of primer modifications makes SNP identification in genomic samples much faster and with greater probability of accuracy.

The present invention also provides a method for SNP (single nucleotide polymorphism) detection by using a a modified nucleotide, such as a deoxynucleotide or ribonucleotide modification or a 2'- or 3'-substituted modification, for example, without limitation, a 2'- or 3'-alkyl, alkyloxy, alkylamino, alkylthio, aryl, or aryloxy modification, or a 2'- or 3'-O-alkyl or 2'- or 3'-O-aryl modification or preferably, a 2-O-methyl ribonucleotide modification at or near the 3'-terminal nucleotide of primers e.g. in a DNA Synthesis reaction. For example, 2-O-methyl ribose terminated primers can be extended by DNA polymerases such as Taq, albeit with lower efficiency compared to the canonical unmodified primers with deoxynucleotide at the 3'-termini. The extension efficiency of a 3'-termini that forms a single base pair mismatch catalyzed by DNA polymerase is severely compromised, if the 3'-terminal nucleotide contains a 2-O-substituted moiety, specifically, a 2-O-methyl moiety. The relative rate difference of nucleotide insertion into a 3'-end of a primer that is correctly annealed compared to that with a frayed termini can be utilized in order to detect single nucleotide variations in DNA samples. This technology, utilizing 2-O-substituted or preferably 2-O-methyl terminated primers in a PCR set-up, is a very cost effective and reliable approach to detect single nucleotide variations between DNA samples and can easily be adapted for high-through put screening. Examples are given below that exemplify PCR amplification of target sequences using primers that contain the 2-O-methyl modification at the 3'-terminal nucleotide. Primers that correctly base-pair at the 3'-termini and those that form a mis-matched end gave significantly varied amount of amplified yield. In a preferred embodiment, primers that form mismatch 3'-termini gave substantially reduced (e.g. less than 20%, more preferably less than 10%) or no amplified product.

The present invention also provides a composition comprising one or more nucleic acid molecules and at least one oligonucleotide, wherein at least a portion of said oligonucleotide is capable of hybridizing with at least a portion of said nucleic acid molecule and wherein said oligonucleotide comprises a a modified nucleotide, such as a deoxynucleotide or ribonucleotide modification or a 2'- or 3'-substituted modification, for example, without limitation, a 2'- or 3'-alkyl, alkyloxy, alkylamino, alkylthio, aryl, or aryloxy modification, or a 2'- or 3'-O-alkyl or 2'- or 3'-O-aryl modification or preferably a 2'-O-methyl ribonucleotide modification at or near the 3'-terminal nucleotide. Such reaction mixtures or compositions of the present invention may further comprise one or more components selected from the group consisting of one or more nucleotides, one or more DNA polymerases, one or more reverse transcriptases, one or more buffers or buffering salts, one or more target or template molecules and one or more products produced by a hybridization or synthesis/amplification reaction of the present invention.

The present invention also provides a method for amplifying a double-stranded nucleic acid molecule, comprising:

(a) providing a first and second primer, wherein said first primer is complementary to a sequence within or at or near the 3'-termini of the first strand of said nucleic molecule and said second primer is complementary to a sequence within or at or near the 3'-termini of the second strand of said nucleic acid molecule;

(b) hybridizing said first primer to said first strand and said second primer to said second strand in the presence of one or more of the polymerases, under conditions such that a third nucleic acid molecule complementary to all or a portion of said first strand and a fourth nucleic acid molecule complementary to all or a portion said second strand are synthesized;

(c) denaturing said first and third strand, and said second and fourth strands; and repeating the above steps one or more times, wherein one or more of the primers comprise a nucleotide modification at or near the 3'-terminal nucleotide.

In another aspect, the invention provides a method of determining the presence of at least one nucleotide of interest at a specific position in a target nucleic acid molecule, comprising:

(a) contacting at least one target nucleic acid molecule having said nucleotide of interest at a specific position on a target nucleic acid molecule with at least one oligonucleotide, wherein at least a portion of the oligonucleotide is capable of forming base pairs or hybridizing with at least a portion of the target nucleic acid molecule and wherein the oligonucleotide comprises a nucleotide modification at or near the 3'-terminal nucleotide; and (b) incubating the oligonucleotide and the target nucleic acid molecule under conditions sufficient to cause extension of the oligonucleotide when the 3'-most nucleotide of the oligonucleotide base pair with the nucleotide at the specific position of the target nucleic acid molecule, wherein the presence of or increased production of an extension product indicates the presence of the particular nucleotide at the specific position.

The present invention also provides a method of determining the absence of at least one nucleotide at a specific position in a target nucleic acid molecule, comprising:

(a) contacting at least one target nucleic acid molecule having said nucleotide of interest at a specific position on the target nucleic acid molecule with at least one oligonucleotide, wherein at least one portion of the oligonucleotide is capable of forming base pairs or hybridizing with at least a portion of the target nucleic acid molecule and wherein the oligonucleotide comprises a nucleotide modification at or near the 3'-terminal nucleotide; and (b) incubating the oligonucleotide and target nucleic acid molecule under conditions sufficient to inhibit or prevent extension of the oligonucleotide when the 3'-most nucleotide of the oligonucleotide does not substantially base pair with the nucleotide of the specific position of the target nucleic acid molecule, wherein the lack of or reduced production of an extension product indicates the absence of the particular nucleotide at the specific position.

In another aspect, the invention provides a method of determining the presence or absence of a nucleotide at a specific position in a target nucleic acid molecule, comprising:

(a) contacting at least first oligonucleotide with at least one target nucleic acid molecule under conditions sufficient to cause extension of the first oligonucleotide when the 3'-most nucleotide of the oligonucleotide base pairs with the nucleotide at the specific position of the target nucleic acid molecule, wherein said first oligonucleotide comprises a nucleotide modification at or near the 3'-terminal nucleotide;

(b) contacting at least a second oligonucleotide with at least one target nucleic acid molecule under conditions sufficient to inhibit or prevent extension of the oligonucleotide when the 3'-most nucleotide of the oligonucleotide do not substantially base pair with the nucleotide at the specific position of the target nucleic acid molecule, wherein said second oligonucleotide comprises a nucleotide modification at or near the 3'-terminal nucleotide; and (c) comparing the level of extension or the amount of extension or presence or absence of extension product accomplished with the first oligonucleotide compared to the second oligonucleotide.

The amount of product can be determined using any methodology known to those of skill in the art, for example, by running the product on an agarose gel and staining with ethidium bromide and comparing to known amounts of similarly treated nucleic acid standards.

The present invention provides a method for synthesizing or amplifying one or more nucleic acid molecules comprising:

(a) mixing one or more nucleic acid templates or targets with one or more oligonucleotides, wherein said one or more of said oligonucleotides comprise a nucleotide modification at or near the 3'-terminal nucleotide; and (b) incubating said mixture under conditions sufficient to synthesize or amplify one or more nucleic acid molecules complementary to all or a portion of said templates or targets.

In another aspect, the invention provides a method for synthesizing or amplifying one or more nucleic acid molecules, wherein the specificity of the nucleic acid synthesis or amplification is increased, comprising:

(a) mixing one or more nucleic acid templates or targets with one or more oligonucleotides, wherein said one or more of said oligonucleotides comprises a nucleotide modification at or near the 3'-terminal nucleotide; and (b) incubating said mixture under conditions sufficient to synthesize or amplify one or more nucleic acid molecules complementary to all or a portion of said templates or targets, wherein the synthesis or amplification has increased specificity when compared to amplification or synthesis conducted with an oligonucleotide not modified with a nucleotide modification at or near the 3'-terminal nucleotide.

In another aspect, this present invention provides a method of protecting oligonucleotides from degradation with modified oligonucleotides of the present invention. The methods of the present invention are adaptable to many methods for amplification of nucleic acid sequences, including, without limitation, PCR (e.g. "RT-PCR," "5'-RACE," "anchor PCR" and "one-sided PCR"), LCR, SDA and NASBA, and other amplification systems known to those of ordinary skill in the art. A modified nucleotide or specifically a 2'-O-methyl ribonucleotide at or near the 3'-terminal nucleotide protects the oligonucleotide from degradation. See Example 26. In yet another aspect, this present invention provides a method of inhibiting degradation in oligonucleotides comprising protecting oligonucleotides with modified oligonucleotides of the present invention.

In yet another aspect, this present invention provides oligonucleotides that are oligonucleotides of the present invention or are oligonucleotides comprising one or more of nucleotide analogues of the present invention.

The present invention provides a composition comprising one or more nucleic acid molecules and at least one oligonucleotide, wherein at least a portion of said oligonucleotide is capable of hybridizing with at least a portion of said nucleic acid molecule and wherein said oligonucleotide is an oligonucleotide of the present invention or is an oligonucleotide which comprises one or more nucleotide analogues of the present invention.

In another aspect, the invention provides a method of making a composition, comprising the steps of:

(a) providing at least one oligonucleotide; and (b) contacting said oligonucleotide with at least one nucleic acid molecule, wherein at least a portion of said oligonucleotide is capable of hybridizing with at least a portion of said nucleic acid molecule and wherein said oligonucleotide is an oligonucleotide of the present invention or is an oligonucleotide which comprises one or more nucleotide analogues of the present invention.

The present invention provides a composition for quantifying or detecting one or more target nucleic acid molecules in a sample comprising one or more oligonucleotides and one or more target nucleic acid molecules to be detected or quantified, wherein said oligonucleotides are oligonucleotides of the present invention or are oligonucleotides that contain one or more nucleotide analogues of the present invention.

In another aspect, the invention provides a method for the quantification or detection of one or more target nucleic acid molecules in a sample comprising hybridizing one or more oligonucleotides with one or more molecules to be detected or quantified, and detecting the presence or absence and/or quantifying the amount of said target nucleic acid molecules, wherein said oligonucleotides are oligonucleotides of the present invention or are oligonucleotides that contain one or more nucleotide analogues of the present invention.

The present invention provides a method for the quantitation or detection of one or more nucleic acid molecules in a sample during nucleic acid synthesis comprising:

(a) mixing one or more nucleic acid templates with one or more oligonucleotides, wherein said oligonucleotides are oligonucleotides of the present invention or are oligonucleotides that contain one or more nucleotide analogues of the present invention;

(b) incubating said mixture under conditions sufficient to synthesize one or more nucleic acid molecules complementary to all or a portion of said templates, said synthesized nucleic acid molecule comprising said oligonucleotides; and (c) detecting the presence or absence or quantifying the amount of said synthesized nucleic acid molecules by measuring the amount of nucleic acid molecules synthesized in said sample.

In another aspect, the invention provides a method for quantitation or detection of one or more nucleic acid molecules in a sample during nucleic acid amplification comprising:

(a) mixing one or more nucleic acid templates with one or more oligonucleotides, wherein said oligonucleotides are oligonucleotides of the present invention or are oligonucleotides that contain one or more nucleotide analogues of the present invention; and (b) incubating said mixture under conditions sufficient to amplify one or more nucleic acid molecules complementary to all or a portion of said templates, said amplified nucleic acid molecule comprising said oligonucleotides; and (c) detecting the presence or absence or quantifying the amount of said nucleic acid molecules by measuring the amount of nucleic acid molecules amplified in said sample.

The present invention provides a method for amplifying a double stranded nucleic acid molecule, comprising:

(a) providing a first and second primer, wherein said first primer is complementary to a sequence within or at or near the 3'-termini of the first strand of said nucleic molecule and said second primer is complementary to a sequence within or at or near the 3'-termini of the second strand of said nucleic acid molecule;

(b) hybridizing said first primer to said first strand and said second primer to said second strand in the presence of one or more of the polymerases, under conditions such that a third nucleic acid molecule complementary to all or a portion of said first strand and a fourth nucleic acid molecule complementary to all or a portion said second strand are synthesized;

(c) denaturing said first and third strand, and said second and fourth strands; and (d) repeating the above steps one or more times, wherein one or more of the primers comprise one or more of the nucleotide analogues of the present invention.

In another aspect, the invention provides a method of determining the presence of one or more particular nucleotides at a specific position or positions in a target nucleic acid molecule, comprising:

(a) contacting at least one target nucleic acid molecule having one or more nucleotides of interest at a specific position or positions on a target nucleic acid molecule with at least one oligonucleotide, wherein at least a portion of the oligonucleotide is capable of forming base pairs or hybridizing with at least a portion of the target nucleic acid molecule and wherein the oligonucleotide is an oligonucleotide of the present invention or is an oligonucleotide which comprises one or more nucleotide analogues of the present invention; and (b) incubating the oligonucleotide and the target nucleic acid molecule under conditions sufficient to cause extension of the oligonucleotide when the 3'-most nucleotide or nucleotides of the oligonucleotide base pair with the nucleotide or nucleotides at the specific position or positions of the target nucleic acid molecule, wherein the production of an extension product indicates the presence of the particular nucleotide at the specific position.

The present invention provides a method of determining the absence of one or more particular nucleotides at a specific position or positions in a target nucleic acid molecule, comprising:

(a) contacting at least one target nucleic acid molecule having one or more nucleotides of interest at a specific position or positions on the target nucleic acid molecule with at least one oligonucleotide, wherein at least one portion of the oligonucleotide is capable of forming base pairs or hybridizing with at least a portion of the target nucleic acid molecule and wherein the oligonucleotide is an oligonucleotide of the present invention or is an oligonucleotide which comprises one or more nucleotide analogues of the present invention; and (b) incubating the oligonucleotide and target nucleic acid molecule under conditions sufficient to inhibit or prevent extension of the oligonucleotide when the 3'-most nucleotide or nucleotides of the oligonucleotide does not substantially base pair with the nucleotide or nucleotides of the specific position or positions of the target nucleic acid molecule, wherein the lack of or reduced production of an extension product indicates the absence of the particular nucleotide at the specific position.

In another aspect, the invention provides a method of determining the presence or absence of one or more particular nucleotides at a specific position or positions in a target nucleic acid molecule, comprising:

(a) contacting at least first oligonucleotide with at least one target nucleic acid molecule under conditions sufficient to cause extension of the first oligonucleotide when the 3'-most nucleotide or nucleotides of the oligonucleotide base pairs with the nucleotide or nucleotides at the specific position or positions of the target nucleic acid molecule;

(b) contacting at least a second oligonucleotide with at least one target nucleic acid molecule under conditions sufficient to inhibit or prevent extension of the oligonucleotide when the 3'-most nucleotide or nucleotides of the oligonucleotide do not substantially base pair with the nucleotide or nucleotides at the specific position or positions of the target nucleic acid molecule; and (c) comparing the level of extension or the amount of extension product accomplished with the first oligonucleotide compared to the second oligonucleotide, wherein said first and/or second oligonucleotide is an oligonucleotide of the present invention or is an oligonucleotide which comprises one or more nucleotide analogues of the present invention.

The present invention provides a method of determining the presence or absence of at least one particular nucleotide of interest at a specific position in a target nucleic acid molecule, comprising:

(a) providing at least one target nucleic acid molecule having said nucleotide of interest at a specific position;

(b) contacting said target nucleic acid molecule with at least one oligonucleotide, wherein at least a portion of the oligonucleotide is capable of forming base pairs or hybridizing with at least a portion of the nucleic acid molecule and wherein the oligonucleotide is an oligonucleotide of the present invention or is an oligonucleotide which comprises at least one nucleotide analogues of the present invention; and (c) contacting the oligonucleotide and the target nucleic acid molecule with a polymerase less able to extend the oligonucleotide when the 3'-most nucleotide of the oligonucleotide does not base pair with the target nucleic acid and more able to extend the oligonucleotide when the 3'-most nucleotide of the oligonucleotide base pairs with the target nucleic acid molecule; and measuring the level of extension of the oligonucleotide.

In another aspect, the invention provides a method for synthesizing or amplifying one or more nucleic acid molecules comprising:

(a) mixing one or more nucleic acid templates or targets with one or more oligonucleotides, wherein said oligonucleotides is an oligonucleotide of the present invention or is an oligonucleotide which comprises one or more nucleotide analogues of the present invention; and (b) incubating said mixture under conditions sufficient to synthesize or amplify one or more nucleic acid molecules complementary to all or a portion of said templates or targets.

In another aspect, the invention provides a method of detecting a single nucleotide polymorphism comprising the steps of:

(a) contacting at least a first oligonucleotide with at least one target nucleic acid molecule under conditions sufficient to cause extension of the first oligonucleotide when the 3'-most nucleotide or nucleotides of the oligonucleotide base pairs with the nucleotide or nucleotides at the specific position or positions of the target nucleic acid molecule;

(b) contacting at least a second oligonucleotide with at least one target nucleic acid molecule under conditions sufficient to inhibit or prevent extension of the oligonucleotide when the 3'-most nucleotide or nucleotides of the oligonucleotide do not substantially base pair with the nucleotide or nucleotides at the specific position or positions of the target nucleic acid molecule; and (c) comparing the level of extension or the amount of extension product or the presence of absence of extension product accomplished with the first oligonucleotide compared to the second oligonucleotide, wherein said first and/or second oligonucleotide is an oligonucleotide of the present invention or is an oligonucleotide which comprises one or more nucleotide analogues of the present invention.

Kits

The present invention also relates to kits for the detection or measurement of nucleic acid molecules or for polymerase activity in a sample. Such kits may also be designed to detect/quantitate nucleic acid molecules of interest during or after nucleic acid synthesis or amplification reactions. Such kits may be diagnostic kits wherein the presence of the nucleic acid is correlated with the presence or absence of a disease or disorder. The invention also relates to kits for carrying out extension, synthesis and/or amplification reactions of the invention and to kits for making the compositions of the invention.

In specific embodiments, the kits comprise one or more oligonucleotides of the invention (including primers and/or probes). The kit can further comprise additional components for carrying out the detection/quantification assays or other methods of the invention. Such kits may comprise one or more additional components selected from the group consisting of one or more polymerases (e.g., DNA polymerases and reverse transcriptases), one or more nucleotides, one or more buffering salts (including nucleic acid synthesis or amplification buffers), one or more control nucleic acid target molecules (to act as positive controls to test assays or assist in quantification of the amount of nucleic acid molecules in unknown samples), one or more quenchers (single-stranded binding proteins, blocking oligonucleotides, etc.), instructions for carry one out the methods of the invention and the like. Control nucleic acid molecules are preferably provided in the kits of the invention at known concentrations to establish control samples of known amounts of target molecules to assist one in establishing the amount of nucleic acid molecule of interest in an unknown sample. Thus, the measurement of activity of the labeled oligonucleotide for a known sample may be compared to such measurement for an unknown sample to quantify the amount of the target nucleic acid molecule in the unknown sample. The kits of the invention preferably comprise a container (a box, a carton, or other packaging) having in close confinement therein one and preferably more containers (tubes, vials and the like) which comprise various reagents for carrying out the methods of the invention. The reagents may be in separate containers or may be combined in different combinations in a single container. Such kits of the invention may further comprise instructions or protocols for carrying out the methods of the invention and optionally, may comprise an apparatus or other equipment for detecting the detectable labels associated with the oligonucleotides of the invention.

In another embodiment, kits of the invention may be used to carry out hybridization, synthesis, amplification or other extension reactions using modified nucleotides, such as a deoxynucleotide or ribonucleotide modifications or 2'- or 3'-substituted modifications, for example, without limitation, 2'- or 3'-alkyl, alkyloxy, alkylamino, alkylthio, aryl, or aryloxy modifications, or 2'- or 3'-O-alkyl or 2'- or 3'-O-aryl modifications, 2'-O-alkyl or preferably, 2'-O-methyl modified oligonucleotides of the invention. Preferred kits of the invention may comprise one or more containers (such as vials, tubes, and the like) configured to contain the reagents used in the methods of the invention and optionally may contain instructions or protocols for using such reagents. The kits of the invention may comprise one or more components selected from the group consisting of one or more oligonucleotides of the invention (including, but not limited to, oligonucleotides, probes and/or primers and nucleotide modified oligonucleotides, probes and/or primers), one or more DNA polymerases, such as a thermostable polymerase, one or more reverse transcriptases, or any other DNA or RNA polymerase, one or more buffers or buffering salts, one or more nucleotides, one or more target/template molecules (which may used for determining reaction performance, i.e., control reactions) and other reagents for analysis or further manipulation of the products or intermediates produced by the methods of the invention. Such additional components may include components used for cloning and/or sequencing and components or equipment needed for the detection or quantification of the nucleic acid molecule of interest.

The present invention provides a kit for use in synthesis of a nucleic acid molecule, said kit comprising one or more oligonucleotides that are oligonucleotides of the invention or oligonucleotides comprising one or more of the nucleotide analogues of the present invention.

In another aspect, the invention provides a kit for use in amplification of a nucleic acid molecule, said kit comprising one or more oligonucleotides that are oligonucleotides of the invention or oligonucleotides comprising one or more of the nucleotide analogues of the present invention.

The present invention provides a kit for the detection or measurement of nucleic acid synthesis or amplification products comprising one or more oligonucleotides that are oligonucleotides of the invention or oligonucleotides comprising one or more nucleotide analogues of the present invention.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

Example 1

Preparation of Oligonucleotides

Oligonucleotides may be prepared using any known methodology. In some preferred embodiments, oligonucleotides may be synthesized on solid supports using commercially available technology. Oligodeoxynucleotides were synthesized using DNA synthesizer-8700 (Milligen/Biosearch). Fluorescent moieties may be incorporated into the oligonucleotides of the present invention using any conventional technology and at any number of locations (e.g. at any nucleotide) within the oligonucleotide. For example, fluorescent labels may be incorporated into nucleoside phosporamidites and directly incorporated into the oligodeoxynucleotides during automated chemical synthesis. In some preferred embodiments, the modified nucleotide may be a fluorescein-dT phosphoramidite (Glen Research, cat. #10-1056) which may be inserted into designated position during chemical synthesis of oligonucleotide. 5'-fluorescein phosphoramidite (FAM) (Glen Research, cat. #10-5901) and 3'-TAMRA-CPG 500 (Glen Research, cat. #20-5910) were used to add the indicated labels to the 5'- and 3'-ends, respectively, of the oligodeoxynucleotide during chemical synthesis. Alternatively, a nucleotide containing a reactive functional moiety may be incorporated into the oligonucleotide during synthesis. After the completion of the synthesis and removal of the oligonucleotide from the solid support, the reactive functional moiety may by used to couple a fluorescent moiety containing molecule to the oligonucleotide. In some preferred embodiments, the reactive functional moiety may be an amino-modified C6-dT (Glen Research, cat. #10-1039) which may be inserted into a designated position during chemical synthesis of the oligonucleotide and used for further modification. The further modification may include the incorporation of a fluoresently labeled molecule. In some preferred embodiments, the fluorescently labeled molecule may be a 6-carboxyfluorescein succinimidyl ester (6-FAM, SE, cat. #C6164, Molecular Probes), fluorescein-5-isothiocyanate (FITC) (Molecular Probes, cat. #F-1907), 5-(6-)-carboxytetramethylrhodamine (TAMRA) succinimidyl ester (Molecular Probes), or BODIPY 530/550 succinimidyl ester (Molecular Probes).

All labeled oligonucleotides may be purified using reverse-phase HPLC, for example, on a C-18 column using a gradient of acetonitrile in 0.2 M triethyl ammonium acetate.

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al., Nucl. Acids Res. 16:3209 (1988), and methylphosphonate oligonucleotides can be prepared by use of controlled pore glass polymer supports (Sarin et al., Proc. Natl. Acad. Sci. USA 85:7448-7451 (1988)). Oligonucleotides may also be prepared by standard phosphoramidite chemistry, or by cleavage of a larger nucleic acid fragment using non-specific nucleic acid cleaving chemicals or enzymes or site-specific restriction endonucleases. Labeled oligonucleotides of the invention may also be obtained commercially from Invitrogen Corporation (Life Technologies Division) or other oligonucleotide manufacturers.

A preferable method for synthesizing oligonucleotides is to use an automated DNA synthesizer using methods known in the art. Once the desired oligonucleotide is synthesized, it is cleaved from the solid support on which it was synthesized and treated, by methods known in the art, to remove any protecting groups present. The oligonucleotide may then be purified by any method known in the art, including extraction and gel purification. The concentration and purity of the oligonucleotide may be determined by examining the oligonucleotide that has been separated on an acrylamide gel or by measuring the optical density at 260 nm in a spectrophotometer.

Oligonucleotides of the invention may be labeled during chemical synthesis or the label may be attached after synthesis by methods known in the art. In a specific embodiment, the label moiety is a fluorophore. Suitable moieties that can be selected as fluorophores or quenchers are set forth in Table 1.

TABLE 1

4-acetamido-4'-isothiocyanatostilbene-2,2'disulfonic acid
acridine and derivatives:

acridine
acridine isothiocyanate
5-(2'-aminoethyl)aminonaphthalene-1-sulfonic acid (EDANS)
4-amino-N-3-vinylsulfonyl)phenylnaphthalimide-3,5 disulfonate (Lucifer Yellow VS)
N-(4-anilino-1-naphthyl)maleimide
anthranilamide
Brilliant Yellow
coumarin and derivatives:

7-amino-4-methylcoumarin (AMC, Coumarin 120)
7-amino-4-trifluoromethylcoulaurin (Coumaran 151)
cyanosine
4',6-diaminidino-2-phenylindole (DAPI)
5',5''-dibromopyrogallol-sulfonephthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-dimethylaminonaphthalene-1-sulfonyl chloride (DNS, dansyl chloride)
4-(4'-dimethylaminophenylazo)benzoic acid (DABCYL)
4-dimethylaminophenylazophenyl-4'-isothiocyanate (DABITC)
eosin and derivatives:

eosin
eosin isothiocyanate
erythrosin and derivatives:

erythrosin B
erythrosin isothiocyanate
ethidium
fluorescein and derivatives:

5-carboxyfluorescein (FAM)
5-(4,6-dichlorotriazin-2-yl)aminofluorescein (DTAF)
2'7'-dimethoxy-4'5'-dichloro-6-carboxyfluorescein (JOE)
fluorescein
fluorescein isothiocyanate
QFITC (XRITC)
fluorescamine
IR144
IR1446
Malachite Green isothiocyanate
4-methylumbelliferone
ortho cresolphthalein
nitrotyrosine
pararosaniline TABLE 1-continued Phenol Red
B-phycoerythrin
o-phthaldialdehyde
pyrene and derivatives:

pyrene
pyrene butyrate
succinimidyl 1-pyrene butyrate
Reactive Red 4 (Cibacron ® Brilliant Red 3B-A)
rhodamine and derivatives:

6-carboxy-X-rhodamine (ROX)
6-carboxyrhodamine (R6G)
lissamine rhodamine B sulfonyl chloride
rhodamine (Rhod)
rhodamine B
rhodamine 123
rhodamine X isothiocyanate
sulforhodamme B
sulforhodamine 101
sulfonyl chloride derivative of sulforhodamine 101
(Texas Red)
N,N,N',N'-tetramethyl-6-carboxyrhodaniine (TAMRA)
tetramethyl rhodamine
tetramethyl rhodamine isothiocyanate (TRITC)
riboflavin
rosolic acid
terbium chelate derivative One of ordinary skill in the art can easily determine, using art-known techniques of spectrophotometry, which of the above identified fluorophores or combinations thereof can be used in accordance with the invention. Oligonucleotides are preferably modified during synthesis, such that a modified T-base is introduced into a designated position by the use of Amino-Modifier C6 dT (Glen Research), and a primary amino group is incorporated on the modified T-base, as described by Ju et al. (*Proc. Natl. Acad. Sci., USA* 92:4347-4351 (1995)). These modifications may be used for subsequent incorporation of fluorescent dyes into designated positions of the labeled oligonucleotides.

In yet another embodiment, the labeled oligonucleotides may be further labeled with any other art-known detectable marker, including radioactive labels such as $^{32}P$, $^{35}S$, $^{3}H$, and the like, or with enzymatic markers that produce detectable signals when a particular chemical reaction is conducted, such as alkaline phosphatase or horseradish peroxidase. Such enzymatic markers are preferably heat stable so as to survive the denaturing steps of the amplification or synthesis process.

Oligonucleotides may also be indirectly labeled by incorporating a nucleotide linked covalently to a hapten or to a molecule such as biotin, to which a labeled avidin molecule may be bound, or digoxygenin, to which a labeled anti-digoxygenin antibody may be bound. Oligonucleotides may be supplementally labeled during chemical synthesis or the supplemental label may be attached after synthesis by methods known in the art.

The sequences of the primers used in the following specific examples are provided in Table 2.

TABLE 2

| | |
|---|---|
| Oligo A internally labeled with fluorescein | 5'-cct tct cat ggt ggc tgT aga ac (SEQ ID NO: 1) |
| Oligo B 5'-labeled with fluorescein | 5'-Cct tct cat ggt ggc tgt aga ac (SEQ ID NO: 2) |
| Oligo C complement to oligos A and B | 5'-gtt cta cag cca cca tga gaa gg (SEQ ID NO: 3) |
| Oligo D 3'-labeled with TAMRA | 5'-ggg gct gcg act gtg ctc cgg cA (SEQ ID NO: 4) |
| Oligo E complement to oligo D | 5'-tgc cgg agc aca gtc gca gcc cc (SEQ ID NO: 5) |
| Oligo F 5'-labeled with fluorescein | 5'-Aat aat agg atg agg cag ga (SEQ ID NO: 6) |
| Oligo G 5'-labeled with BODIPY 530/550 | 5'-Aat aat agg atg agg cag ga (SEQ ID NO: 7) |
| Oligo H complement to Oligos F and G | 5'-tcc tgc ctc atc cta tta tt (SEQ ID NO: 8) |
| Oligo I forward primer for IL4 | 5'-gag ttg acc gta aca gac atc tt (SEQ ID NO: 9) |
| Oligo J forward primer for beta-actin internally labeled with fluorescein | 5'-ggc att gcc gac agg aTg tag aag (SEQ ID NO: 10) |
| Oligo K reverse primer for beta-actin | 5'-ggg ccg gac tcg tca tac (SEQ ID NO: 11) |
| Oligo L forward primer for beta-actin labeled with Fluorescein through the tail | 5'-ggt tgT aga gca ctc agc aca atg aag a (SEQ ID NO: 12) |
| Oligo 1 IL 4 forward primer | 5'-gag ttg acc gta aca gac atc tt (SEQ ID NO: 9) |
| Oligo 2 IL 4 reverse primer, 297 WT | 5'-cct tct cat ggt ggc tgt aga ac (SEQ ID NO: 14) |
| Oligo 3 IL 4 reverse primer, 297 MUT | 5'-cct tct cat ggt ggc tgt aga at (SEQ ID NO: 15) |
| Oligo 4 IL 4 reverse primer, 300 WT | 5'-gtg tcc ttc tca tgg tgg ctg tag (SEQ ID NO: 16) |
| Oligo 5 IL 4 reverse primer, 300 MUT | 5'-gtg tcc ttc tca tgg tgg ctg tat (SEQ ID NO: 17) |
| Oligo 6 IL 4 reverse primer, 297 WT-Fluo | 5'-cct tct cat ggt ggc tgT aga ac (SEQ ID NO: 1) |
| Oligo 7 IL 4 reverse primer, 297 MUT-Fluo | 5'-cct tct cat ggt ggc tgT aga at (SEQ ID NO: 19) |
| Oligo 8 IL 4 reverse primer, 300 WT-Fluo | 5'-gtg tcc ttc tca tgg tgg ctg Tag (SEQ ID NO: 20) |
| Oligo 9 IL 4 reverse primer, 300 MUT-Fluo | 5'-gtg tcc ttc tca tgg tgg ctg Tat (SEQ ID NO: 21) |
| Oligo 10 RDS reverse primer-Fluo | 5'-cta ccg ggt gtc tgt gtc tcg gTa g (SEQ ID NO: 22) |
| Oligo 11 RDS forward primer, C-allele | 5'-cgt acc tgg cta tct gtg tc (SEQ ID NO: 23) |
| Oligo 12 RDS forward primer, T-allele | 5'-cgt acc tgg cta tct gtg tt (SEQ ID NO: 24) |
| Oligo 13 RDS forward primer, C-allele/hairpin | 5'-gac acc tgg cta tct gtg tc (SEQ ID NO: 25) |

TABLE 2-continued

| | | |
|---|---|---|
| Oligo 14 RDS forward primer, T-allele/hairpin | 5'-aac aca cct ggc tat ctg tgt t (SEQ ID NO: 26) | |
| Oligo 15 IL 4 reverse primer/hairpin | 5'-cta cag tcc ttc tca tgg tgg ctg tag (SEQ ID NO: 27) | |
| Oligo 16 beta-globin forward primer/linear-A | 5'-ctt cct gag agc cga act gta gtg a (SEQ ID NO: 28) | |
| Oligo 17 beta-globin reverse primer/linear-A | 5'-aca tgt att tgc atg gaa aac aac tc (SEQ ID NO: 29) | |
| Oligo 18 beta-globin forward primer/hairpin-A | 5'-tca cta ctt cct gag agc cga act gta gtg a (SEQ ID NO: 30) | |
| Oligo 19 beta-globin reverse primer/hairpin-A | 5'-gag ttg tac atg tat ttg cat gga aaa caa ctc (SEQ ID NO: 31) | |
| Oligo 20 beta-globin forward primer/linear-B | 5'-gct cag aat gat gtt tcc acc ttc (SEQ ID NO: 32) | |
| Oligo 21 beta-globin reverse primer/linear-B | 5'-aaa tca tac tag ctc acc agc aat g (SEQ ID NO: 33) | |
| Oligo 22 beta-globin forward primer/hairpin-B | 5'-gaa ggt gct cag aat gat gtt tcc acc ttc (SEQ ID NO: 34) | |
| Oligo 23 beta-globin reverse primer/hairpin-B | 5'-cat tgc aaa tca tac tag ctc acc agc aat g (SEQ ID NO: 35) | |
| Oligo 24 NF 1355 forward primer/linear | 5'-tgg cag ttg aat gcc aag taa t (SEQ ID NO: 36) | |
| Oligo 25 NF 1355 reverse primer/linear | 5'-aca gcc act gtg ccc agg tc (SEQ ID NO: 37) | |
| Oligo 26 NF 1355 forward primer/hairpin | 5'-att act tgg cag ttg aat gcc aag taa t (SEQ ID NO: 38) | |
| Oligo 27 NF 1355 reverse primer/hairpin | 5'-gac ctg aca gcc act gtg ccc agg tc (SEQ ID NO: 39) | |
| Oligo 28 NF 1616 forward primer/linear | 5'-att tca tgg ggg aaa caa aga tg (SEQ ID NO: 40) | |
| Oligo 29 NF 1616 reverse primer/linear | 5'-ata cct gcg ctc acc aca gg (SEQ ID NO: 41) | |
| Oligo 30 NF 1616 forward primer/hairpin | 5'-cat ctt tat ttc atg ggg gaa aca aag atg (SEQ ID NO: 42) | |
| Oligo 31 NF 1616 reverse primer/hairpin | 5'-cct gtg ata cct gcg ctc acc aca gg (SEQ ID NO: 43) | |

The nucleotide to which the fluorescent moiety is attached is indicated by a bold capital letter.

Example 2

PCR Targets and Conditions

Those skilled in the art will appreciate that any nucleic acid that can be amplified by PCR may be used in the practice of the present invention. Examples of suitable nucleic acids include, but are not limited to, genomic DNAs, cDNAs and cloned PCR products. The practice of the present invention is not limited to use with DNA molecules. For example, mRNA molecules may be used as templates for an amplification reaction by first conducting a first strand synthesis reaction using techniques well-known in the art. The present invention has been exemplified using cDNAs for IL4 and beta-actin synthesized using total mRNA from the corresponding cells and SuperScript™ System for the First Strand cDNA Synthesis (Gibco BRL, cat. #18089-011) according to the manufacturer's manual. IL4 and beta-actin cDNAs were amplified and cloned into pTEPA plasmid according to Gibco BRL manual (cat. #10156-016).

The selection of suitable PCR conditions is within the purview of one of ordinary skill in the art. Those skilled in the art will appreciate that it may be necessary to adjust the concentrations of the nucleic acid target, primers and temperatures of the various steps in order to optimize the PCR reaction for a given target and primer. Such optimization does not entail undue experimentation. In the specific examples provided herein, PCR was performed in 25 µl of PLATINUM® Taq Reaction Buffer with 0.5 U of PLATINUM® Taq, 0.2 mM dNTPs, 0.2 µM forward and reverse primers, and 1.75 mM MgCl$_2$ using $10^4$-$10^6$ copies of target. PLATINUM® Tsp was used under the same conditions. Thermal cycling was performed on 9600 or ABI PRISM® 7700 Sequence Detector (Perkin Elmer) with 4 minutes denaturation at 94° C., followed by 35-40 cycles: 15 seconds at 94° C., 30 seconds at 55° C. and 40 seconds at 72° C. In two-step PCR, cycling conditions were 15 seconds at 94° C. and 30 seconds at 65° C. Unless otherwise indicated, in all examples, amplification was conducted with PLATINUM® Taq (available from Invitrogen Corporation (Life Technologies Division)).

Example 3

Detection of Nucleic Acids

Nucleic acids may be detected by any conventional technology. In some preferred embodiments, the nucleic acid to be detected may be a PCR product and may be detected either by agarose gel electrophoresis or by homogeneous fluorescence detection method. In this method, a fluorescent signal is generated upon the incorporation of the specifically labeled primer into the PCR product. The method does not require the presence of any specific quenching moiety or detection oligonucleotide. In some preferred embodiments, the detection oligonucleotides are capable of forming a hairpin structure and are labeled with fluorescein attached at or near to the 3'-end.

The fluorescent measurements were performed in the PCR reaction buffer using on ABI PRISM® 7700 Sequence Detector, fluorescent plate reader (TECAN) or KODAK® EDAS Digital Camera. Excitation/emission wavelengths were 490 nm/520 nm for fluorescein and 555 nm/580 nm for TAMRA.

Example 4

Fluorescence Signal of Oligonucleotide Internally Labeled with Fluorescein Increases Upon its Hybridization to the Complementary Oligonucleotide Two oligonucleotides of the same sequence were labeled with fluorescein either internally on T-base (oligo A (SEQ ID NO:1)), or at the 5'-end (oligo B (SEQ ID NO:2)) as described above. 10 pmoles of each oligonucleotide were hybridized to the complementary oligo C (SEQ ID NO:3) (50 pmoles) in 0.05 ml of the PCR buffer, heated at 70° C. for 2 minutes and cooled to 25° C. Melting curves between 25 and 95° C. were determined on ABI PRISM™ 7700 Sequence Detector.

Figure 2B:
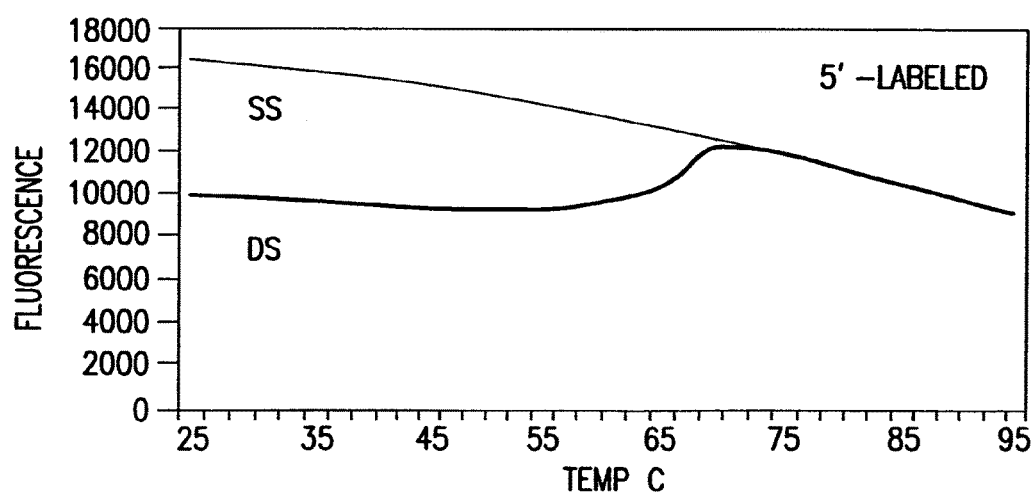

As shown in FIGS. 2A-B, in the case of internally labeled Oligo A (SEQ ID NO:1), a fluorescence signal increases as a result of presence of the non-labeled complementary oligonucleotide. That means the signal increase was caused by the formation of the double-stranded structure. In contrast, when the fluorescein was present on the 5'-end of the same sequence (Oligo B (SEQ ID NO:2)), fluorescence signal decreased upon hybridization.

Example 5

Oligodeoxynucleotide Labeled with TAMRA on its 3'-End, Increases the Fluorescence Signal Upon Hybridization 20 pmoles of Oligo D (SEQ ID NO:4) 3'-labeled with TAMRA as described above were annealed to 100 pmoles of complementary non-labeled oligodeoxynucleotide (Oligo E (SEQ ID NO:5)) in 0.5 ml of the PCR Buffer. Fluorescence emission spectrum was detected on a spectrofluorimeter with 555 nm excitation.

Figure 3:
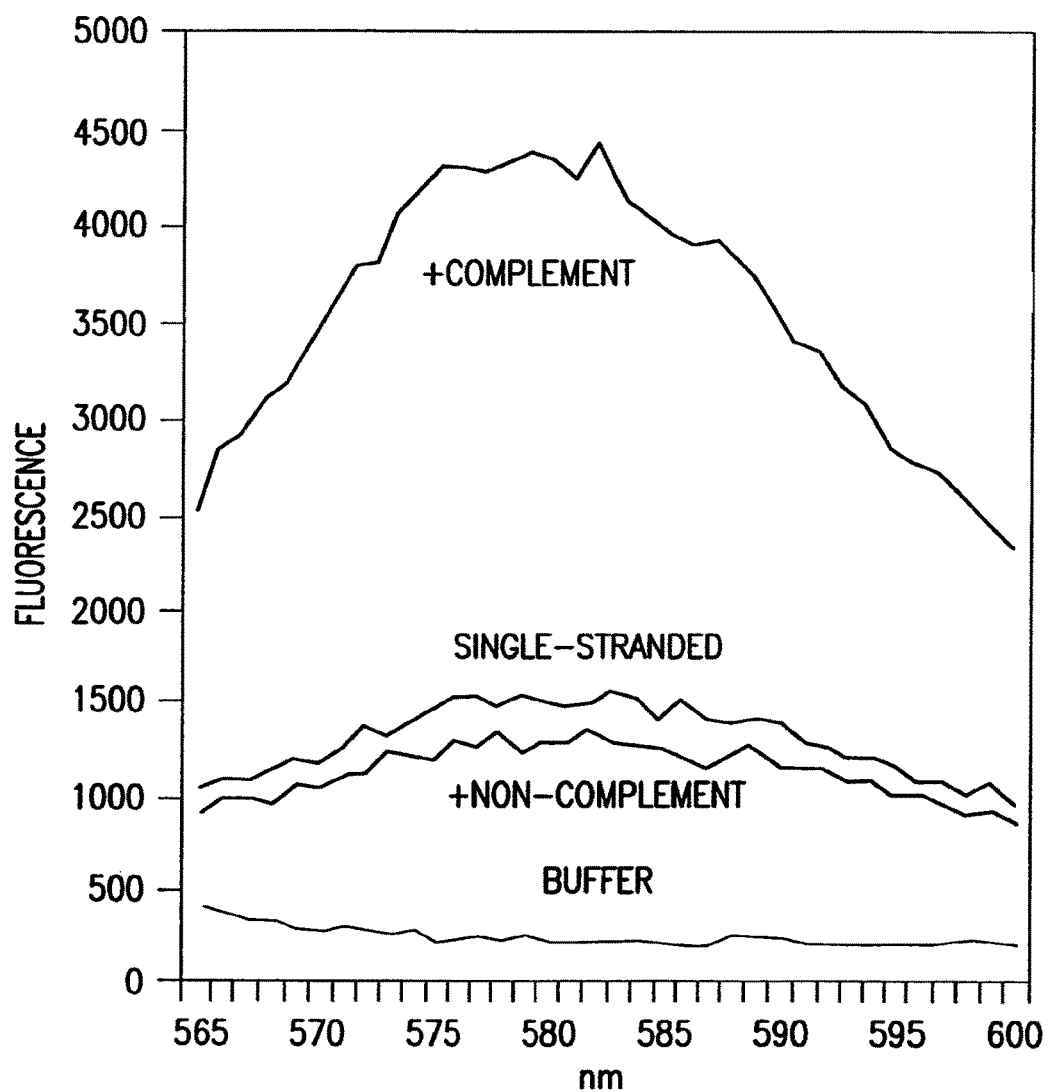
FIG. 3 is a line graph of fluorescent intensity as a function of wavelength which shows fluorescence of 3'-TAMRA oligonucleotide in the presence of complementary and non-complementary oligonucleotides. In the presence of complement (to create a double-stranded molecule), the fluorescence increased compared to the single-stranded form (see Example 5).

As shown in FIG. 3, a significant increase of the signal was observed upon hybridization, indicating that the proposed method can be applied to different fluorophores. The curve labeled buffer shows the fluorescence as a function of wavelength of the buffering solution. The curve labeled single-stranded shows the results obtained with the single-stranded version of oligo D (SEQ ID NO:4) alone. When a non-complementary oligonucleotide was added to oligo D (SEQ ID NO:4) a slight decrease in signal was observed (+non-complement). When complementary oligonucleotide oligo E (SEQ ID NO:5) was added, a large increase in fluorescence was observed (+complement).

Example 6

Oligodeoxynucleotide 5'-Labeled with BODIPY 530/550 Increases the Fluorescence Signal Upon Hybridization In Examples 4 and 5, oligonucleotides internally labeled with fluorescein and 3'-labeled with TAMRA were shown to increase the fluorescence intensity upon hybridization to the complementary oligonucleotide. In contrast, oligonucleotides 5'-labeled with fluorescein demonstrated fluorescence quenching upon hybridization (see Example 4; Cardullo et al., *PNAS* 85: 8790-8794 (1988); U.S. Pat. No. 5,846,729).

However, there are some dyes that can show an enhancement of the fluorescence intensity upon hybridization even though they are located at the 5'-position of an oligonucleotide. For example, an oligodeoxynucleotide labeled at the 5'-end with BODIPY 530/550 shows an increase fluorescence intensity upon hybridization.

The same oligodeoxynucleotide sequence was 5'-labeled with fluorescein (Oligo F (SEQ ID NO:6)) or BODIPY 530/550 (Oligo G (SEQ ID NO:7)). 20 pmoles of each labeled oligonucleotide were annealed to 100 pmoles of complementary non-labeled oligodeoxynucleotide (Oligo H (SEQ ID NO:8)) in 0.5 ml of the PCR Buffer. Fluorescence emission spectrum was detected on a spectrofluorimeter with 490 nm excitation in case of fluorescein and 538 nm excitation in case of BODIPY.

Figure 4:
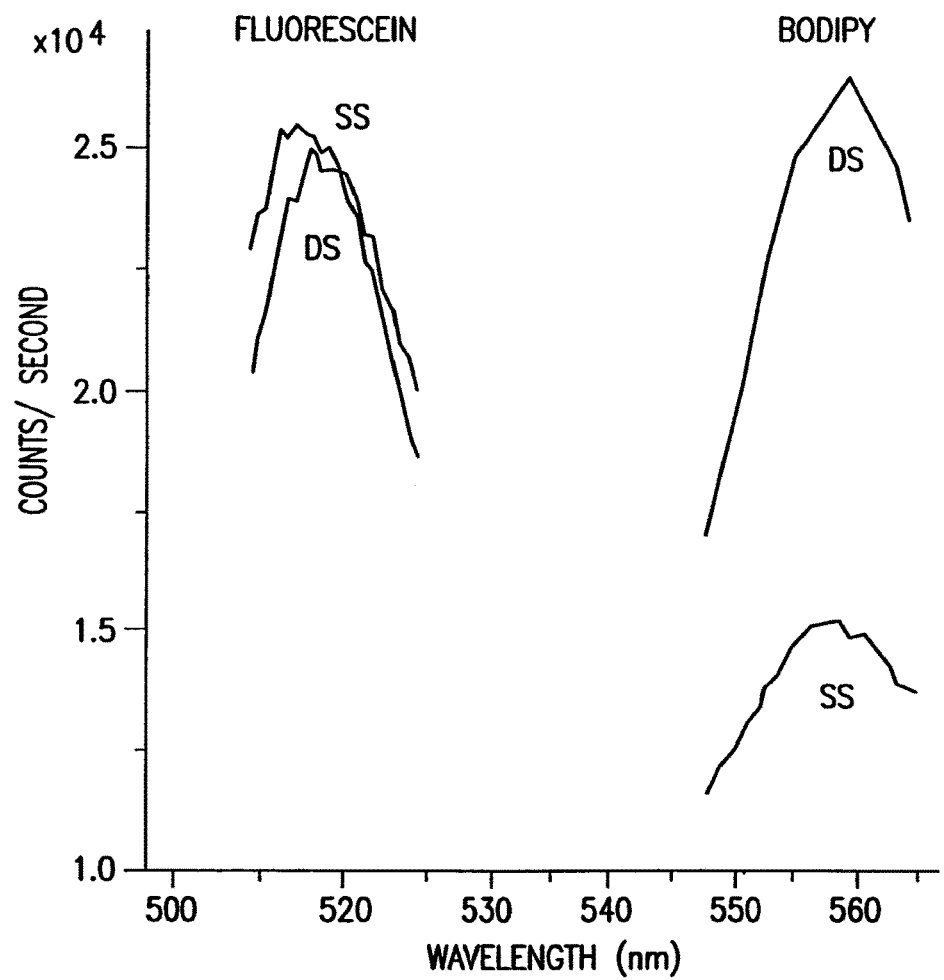
FIG. 4 is a line graph of fluorescence as a function of wavelength which shows the effect of hybridization on the fluorescence of oligonucleotides 5'-labeled with fluorescein and BODIPY 530/550. In the presence of the complement oligonucleotide (to create a double-stranded molecule), the fluorescence increased in case of BODIPY dye and decreased in case of fluorescein.

As shown in FIG. 4, a significant increase of the signal upon hybridization in case of BODIPY dye was observed, in contrast, a decrease in the signal was observed upon hybridization of a fluorescein containing oligonucleotide.

The results shown in Examples 4, 5 and 6 demonstrate that the fluorescent properties of a given fluorophore, in particular, the fluorescent intensity, can be affected upon hybridization without a significant shift of the emission spectrum as a result of the point of attachment of the fluorphore to a given oligonucleotide, i.e., internal, 3' and 5'.

Example 7

Quantitative PCR of IL4 cDNA Using Primer Internally Labeled with Fluorescein

Figure 5A:
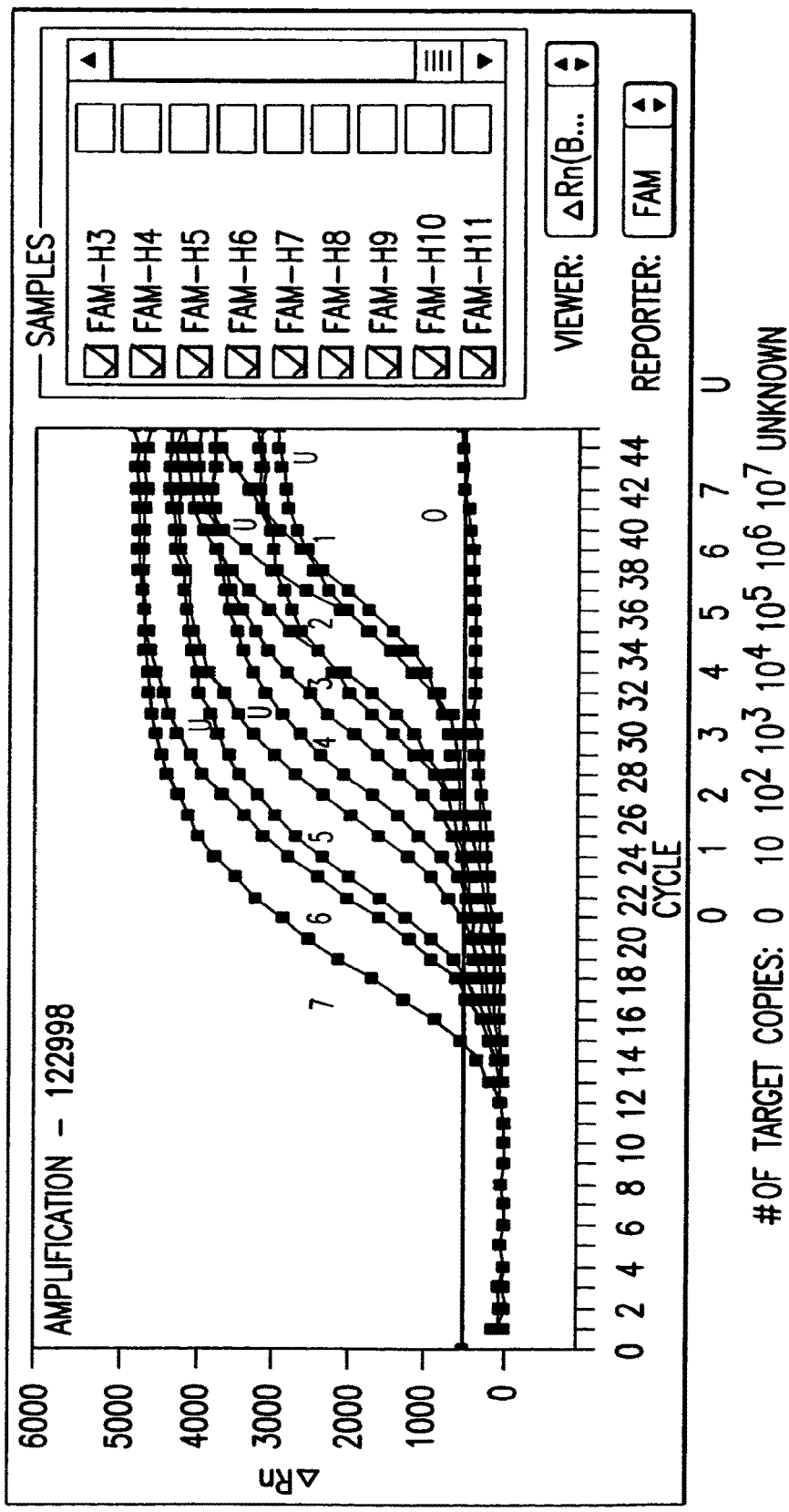
FIG. 5A is a line graph of fluorescent intensity as a function of the number of cycles of amplification performed which shows quantitative PCR of IL4 cDNA with an internally labeled primer. PCR was performed as described in Example 7. Data from ABI PRISM® 7700 Sequence Detector were treated according to the manufacturer's instructions with minor modifications (FIG. 5B).
Figure 5C:
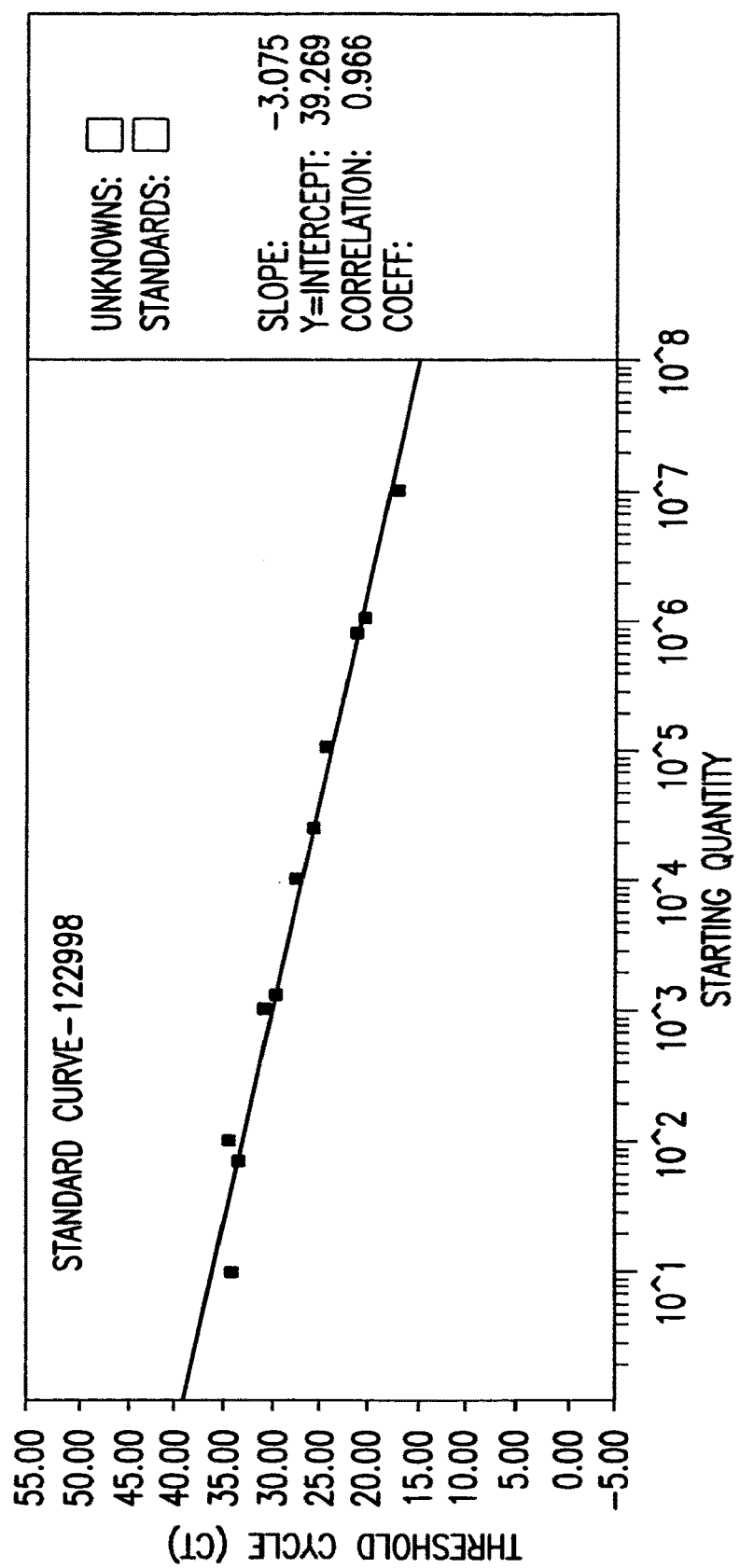
FIG. 5C is a standard curve plotting the number of cycles of amplification against the starting quantity of template DNA.

Fluorescein-dT was directly incorporated into the sequence of IL-4 primer during chemical synthesis using the methods described above. The resulting oligonucleotide (Oligo A (SEQ ID NO:1)) was used as a reverse primer for IL4 cDNA amplification. Quantitative PCR using reverse primer (Oligo A (SEQ ID NO:1)) and forward primer (Oligo I (SEQ ID NO:9)) was performed as described above in the presence of varying amounts of the template DNA. $10^7$, $10^6$, $10^5$, $10^4$, $10^3$, $10^2$, 10 and 0 copies of the cloned IL4 target were used per reaction along with four samples of unknown concentration of the target. As shown in FIG. 5A, all dilutions of the DNA target can be detected with extremely high accuracy.

The results of this experiment demonstrate that although no quencher is present in the structure of the labeled oligonucleotide, it can be successfully used in quantitative PCR.

Example 8

Real-Time PCR of IL4 cDNA Using Primer Post-Synthetically Labeled with FITC

Figure 6:
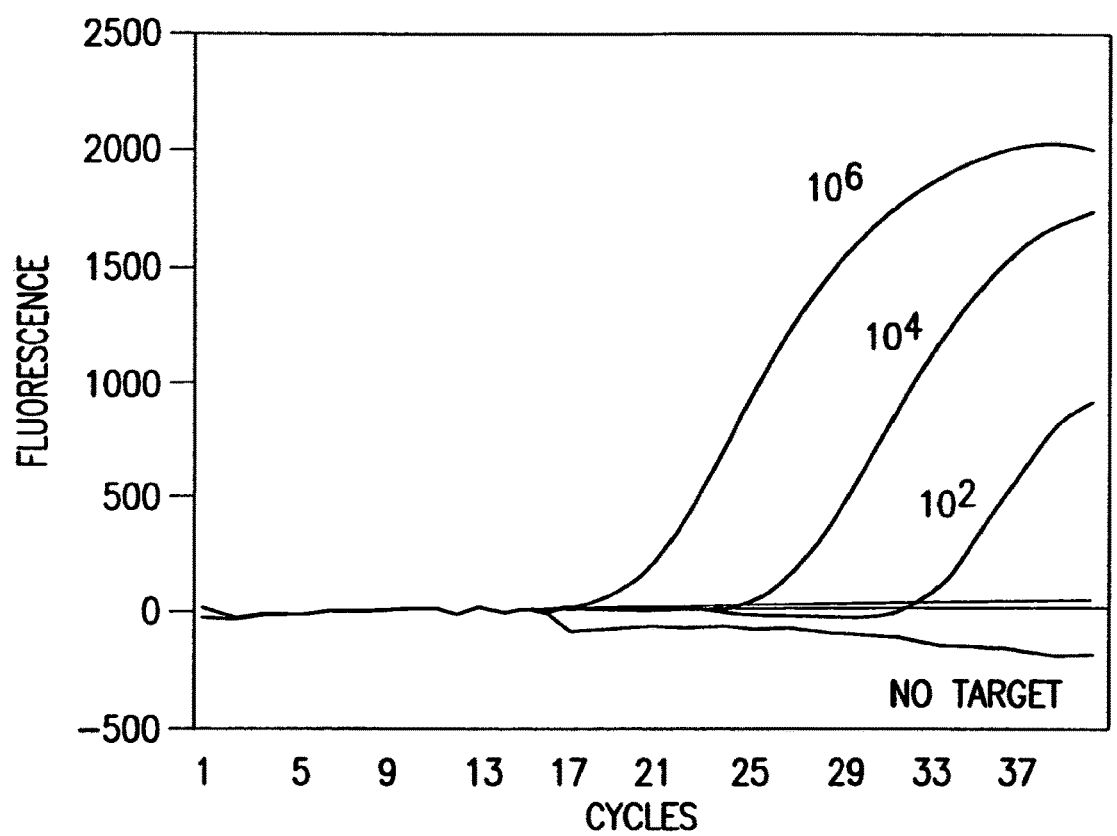
FIG. 6 is a line graph of fluorescent intensity as a function of the number of cycles of amplification performed which shows IL4 cDNA PCR with a primer post-synthetically labeled with fluorescein. PCR was performed as described in Example 8. Real-time amplification data were exported from ABI PRISM® 7700 Sequence Detector in Excel.

Reverse primer for IL4 (Oligo A (SEQ ID NO:1)) was synthesized and labeled post-synthetically as described above. Amplification was performed with $10^6$, $10^4$, $10^2$ and 0 copies of nucleic acid target as described in the previous example. As shown in FIG. 6, all dilutions of the DNA target can be detected.

The experimental results in preceding examples demonstrate that different methods of the labeling of oligonucleotides can be used for achieving the same result. Also, since two methods of synthesis provide different structures of the linker arm between oligonucleotide and fluorophore, different linker arms can be used to attach a fluorophore in the proposed methods.

Example 9

Figure 7:
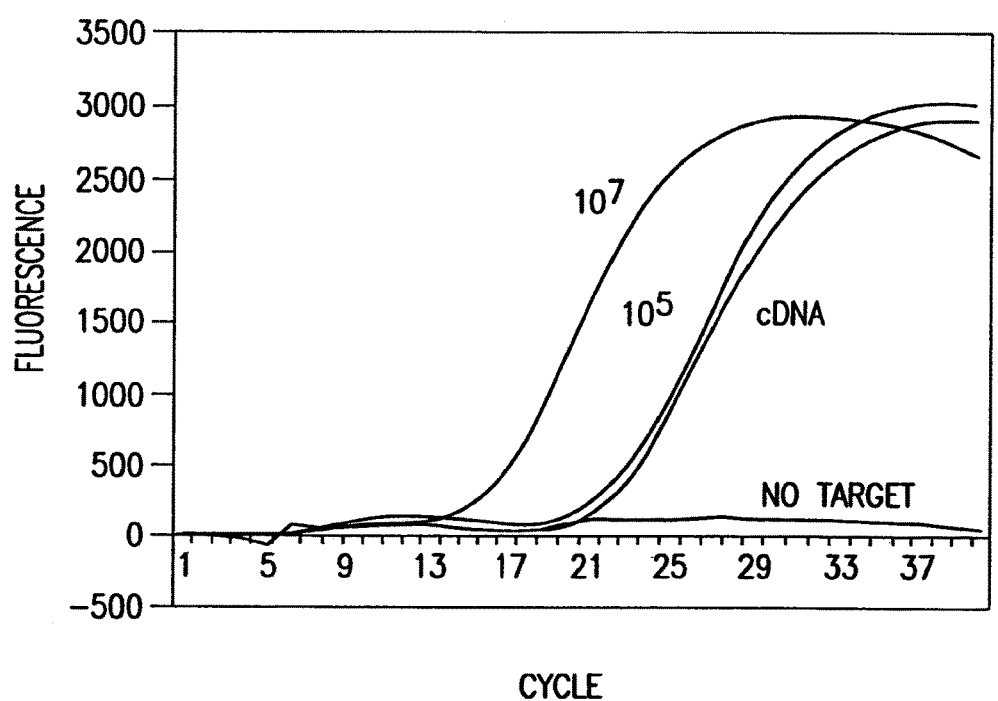
FIG. 7 is a line graph of fluorescent intensity as a function of the number of cycles of amplification performed which shows detection of beta-actin cDNA by PCR with a primer internally labeled with fluorescein. PCR was performed as described in Example 9.

Real-Time PCR of Beta-Actin cDNA with a Primer Internally Labeled with Fluorescein Fluorescein-dT was directly incorporated into the sequence of the forward primer for human beta-actin cDNA (Oligo J (SEQ ID NO:10)) during chemical synthesis. This oligonucleotide and unlabeled reverse primer (Oligo K (SEQ ID NO:11)) were used for the amplification of beta-actin cDNA. cDNA target was obtained by reverse transcription of HeLa cell mRNA and also a cloned cDNA fragment ($10^7$, $10^5$ and 0 copies per reaction). Quantitative PCR was performed as described above. As shown in FIG. 7, all dilutions of the DNA target can be detected.

The results of this experiment demonstrate that different targets can be detected using the proposed method.

Example 10

Real-Time PCR of Beta-Actin cDNA with a Primer Internally Labeled Through a "Tag" Sequence Non-Complementary to the Target All the above experiments show that the label can incorporated into the sequence of an oligonucleotide complementary to the target nucleic acid. However, the same result can be obtained if the label is present on a non-complementary tag sequence attached to the 5'-end of a PCR primer. In this case, a signal will be generated after this tailed primer is copied and incorporated into the double-stranded PCR product. This approach was demonstrated in the beta-actin PCR.

Figure 8:
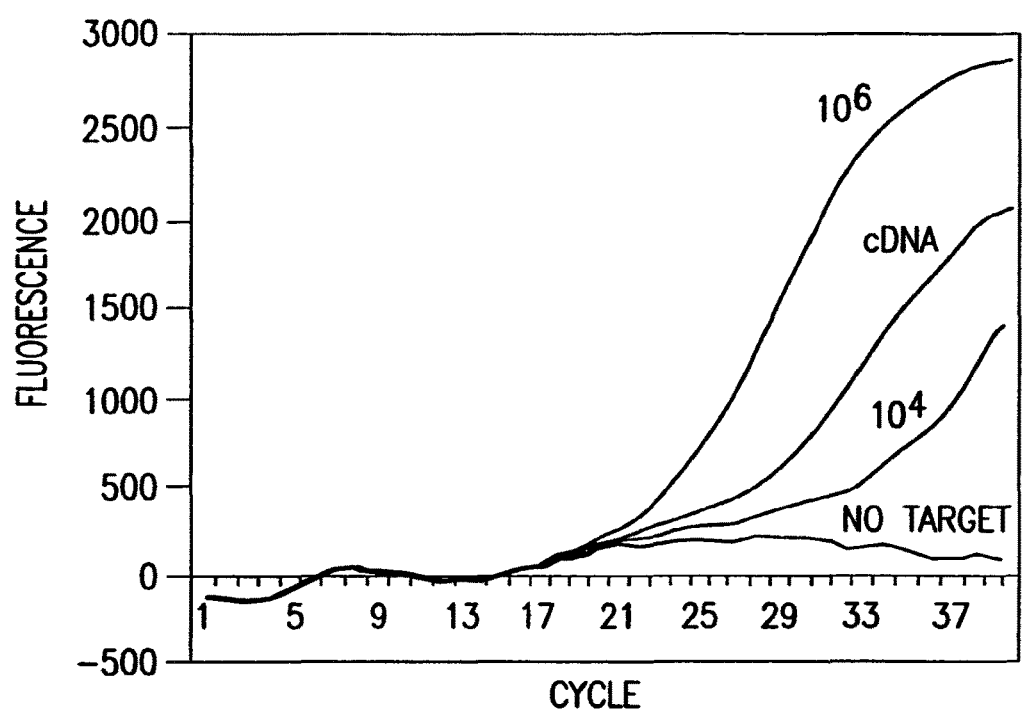
FIG. 8 is a line graph of fluorescent intensity as a function of the number of cycles of amplification performed which shows beta-actin cDNA PCR with a primer internally labeled through a 5'-detection tail. PCR was performed as described in Example 10.

Oligodeoxynucleotide (Oligo L (SEQ ID NO:12)) was synthesized with fluorescein-dT directly incorporated into the structure of a 9-nucleotide tail, non-complementary to the target. This tail was added to the 5'-end of the beta-actin forward primer. Oligo L (SEQ ID NO:12) and unlabeled reverse primer (Oligo K (SEQ ID NO:11)) were used to amplify beta-actin cDNA and $10^6$, $10^4$, and 0 copies of cloned target. As shown in FIG. 8, both cloned target and cDNA in total cDNA population were detected.

Example 11

Allele Specific PCR with Modified Oligonucleotide Primers

Figure 9:
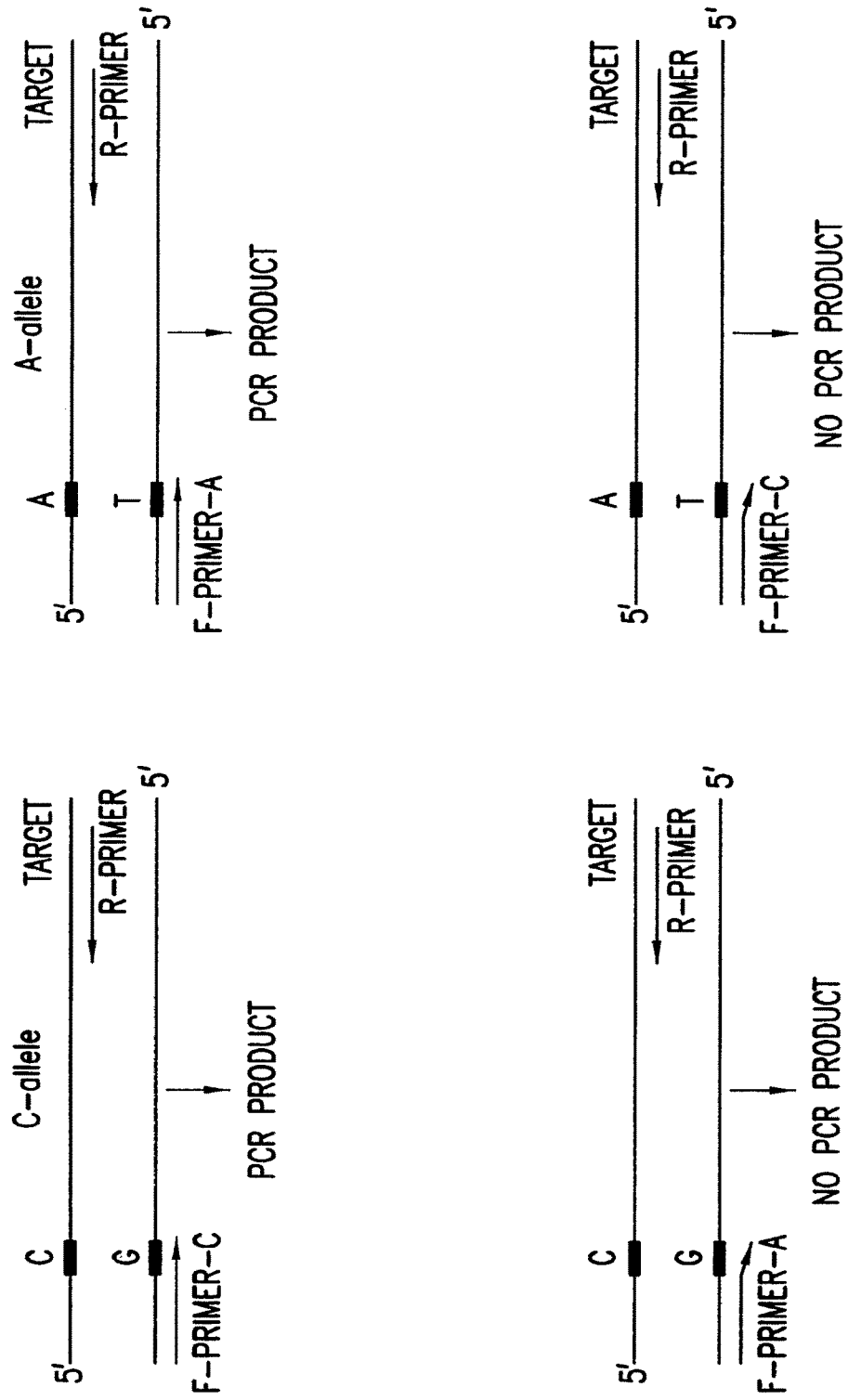
FIG. 9 is a schematic representation of allele specific PCR.

The principle of allele specific PCR is presented in FIG. 9. The method operates on the basis of the specific amplification of a target allele by PCR with primers designed such that their 3'-ends are placed at the mutation site (i.e., the 3'-most nucleotide of the primer corresponds to the mutated nucleotide in the target/template nucleic acid). When this base is complementary to that of the corresponding nucleotide of the specific allele, the target is amplified; when it is not complementary PCR will proceed with a significant delay. The longer the delay, the more efficiently the system can discriminate between alleles. In some preferred embodiments, the present invention provides oligonucleotides useful for allele specific PCR which oligonucleotides comprise a specificity enhancing group that improves discrimination between alleles.

Allele specific PCR was performed using regular PCR primers and the primers labeled with fluorescein at a base close to the 3'-end. Two positions of the IL4 cDNA were chosen for detection, C297 and G300. For each position, two PCRs were performed using the same forward primer (Oligo 1 (SEQ ID NO:9)) and different reverse primers: wild type (WT), complementary to the target, or mutant (MUT) with a mismatch at the 3'-end. The sequences of the primers used are provided in Table 2. Each of these allele specific primers was synthesized with and without chemical modification on a T-base close to the 3'-end. The primers used were 297 WT—primer complementary to the C-allele at position 297 (Oligo 2 (SEQ ID NO:14)), 297 MUT—same primer with C-T mutation at the 3'-end (Oligo 3 (SEQ ID NO:15)), 300 WT—primer complementary to the C-allele at position 300 (Oligo 4 (SEQ ID NO:16)) and 300 MUT—same primer with G-T mutation at the 3'-end (Oligo 5 (SEQ ID NO:17)). Oligonucleotides 6, 7, 8, 9 (SEQ ID NOS:1, 19, 20, 21, respectively) correspond to oligonucleotides 2, 3, 4, 5 (SEQ ID NOS:14, 15, 16, 17, respectively) with fluorescein attached to the designated T-base.

Figure 10:
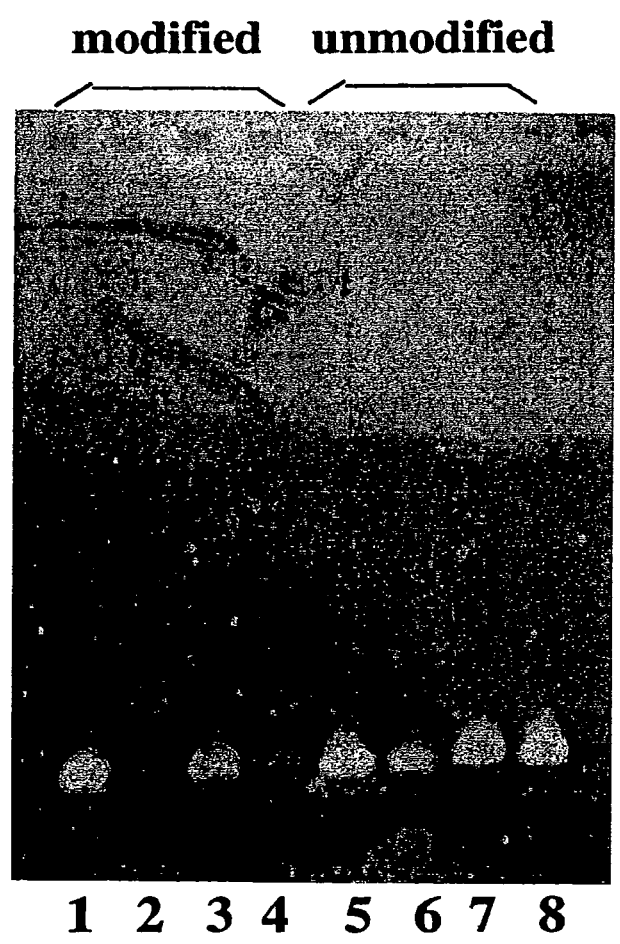
FIG. 10 is a photograph of an agarose gel showing the results of an allele specific PCR reaction comparing the primers of the present invention to standard primers.

Three-step PCR was performed for 40 cycles with PLATINUM® Taq as described above. The results are shown in FIG. 10. Reverse primers with their 3'-end at positions 297 or 300 were either complementary to the target (WT) or had a 3'-mutation (MUT). Lanes 1 through 4 show the results obtained with primers modified with fluorescein as a specificity enhancing group; lanes 5 through 8 show the results obtained with unmodified primers. Lanes 1 and 5 show the results using the primer 297 WT; lanes 2 and 6 show the results using the primer 297 MUT; lanes 3 and 7 show the results using primer 300 WT; and lanes 4 and 8 show the results using primer 300 MUT. A comparison of lanes 2 and 6 and a comparison of lanes 4 and 8 show that the presence of a modification allows discrimination that is almost complete after 40 cycles. The practice of the present invention is not limited to the use of fluorescein, similar results were obtained with TAMRA as a specificity enhancing group.

Example 12

Allele Specific PCR with Hairpin Oligonucleotide Primers

Figure 11:
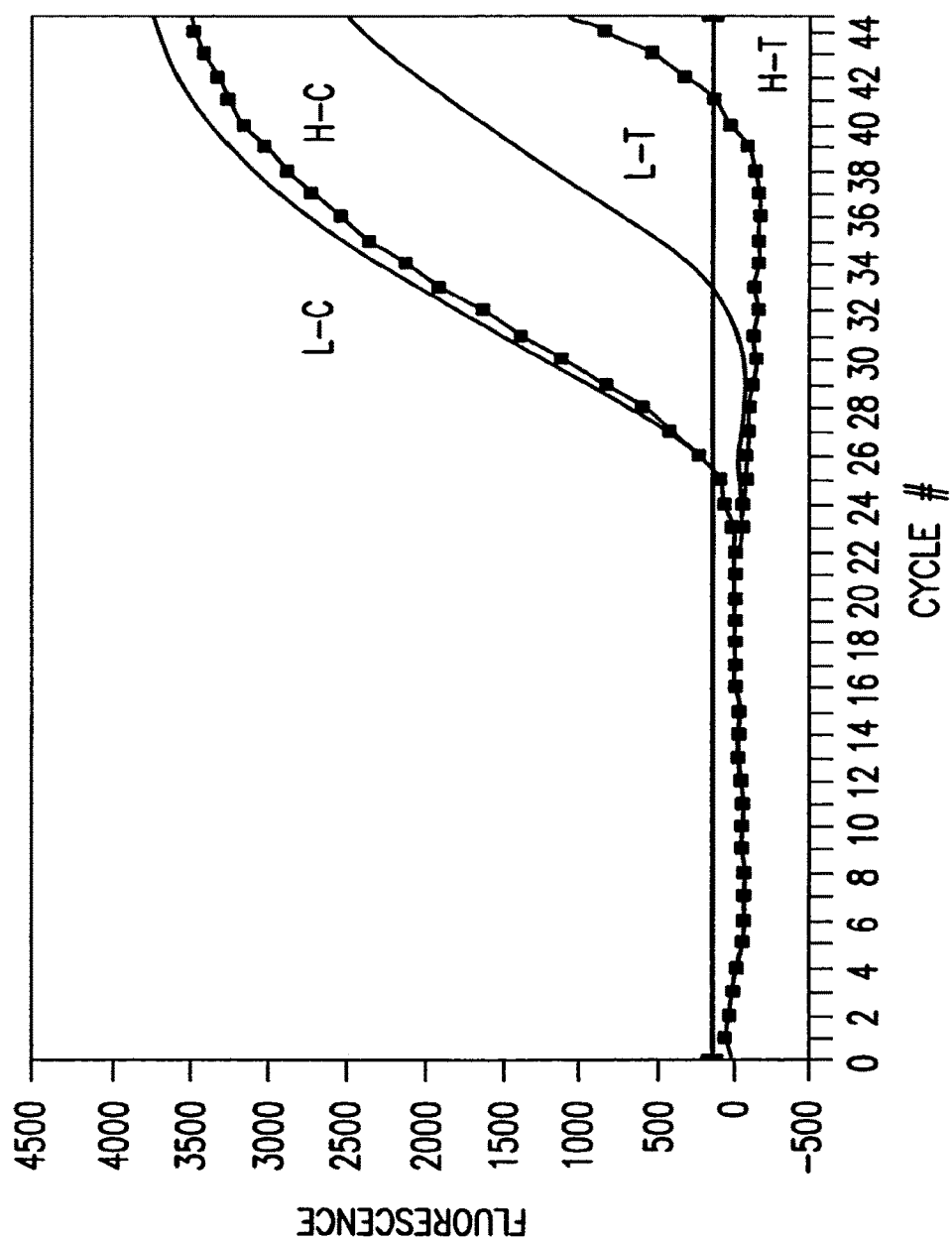
FIG. 11 is a plot of fluorescence as a function of the number of cycles of PCR performed in an allele specific PCR reaction comparing the hairpin primers of the present invention to standard linear primers.

It has been discovered that mutation discrimination can be improved through the secondary structure of the allele specific primers. This feature is exemplified using primers specific for the RDS gene. Forward primers for the RDS gene had their 3'-ends located at position 558, the site of a C/T polymorphism. The DNA target contained the C-allele. The reverse primer was the same for both alleles and contained the label that permitted homogeneous detection of amplification in real time (Oligo 10 (SEQ ID NO:22)). Forward allele specific primers were either of the conventional linear structure (Oligos 11, 12 (SEQ ID NOS:23, 24, respectively)) or had the hairpin structure (Oligos 13, 14 (SEQ ID NOS:25, 26, respectively)). Hairpin primers consisted of the target-specific sequence and a short tail complementary to the 3'-fragment of the primer. Three-step PCR was performed with PLATINUM® Taq DNA polymerase on PRIZM® 7700 as described above. The results in FIG. 11 show that the blunt end hairpin structure of the primer significantly improves mutation discrimination. The primers of the invention were used to discriminate between the C and the T allele of human RDS gene by allele-specific PCR with PLATINUM® Taq DNA polymerase using the same fluorescent reverse primer (Oligo 10 (SEQ ID NO:22)) and different allele specific forward primers. The primers used were designated L-C for the linear primer specific for C-allele (Oligo 11 (SEQ ID NO:23)), L-T for the linear primer specific for T-allele (Oligo 12 (SEQ ID NO:24)), H-C for the hairpin primer specific for C-allele (Oligo 13 (SEQ ID NO:25)) and H-T for the hairpin primer specific for T-allele (Oligo 14 (SEQ ID NO:26)). A comparison of the real time fluorescence of the reactions is plotted as a function of the cycle number. The linear T mismatched primer generated a signal that was detectable well before the hairpin T mismatched primer signal. This demonstrates that the discrimination between the alleles was improved by incorporating the 3'-termini of the primer into a hairpin.

Another example of allele specific PCR using hairpin primers is shown in FIG. 12. Here, two genomic DNA samples were tested by two-step PCR. One of the samples was known to have a 558C-allele of RDS gene, another the 558T allele. All forward primers were hairpin primers and fluorescent reverse primer was used for the detection. Curve 1 was obtained with the C-specific primer with C-target DNA; curve 2 was obtained using the C-specific primer with T-target DNA; curve 3 was obtained using C-specific primer with no target DNA (negative control); curve 4 was obtained using the T-specific primer with T-target DNA; curve 5 was obtained using T-specific primer with C-target DNA; and curve 6 was obtained using T-specific primer with no target (negative control).

Figure 13A:
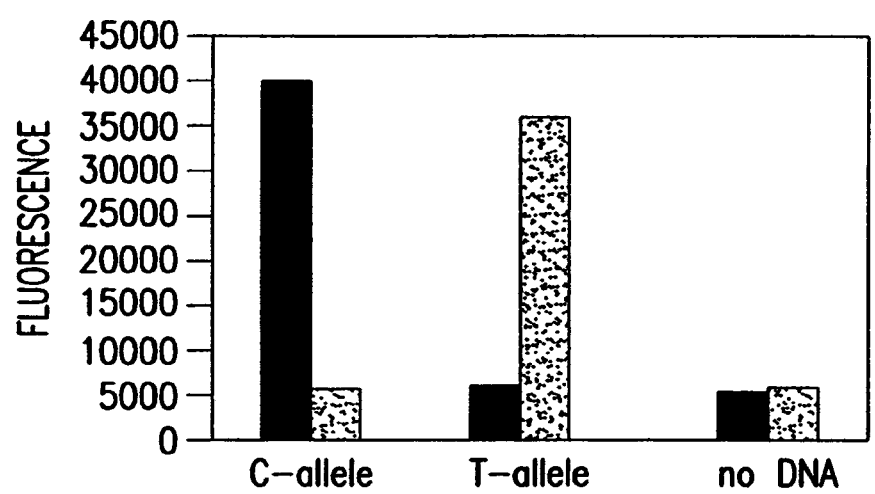
FIG. 13A shows a bar graph of the fluorescence intensity obtained at the end point of an allele specific PCR reaction using the primers of the present invention.
Figure 13B:
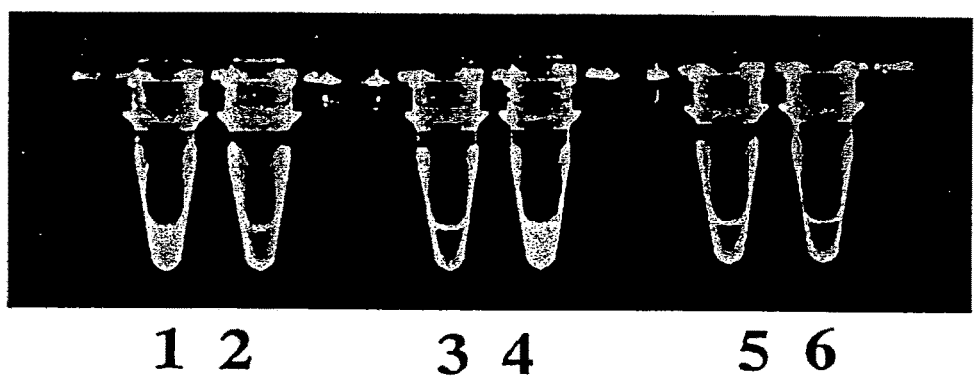
FIG. 13B is a photograph of the PCR tubes in which the allele specific reaction was conducted illuminated with ultraviolet light.

The results demonstrate that only C-allele with C-specific primers and T-allele with T-specific primers give a positive signal when hairpin primers are used. No increase of fluorescence was detected when the primer had a 3'-mismatch. No signal was generated in the absence of target. As shown in FIGS. 13A-B, the alleles can be detected with the same high level of specificity not only in real time, but also at the end point. Fluorescent reverse primer was used for the detection. 1, 3, 5 C-specific primers, 2, 4, 6 T-specific primers, 1 and 2 C-allele target DNA, 3 and 4 T-allele target DNA, and 5 and 6 no DNA (negative controls). FIG. 13A shows a bar graph of the fluorescence obtained while FIG. 13B shows a photograph of the reaction mixture after the amplification reactions. End point detection is permitted by high signal/noise ratio of the detection system and can be performed using a fluorescent plate reader or UV transilluminator and digital camera.

Figure 14:
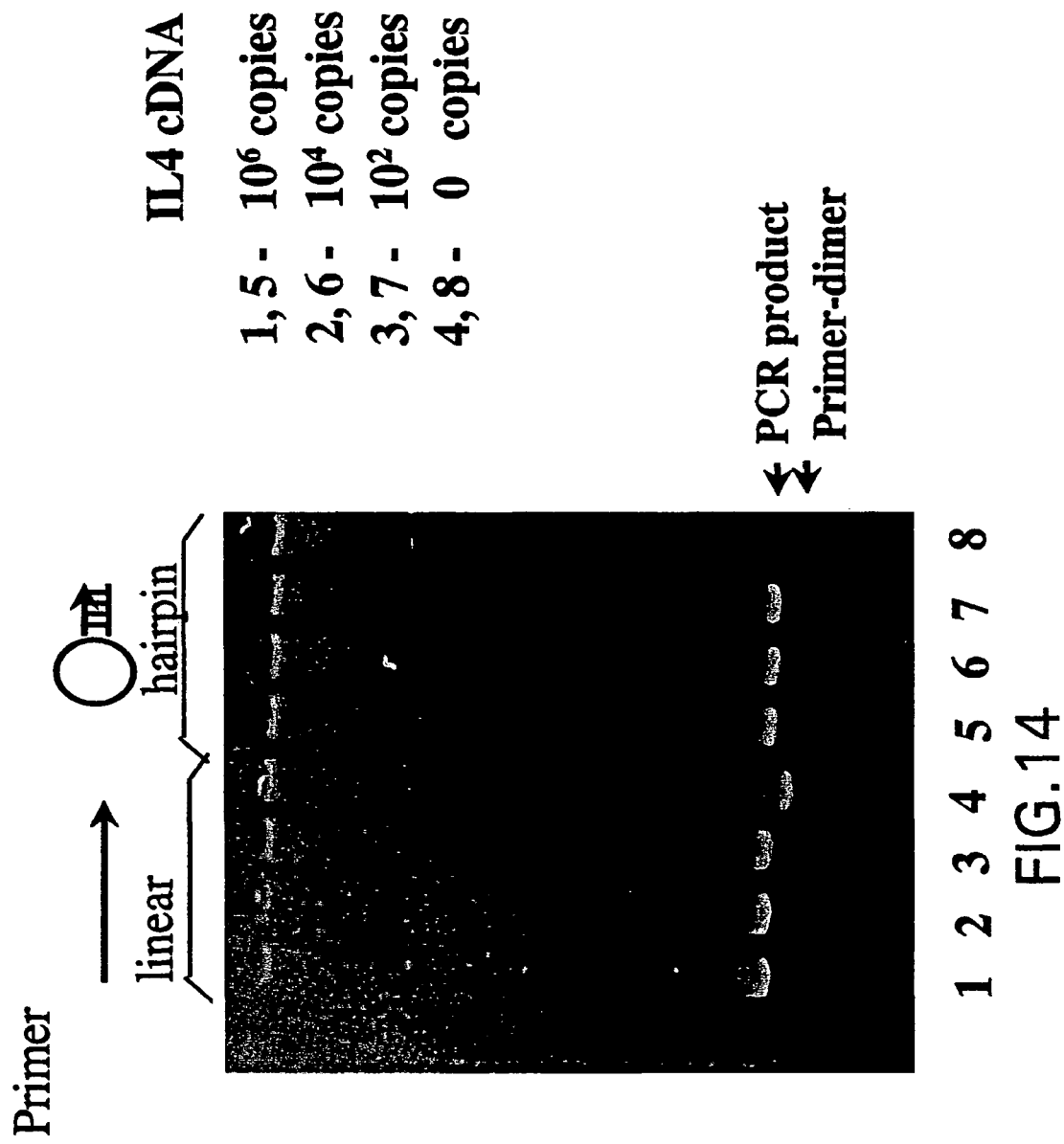
FIG. 14 is a photograph of an agarose gel showing the effects of target DNA concentration on an allele specific PCR reaction using the primers of the present invention.

Another surprising result of the use of the primers of the present invention is the elimination of primer-dimers from the PCR reaction. As shown in FIG. 14, the use of a hairpin oligonucleotide in the PCR reaction eliminates the formation of primer-dimers. IL4 cDNA was used as a PCR target. Oligo 1 (SEQ ID NO:9) was used as a forward primer, oligo 2 (SEQ ID NO:14) as a linear reverse primer and Oligo 15 (SEQ ID NO:27) as a hairpin reverse primer. PCR was performed with PLATINUM® Taq for 50 cycles. Lanes 1, 5 contained $10^6$ copies of target; lanes 2, 6 contained $10^4$ copies of target; lanes 3, 7 contained $10^2$ copies of target; and lanes 4, 8 contained no target. Comparison of lanes 4 and 8 shows that primer-dimer was formed with linear reverse primer, but not with the hairpin.

Example 13

Use of Mismatch Discriminating Polymerases in Allele Specific PCR

The ability to discriminate between alleles by allele specific PCR may be improved by using DNA polymerases modified to be substantially unable to extend an oligonucleotide when the 3'-most nucleotide of the oligonucleotide is not base paired with the target nucleic acid sequence. The preparation of such modified DNA polymerases is disclosed in WO 99/10366 and WO 98/35060. These publications disclose the cloning and mutagenesis of thermostable polymerases, in particular, the thermostable DNA polymerase isolated from *Thermatoga* spp. In some preferred embodiments of the present invention, allele specific PCR is performed using a mutant DNA polymerase derived from the DNA polymerase of *Thermotoga neopolitana* (Tne). Suitable mutations include deletion of one or more amino acids, frame shift mutations, point mutations that result in one or more amino acid substitutions at one or more sites in the enzyme, insertion mutations and combinations thereof. In a preferred embodiment, the mutations may include a deletion of the first 283 amino acids of the wild type enzyme leaving a fragment that begins with methionine 284 (Δ283), a point mutation changing amino acid 323 from aspartic acid to alanine (D323A) and a point mutation changing amino acid 722 from arginine to lysine (R722K). In some preferred embodiments, the mutant Tne DNA polymerase will have at least all three mutations, i.e., will be Δ283, D323A and R722K.

Figure 15:
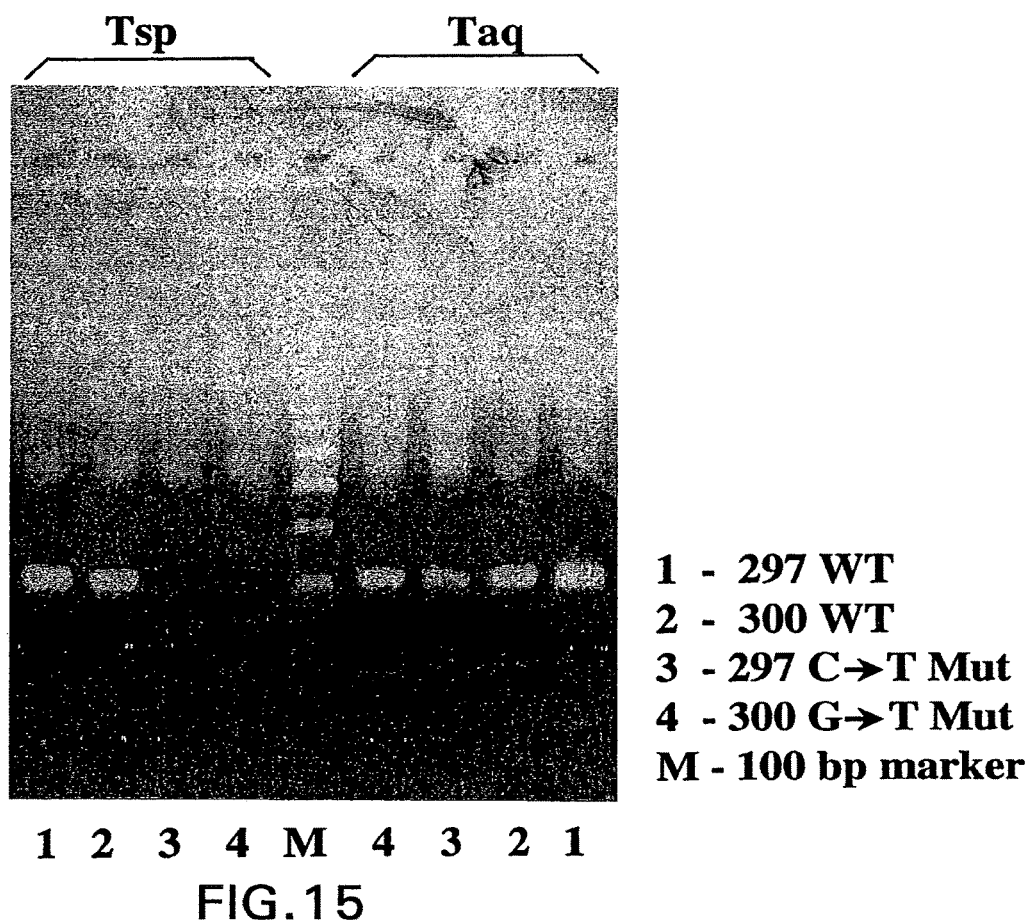
FIG. 15 is a photograph of an agarose gel showing the results of an allele specific reaction comparing the results obtained using Tsp DNA polymerase to PLATINUM® Taq DNA polymerase using standard primers.

PLATINUM® Tsp DNA polymerase is a proprietary enzyme of Invitrogen Corporation (Life Technologies Division) that can be activated by temperature thus providing a hot start for PCR (U.S. Pat. Nos. 5,338,671 and 5,587,287). Here, a new property of this enzyme is described, i.e., increased specificity towards the base paired 3'-end of the primer. PCR was performed for 45 cycles with PLATINUM® Tsp or PLATINUM® Taq DNA polymerase using IL4 cDNA as a target. Two positions of the IL4 cDNA were chosen for detection, C297 and G300. For each position, two PCR reactions were performed using the same forward primer (Oligo 1 (SEQ ID NO:9)) and different reverse primers. Primer sequences are described in Table 2 (Oligos 1-5 (SEQ ID NOS:9, 14-17)). The oligonucleotides are designated wild type (WT) when the 3'-nucleotide is complementary to the target, or mutant (MUT) with a mismatch at the 3'-end. The oligonucleotides used were the 297 WT primer which is complementary to the C-allele at position 297 (Oligo 2 (SEQ ID NO:14), lane 1), the 297 MUT primer which has the same sequence as the 297 WT primer except for a C-T mutation at the 3'-end (Oligo 3 (SEQ ID NO:15), lane 3), the 300 WT primer which is complementary to the C-allele at position 300 (Oligo 4 (SEQ ID NO:16), lane 2) and the 300 MUT primer which has the same sequence as the 300 WT primer except for a G-T mutation at the 3'-end (Oligo 5 (SEQ ID NO:17), lane 4). As seen in FIG. 15, a comparison of the results obtained with PLATINUM® Tsp DNA polymerase to those obtained with PLATINUM® Taq DNA polymerase show that PLATINUM® Tsp has better discriminatory properties than PLATINUM® Taq.

Example 14

Use of Hairpin Primers to Enhance Specificity of PCR

In this experiment, a 3.6 kb fragment of the human beta-globin was amplified from human genomic DNA using PLATINUM® Pfx thermostable polymerase in Pfx buffer (Invitrogen Corporation (Life Technologies Division)). Two different sets of primers were used. Each set of primers consisted of two primer pairs, one pair of linear primers and another pair of primers having a hairpin version of the same gene specific primer sequence. The hairpin version of each pair of oligonucleotides was constructed by adding bases to the 5'-end of the primer sequence that are complementary to the 3'-end of the oligonucleotide as discussed above. Typically, the number of bases added to the 5'-end is selected such that the oligonucleotide forms a hairpin at temperatures below the annealing temperature and assumes a linear form at or near the annealing temperature. Those skilled in the art can readily determine the number of nucleotides to be added to the 5'-end of the primer so as to control the temperature at which the primer assumes a linear form.

Figures 16A, 16B:
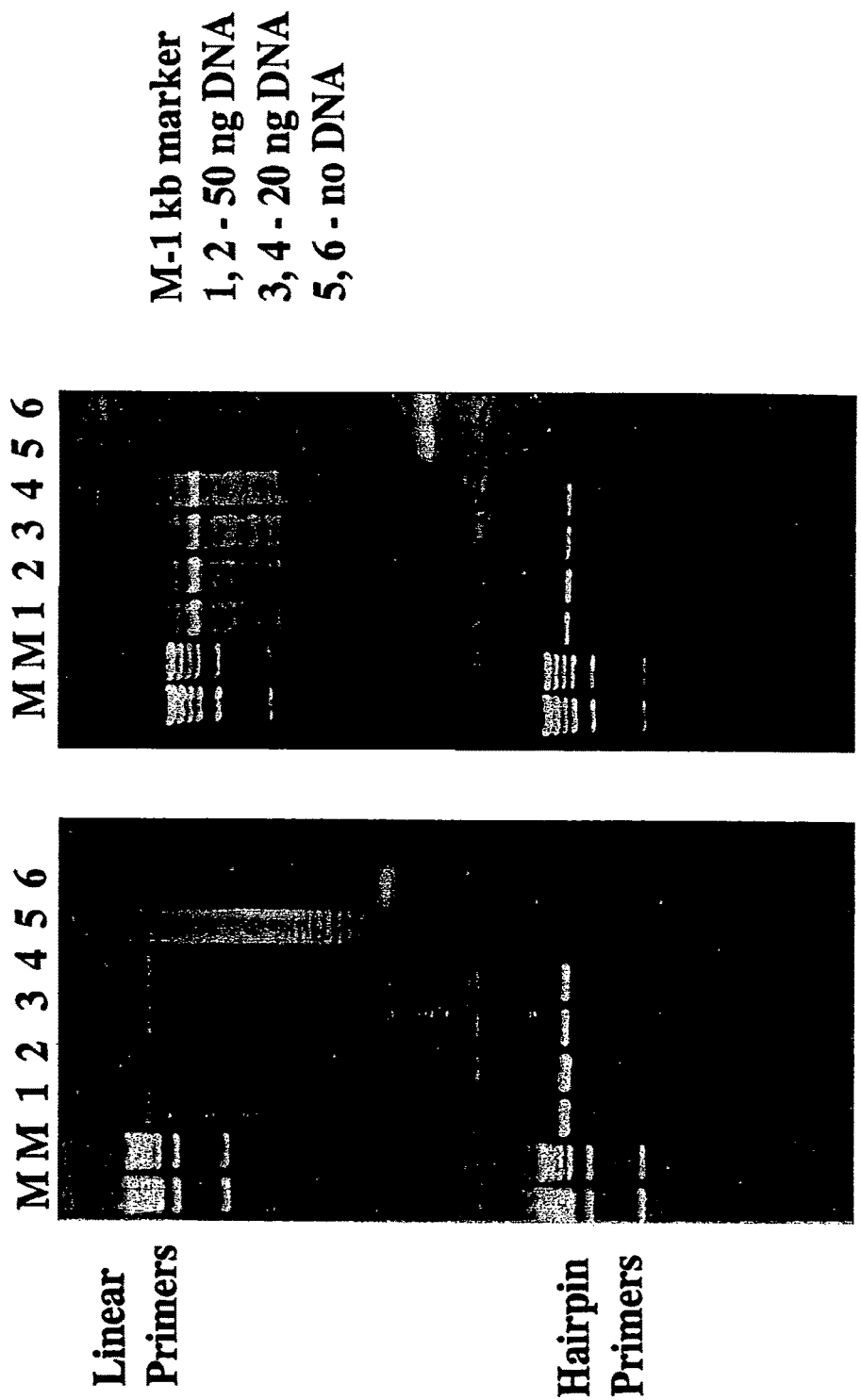
FIGS. 16A-B are photographs of an ethidium bromide stained agarose gel showing the results of comparison of the hairpin oligonucleotides of the present invention to linear oligonucleotides in an amplification reaction using varying amounts of template DNA.

For the amplification of the beta globin gene, two sets of primers were used. Set A—oligos 16 (SEQ ID NO:28) and 17 (SEQ ID NO:29) (linear) or 18 (SEQ ID NO:30) and 19 (SEQ ID NO:31) (hairpin) and Set B—oligos 20 (SEQ ID NO:32) and 21 (SEQ ID NO:33) (linear) or 22 (SEQ ID NO:34) and 23 (SEQ ID NO:35) (hairpin). PCR was performed as follows: 2 minutes at 94° C. followed by 35 cycles of: 15 seconds at 94° C. then 30 seconds at 60° C. followed by 4 minutes at 68° C. using varying amounts of template DNA. The results are shown in FIGS. 16A-B. The lanes labeled M contain molecular weight markers. Lanes 1 and 2 show the results obtained using 50 ng of template DNA, lanes 3 and 4 show the results obtained using 20 ng of template and lanes 5 and 6 show the no DNA controls. It is clear that both linear sets of primers generated various mis-priming products and primer-dimers, while amplification with the corresponding hairpin primers produced the expected size amplification product with very little incorrect product.

Figure 17A:
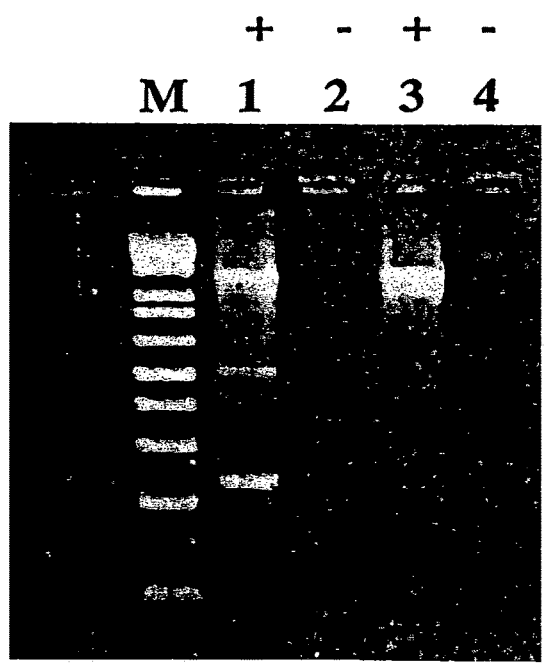
FIGS. 17A-B are photographs of an ethidium bromide stained agarose gel showing the results of comparison of the hairpin oligonucleotides of the present invention to linear oligonucleotides in an amplification reaction to produce varying sized amplification products.
Figure 17B:
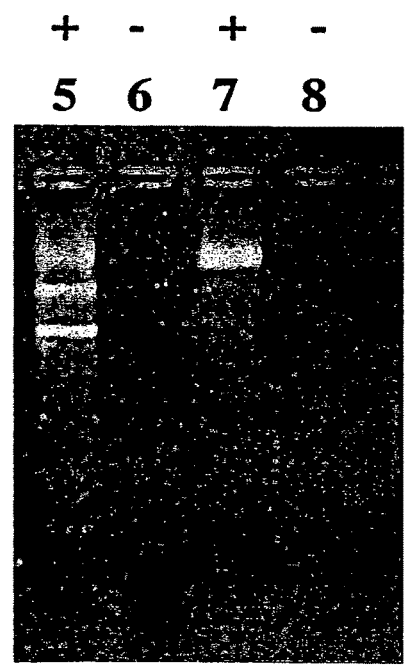
Figure 18A:
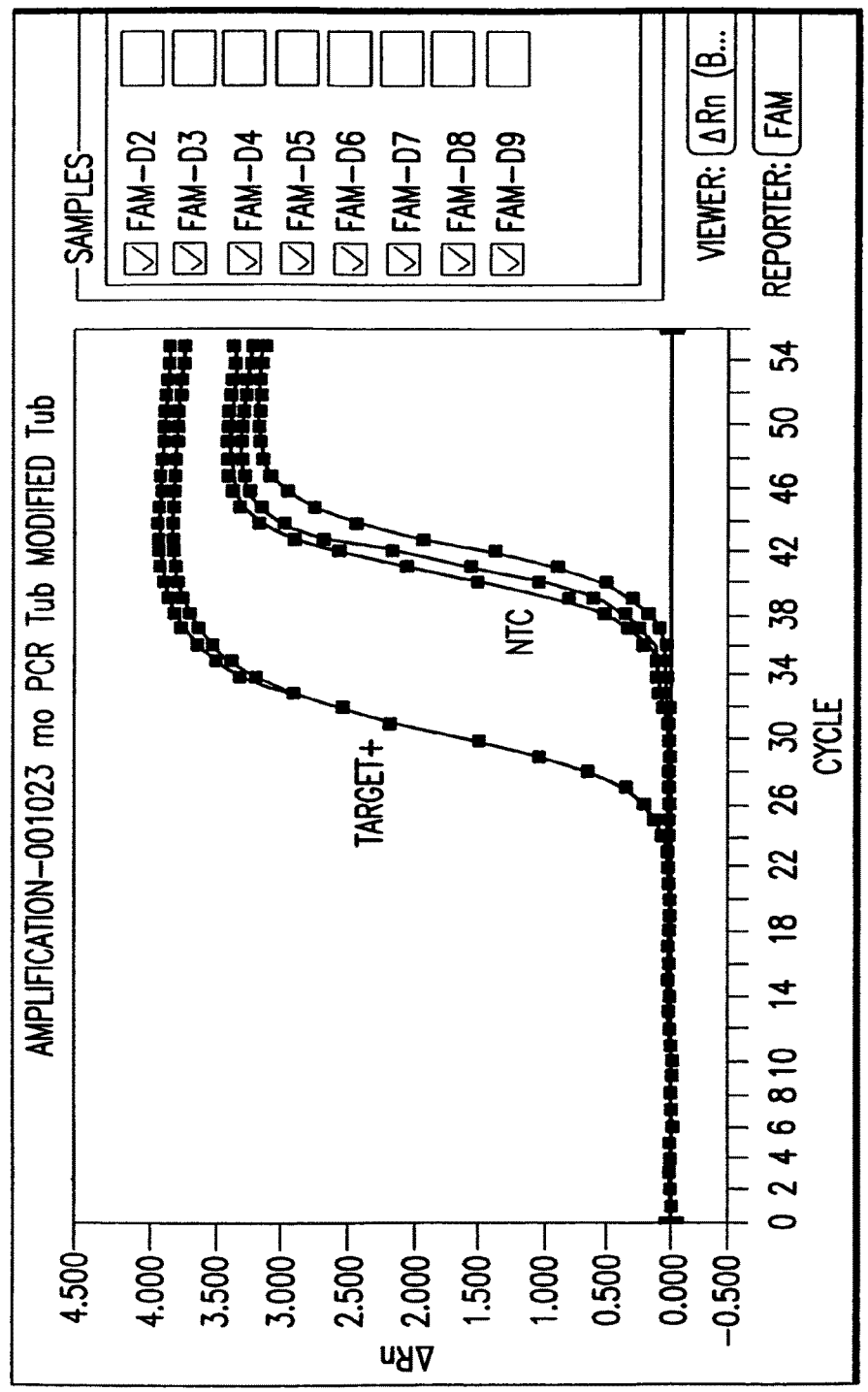
FIG. 18A-D are line graphs of fluorescence intensity as a function of number of cycles of amplification performed which show detection of human tuberin cDNA by PCR with hairpin primers nonmodified (18A) and modified at the 5'-ends of both primers with 2'-O-Me (18B), 5'-5' linkage (18C) and forward primer modified with 2'-O-Me and reverse primer with 5'-5' linkage (18D). PCR was performed as described in Example 15. "F"=forward primer; "R"=reverse primer; and "NTC"=no target control.
Figure 18B:
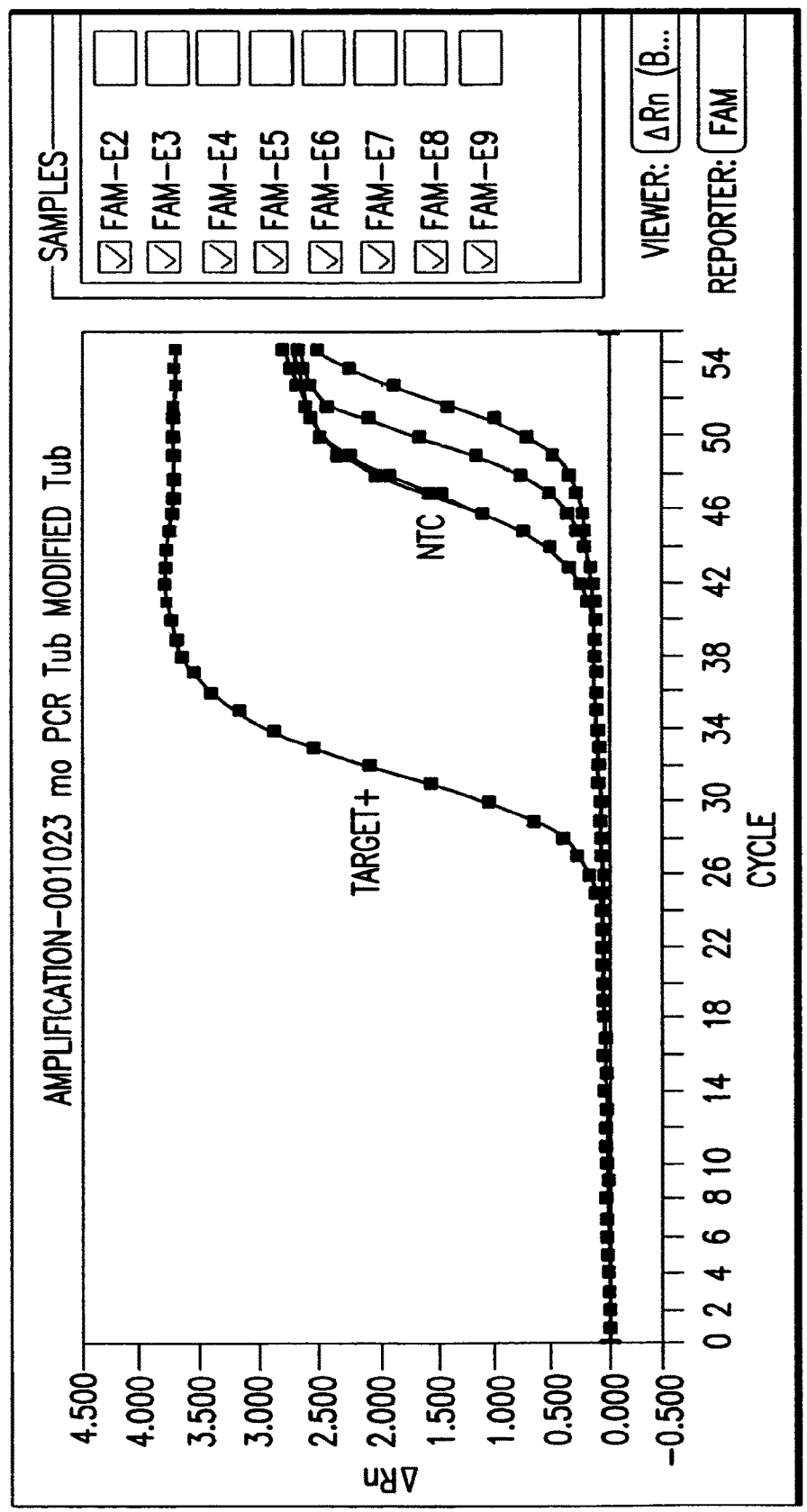
Figure 18C:
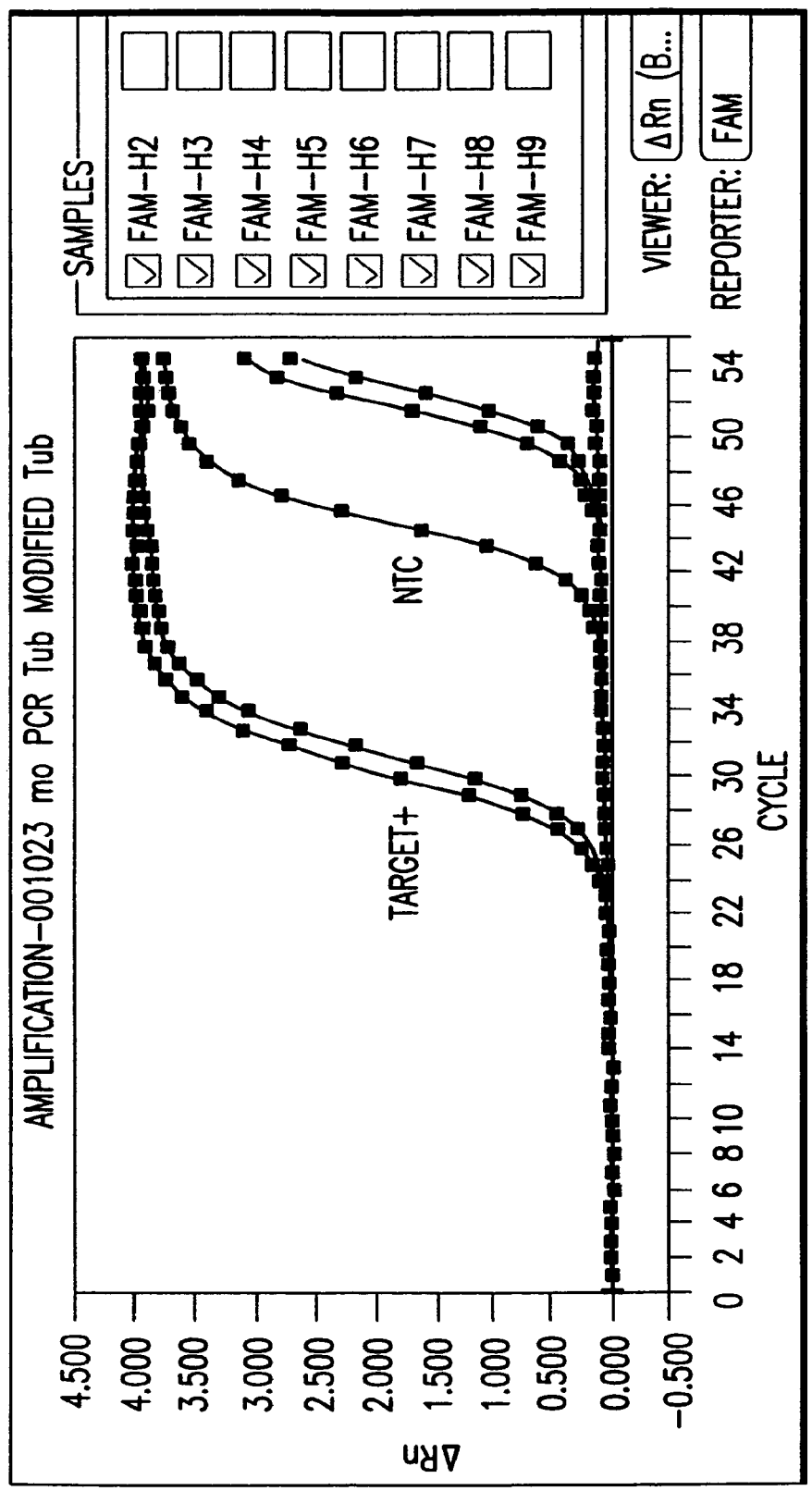
Figure 18D:
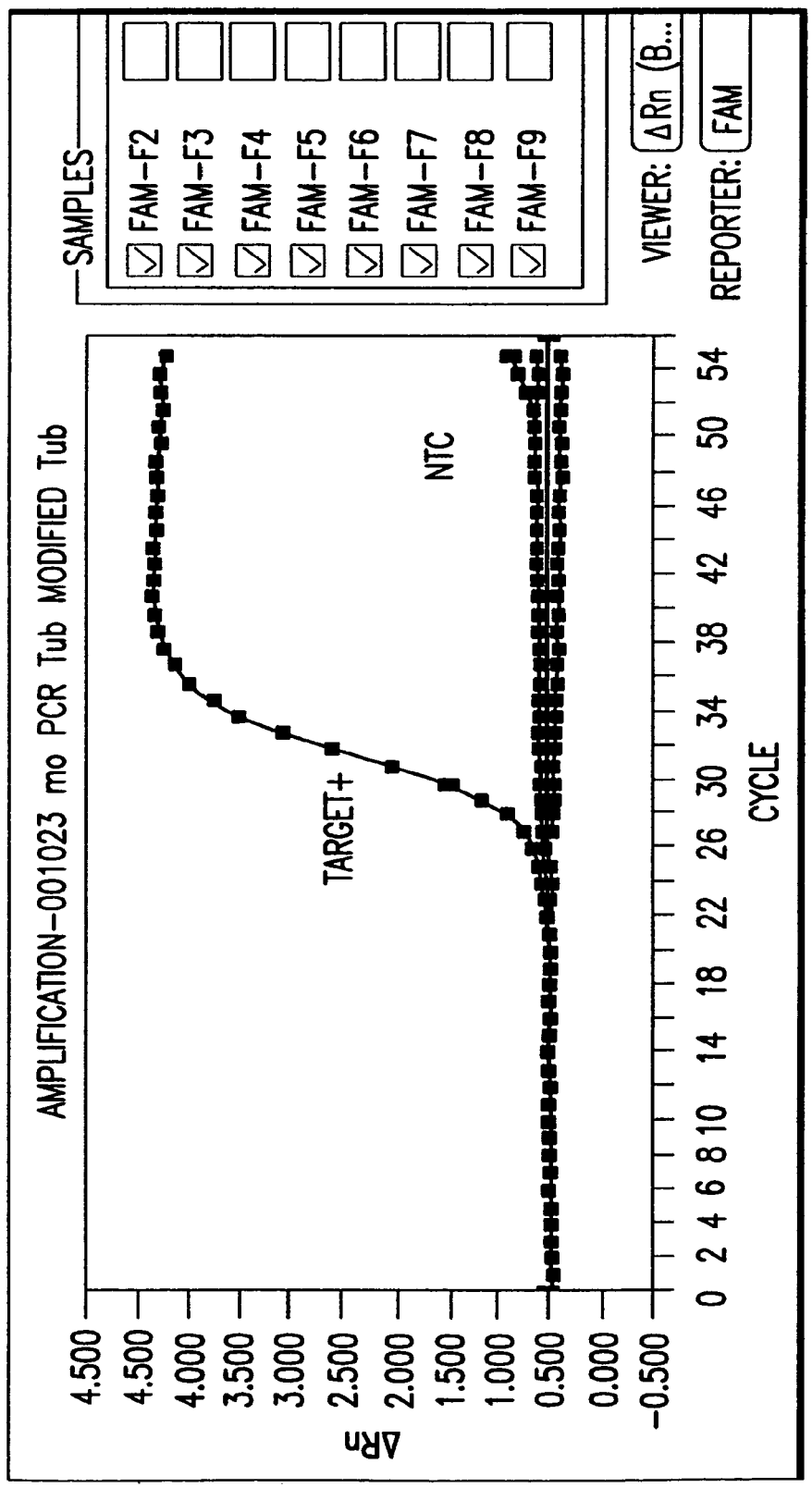
Figure 19A:
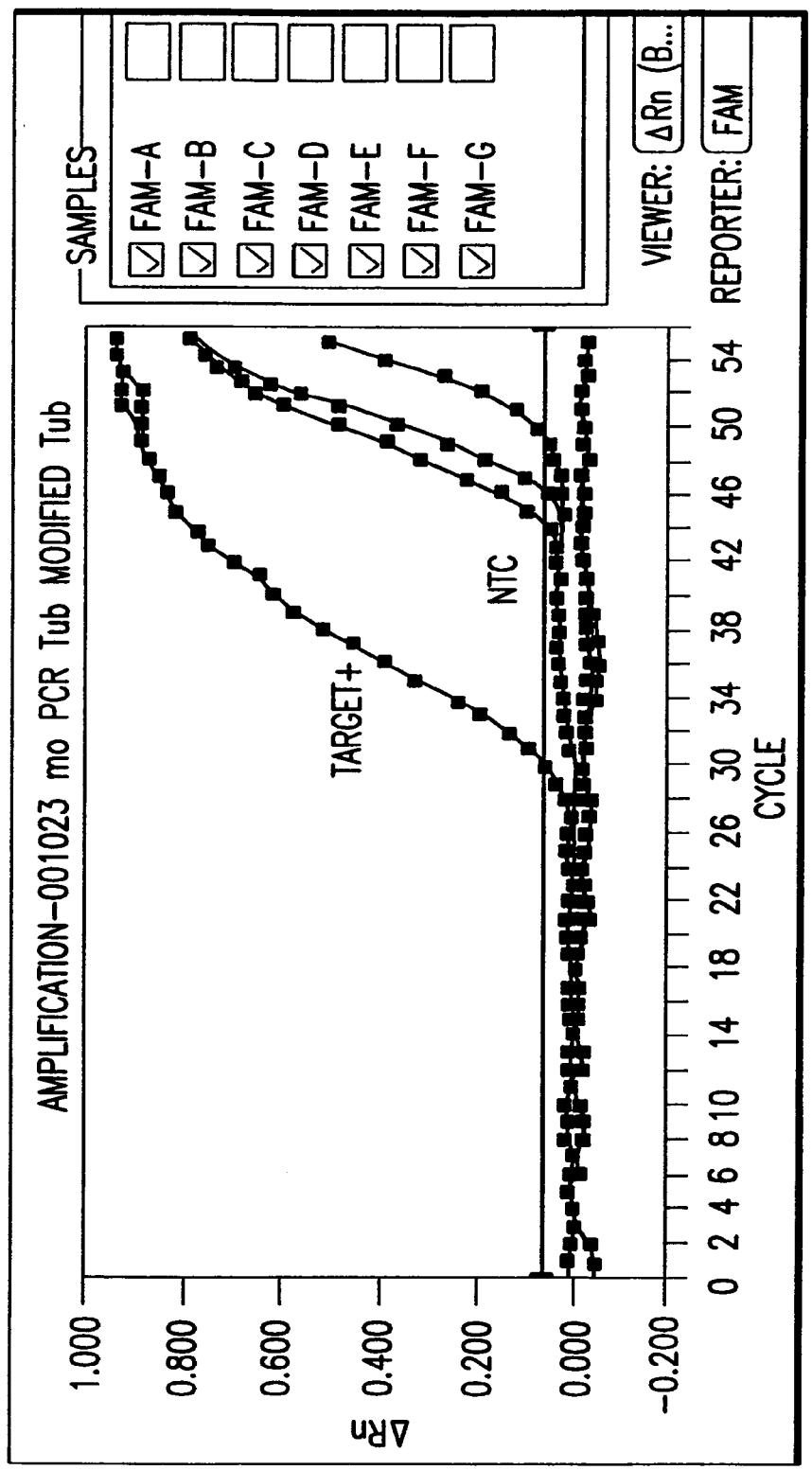
FIGS. 19A-D are line graphs of fluorescence intensity as a function of number of cycles of amplification performed which show detection of human tuberin cDNA by PCR with hairpin primers nonmodified (FIG. 19A) and modified at the 5'-ends with C3-amino (FIG. 19B), C6-amino (FIG. 19C) and biotin (FIG. 19D). PCR was performed as described in Example 16. "R"=reverse primer.
Figure 19B:
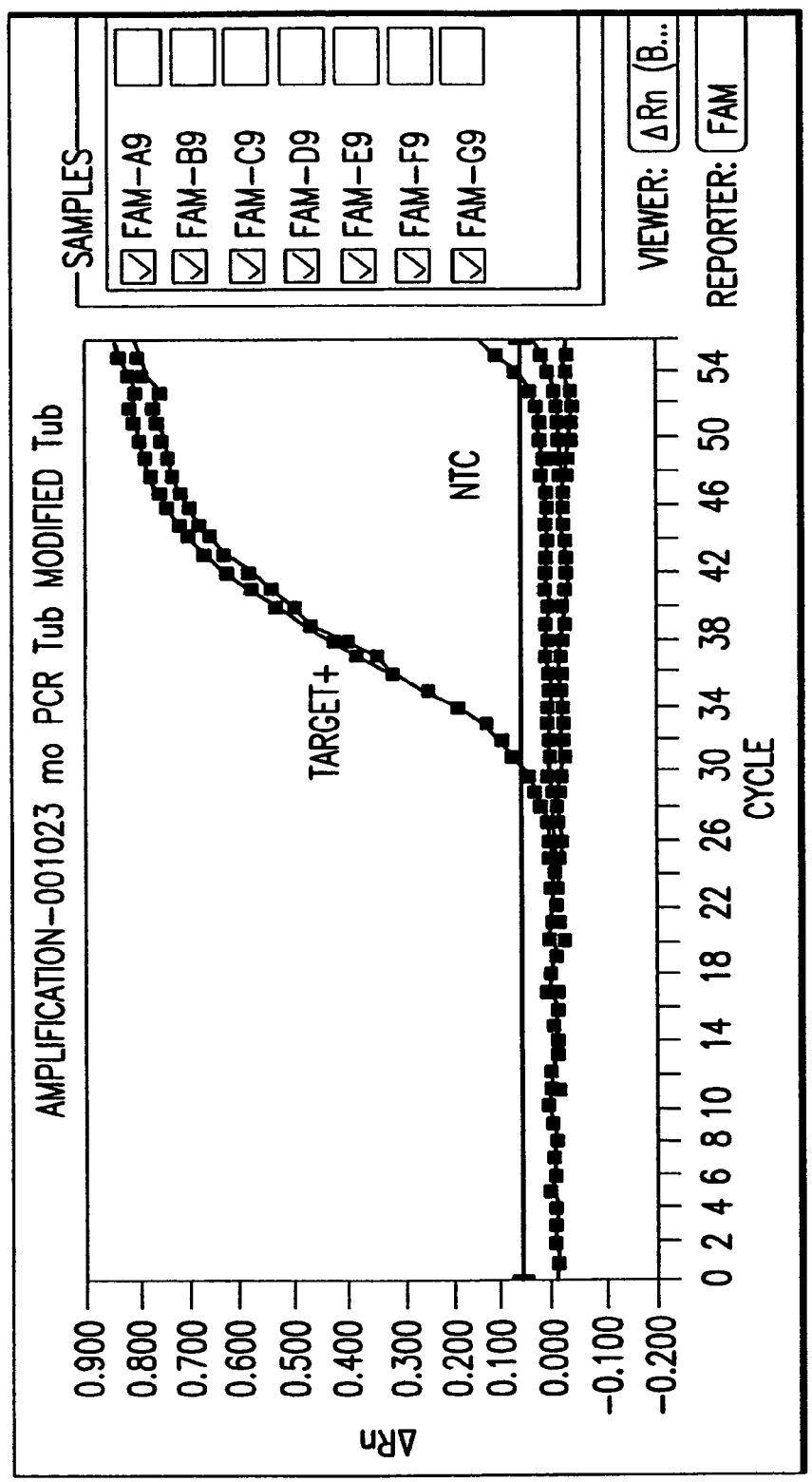
Figure 19C:
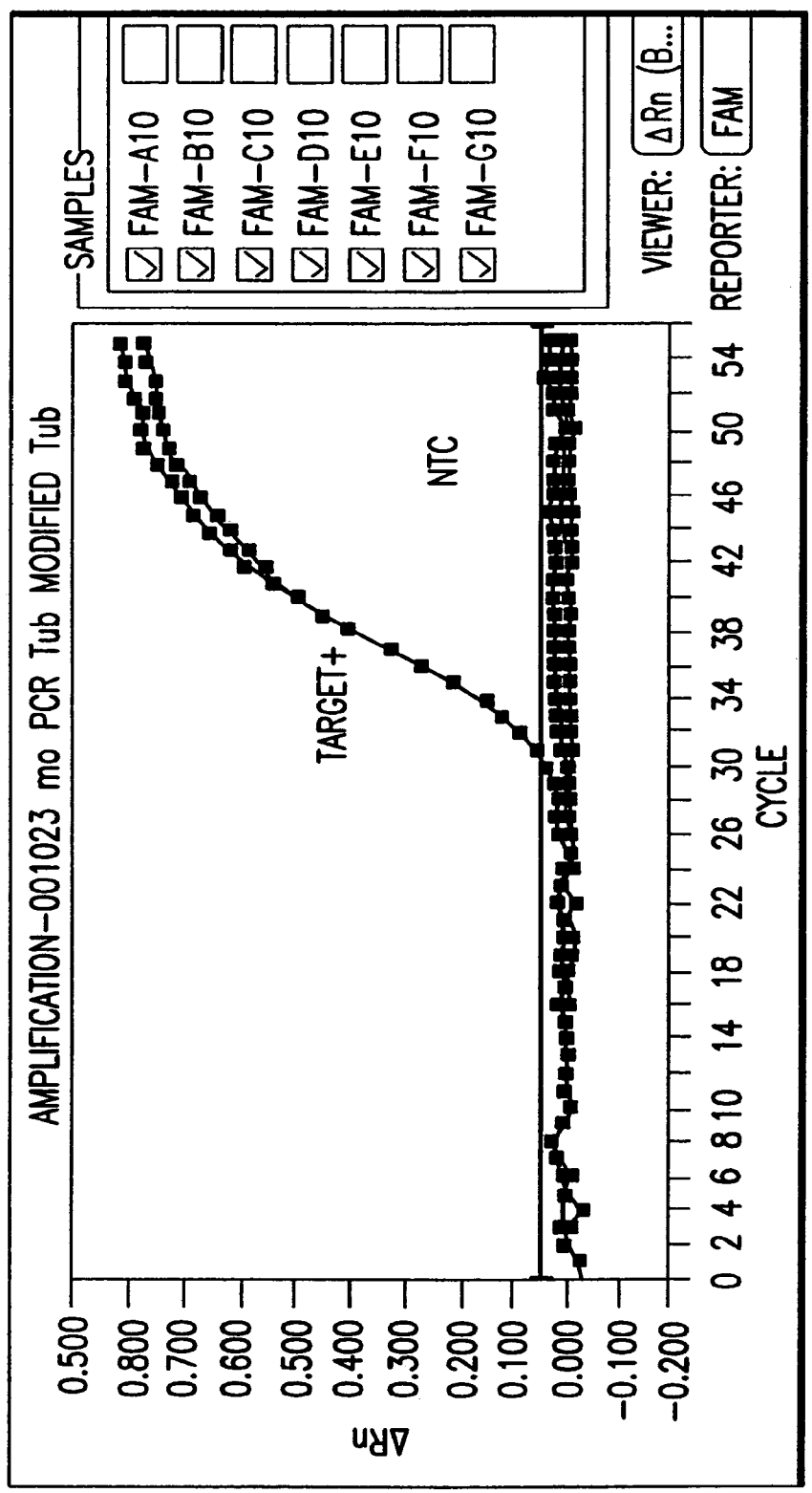
Figure 19D:
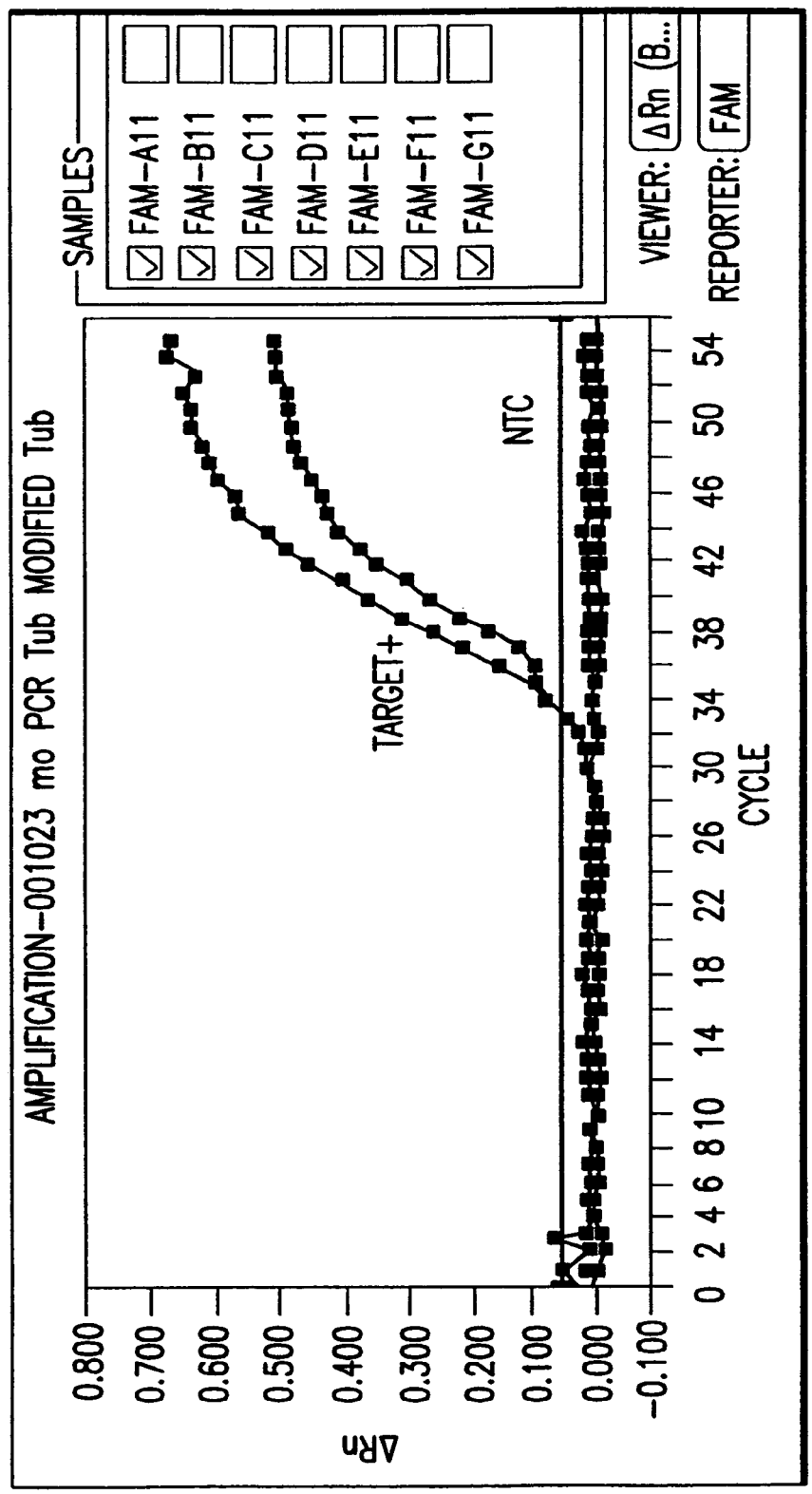
Figure 20A:
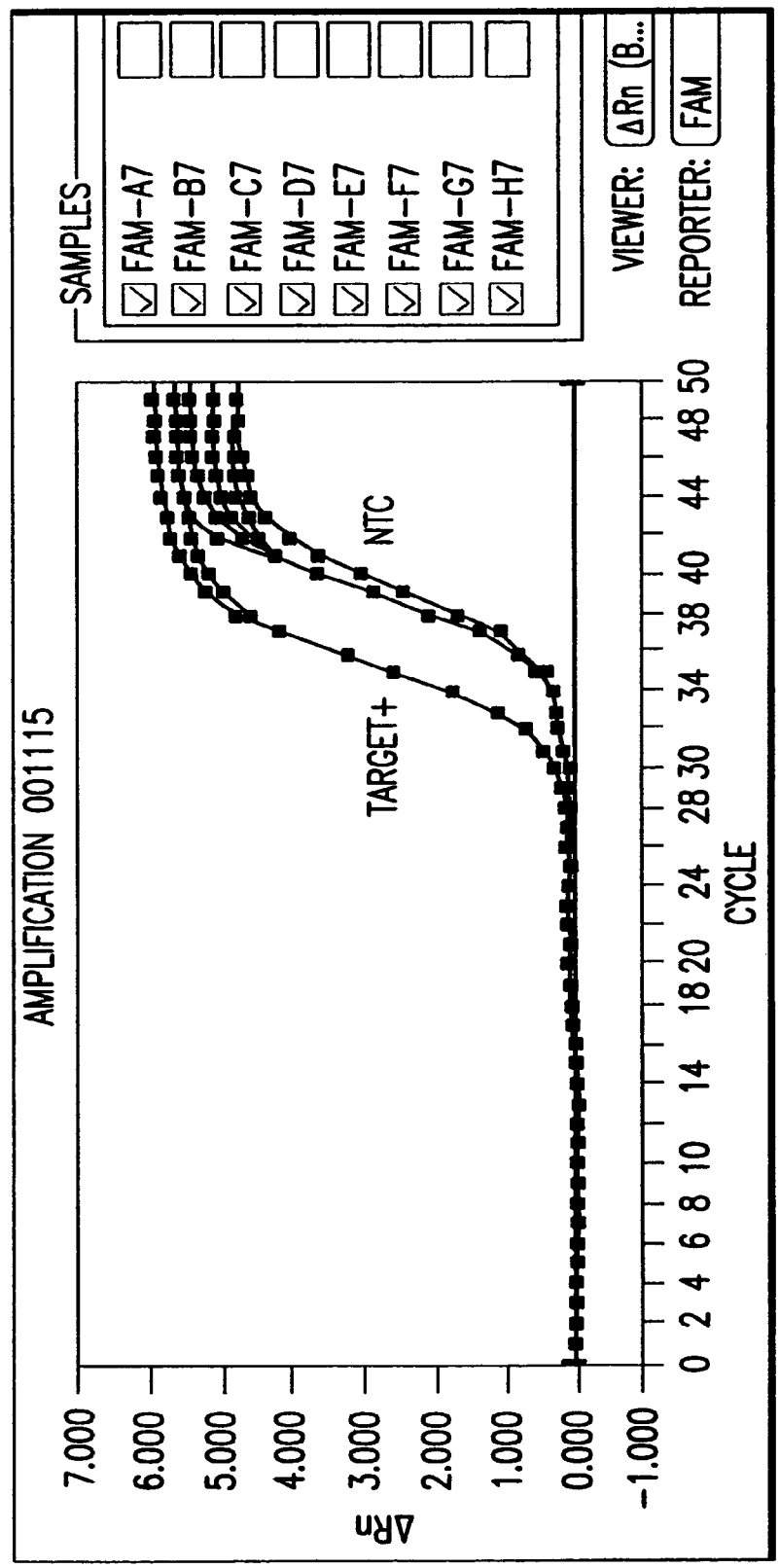
FIGS. 20A-D are line graphs of fluorescence intensity as a function of number of cycles of amplification performed which show detection of human tuberin cDNA (FIGS. 20A, 20B) and RDS genomic DNA (FIGS. 20C, 20D) by PCR with blunt end hairpin primers (FIGS. 20A, 20C) and hairpin primers with extended 3'-ends (FIGS. 20B, 20D). PCR was performed as described in Example 17.
Figure 20B:
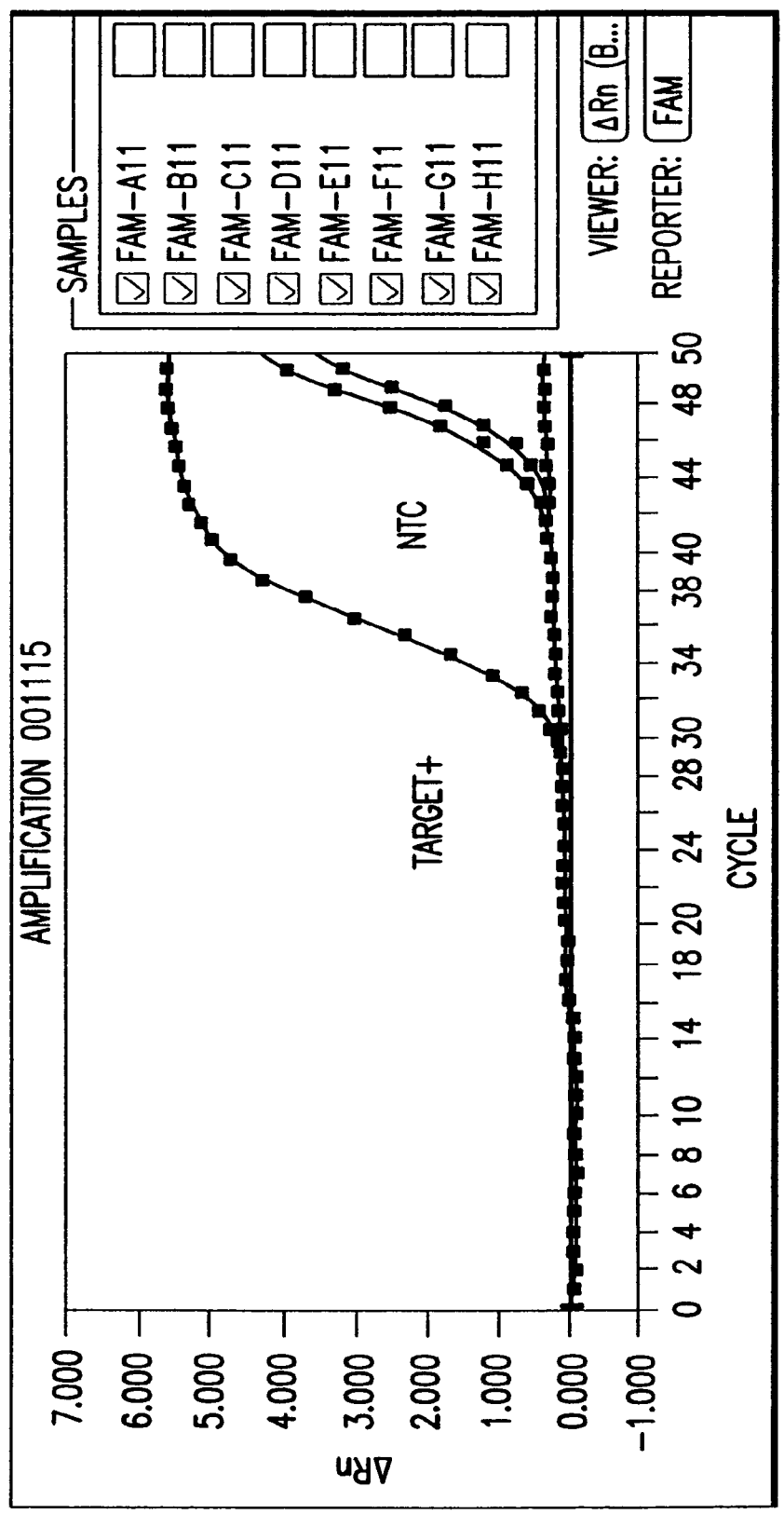
Figure 20C:
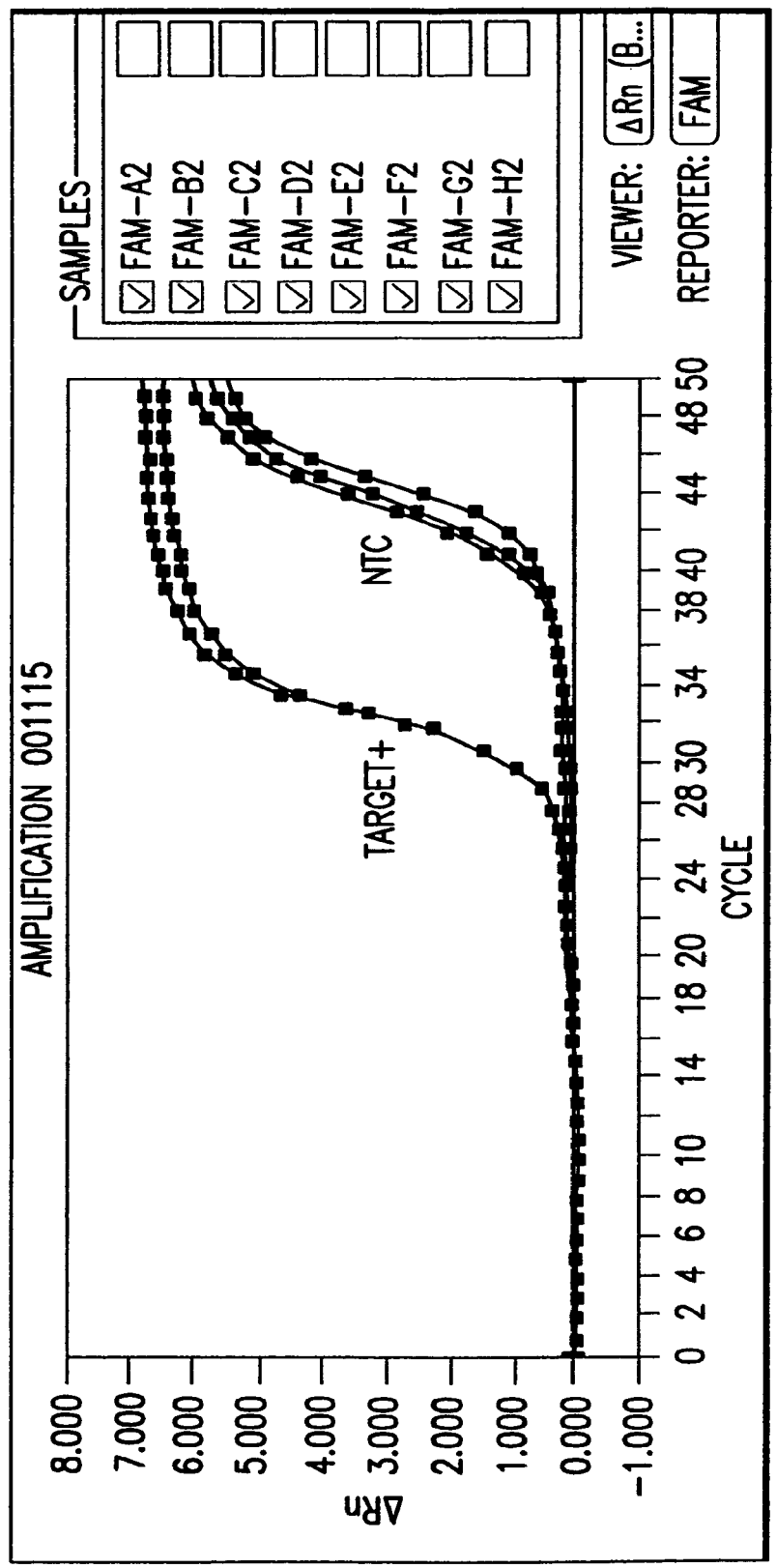
Figure 20D:
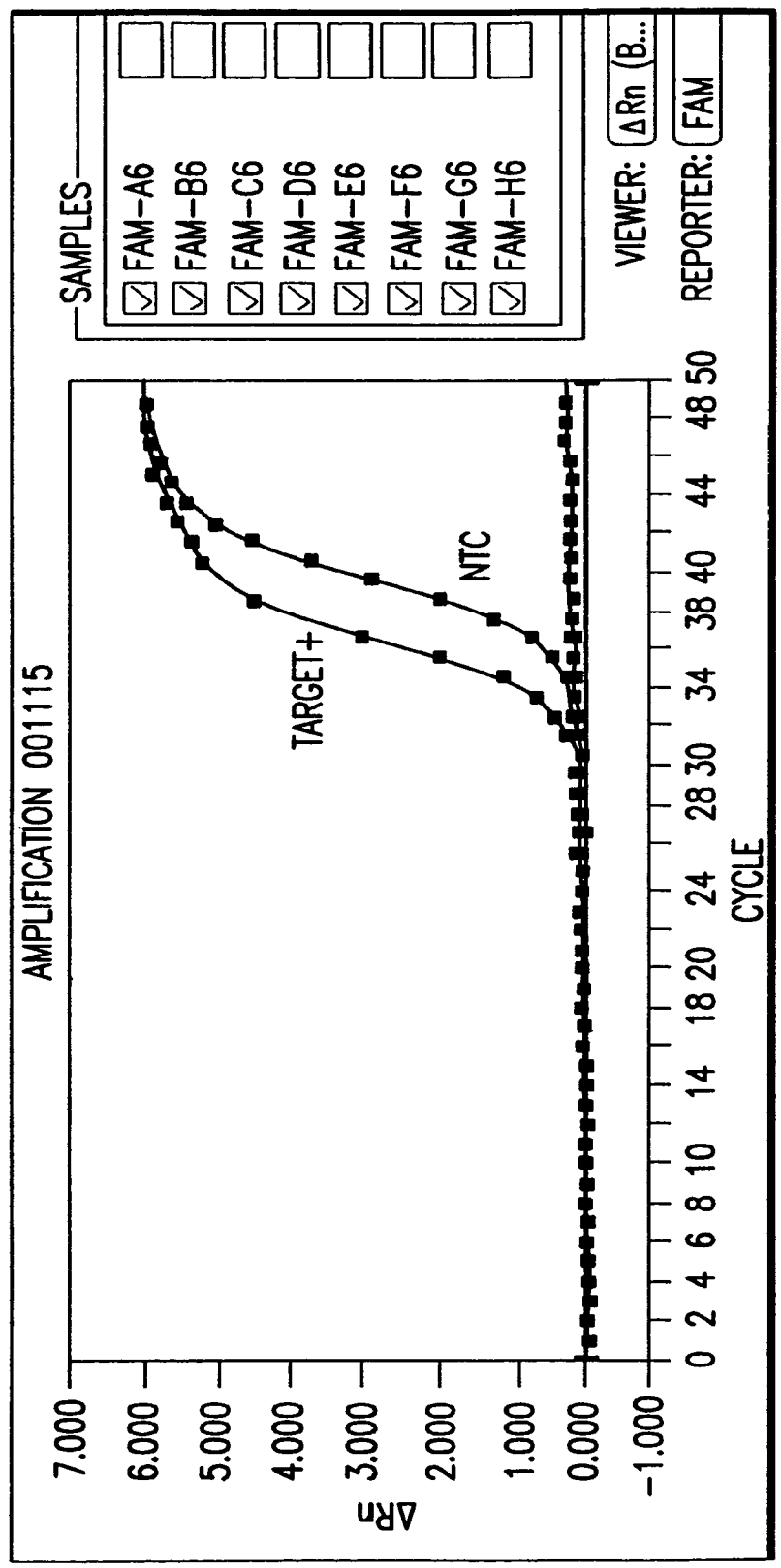

Similar results were obtained during the amplification of another human gene Necrosis Factor 2 (NF2). 1.3 and 1.6 kb fragments were amplified using PLATINUM® Taq DNA polymerase in PCR SuperMix (Invitrogen Corporation (Life Technologies Division)). For the amplification of the 1.3 kb fragment, oligos 24 (SEQ ID NO:36) and 25 (SEQ ID NO:37) (linear) or 26 (SEQ ID NO:38) and 27 (SEQ ID NO:39) (hairpin) were used as primers. For the amplification of the 1.6 kb fragment oligos 28 (SEQ ID NO:40) and 29 (SEQ ID NO:41) (linear) or 30 (SEQ ID NO:42) and 31 (SEQ ID NO:43) (hairpin) were used as primers. PCR was performed on 50 ng of human genomic DNA as follows: 2 minutes at 94° C. followed by 35 cycles of: 30 seconds at 94° C., 30 seconds at 62° C. and 4 minutes at 68° C. The results are shown in FIGS. 17A-B. Lane M contains molecular weight markers. + indicates the presence of template DNA and – indicates the no DNA control. Lane 1 shows the results using linear primers for the 1.3 kb fragment in the presence of template DNA. Lane 2 shows the no DNA control for lane 1. Lane 3 shows the results obtained using the hairpin primer for the 1.3 kb fragment while lane 4 is the no DNA control for lane 3. Lane 5 shows the results obtained using the linear primers for the 1.6 kb fragment while lane 6 is the no DNA control for lane 5. Lane 7 shows the results obtained using the hairpin primers for the 1.6 kb fragment while lane 8 is the no DNA control for lane 7. In both instances, the hairpin primers gave more and cleaner amplification products of the appropriate size than linear primers of the same gene specific sequence.

Example 15

The Occurrence of Primer-Dimers can be Reduced if the 5' End of Hairpin Primers is Modified with 2'-O Methyl, 5'-5' Phosphodiester Bond Human tuberin cDNA was amplified by PCR as in Example 2, except the concentration of $MgCl_2$ was 3 mM and 3% glycerol was added. SYBR Green was used for detection (Molecular probes, 30,000 fold dilution). For each primer set, 8 reactions were performed: two with target added and six as no target controls (NTC). The frequency of primer-dimer formation and the cycle number where they occur were used as a measure of primer-dimer artifact.

Oligonucleotides 32 and 33 were used as forward and reverse primers:

| | |
|---|---|
| Oligo 32 tuberin forward primer/Hp | 5'-caa cat aag atc gcc gtc ctg tat gtt g (SEQ ID NO: 44) |
| Oligo 33 Tuberin reverse primer/Hp | 5'-cat caa aag ttg aac tgg ccc ttg atg (SEQ ID NO: 45) |

The results in FIGS. 18A-D show that modifications do not have any negative effect on target amplification (target +). However primer-dimer formation was greatly reduced. Similar results may also be obtained with modifications near the 5' end of the primers. In FIGS. 18A-D:

18A—forward and reverse primers not modified at the 5'-ends;

18B—nucleotides at the 5'-ends of both primers were substituted with 2'-O-methyl analogues;

18C—nucleotides at the 5'-ends of both primers utilize a 5'-5' phosphodiester bond;

18D—forward primer was modified with 2'-O-methyl and reverse one with a 5'-5' link.

Example 16

The occurrence of primer-dimers can be reduced if the 5'-end of hairpin primers is modified with C3-amino, C6-amino or biotin.

Human tuberin cDNA was amplified by PCR as in Example 2. Fluorescein-labeled forward primers were used for detection. For each primer set, 8 reactions were performed: two with target added and six as no target controls (NTC). The frequency of primer-dimer formation and the cycle number where they occur were used as a measure of primer-dimer artifact.

Oligonucleotides 34 and 33 were used as forward and reverse primers:

```
Oligo 34 tuberin forward   5'-caa cat aag atc gcc gtc
primer/Hp/FLUO             ctg tat gTt g
                           (SEQ ID NO: 46)

Oligo 35 tuberin forward   5'-aac ata caa aga tcg ccg
primer/H4                  tcc tgt atg ttg
                           (SEQ ID NO: 47)
```

The results in FIGS. 19A-D show that primer-dimer formation in no-target controls was greatly reduced. Similar results may be obtained with modifications near the 5' end of the primers. In FIGS. 19A-D:

19A—forward and reverse primers not modified at the 5'-ends;

19B—5'-ends of both primers were modified with C3-amino modifier (Glen Research);

19C—5'-ends of both primers were modified with C6-amino modifier (Glen Research);

19D—5' ends of both primers were modified with biotin (Glen Research).

Example 17

Effect of 3'-Extending Nucleotide on Primer-Dimer Formation

As noted above, an alternative method of minimizing primer-dimer formation while using hairpin primers is to make oligonucleotides with the 3'-end extended by 1 or 2 or more nucleotides that are not complementary to each other. For this example, two targets were selected that demonstrated significant primer-dimer artifacts under certain conditions: human tuberin cDNA and human RDS gene. PCR was performed as in Example 2, except the concentration of $MgCl_2$ was 3 mM and 3% glycerol was added. SYBR Green was used for detection (Molecular probes, 30,000 fold dilution). For each primer set, 8 reactions were performed: two with target added and six as no target controls (NTC). The frequency of primer-dimer formation and the cycle number where they occur were used as a measure of primer-dimer artifact.

```
Oligo 32 tuberin  5'-caa cat aag atc gcc gtc ctg tat
forward primer/   gtt g (SEQ ID NO: 44)
Hp Oligo 33 Tuberin  5'-cat caa aag ttg aac tgg ccc ttg
reverse primer/   atg (SEQ ID NO: 45)
Hp Oligo 35 tuberin  5'-aac ata caa aga tcg ccg tcc tgt
forward primer/   atg ttg (SEQ ID NO: 47)
H4

Oligo 36 Tuberin  5'-atc aag aag ttg aac tgg ccc ttg
reverse primer/   atg (SEQ ID NO: 51)
H4

Oligo 37 fr RDS   5'-cta aac tga cgg tgg aat tta agt
forward primer/   tta g (SEQ ID NO: 52)
Hp Oligo 38 frRDS    5'-gat tct ctt gct cca tga tta aag
reverse primer/   aat c (SEQ ID NO: 53)
Hp Oligo 39 fr RDS   5'-aaa ctt act gac ggt gga att taa
forward primer/   gtt ta (SEQ ID NO: 54)
H4

Oligo 40 frRDS    5'-att ctt ctt gct cca tga tta aag
reverse primer/   aat c (SEQ ID NO: 55)
H3
```

The results in FIGS. 20A-D show that primer-dimer artifact is significantly reduced when hairpin primers with extended 3'-ends were used. In FIGS. 20A-D:

20A—tuberin cDNA was amplified using forward and reverse primers as blunt end hairpins (Oligos 32 and 33);

20B—tuberin cDNA was amplified using forward and reverse primers with extended 3'-ends (Oligos 35 and 36);

20C—human RDS gene was amplified using forward and reverse primers as blunt end hairpins (Oligos 37 and 38);

20D—human RDS gene was amplified using forward and reverse with one extended 3'-nucleotide (Oligos 39 and 40).

Example 18

Figure 21:
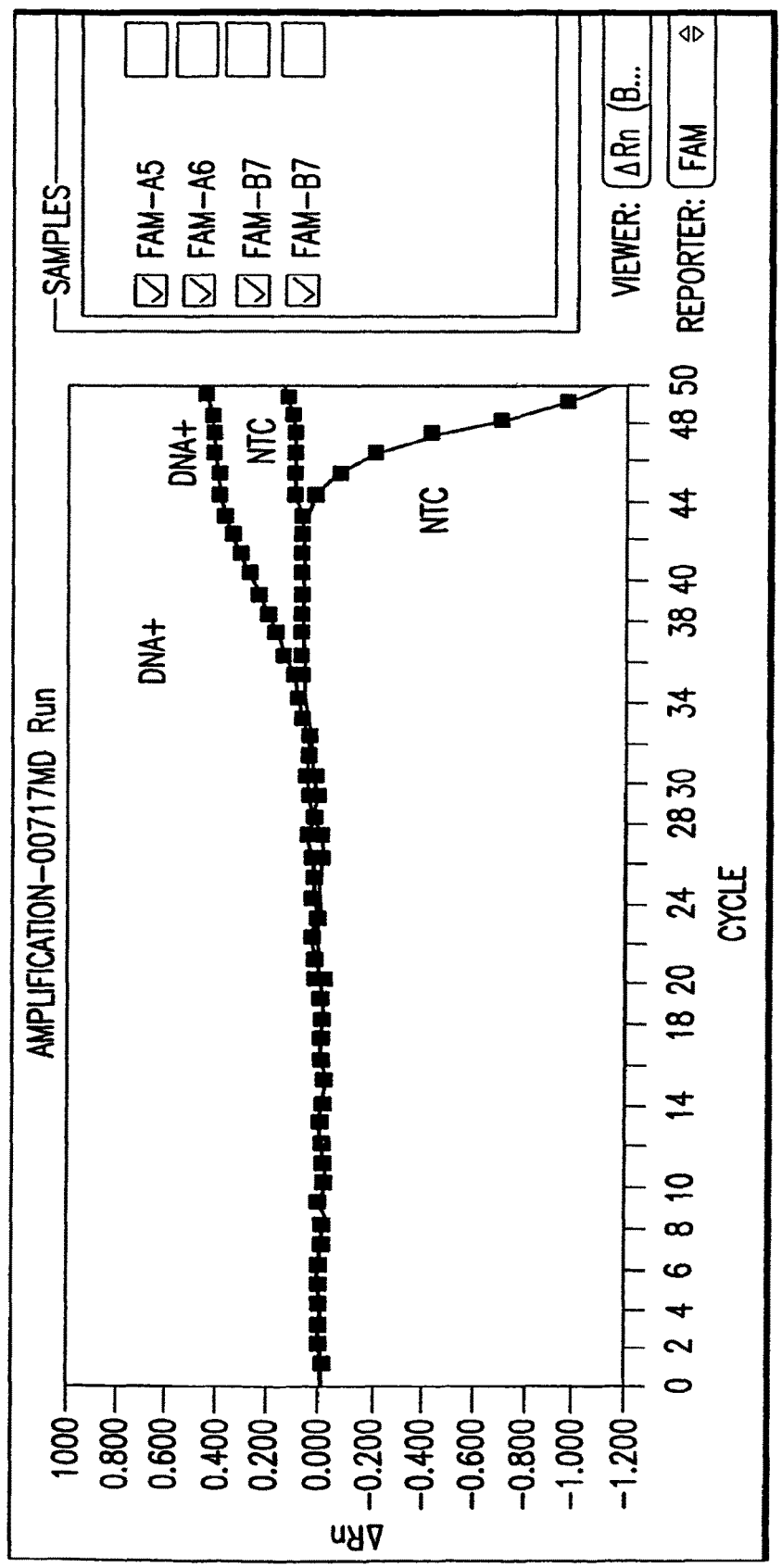
FIG. 21 is a line graph of fluorescence intensity as a function of number of cycles of amplification performed which shows detection of 5 ng of genomic DNA (A-allele) by PCR with A-specific or B-specific forward primers (Oligos 41, 42) labeled with DABCYL and reverse primer labeled with FAM (Oligo 43). PCR was performed as described in Example 18.

Primer-Dimer can be Made Non-Fluorescent by Putting a Fluorophore on One of the Primers and a Quencher on Another The method described in this example does not prevent primer-dimer formation, but makes them invisible. This approach was demonstrated in allele-specific PCR of human gene WIAE-1328. PCR conditions are described in Example 2. Reverse primer was the same Oligo 43 labeled with fluorescein. Forward primers for A and B alleles were labeled with DABCYL as a quencher (Oligos 41 and 42). In FIG. 21, one can see that the fluorescent signal in the no-target control is going down along with primer-dimer formation. At the same time, the normal increase of the signal in the presence of target is observed.

```
Oligo 41 WIAF-forward   5'-tga ggc cgc cat atc tcc
primer 1328A/dabcyl     Tca (SEQ ID NO: 56)

Oligo 42 WIAF-forward   5'-gga ggc cgc cat atc tcc
primer 1328B/dabcyl     Tcc( SEQ ID NO: 57)

Oligo 43 WIAF-reverse   5'-gag ata aaa taa aat tca
primer 1328A/FAM        tgg tgt atc Tc (SEQ ID
                        NO: 58)
```

Example 19

Multiplex PCR of IL4 cDNA and Beta-Actin

Figure 22A:
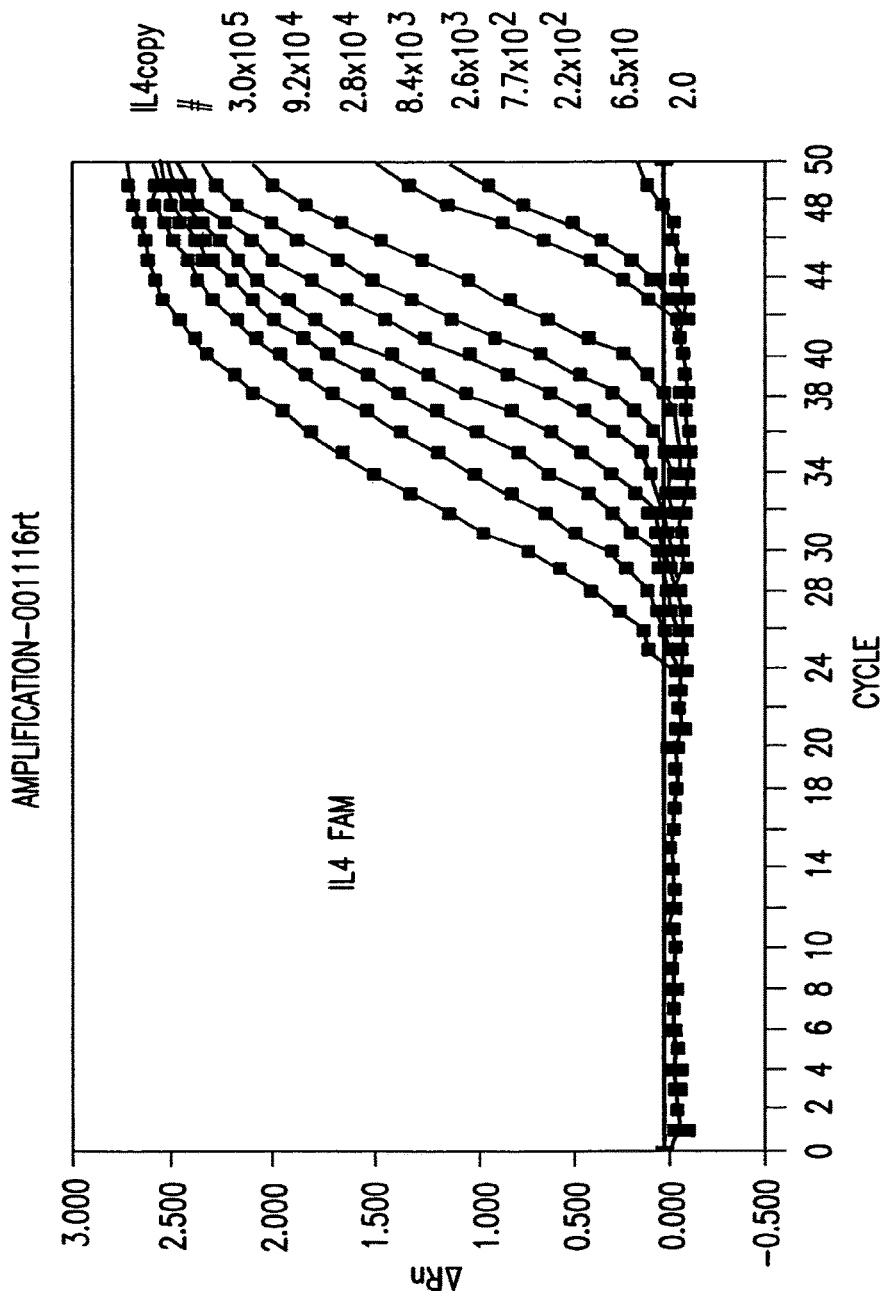
FIGS. 22A-B are line graphs of fluorescence intensity as a function of number of cycles of amplification performed which show detection of IL4 cDNA using FAM labeled primer (FIG. 22A) and human beta-actin using JOE labeled primer (FIG. 22B). PCR was performed as described in Example 19.
Figure 22B:
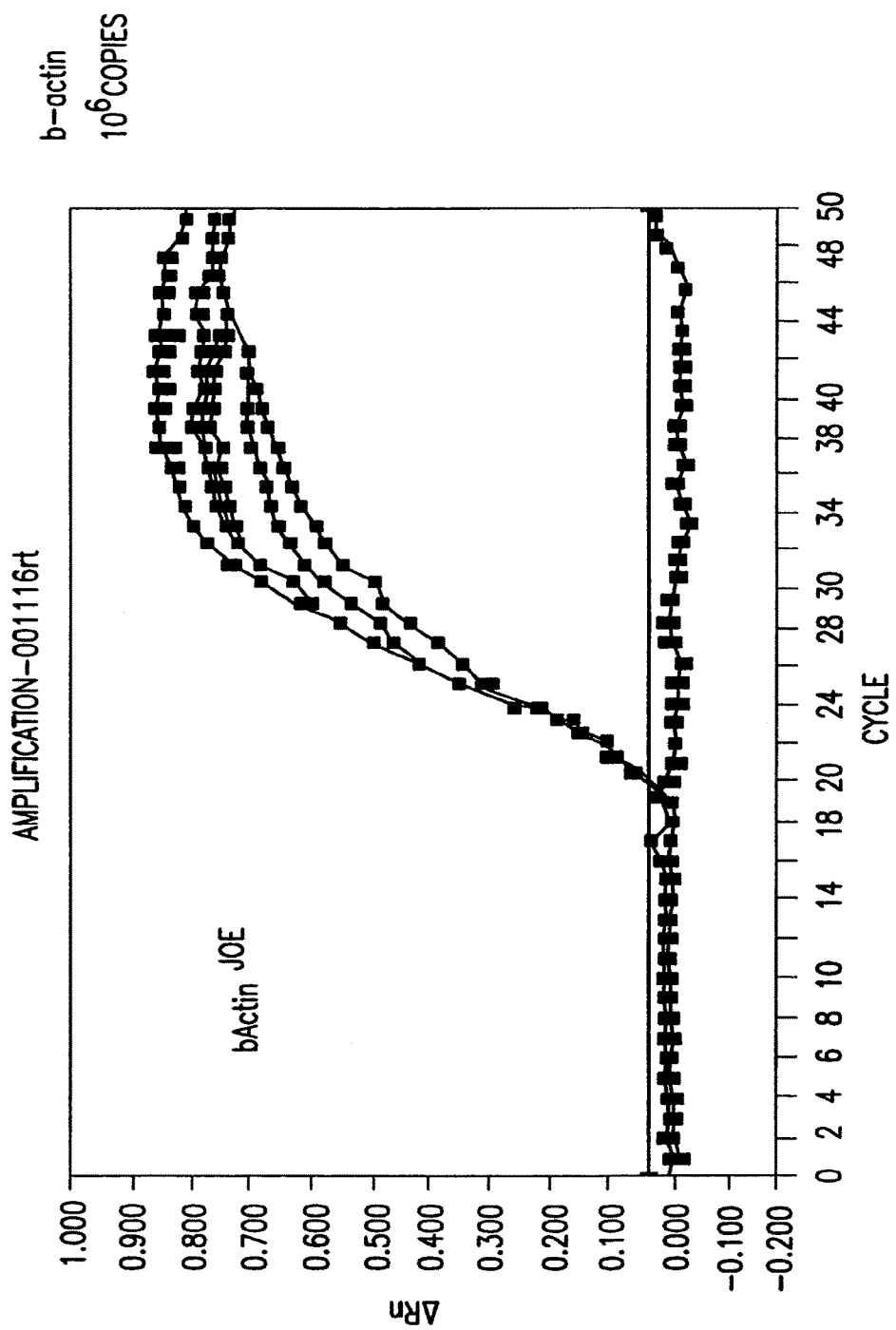

This example demonstrates the multiplex capability of the inventive method of detection. Two primers for IL4 cDNA were used forward (Oligo 46) and reverse labeled with fluorescein (Oligo 47). To amplify beta actin, forward primer was labeled with JOE (Oligo 44) and the reverse primer was unlabeled (Oligo 45). All four primers were amplified in the same tube under the conditions described in Example 2. The concentration of beta actin target was kept constant ($10^6$ copies per reaction) and the concentration of IL4 target varied from 2 copies to $3 \times 10^5$ copies. Fluorescence of two fluorophores was detected in real time. Results presented in FIGS. 22A-B demonstrate high sensitivity and dynamic range of the detection.

Oligo 44 HumAct 5'-gat ctt cgg cac cca gca caa tga
forward 1022-Hp/ aga Tc (SEQ ID NO: 59)
JOE
Oligo 45 HumAct 5'-atg ctt caa gtc ata gtc cgc cta
reverse 1160-Hp2 gaa gca t (SEQ ID NO: 60)

Oligo 46 IL4 5'-aag atg tcg agt tga ccg taa cag
forward 211-Hp2 aca tct t (SEQ ID NO: 61)
Oligo 47 IL4 5'-cta cag tcc ttc tca tgg tgg ctg
reverse 300-Hp1/ Tag (SEQ ID NO: 62)
FAM Example 20

Universal Detection Primer Format Coupled to
Allele Specific PCR

Figure 33:
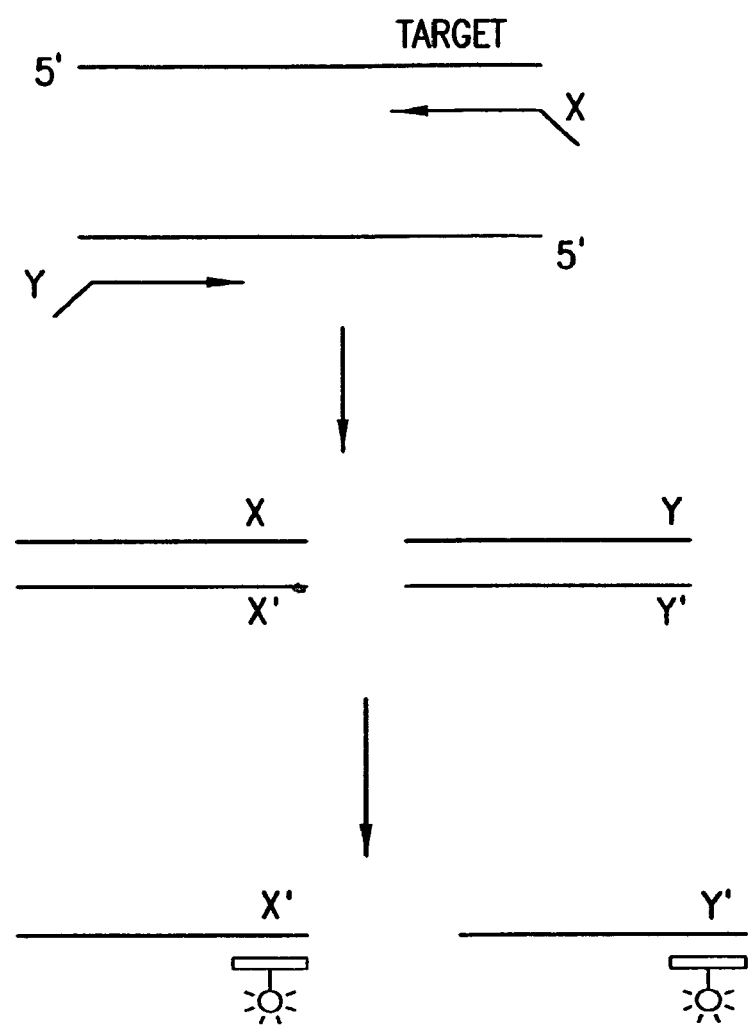
FIG. 33 is a schematic representation of using a universal detection oligonucleotide and an adapter coupled to allelic specific PCR. See Example 20.

The fluorescent modified oligonucleotides can be used in a format which will allow the primer to detect any gene-specific nucleotide target sequence. More specifically, fluorogenic detection primers of a design described in previous examples were used to detect the presence of PCR product in a "universal" primer format which requires three primers. The methodology requires adding a sequence tail (tail X) to the 5'-end of a gene-specific target primer used in the PCR. Tail X is non-complementary to the target. The tailed sequence is identical to the 3'-sequence of the fluorogenic detection primer. The second primer is the universal primer which is at least partially identical to tail X and labeled with a fluorescent moiety (linear or hairpin). The third primer is a regular PCR primer. If the first primer is forward, then the third primer is reverse and opposite. Thus, both forward and reverse primers and a Universal primer may be used. The forward and reverse primers may have X tails or one may have an X tail and the other may have a Y tail. The universal primer may contain the X tail sequence or two universal primers may be used wherein one contains the X tail sequence and one contains the Y tail sequence. The amplicon generated in the early cycles of PCR serves as template for the universal detection primer in the later cycles. See FIG. 33.

In this example, the gene specific sequences were designed for allele-specific PCR, but the universal detection format can be used for any target by adding a 5' tail of appropriate sequence to the gene specific primer. PCR was performed in a 50 µl volume of reaction buffer (20 mM Tris-HCl (pH 8.4), 50 mM KCl) containing 1.5 mM MgCl₂, 0.2 mM each dNTP, 2.5 U PLATINUM® Taq DNA polymerase, 0.2 µM forward universal labeled detection primer, 0.02 µM forward allele specific tailed primer, and 0.2 µM reverse primer. Thermal cycling and fluorescent detection were performed on an ABI 7700 Sequence Detection System using a 2 minute hold at 25° C., a 2 minute hold at 94° C., and 40 cycles of 30 seconds at 94° C., 30 seconds at 55° C. and 30 seconds at 72° C., and a 2 minute hold at 25° C.

Figure 23:
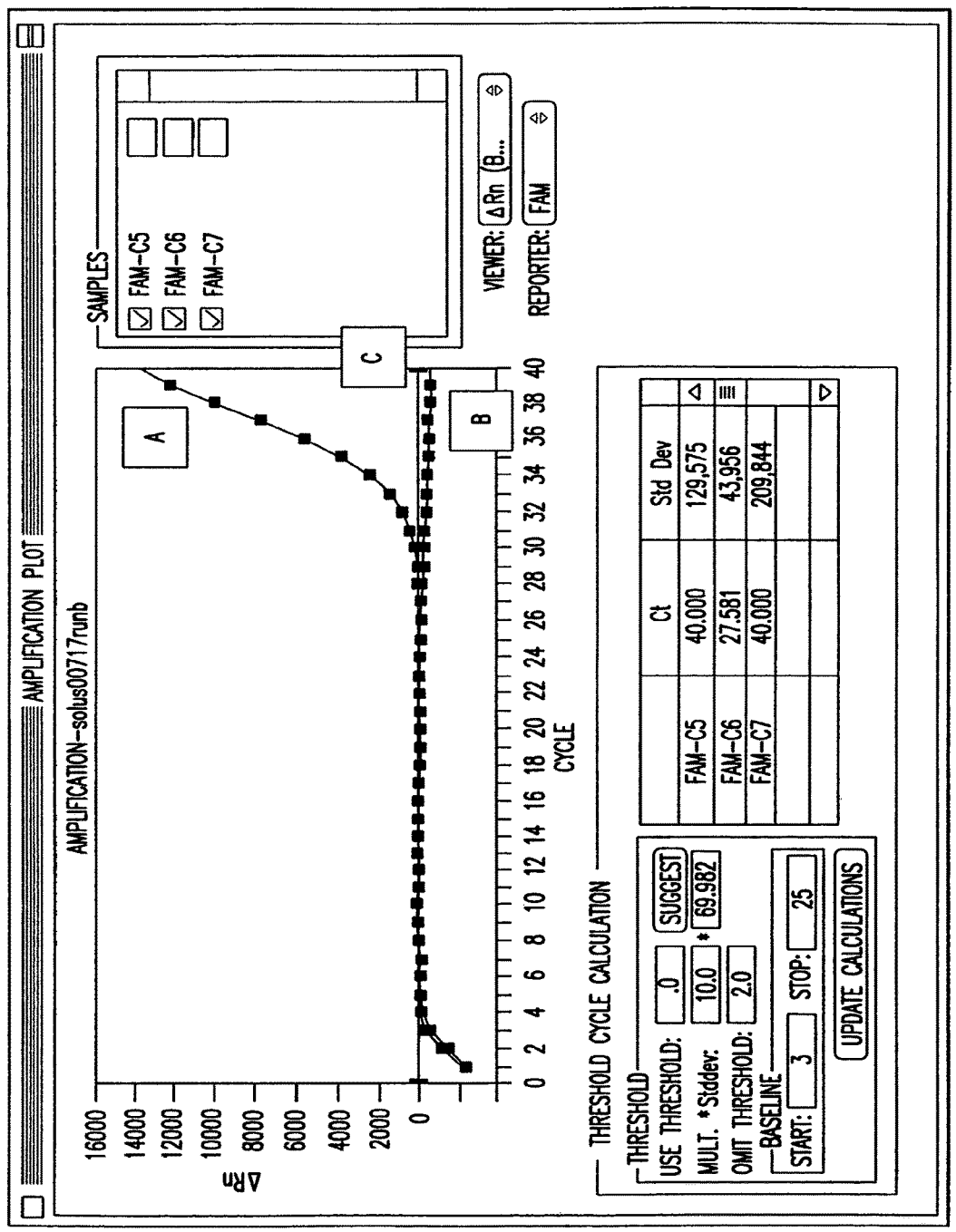
FIG. 23 is a line graph of fluorescence intensity as a function of number of cycles of amplification performed which shows detection of human RDS alleles using FAM labeled universal detection primer. PCR was performed as described in Example 20. (23A) shows the detection of the RDS A allele using the A-specific primer on AA homozygote human DNA. (23B) indicates the discrimination of the A-specific primer (inability of the A-specific primer to detect BB homozygote DNA). (23C) indicates that there is no detectable amplification in a no DNA template control.

Primer sequences used in FIG. 23 were Oligo 48 for the universal detection primer, Oligo 49 for the forward allele A-specific primer, and Oligo 50 for the reverse primer. Universal format detection and allelic discrimination were equivalent using forward allele B-specific primer (Oligo 51). Other universal detection sequences (Oligos 52-58) were used in the same experiment and gave similar results. These and other universal primer sequences were labeled with dyes other than FAM (JOE, TAMRA, ALEXA 450, ALEXA 594, HEX, and TET), giving similar results.

Oligo 48 5'-cta ccg ggt gtc tgt gtc tcg gTa g
(SEQ ID NO: 63)

Oligo 49 5'-ggg tgt ctg tgt ctc ggt aga cct
ggc tat ctg tgt c (SEQ ID NO: 64)

Oligo 50 5'-ggt agt act tca tgc cgt tct tga g
(SEQ ID NO: 65)

Oligo 51 5'-ggg tgt ctg tgt ctc ggt aga cct
ggc tat ctg tgt t (SEQ ID NO: 66)

Oligo 52 5'-cta ccg ggc atc tga gta tcg gTa g
(SEQ ID NO: 67)

Oligo 53 5'-cga ctg ggc atc tga gta tca gTc g
(SEQ ID NO: 68)

Oligo 54 5'-gta ccg gag gac tgt gtt tcg gTa c
(SEQ ID NO: 69)

Oligo 55 5'-caa ccg gag gac tgt gtt tcg gTt g
(SEQ ID NO: 70)

Oligo 56 5'-caa ccg gag gac tgt gtt tcg gTt g
(SEQ ID NO: 70)

Oligo 57 5'-gac cgg agg act gtg ttt cgg Tc
(SEQ ID NO: 72)

Oligo 58 5'-cac cgg agg act gtg ttt cgg Tg
(SEQ ID NO: 73)

Example 21

Determining Sequences of Labeled
Oligonucleotides

To find a sequence for a labeled oligonucleotide on each strand of the target, find the labeled primer by:

Step 1—Find T.

Step 2—3' from T should be: AG, TG, AC, TC, C or G.

Step 3—5' from T should be at least one G out of three nucleotides such as NGG/GNG/GGN, NNG, NGN, GNN or GGG (sequences located in the order of preference).

Step 4—Create a primer with the 3'-end found in step 2 with a temperature of 64-70° C., preferably, 66-68° C. See Rozen, S. and H. J. Skaletsky (1996, 1997, 1998) Primer 3 (Code available at http:/www-genome.wi.mit.edu/genome_software/other/primer3.html or http:/www.genome.wi.mit-.edu/cgi-bin/primer/primer3_www.cgi).

Step 5—Add a tail to the primer to make a hairpin (example: ctaccgGGTGTCTGTGTCTCGGTAG (SEQ ID NO:74)) by adding to the 5'-end, nucleotides complementary to the 3'-end, checking delta G, i.e., measurement of energy which characterizes the stability of the resulting hairpin structure. Delta G is calculated using Primer 3. Resulting delta G should be between 2.5 and 5.5. The lower the delta G, the more stable the hairpin structure.

As a result of steps 1-5, labeled primers for both strands can be obtained.

Additionally, one can combine the steps described above with an existing program for primer design, e.g., Primer 3

(available to public). Labeled primer and unlabeled counterpart should be found on each strand of the DNA target. Then, Step 1—Find T.

Step 2—3' from T should be AG, TG, AC, TC, C or G.

Step 3—5' from T should be at least one G out of three nucleotides such as NGG/GNG/GGN, NNG, NGN, GNN or GGG.

Step 4—Create a primer with the 3'-end found in step 2 with a temperature of 64-70° C., preferably, 66-68° C. See Rozen, S. and H. J. Skaletsky (1996, 1997, 1998) Primer 3 (Code available at http:/www-genome.wi.mit.edu/genome_software/other/primer3.html or http:/www.genome.wi.mit.edu/cgi-bin/primer/primer3_www.cgi).

Step 5—Apply functions of Primer 3 to labeled primers to select the best ones. Find the counter-part primer for each labeled primer selected (left for the right-labeled and right for the left-labeled).

Step 6—Add a tail to the primer to make a hairpin (example: ctaccgGGTGTCTGTGTCTCGGTAG (SEQ ID NO:74)) by adding to the 5'-end, nucleotides complementary to the 3'-end, checking delta G of the resulting hairpin. Delta G can be calculated using Primer 3. Resulting delta G should be between 2.5 and 5.5.

Example 22

2'-O-Methyl Modification of the Nucleotide Residue on the 3'-End of a PCR Primer can Improve the Specificity of Allele-Specific PCR The principle of allele-specific PCR is presented in FIG. 9 and described in Example 11. In this experiment, two sets of PCR primers (sets A and B) were used to amplify 20 ng of pUC19 linearised plasmid. PCR was performed as described in Example 2. Detection was performed using SYBR Green as described in Example 15.

Set A was comprised of regular liner oligonucleotides. Four different oligonucleotides were used as forward primers: with A, T, C and G at the 3'-end. Only C-ended oligonucleotide was completely complementary to the target (G/C), the rest had a mismatch at the 3'-end (G/T; G/A; G/G). Reverse primer was Oligo 63.

Set B had the same sequences of oligonucleotides, but all the forward primers had modified 3'-nucleotide-2'-O-methyl. Reverse primer was Oligo 63.

```
Oligo 59 pUC19          5'-gcc ggt gag cgt ggg
forward primer, 3'-A    tct a (SEQ ID NO: 75)

Oligo 60 pUC19          5'-gcc ggt gag cgt ggg
forward primer, 3'-T    tct t (SEQ ID NO: 76)

Oligo 61 pUC19          5'-gcc ggt gag cgt ggg
forward primer, 3'-C    tct c (SEQ ID NO: 77)

Oligo 62 pUC19          5'-gcc ggt gag cgt ggg
forward primer, 3'-G    tct g (SEQ ID NO: 78)

Oligo 63 pUC19 reverse  5'-ctc tgc tga agc cag
primer                  tta cct tc (SEQ ID NO: 79)

Oligo 64 pUC19 forward  5'-gcc ggt gag cgt ggg
primer, 3'-A/2'-O-Me    tct a (SEQ ID NO: 80)

Oligo 65 pUC19 forward  5'-gcc ggt gag cgt ggg
primer, 3'-T/2'-O-Me    tct t (SEQ ID NO: 81)
```

-continued

```
Oligo 66 pUC19 forward  5'-gcc ggt gag cgt ggg
primer, 3'-C/2'-O-Me    tct c (SEQ ID NO: 82)

Oligo 67 pUC19 forward  5'-gcc ggt gag cgt ggg
primer, 3'-G/2'-O-Me    tct g (SEQ ID NO: 83)
```

Figure 24A:
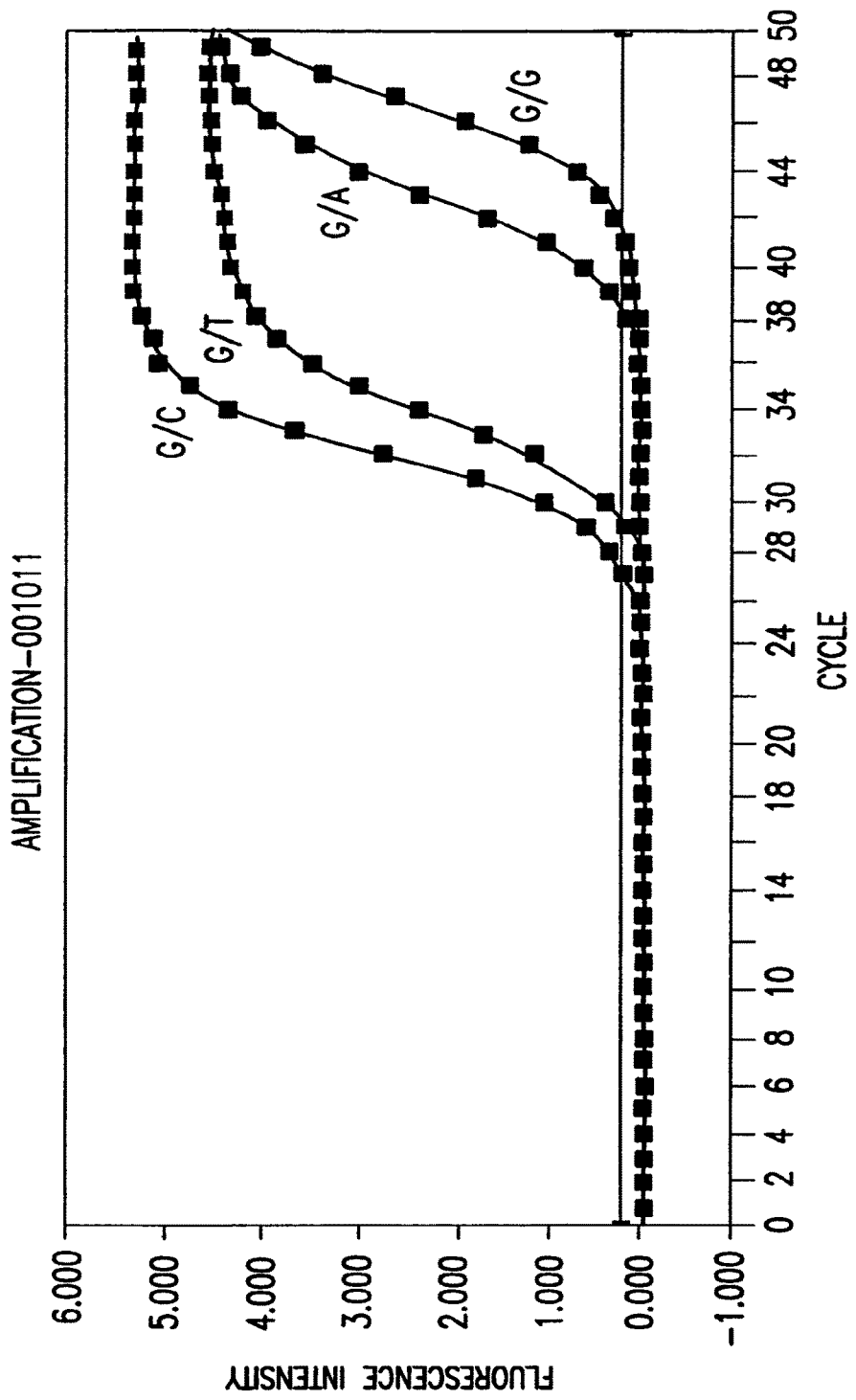
FIGS. 24A-B are line graphs of fluorescence intensity as a function of number of cycles of amplification performed.
Figure 24B:
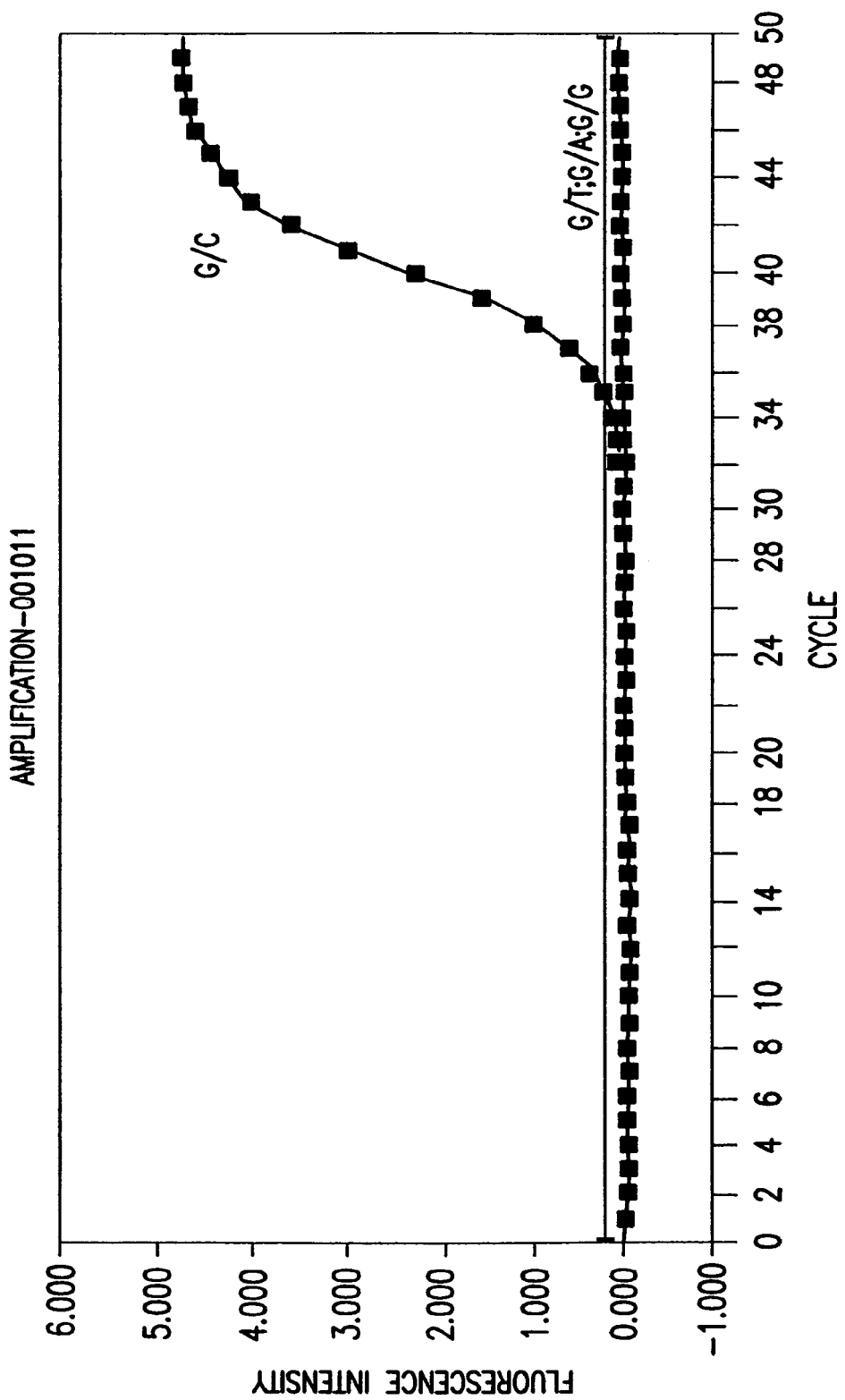

The results of real-time PCR are shown in FIGS. 24A-B. The results demonstrate that the presence of a modification increases window discrimination (the difference between the number of cycles when the product with matched and mismatched primers appears).

Figure 26B:
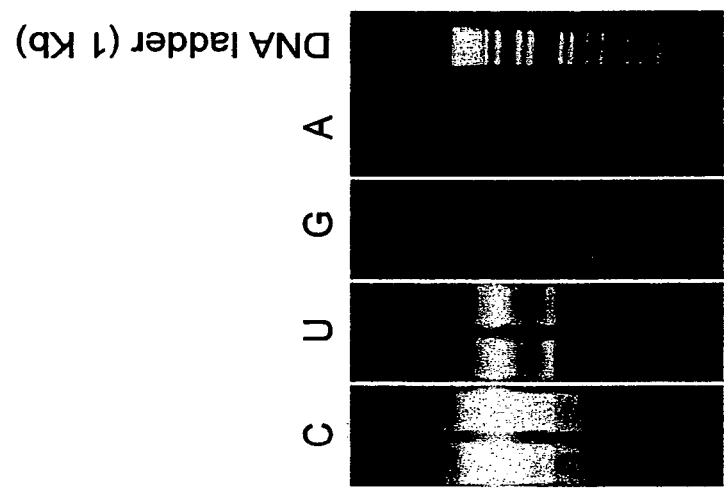
FIGS. 26A-B are photographs of an agarose gel stained with ethidium bromide showing amplification of a 2.7 Kb target DNA sequence (pUC19). Amplification cycle was repeated for 30-times.
Figure 26A:
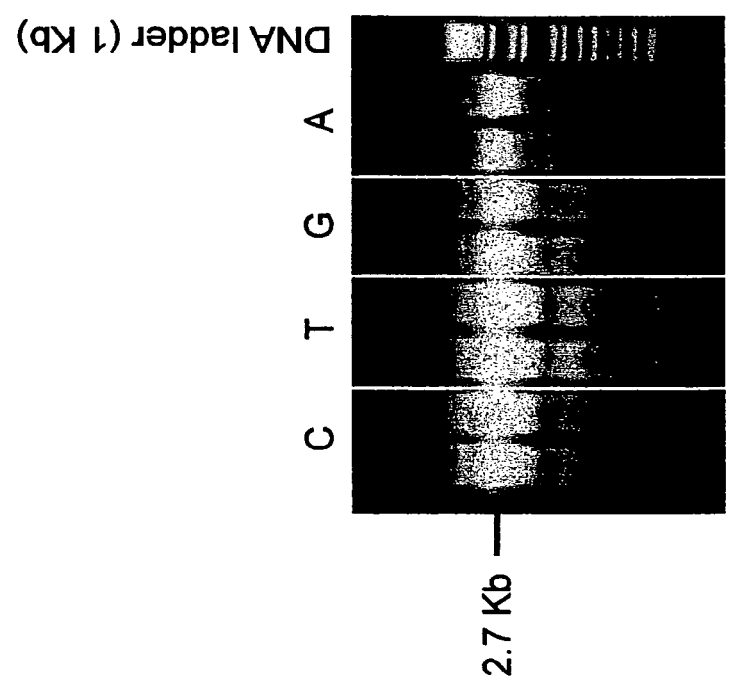

Additional amplification experiments of a 2.7 Kb target DNA sequence (pUC19) was performed using four different sequences for the forward primer denoted below as oligos 68, 69, 70 and 71. Each forward primer has an analogous primer with a dNTP or 2'-O-methyl ribonucleotide at the 3'-terminal nucleotide. FIG. 25A represents amplification using forward primers with the canonical nucleotide at the 3'-termini (deoxynucleotide); whereas FIG. 25B represents amplification using forward primers that contain a 2'-O-methyl ribonucleotide modification at the 3'-termini. The reverse primer for each of the amplification assays was the same (see Oligo 72). The lanes marked C, T(U), G, and A denote the sequence of the 3'-terminal nucleotide of each of the forward primer where C forms the correct Watson/Crick base-pair with the target sequence. The target sequence was amplified by Taq DNA polymerase and the amplification cycle was repeated for 40-times. Each amplification reaction was done in duplicate. FIGS. 26A-B depict the amplification cycle repeated for 30-times.

```
Oligo 68 pUC19          5'-
forward primer, 3'-C    ATGCGCCGGTGAGCGTGGGTCT
                        C-3' (SEQ ID NO: 84)

Oligo 69 pUC19          5'-
forward primer,         ATGCGCCGGTGAGCGTGGGTCTT(U)-3'
3'-T/U                  (SEQ ID NO: 85)

Oligo 70 pUC19          5'-ATGCGCCGGTGAGCGTGGGTCTG-3'
forward primer, 3'-G    (SEQ ID NO: 86)

Oligo 71 pUC19          5'-ATGCGCCGGTGAGCGTGGGTCTA-3'
forward primer, 3'-A    (SEQ ID NO: 87)

Oligo 72 pUC19          5'-ATGCACCGCCTCCAGATTTATC-3'
reverse primer          (SEQ ID NO: 88)
```

The results shown in FIGS. 25A-B and 26A-B demonstrate the increased specificity in amplified product using 2'-O-methyl modified primers in relation to unmodified primers.

Example 23

Figure 27A:
FIGS. 27A-C are autoradiographs showing the relative extension of primers containing deoxynucleotide (FIG. 27A), ribonucleotide (FIG. 27B) and 2'-O-methyl ribonucleotide (FIG. 27C) modifications at the 3'-terminal nucleotide by Taq DNA polymerase at 60° C.
Figure 27B:
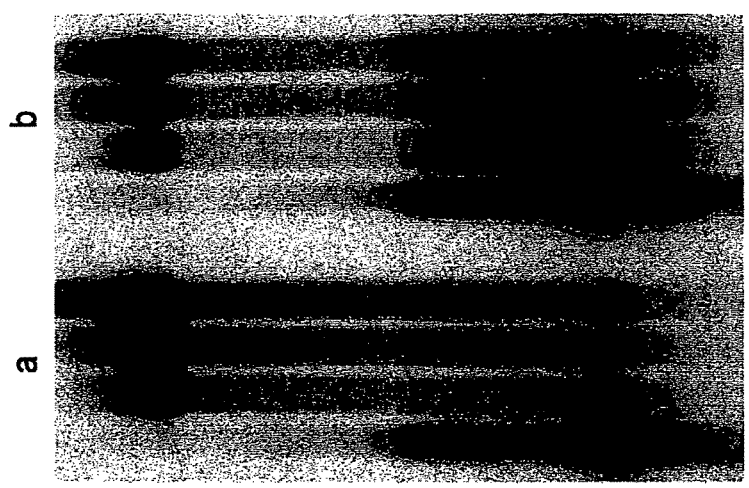
Figure 27C:
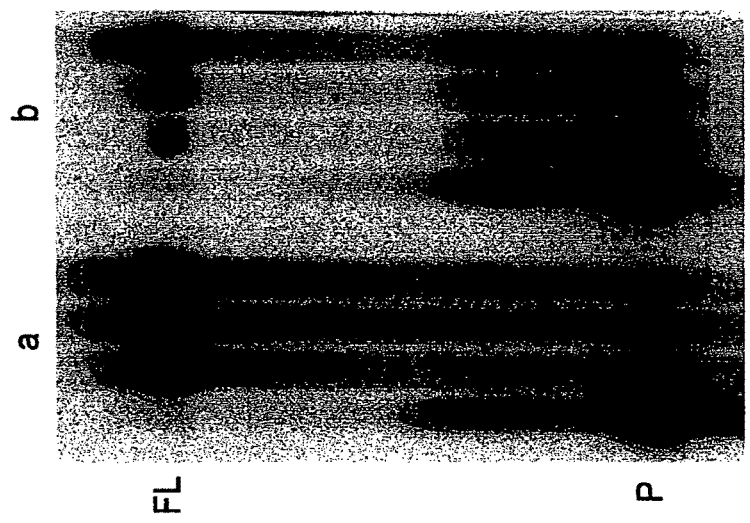

2'-O-Methyl Modification of the Nucleotide Residue on the 3'-End Forming a Single-Pair Mismatch at the 3'-Termini Nucleotide are Extended with Significantly Reduced Efficiency by Taq Polymerase In this experiment, the relative extension of primers containing deoxynucleotide, ribonucleotide and 2'-O-methyl ribonucleotide modifications at the 3'-terminal nucleotide by Taq DNA polymerase at 60° C. was analyzed. The results are shown in FIGS. 27A-C. For each type of 3'-terminal nucleotide modification (including the canonical unmodified primer) a totally complimentary (sub-panel a) and a primer sequence that forms a single base-pair mismatch at the 3'-terminal position (sub-panel b) primer/template substrates were used for the assay. The primer sequences used for these assays are Oligo 73 and Oligo 74. The template sequence for Oligo 73 is:

```
                                         (SEQ ID NO: 89)
5'-CGAGGCGCTGCCGTCGGTGCCGCAGCCGGCCGGTTTCTGCTACG

CCGGTAGGCTAACGTTA-3'.
```

The template sequence for Oligo 74 is:

```
                                         (SEQ ID NO: 90)
5'-CGAGGCGCTGCCGTCGGTGCCGCAGCCGGCCGGTTTCTGC

TACGCCGGTAGGCTAACGT-3'.
```

In the case of the ribonucleotide and 2'-O-methyl terminated oligonucleotides, uracil was used at the 3'-terminal nucleotide instead of thymine (see Oligo 74).

```
Oligo 73 forward primer,  5'-
3'-C (32-mer)             GCTCCGCGACGGCAGCCACGGCGTC
                          GGCCGGC (SEQ ID NO: 91)

Oligo 74 forward primer,  5'-
3'-T/U 2'-O-Me (32-mer)   GCTCCGCGACGGCAGCCACGGCGTC
                          GGCCGGT(U) (SEQ ID NO: 92)
```

In each case, a DNA substrate (32/60 mer) was used where the 5'-termini of the primer strand was labeled with $^{32}$P using T4 polynucleotide kinase. A polymerization reaction was initiated by the addition of Taq (1 µL of 5 unit/µl) which is available commercially (Invitrogen Corporation, Life Technologies Division; Rockville, Md.) to a 9 µL solution of the DNA substrate in the presence of dNTP and MgCl$_2$ at 60° C. The reaction concentration of the DNA was about 12 nM, each of the four dNTP was 200 µM and the MgCl$_2$ was 1.5 mM. P denotes the position of the DNA primer (32-mer) and FL is the fully extended product (60-mer). The most left lane for each sub-panel represents the control oligonucleotide substrate. T denotes the time interval in minute of time elapsed prior to quenching of the reaction following the addition of Taq Polymerase.

The result of this assay suggests the following: (i) primers that contain a ribonucleotide or 2'-O-methyl ribonucleotide at the 3'-termini can be extended by Taq polymerase (FIGS. 27B and C). However, the efficiency of extension of the 2'-O-methyl ribonucleotide modified 3'-termini was lower compared to primers that contain dNTP or rNTP at the 3'-termini (comparison of data between FIGS. 27A and B); (ii) DNA substrates that form a single base-pair mismatch at the 3'-terminal nucleotide of the primer are extended by Taq with reduced efficiency compared to the fully annealed DNA substrate for each of the 3'-ribose modification (comparison of data between panels a and b for FIGS. 27A-C); and (iii) primers containing 2'-O-methyl ribonucleotides that form a single base-pair mismatch at the 3'-terminal nucleotide are extended with significantly reduced efficiency by Taq (as shown in FIG. 27C, panel b).

Example 24

Figure 28:
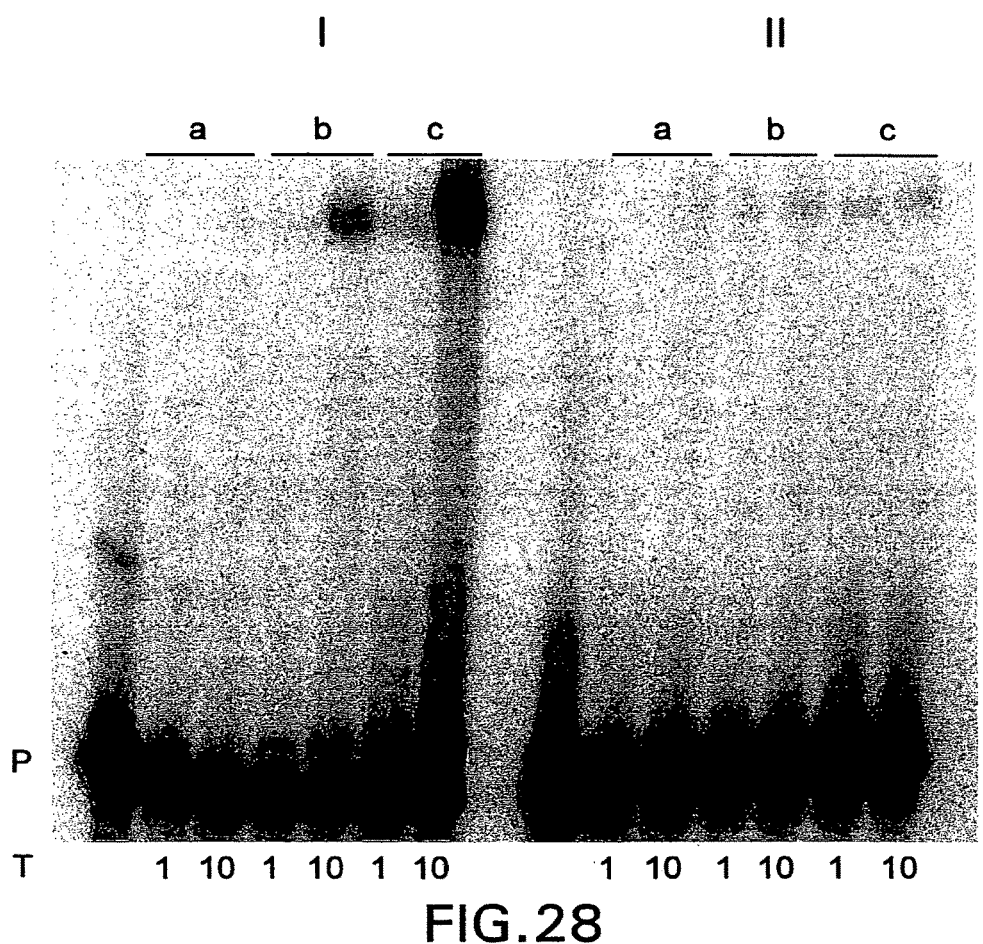
FIG. 28 is an autoradiograph showing the relative extension efficiency of primers that contain a 2'-O-methyl ribose modification at the 3'-terminal nucleotide by Taq at ambient temperature (lanes a), 55° C. (lanes b), and 72° C. (lanes c).

DNA Substrates that Form a Single Base-Pair Mismatch at the 3'-Terminal Nucleotide of a 2'-O-Methyl Modified Primer have Negligible Levels of Extension by Taq Polymerase FIGS. 28A-B show the relative extension efficiency of primers that contain a 2'-O-methyl ribose modification at the 3'-terminal nucleotide by Taq at ambient temperature (lanes a), 55° C. (lanes b), and 72° C. (lanes c). FIG. 28A represent a totally complimentary primer/template substrate, whereas FIG. 28B represent a primer/template substrate that forms a single base-pair mismatch at the 3'-terminal nucleotide of the primer.

In each case, the DNA substrate (32/60 mer) was used where the 5'-terminus of the primer strand was labeled with $^{32}$P using T4 polynucleotide kinase. A polymerization reaction was initiated by the addition of Taq (1 µL of 5 unit/µl) to a 9 µL solution of the DNA substrate in the presence of dNTP and MgCl$_2$ set at ambient temperature, 55° C. and 72° C. The reaction concentration of the DNA was about 12 nM, each of the four dNTP was 200 µM and the MgCl$_2$ was 1.5 mM. P denotes the position of the DNA primer (32-mer) and FL is the fully extended product (60-mer). The most left lane for each panel represents the control oligonucleotide substrate. T denotes the time interval in minute of time that elapsed prior to quenching of the reaction following the addition of Taq.

The results suggest the following: (i) primers that contain a 2'-O-methyl ribonucleotide at the 3'-terminus have a much lower efficiency of extension by Taq at ambient temperature and (ii) DNA substrates that form a single base-pair mismatch at the 3'-terminal nucleotide of the primer (FIG. 28B) have negligible level of extension by Taq at each of the assay temperature following 10 min of reaction time.

Example 25

Figure 29:
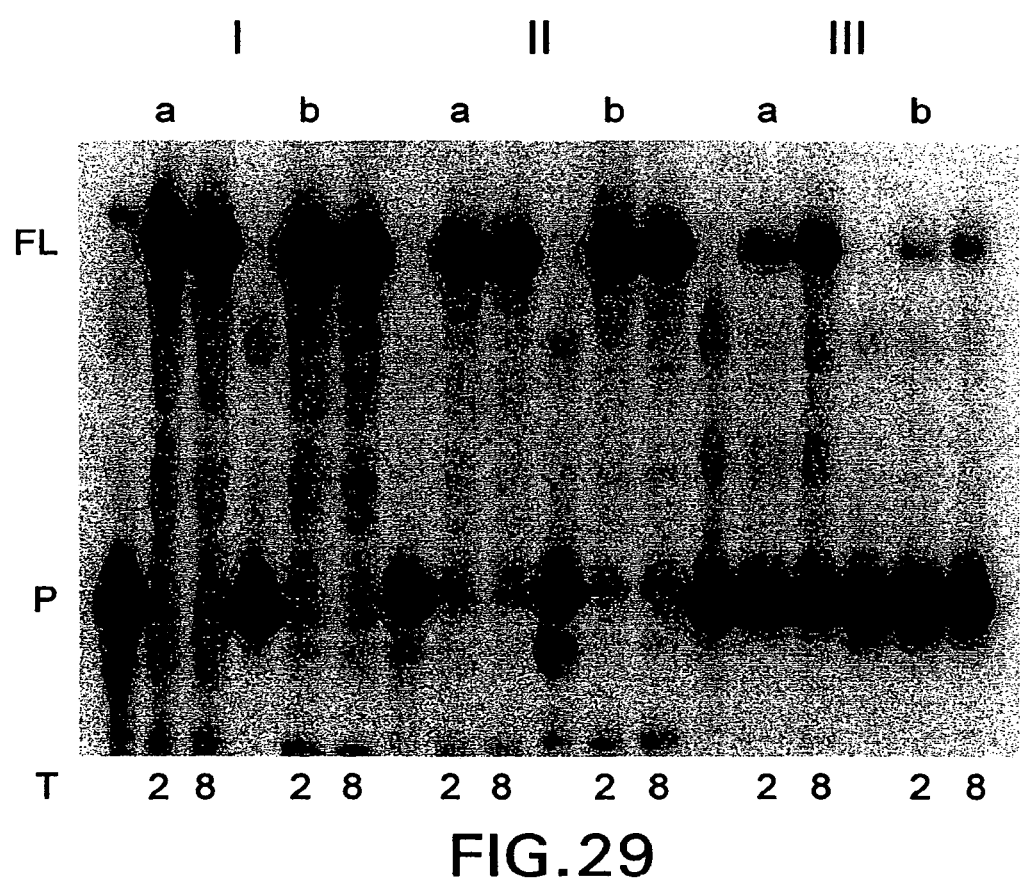
FIG. 29 is an autoradiograph showing the relative extension efficiency of primers with deoxynucleotide (panel I), ribonucleotide (panel II) and 2'-O-methyl ribonucleotide (panel III) modifications at the 3'-terminal nucleotide by the Klenow fragment of DNA polymerase of E. coli at 37° C.

2'-O-Methyl Ribonucleotide Modified Primers that Form a Single Base-Pair Mismatch at the 3'-Terminal Nucleotide was Extended with Significantly Reduced Efficiency in Relation to the Analogous Primer/Template Substrate FIG. 29 shows the relative extension efficiency of primers with deoxynucleotide (panel I), ribonucleotide (panel II) and 2'-O-methyl ribonucleotide (panel III) modifications at the 3'-terminal nucleotide by the Klenow fragment of DNA polymerase of E. coli at 37° C. For each type of 3'-terminal modification, a totally base-paired (sub-panel a) and a primer sequence that forms a single mismatch base-pair (sub-panel b) primer/template substrates were used for the assay.

In each case, the DNA substrate (32/60 mer) was used where the 5'-terminus of the primer strand was labeled with $^{32}$P using T4 polynucleotide kinase. A polymerization reaction was initiated by the addition of Klenow fragment to a solution of the DNA substrate in the presence of dNTP and MgCl$_2$ set at 37° C. The reaction concentration of the DNA was about 12 nM, each of the four dNTP was 200 µM and the MgCl$_2$ was 1.5 mM. For each reaction condition the DNA substrate and the Klenow fragment concentration were maintained at about 12 nM and 75 nM, respectively. P denotes the position of the DNA primer (32-mer) and FL is the fully extended product (60-mer). The most left lane for each sub-panel represents the control oligonucleotide substrate. T denotes the time interval in minute of the time that elapsed prior to quenching of the reaction following the addition of the Klenow fragment.

The results as depicted in FIG. 29 suggest the following: (i) primers that contain a ribonucleotide (rNTP) or 2'-O-methyl ribonucleotide at the 3'-termini can be readily extended by the Klenow fragment (panels II and III). However, the efficiency of extension of the 2'-O-methyl ribonucleotide modified oligonucleotide was lower compared to the primers that contain dNMP or rNMP at the 3'-termini (panel III); (ii) under our experimental condition, DNA substrates that form a single base-pair mismatch at the 3'-terminal nucleotide of the primer are extended by Klenow fragment with comparable efficiencies to that of the totally complimentary DNA substrate in the case of the deoxynucleotide or ribonucleotide terminated primers (comparisons between sub-panels a and b for Panels I and II). This result is indicative of the 3'→5' exo-nuclease directed excision of the mismatch at the 3'-termini of the primer; and (iii) under our experimental conditions, in the case of the 2'-O-methyl ribonucleotide modified primer sequences that form a single base-pair mismatch at the 3'-terminal nucleotide was extended with significantly reduced efficiency in relation to the analogous primer/template substrate (comparison between sub-panels a and b for panel III).

Figure 30:
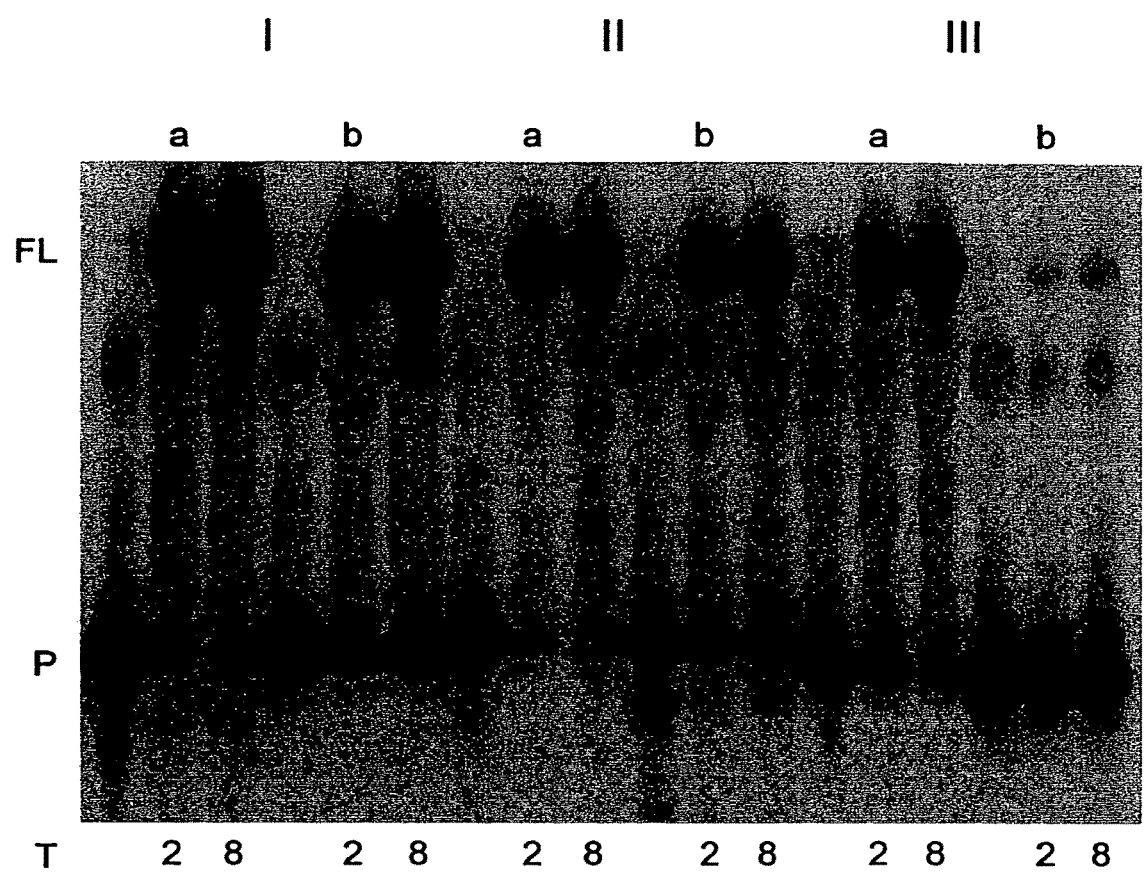
FIG. 30 is an autoradiograph showing the relative extension efficiency of primers with deoxynucleotide (panel I), ribonucleotide (panel II) and 2'-O-methyl ribonucleotide (panel III) modifications at the 3'-terminal nucleotide by the Klenow fragment (exo-nuclease deficient mutant derivative; Asp424Ala) of DNA polymerase of E. coli at 37° C.

The same above experiment was performed using a mutant Klenow fragment (exo-nuclease deficient mutant derivative; Asp424Ala). FIG. 30 shows the relative extension efficiency of primers with deoxynucleotide (panel I), ribonucleotide (panel II) and 2'-O-methyl ribonucleotide (panel III) modifications at the 3'-terminal nucleotide by the Klenow fragment (exo-nuclease deficient mutant derivative; Asp424Ala) of DNA polymerase of E. coli at 37° C. For each type of 3'-termination a totally base-paired (sub-panel a) and a primer sequence that forms a single mismatch base-pair (sub-panel b) primer/template substrates were used for the assay.

In each case, the DNA substrate (32/60 mer) was used where the 5'-terminus of the primer strand was labeled with $^{32}P$ using T4 polynucleotide kinase. A polymerization reaction was initiated by the addition of the Klenow fragment mutant derivative (3'→5' exo-nuclease deficient) to a solution of the DNA substrate in the presence of dNTP and $MgCl_2$ set at 37° C. The reaction concentration of the DNA was about 12 nM, each of the four dNTP was 200 µM and the $MgCl_2$ was 1.5 mM. For each reaction condition the DNA substrate and the Klenow fragment concentration were maintained at about 12 nM and 75 nM, respectively. P denotes the position of the DNA primer (32-mer) and FL is the fully extended product (60-mer). The most left lane for each sub-panel represents the control oligonucleotide substrate. T denotes the time interval in minute that elapsed prior to quenching of the reaction following the addition of the Klenow fragment.

The results suggest the following: (i) primers that contain a ribonucleotide and 2'-O-methyl ribonucleotide at the 3'-termini can be readily extended by the Klenow fragment (panels II and III). However, the efficiency of extension of the 2'-O-methyl ribonucleotide modified oligonucleotide was lower compared to the primers that contain dNMP or rNMP at the 3'-termini (panel III); (ii) under our experimental conditions, DNA substrates that form a single base-pair mismatch at the 3'-terminal nucleotide of the primer are extended by Klenow fragment with lower efficiency compared to that of the totally complimentary DNA substrate for each set of DNA substrates (comparison of data between sub-panels a and b for each Panel); and (iii) under our experimental conditions, in the case of the 2'-O-methyl ribonucleotide modified primer that form a single base-pair mismatch at the 3'-terminal nucleotide was extended with reduced efficiency in relation to the totally complimentary primer/template substrate by the Klenow fragment (3'→5' exo-nuclease deficient protein) (comparison of the data between sub-panels a and b of panel III).

Example 26

Figure 31:
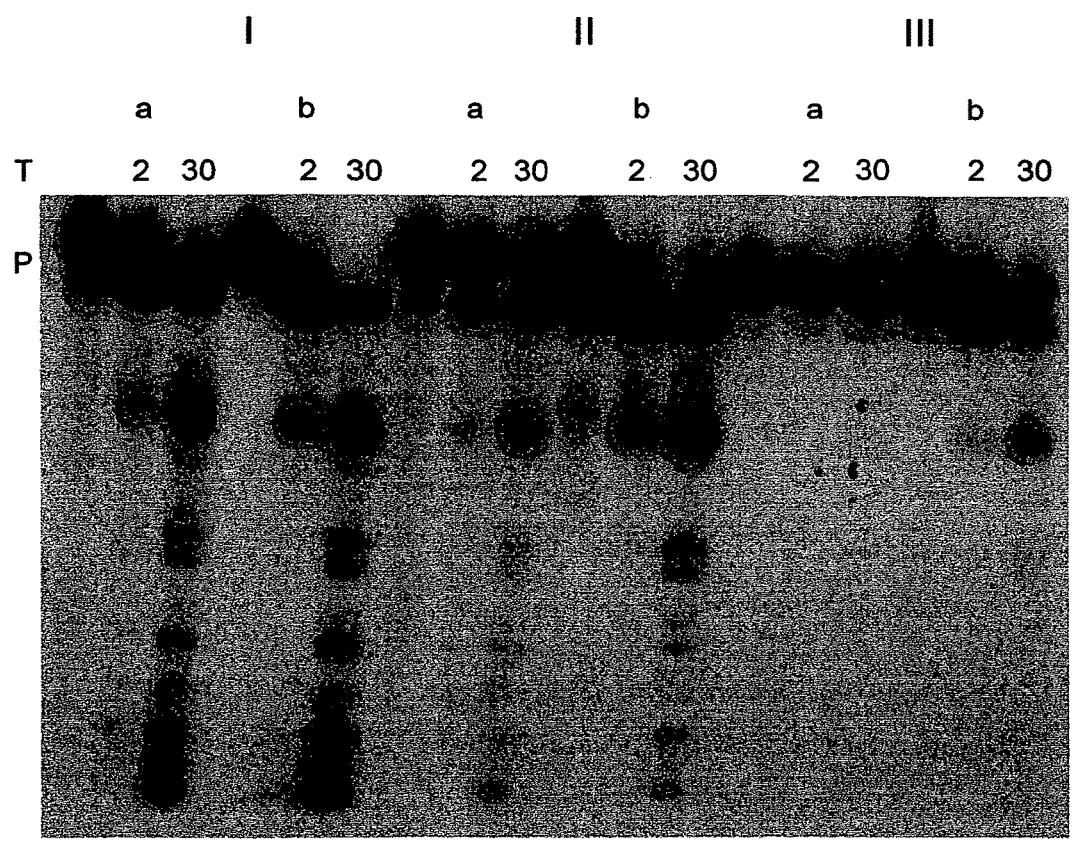
FIG. 31 is an autoradiograph showing the relative rate of 3'→5' exo-nuclease directed degradation catalyzed by the Klenow fragment of DNA polymerase of E. coli at 37° C.

2'-O-Methyl Modification Significantly Protects the Oligonucleotide from Degradation The relative rate of 3'→5' exo-nuclease directed degradation catalyzed by the Klenow fragment of DNA polymerase of E. coli at 37° C. is shown in FIG. 31. The primer/template substrates contain a deoxynucleotide (panel I), ribonucleotide (panel II) and 2'-O-methyl ribonucleotide (panel III) at the 3'-terminal nucleotide of the primer strand. For each type of the 3'-terminal nucleotide modification, a totally base-paired (sub-panel a) and a primer sequence that forms a single base-pair mismatch at the 3'-termini nucleotide position (sub-panel b) primer/template substrates were used for the assay.

In each case, the DNA substrate (32/60 mer) was used where the 5'-termini of the primer strand was labeled with $^{32}P$ using T4 polynucleotide kinase. An exo-nuclease directed degradation was initiated by the addition of the Klenow fragment to a solution of the DNA substrate in the presence of $MgCl_2$ and NaCl at 37° C. The reaction concentration of the DNA was about 12 nM, the Klenow fragment was about 75 nM and the concentrations of $MgCl_2$ and NaCl were 6 mM and 50 mM, respectively. P denotes the position of the DNA primer (32-mer). For each reaction condition the DNA substrate and the Klenow fragment concentration were maintained at about 12 nM and 75 nM, respectively. The most left lane for each sub-panel represents the control oligonucleotide substrate. T denotes the time interval in minute of time elapsed prior to quenching of the reaction following the initiation of degradation.

The results suggest the following: (i) primers that contain a ribonucleotide and 2'-O-methyl ribonucleotide modifications at the 3'-terminus can be excised by the Klenow fragment, albeit at different rate. For the totally complimentary primer/template substrates, the rate of excision is higher in the order of dNTP, rNTP and 2'-O-methyl-NTP at the 3'-termini. The above result implies that the 2'-O-methyl modification significantly protects the oligonucleotide from degradation by the 3'→5' exo-nuclease activity of the Klenow fragment; and (ii) under our experimental conditions, DNA substrates that form a single base-pair mismatch with a dNTP or rNTP at the 3'-termini of the primer are degraded with comparable efficiencies by the Klenow fragment (comparison of data between sub-panels b of panels I and II).

Figure 32:
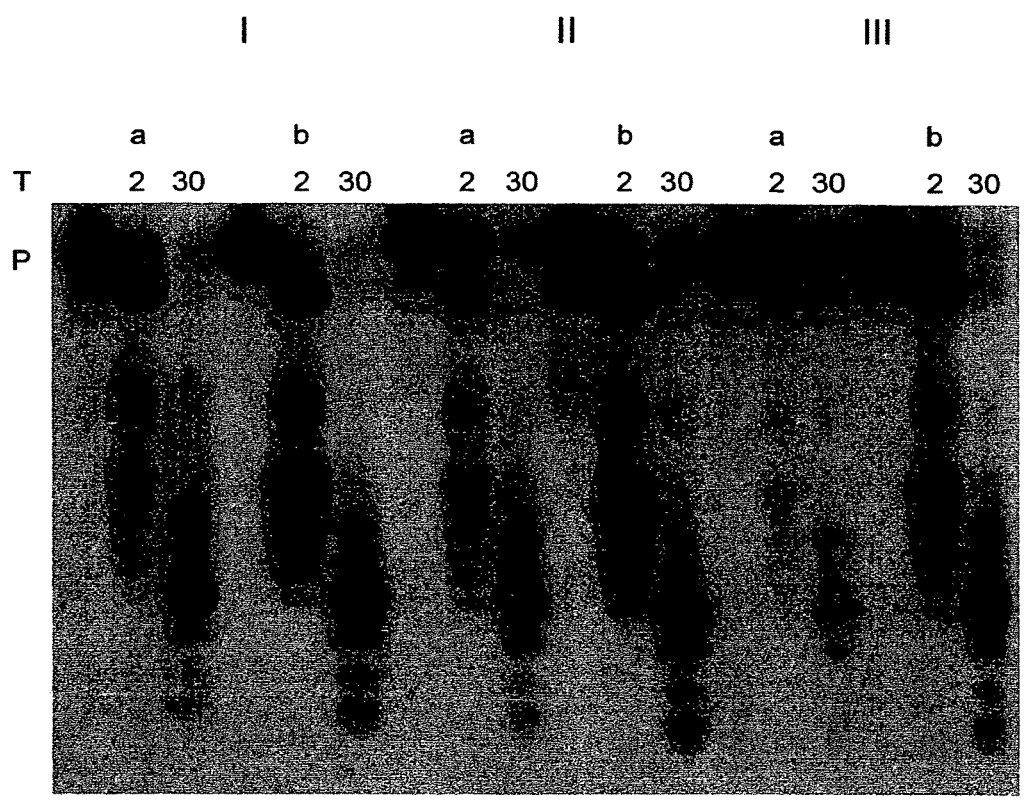
FIG. 32 is an autoradiograph showing the relative rate of 3'→5' exo-nuclease directed degradation catalyzed by Tne DNA polymerase (Asp137Ala mutant derivative; confers 5'→3' exo-nuclease deficient) at 72° C.

Further experiments using Tne Polymerase show the 2'-O-methyl modification significantly protects the oligonucleotide from degradation by 3'→5' exo-nuclease activity of Tne. FIG. 32 shows the relative rate of 3'→5' exo-nuclease directed degradation catalyzed by Tne DNA polymerase (Asp137Ala mutant derivative; confers 5'→3' exo-nuclease deficient) at 72° C. The primer/template substrates contain a deoxynucleotide (panel I), ribonucleotide (panel II) and 2'-O-methyl ribonucleotide (panel III) at the 3'-terminal of the primer strand. For each type of 3'-terminal nucleotide modification, primer/template substrates that form a totally base-paired (sub-panel a) and a single base-pair mismatch at the 3'-terminal nucleotide of the primer (sub-panel b) were used for the assay.

In each case, the DNA substrate (32/60 mer) was used where the 5'-terminus of the primer strand was labeled with $^{32}P$ using T4 polynucleotide kinase. An exo-nuclease directed degradation was initiated by the addition of Tne to a solution of the DNA substrate in the presence of $MgCl_2$ and NaCl at 37° C. The reaction concentration of the DNA was about 12 nM, Tne polymerase was 75 nM and the concentrations of MgCl$_2$ and NaCl were 6 mM and 50 mM, respectively. P denotes the position of the DNA primer (32-mer). The most left lane for each sub-panel represents the control oligonucleotide substrate. T denotes the time interval in minute of the time that elapsed prior to quenching of the reaction following the addition of Tne.

Results suggest the following: (i) primers that contain a ribonucleotide and 2'-O-methyl ribonucleotide modifications at the 3'-terminus can be excised by Tne, albeit at different rate. For the totally complimentary primer/template substrates, the rate of excision is higher in the order of dNTP, rNTP and 2'-O-methyl-NTP at the 3'-termini of the primer. This result suggests that the 2'-O-methyl modification significantly protects the oligonucleotide from degradation by 3'→5' exo-nuclease activity of Tne; and (ii) under our experimental conditions, DNA substrates that form a single base-pair mismatch with dNTP or rNTP at the 3'-termini are degraded with comparable efficiencies by Tne (comparison of the data between sub-panels b of Panels I and II).

Example 27

Effect of Terminal Base Pair on the Fluorescence of Conjugated Fluorescein

Fluorescence intensity, polarization and lifetime of some commonly used fluorophores conjugated to oligodeoxynucleotes with different primary and secondary structures were studied. Fluorescence intensity may increase or decrease upon hybridization of the labeled strand to its complement depending on the sequence and position of the fluorophore. Quenching of the fluorescence in a single strand may occur through a charge transfer process between the dye and guanosine, the most efficient donor of electrons. The formation of the double stranded structure prevents charge separation and the fluorescence intensity increases. Measurements of polarization and lifetime of fluorescein labeled oligonucleotides indicate that base-conjugated fluorophore exist in two conformations, "dark" and "bright," with lower mobility and shorter lifetime of the quenched state. The significance of secondary structure on fluorescence has been investigated through the use of single stranded and double stranded oligonucleotides.

Oligodeoxynucleotide synthesis reagents were purchased from Glen Research, except for wash acetonitrile, which was purchased from Fisher, and standard CPG, which was obtained from ABI. Fluorescent oligodeoxynucleotides were synthesized on a Perceptive Biosystems Expedite DNA synthesizer through direct incorporation of the fluorescein-phosphoramidite to the 5'-end, fluorescein CPG to the 3'-end and C5-fluorescein-dT phosphoramidite internally. Other dyes were incorporated post-synthetically. A two-step procedure included the coupling of the amino modifier C6 T phosphoramidite (phosphoramidite (5-[N-(trifluoroacetylaminohexyl)-3-acrylimido]-2'-deoxyuridinephosphoramidite) during synthesis and post-synthetic modification with N-hydroxy succinimidyl ester of a fluorescent dye from Molecular Probes (Ju, J. et al., *Proc. Natl. Acad. Sci. USA* 92:4347-4351 (1995)). Reverse phase HPLC analysis and purification of oligonucleotides was done using a Waters Alliance HPLC connected to a computer equipped with the Millennium software package (Version 3.1).

The fluorescent intensity, lifetime and polarization were measured for 200 nM fluorescent oligonucleotides in 20 mM tris-HCl, pH 8.4, 50 mM KCl, mM MgCl$_2$, and the concentration of unlabeled complementary oligonucleotide used for duplex formation was 1 µM, unless specified. Melting curves of fluorescent oligonucleotides and duplexes were measured on ABI PRISM 7700 in 50 µl of the above buffer using the following protocol: 25° C. for 2 min, 95° C. for 2 min, then decreasing the temperature to 25° C. in 2° C. per 15 s increments, incubation at 25° C. for 2 min, then increasing the temperature to 25° C. in 2° C. per 15 s increments. For accurate comparison of the fluorescence of single-stranded oligonucleotides versus corresponding duplexes, normalization at 93-95° C. was performed. At this temperature duplexes are completely melted and normalization procedure permitted to eliminate the well-to-well variation of the fluorescence readings.

For some experiments labeled oligonucleotides were hybridized to the complementary oligonucleotides with the protruding 5'-ends. In order to create the blunt end duplex, the complex was incubated for 15 min at 37° C. with 1 unit of Taq DNA polymerase (Invitrogen Corporation) and 200 nM corresponding dNTP in 50 µl of 20 mM tris-HCl, pH 8.4, 50 mM KCl, 2 mM MgCl$_2$. Melting of the created duplexes was performed as described above.

PCR product of IL4 cDNA 133 bp fragment was synthesized with d(gagttgaccgtaacagacatctt) (SEQ ID NO:9) as a forward primer and d(ccttctcatggtggctgtag) (SEQ ID NO:94) as a reverse primer where bold (t) marks the position where the fluorescein is attached. In another experiment linear labeled primer was replaced with the labeled hairpin oligonucleotide d(<u>ctacagt</u>ccttctcatggtggctgtag) (SEQ ID NO:95), where underlined sequence is complementary to the 3'-end of the primer. 50 µl PCR mixture contained 200 nM of each primer, 10$^6$ copies of cloned IL4 cDNA in 1× Platinum q PCR Supermix buffer (Invitrogen Corporation) including 200 µM each dATP, dGTP, dCTP and TTP, 2 mM MgCl$_2$, 20 mM tris-HCl, pH 8.4, 50 mM KCl, and 1 U Platinum™. Reactions were incubated at 25° C. for 2 min, 95° C. for 2 min, followed by 40 cycles: 95° C. for 15 s, 55° C. for 30 s and 72° C. for 30 s.

To examine the effect that the 5'-terminal base has on fluorescence, four oligonucleotides labeled at the 5'-end with 6-carboxyfluoroscein were synthesized. Their sequences were identical, except for the two bases at the 5'-end, which were d(AA), TT, d(CC) or d(GG). These labeled oligonucleotides were hybridized to an excess of unlabeled complementary sequences of the same length and melting curves were measured on an ABI PRISM 7700. Normalized fluorescence at 25° C. was calculated for single-stranded oligonucleotides and duplexes as described above and presented in FIG. 34. The data shows the fluorescence signal does not change upon hybridization when the oligonucleotide contains AA or TT at the 5'-end. On the other hand, there is approximately a 40% decrease in fluorescence upon hybridization when the fluorescent oligonucleotide contains CC at the 5'-end, and about a 30% decrease when the fluorescent oligonucleotide contains GG at the 5'-end.

To examine the effect that the 3'-terminal base has on fluorescence, the fluorescein was attached to a thymidine near the 3'-end of oligonucleotide. Four labeled single-stranded oligonucleotides differed only at the base on the 3'-end, which was C, G, T or A (Table 3). These oligonucleotides were hybridized to a series of complementary strands of different length to form either a blunt end duplexes or a 5'-overhang. Based on 5'-overhangs, a number of duplexes with various ends have been generated by using appropriate dNTPs and DNA polymerase. Some duplexes contained a mismatch between the 3'-end of the labeled strand and the 5'-end of the complementary oligonucleotide. The change of fluorescence upon duplex formation was calculated from the melting curves as described above and presented in Table 3.

A labeled oligonucleotide containing a 3'-terminal C was quenched by 87% upon duplex formation (series A, duplex A1). The same duplex extended by the addition of a single A-T base pair completely eliminates the quenching (duplex A2). Replacing that A-T base pair at the end with a C-G base pair restored the quenching (duplex A3). A 5'-G overhang on the complementary unlabeled strand provides much less quenching than C-G blunt end base pair (duplex A4). Adding a second G to the complimentary strand to give a 2 base overhang reduces the quenching effect even further (duplex A5). Similar results were obtained when the labeled oligonucleotide ended with G (series B, Table 3). 71% quenching was observed in the duplex containing a G-C base pair at the end (duplex B1). Extending the duplex by the addition of an A-T base pair after the G-C base pair eliminated the quenching effect (duplex B2)

Figure 35:
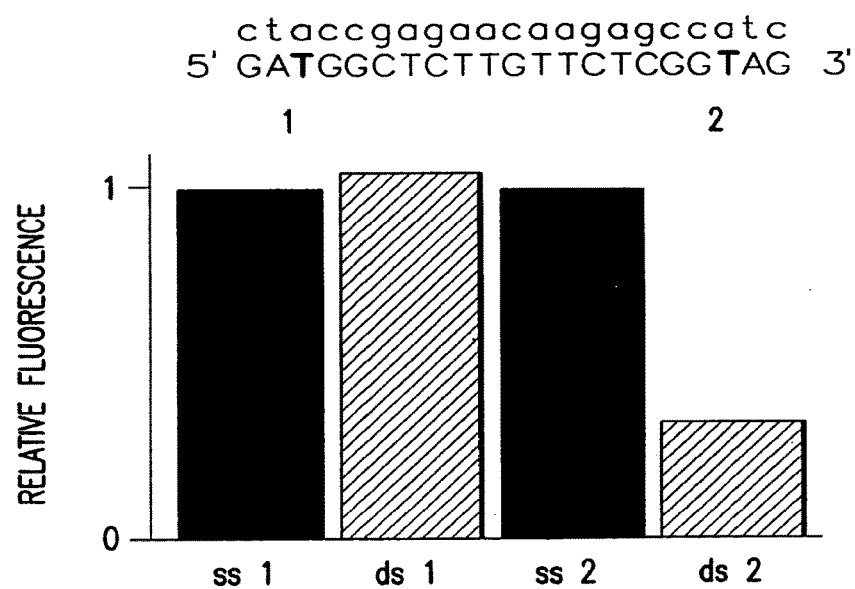
FIG. 35 is a bar graph of relative fluorescence showing a change of fluorescence upon duplex formation for oligonucleotides labeled with fluorescein internally close to the 3'-end or 5'-end. The labeling positions are shown in bold.

The effect of hybridization on fluorescence was compared for a fluorophore located on a base near the 3'-end versus 5'-end. Two oligonucleotides of the same sequence were synthesized so that their 3'-half was a mirror image of the 5'-half (FIG. 35 and Table 4). The 3'-terminal base and the 5'-terminal base were Gs. One of the oligonucleotides had fluorescein attached to the thymidine closest to the 5'-end, while the other oligonucleotide was labeled on the thymidine closest to the 3'-end. The labeled oligonucleotides were hybridized to the unlabeled complementary sequence of the same size. The fluorescence intensity of the single-stranded and double-stranded structures was determined and shown in Table 4 and FIG. 35. The oligonucleotide labeled close to the 3'-end shows substantial quenching upon hybridization, while the oligonucleotide labeled close to the 5'-end exhibits no fluorescence decrease.

TABLE 3

| Duplex A | | Duplex B | | Duplex C | | Duplex D | |
|---|---|---|---|---|---|---|---|
| A1 ...TC-3'<br>...AG-5' | 0.13 | B1 ...TG-3'<br>...AC-5' | 0.27 | C1 ...TT-3'<br>...AA-5' | 1.14 | D1 ...TA-3'<br>...AT-5' | 1.09 |
| A2 ...TCA-3'<br>...AGT-5' | 1.07 | B2 ...TGA-3'<br>...AGT-5' | 1.08 | C2 ...TTC-3'<br>...AAG-5' | 0.35 | D2 ...TAG-3'<br>...ATC-5' | 0.19 |
| A3 ...TCC-3'<br>...AGG-5' | 0.27 | | | C3 ...TT-3'<br>...AAG-5' | 0.72 | | |
| A4 ...TC-3'<br>...AGG-5' | 0.61 | | | C4 ...TT-3'<br>...AAGG-5' | 0.82 | | |
| A5 ...TC-3'<br>...AGGG-5' | 0.76 | | | C5 ...TTT-3'<br>...AAG-5' | 0.76 | | |
| A6 ...TCCC-3'<br>...AGGG-5' | 0.33 | | | C6 ...TTAC-3'<br>...AATG-5' | 0.50 | | |
| | | | | C7 ...TTAAC-3'<br>...AATTG-5' | 1.06 | | |
| | | | | C8 ...TTAAAC-3'<br>...AATTTG-5' | 1.80 | | |

An oligonucleotide containing a 3'-terminal T and a fluorescein on the penultimate base showed no decrease in fluorescence upon duplex formation (series C, duplex C1). Extending this duplex by the addition of a single G-C base pair to the blunt end resulted in significant quenching of the fluorescence (duplex C2). Replacing that G-C base pair with a 5'-G overhang or a terminal G-T mismatch substantially reduces the quenching observed (duplexes C3, C4 and C5). A labeled oligonucleotide ended with adenosine (series D), demonstrated results similar to the T-ended oligonucleotides. Only when the duplex was extended by the addition of a G-C base pair to the end was the fluorescence quenching observed (duplex D2).

The results in Table 3 also show that the quenching of fluorescence by the terminal G-C or C-G base pair is dependent on the distance between the fluorophore and the blunt end. When the fluorophore is positioned further from the 3'-end, the quenching upon hybridization decreases (duplexes A1, A3 and A6; C2, C6-C8). When the fluorophore is at the 6$^{th}$ base from the end (duplex C8), the quenching effect disappears completely, and a strong enhancement of fluorescence is observed.

TABLE 4

| Oligonucleotide duplex | Fluorescence DS/ Fluorescence SS |
|---|---|
| 5'-GATGGCTCTTGTTCTCGGTAG<br>(SEQ ID NO: 133)<br>ctaccgagaacaagagccatc<br>(SEQ ID NO: 134) | 1.05 |
| 5'-GATGGCTCTTGTTCTCGGTAG<br>(SEQ ID NO: 135)<br>ctaccgagaacaagagccatc<br>(SEQ ID NO: 134) | 0.30 |

Example 28

Figure 36:
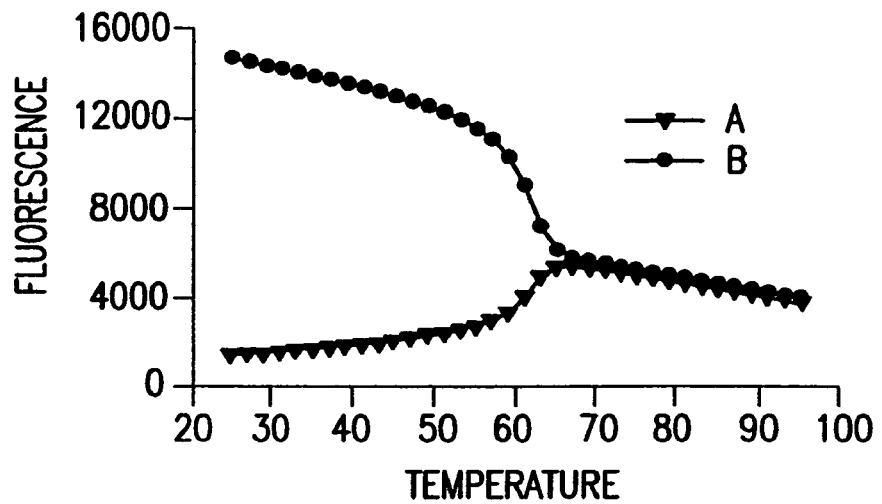
FIG. 36 is a line graph showing the melting curves of oligodeoxynucleotide duplexes labeled with fluorescein. (A) d(CCTTCTCATGGTGGCTGTAG) (SEQ ID NO:94) (B) d(CCTTCTCATGGTGGCTGTAG-AACT) (SEQ ID NO:132). The labeling positions are shown in bold. The complementary strand of the same size as labeled oligonucleotide was used to form the duplex and melting curves were measured as described in Example 27.

Increase of Fluorescence Intensity of the Internally Conjugated Fluorescein Upon Duplex Formation As shown by the results in Table 3, when the fluorophore is moved away from the 3'-terminal G-C base pair, the quenching became less pronounced and eventually an enhancement of fluorescence is observed (duplexes C7 and C8). To examine this further, another set of oligonucleotides was synthesized. The first oligonucleotide was labeled at the third base from the 3'-end of the oligonucleotide. A second oligonucleotide was identical in sequence, except for three extra nucleotides added to the 3'-end. Thus, the second oligonucleotide had the fluorescein 6 bases away from the 3'-end. Each oligonucleotide was hybridized to its complementary sequence. Melting curves of both duplexes are presented in FIG. 36. The fluorescence intensity decreased upon hybridization when two nucleotides separated the label and the 3'-terminal G-C base pair, but increased when the fluorophore was six nucleotides away from the 3'-end.

Figure 37:
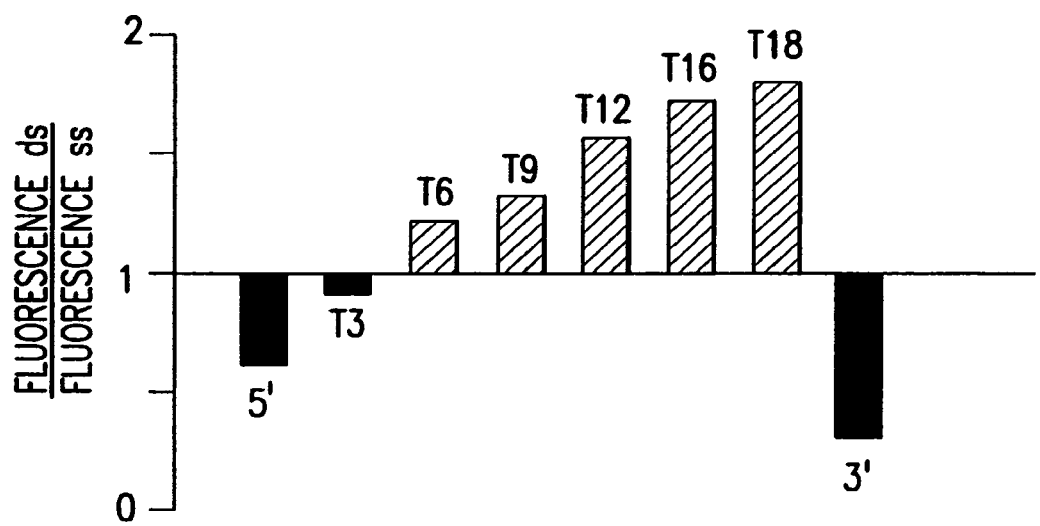
FIG. 37 is a bar graph of fluorescent intensity showing a change of the fluorescence intensity upon hybridization of oligodeoxy nucleotides labeled with FAM at the 5'-end, 3'-end or internally. The internal labeling positions are shown in bold. The complementary strand is shown in lower case. The ratio of the fluorescence between the double-stranded and single-stranded labeled oligonucleotides was determined from the melting curves as described in Example 27.

This increase of fluorescence upon hybridization is dependent on the position of fluorophore within the oligonucleotide sequence (FIG. 37). Eight oligonucleotides of the same sequence were synthesized which were different only in the position of fluorescein: 5', 3' or internally at one of six different T bases. Melting curves of the single-stranded oligonucleotides and duplexes were analyzed the relative fluorescence data are presented in FIG. 37. The fluorescence of the oligonucleotides labeled at the 5'-end, 3'-end or T3 was quenched upon hybridization. However, for oligonucleotides labeled at internal positions starting with T6, an increase in fluorescence was observed. The further the label was away from the 5'-end, the larger was the fluorescence increase upon hybridization.

A possible explanation for the increase of fluorescence upon hybridization is that a quenched state of fluorophore in the single strand may be dequenched as a result of duplex formation. If so, then various labeled oligonucleotides that increase the fluorescence in duplex to a different degree should be quenched to a similar degree in the single-stranded form. Measuring the fluorescence intensity per pmol for the labeled single-stranded oligonucleotides labeled at different positions is shown in FIG. 37. The homogeneity of these oligonucleotides was confirmed by HPLC. As shown in Table 5, the specific fluorescence of free fluorescein is substantially higher than that of the dye-labeled nucleotide, which in its turn is higher than the fluorescence of the dye conjugated to oligonucleotides. Interestingly, the fluorescence/pmol of single-stranded oligonucleotides labeled at positions T3 through T18 is inversely related to the fluorescence enhancement for the corresponding duplexes. Thus, the oligonucleotide labeled at positions T16 and T18 are least fluorescent in the single-stranded state, but result in the most fluorescence enhancement upon duplex formation. Therefore, hybridization appears to attenuate the quenching observed in the single-stranded oligonucleotides. In order to determine how the sequence around the fluorophore affects the increase of fluorescence in duplexes, a large number of internally labeled oligodeoxynucleotides were analyzed. The results show no significant effect of 3'- or 5'-terminal bases on the fluorescence increase when the label is located at least 6 nucleotides from either end. However, the presence of at least one guanosine within four nucleotides of the label is required for the fluorescence to increase upon duplex formation. For example, when Gs around the label in d(CCT-TCTCATGGTGGCTGTAGAAC) (SEQ ID NO:1) were replaced with As, d(CCTTCTCATGGTGATAATAATAC) (SEQ ID NO:97), no fluorescence increase upon hybridization was observed.

To determine whether there are any differences in the charge or accessibility of the dye in the duplex structure as compared to the single strand, the fluorescence intensity of the fluorescein labeled single-stranded and double-stranded oligonucleotides was measured in the presence of 25 mM NaI, a known fluorescence quencher. NaI slightly decreased the fluorescence on both single-stranded and double-stranded oligonucleotides. This implies that the dye is equally accessible for NaI in both forms and argues against dye intercalation into the duplex.

TABLE 5

| Fluorescent material | Fluorescence per pmol | Fluorescence ds/ss |
|---|---|---|
| Fluorescein | 2.84 | |
| Fluorescein-dUTP | 1.36 | |
| d(CCTTCTCATGGTGGCTGTA GAAC) (SEQ ID NO: 98) | 1.07 | 0.9 |
| d(CCTTCTCATGGTGGCTGTA GAAC) (SEQ ID NO: 99) | 0.98 | 1.2 |
| d(CCTTCTCATGGTGGCTGTA GAAC) (SEQ ID NO: 100) | 0.83 | 1.3 |
| d(CCTTCTCATGGTGGCTGTA GAAC) (SEQ ID NO: 101) | 0.72 | 1.55 |
| d(CCTTCTCATGGTGGCTGTA GAAC) (SEQ ID NO: 102) | 0.64 | 1.7 |
| d(CCTTCTCATGGTGGCTGTA GAAC) (SEQ ID NO: 1) | 0.70 | 1.8 |

Example 29

Effect of Primary and Secondary Structure of Oligonucleotide on Fluorescence Polarization and Lifetime of the Conjugated Fluorescein Fluorescence intensity and polarization of oligonucleotides labeled with fluorescein at positions T3, T18 and at the 5'-end were compared to the intensity and polarization of the 133 bp double-stranded PCR products derived from the use of these oligonucleotides as primers. In addition to linear oligonucleotides, a hairpin forming oligonucleotide labeled at position T18 was examined. In this oligonucleotide, six nucleotides were added to the 5'-end of the linear oligonucleotide in order to form a blunt end hairpin. The fluorescence intensity and polarization of the single- and double-stranded structures are shown in Table 6. For the fluorescein attached to the 5'-position of oligonucleotide, the fluorescence intensity decreased upon the formation of the double-stranded structure and the polarization increased. The opposite effect was observed for the internally labeled oligonucleotides. In this case, the increased intensity was accompanied by decreased polarization. The internally labeled hairpin oligonucleotide exhibited the largest change in both intensity and polarization upon the formation of the PCR product.

The fluorescence lifetimes were determined for the fluorescein labeled single-stranded oligonucleotide and its duplex that demonstrated 1.8 difference in fluorescence intensity (T18, Table 5). Measurements were performed at 25° C. in the solution described in Methods in frequency domain mode using a SPEX spectrofluorometer. Data were analyzed with DataMax software (Table 7). A biexponetial decay model provided the best fit to the data for both the single-stranded and double-stranded oligonucleotides with decay components of approximately 4 ns and 1 ns. The lifetime of the primary component was similar to the lifetime of free fluorescein and its fractional amplitude is much higher than that of the short lifetime component. No significant difference in lifetime parameters between the single- and double-stranded structures was discovered. However, values of $\chi^2$ indicate that other multiexponential decay models may provide a better fit to the data and resolve a more complex mixture of the decay components.

TABLE 6

| Labeled oligonucleotide | Fluorescence Polarization PCR product Fluorescence oligo- nucleotide | PCR product Polarization oligo- nucleotide |
|---|---|---|
| 5'Fluo- d(CCTTCTCATGGTGGCTGTA G) (SEQ ID NO: 103) | 0.45 | 1.35 |
| d(CCTTCTCATGGTGGCTGTA G) (SEQ ID NO: 104) | 1.05 | 0.80 |
| d(CCTTCTCATGGTGGCTGTA G) (SEQ ID NO: 94) | 1.65 | 0.75 |
| d(CTACAGTCCTTCTCATGGTG GCTGTAG) (SEQ ID NO: 95) | 8.20 | 0.25 |

TABLE 7

| Oligonucleotide | $\tau_1$ (ns) | $\alpha_1$ | $\tau_2$ (ns) | $\alpha_2$ | $\chi^2$ |
|---|---|---|---|---|---|
| d (CCTTCTCATGGTGGCTGTAG AAC) (SEQ ID NO: 1) | 4.22 | 0.93 | 1.15 | 0.07 | 0.68 |
| d(CCTTCTCATGGTGGCTGTAGAAC) (SEQ ID NO: 1) taccaccgacggaagacatcttg (SEQ ID NO: 139) | 4.01 | 0.95 | 1.05 | 0.05 | 2.86 |

Example 30

Effect of Primary and Secondary Structure of Oligonucleotides on Fluorescence of Dyes Other than Fluorescein All of the data presented in Examples 27-29 were obtained with oligonucleotides containing fluorescein conjugated through the C5 position of thymidine, or attached to the terminus by a short alkyl linker. In addition to fluorescein, a variety of other fluorophores were examined. Similar to fluorescein, JOE, HEX, TET, Alexa 594, ROX, MAX and TAMRA are quenched at the proximity of terminal G-C and C-G base pair and enhance their fluorescence upon duplex formation when located internally at least six nucleotides away from the ends of oligonucleotide. Certain other dyes, such as Texas Red, BODIPY TR and the Cy3 and Cy5 did not follow this pattern.

Example 31

Design and Properties of Fluorogenic PCR Primers

Fluorogenic primers were designed to increase their fluorescent intensity when incorporated into a double-stranded PCR product. This design is based on a study of the effects that the primary and secondary structure of oligonucleotides have on the properties of the conjugated fluorophores. The design factors or rules to consider are: the existence of either a C or G as the terminal 3'-nucleotide of the primer; the fluorophore being attached to the second or third base (thymidine) from the 3'-end; the existence of one or more Gs within the three nucleotides flanking the labeled nucleotide on the 5'-side; and for hairpin primers, the existence of a 5'-tail that is complementary to the 3'-end of the primer. The 5'-tail forms a blunt-end hairpin at temperatures below its melting point, which is approximately the annealing temperature of the primer to the template. The stem of the hairpin primers had a ΔG ranging from −1.6 to −5.8 kcal/mol (Table 8). The above characteristics and other standard characteristics of the primers, such as length and Tm, were included in the primer design by proprietary software. Users may use the software to input their target or template sequence and the software will design primers following the design factors or rules previously mentioned (see Example 21 for steps involved in determining sequence). These design rules enable the software to output numerous primer pairs that are located throughout the target sequence. For example, the software output 94 usable primer pairs for the GAPDH sequence (1310 base pairs).

TABLE 8

| Primer set | Gene target | Dye | Forward primer sequence | Reverse primer sequence | Hairpin ΔG kcal/mol | PCR product bp |
|---|---|---|---|---|---|---|
| 1 | IL-4 | FAM | d(gagttgaccgta acagacatctt) (SEQ ID NO: 9) | d- (ccttctcatggtggct gtag) (SEQ ID NO: 94) | NA | 133 |
| 2 | IL-4 | FAM | d(gagttgaccgta acagacatctt) (SEQ ID NO: 9) | d- (ctacagtccttctcat ggtggctgtag) (SEQ ID NO: 95) | −1.6 | 139 |
| 3 | RDS | FAM | d- (cctggttatctgtgt c) (SEQ ID NO: 105) | d- (ggtgtctgtgtctcgg tag) (SEQ ID NO: 106) | N/A | 136 |
| 4 | RDS | FAM | d- (cctggttatctgtgt c) (SEQ ID NO: 105) | d- (ctaccgggtgtctgtg tctcggtag) (SEQ ID NO: 74) | N/A | 142 |

TABLE 8-continued

| Primer set | Gene target | Dye | Forward primer sequence | Reverse primer sequence | Hairpin ΔG kcal/mol | PCR product bp |
|---|---|---|---|---|---|---|
| 5 | c-myc | FAM | d-(gacgcggggagg ctattctg) (SEQ ID NO: 109) | d-(gactcgtagaaatac ggctgcaccgagtc) (SEQ ID NO: 110) | -3.3 | 236 |
| 6 | c-myc | FAM | d-(cacgaaactttgcc catagca) (SEQ ID NO: 111) | d-(cactggtcgggtgtt gtaagttccagtg) (SEQ ID NO: 112) | -3.7 | 66 |
| 7 | c-myc | FAM | d-(gatctcgtcctggg aagggagatc) (SEQ ID NO: 113) | d-(agggtgtgaccgca acgta) (SEQ ID NO: 114) | -3.0 | 562 |
| 8 | c-myc | FAM | d-(gacgcggggagg ctattctg) (SEQ ID NO: 109) | d-(cagcggagtggagg gaggcgctg) (SEQ ID NO: 116) | -5.0 | 1107 |
| 9 | GAPDH | FAM | d-(agctgaacgggaa gctcact) (SEQ ID NO: 117) | d-(caacgtaggtccacc actgacacgttg) (SEQ ID NO: 118) | -4.2 | 74 |
| 10 | GAPDH | FAM | d-(gcaccgtcaaggc tgagaa) (SEQ ID NO: 119) | d-(caacgtaggtccacc actgacacgttg) (SEQ ID NO: 118) | -4.2 | 570 |
| 11 | GAPDH | FAM | d-(gcaccgtcaaggc tgagaa) (SEQ ID NO: 119) | d-(cacactggtgagga ggggagattcagtgtg) (SEQ ID NO: 122) | -3.8 | 956 |
| 12 | GAPDH | JOE | d-(cacgactggcgct gagtacgtcgtg) (SEQ ID NO: 123) | d-(atggcatggactgtg gtcat) (SEQ ID NO: 124) | -4.5 | 280 |
| 13 | β-Actin | JOE | d-(gatcttcggcaccc agcacaatgaagat c) (SEQ ID NO: 59) | d-(aagtcatagtccgcct agaagcat) (SEQ ID NO: 126) | -4.0 | 191 |
| 14 | 18 S rRNA | JOE | d-(gactcattggccct gtaattggaatgagt c) (SEQ ID NO: 127) | d-(ccaagatccaactac gagctt) (SEQ ID NO: 128) | -5.8 | 155 |
| 15 | RDS | FAM | d-(cctggttatctgtgt [c/t]) (SEQ ID NO: 129) | d-(ctaccgggtgtctgtg tctcggtag) (SEQ ID NO: 130) | -5.4 | 143 |

Primers bearing fluorophores were supplied by Synthetic Genetics (San Diego, Calif.) or by the chemistry department of Invitrogen Corporation (Life Technologies Division, Rockville, Md.). The chemical synthesis of FAM-labeled oligonucleotides was performed either through direct incorporation of the fluorescein-dT phosphoramidite or by a two-step process, which included the coupling of the amino modifier C6 T phosphoramidite (Glen Research) and post-synthetic modification using carboxyfluorescein NHS ester (mixture of 5 and 6-isimers, Molecular Probes). The two-step process was used to synthesize all JOE-labeled oligonucleotides, using 5-carboxy JOE NHS ester (Molecular Probes). Reverse phase purification of the modified primers was performed by absorption on polystyrene resin. Unlabeled Primers were supplied by Invitrogen Corporation Total RNA was isolated from Hela cells and human blood lymphocytes using the Trizol reagent (Invitrogen Corporation) as proscribed by the vendor protocol. The samples of RNA isolated from stimulated or aspirin-treated peripheral-blood T-cells (PBTs) were a generous gift from Dr. Vincenzo Casolaro (Johns Hopkins University, Baltimore, Md.). First-strand cDNAs were synthesized from total RNA by reverse transcription using the Superscript II™ kit (Invitrogen Corporation) with oligo-d ($T_{12-18}$) or random hexamer primers; as proscribed by the vendor protocol. The cloned cDNA template of interleukin-4 (IL-4) was generated by RT-PCR of total RNA from stimulated lymphocytes. Standard "hot-start" PCR was performed using gene-specific primers (primer sequences not shown) and Taq polymerase with Taq polymerase antibodies (Platinum Quantitative PCR Supermix-UDG; Invitrogen Corporation). The PCRs amplified the appropriate cDNAs, nearly full-length, which were then cloned into bacteria using the TOPO T/A cloning kit (Invitrogen Corporation). Finally, plasmid DNAs from clones were purified by alkaline lysis followed by centrifugation, then linearized and further purified by phenol extraction and ethanol precipitation before use as PCR templates. Copy number of plasmids was calculated using absorbance measurements at 260 nm excitation wavelength. The other cloned cDNA templates, c-myc oncogene, β-actin, glyceraldehyde-6-phosphate dehydrogenase (GAPDH) and 18S ribosomal RNA, were generated from Hela cell RNA using similar methods.

Each 50 μl reaction contained the relevant template cDNA, 80-200 nM of each gene-specific primer, 1× Platinum Quantitative PCR Supermix-UDG (Invitrogen Corporation) including 200 μM each dATP, dGTP, dCTP and 400 μM dUTP, 1 U uracil DNA glycosylase, 3 mM $MgCl_2$, 20 mM tris-HCl, pH 8.4, 50 mM KCl, DNA polymerase antibodies, stabilizers, and 1.5 U Taq-polymerase and 1× ROX reference dye (Invitrogen Corporation). For 3-step cycling, reactions were incubated at 25° C. for 2 min, 95° C. for 2 min, then cycled using 95° C. for 15 s, 55° C. for 30 s and 72° C. for 30 s, then reactions were incubated at 25° C. for 2 min. Exceptions were made for amplicons longer than 500 base pairs. These included an extension time of 120 s and a post-cycling hold of 4 min at 72° C. Two-step cycling consisted of 95° C. for 15 sec and 65° C. for 30 sec. Reactions were conducted in a 96-well spectrofluorometric thermal cycler (ABI PRISM 7700, Applied Biosystems, Inc.) or i-Cycler (BioRad). Fluorescence was monitored during every PCR cycle at the annealing step.

Figure 38:
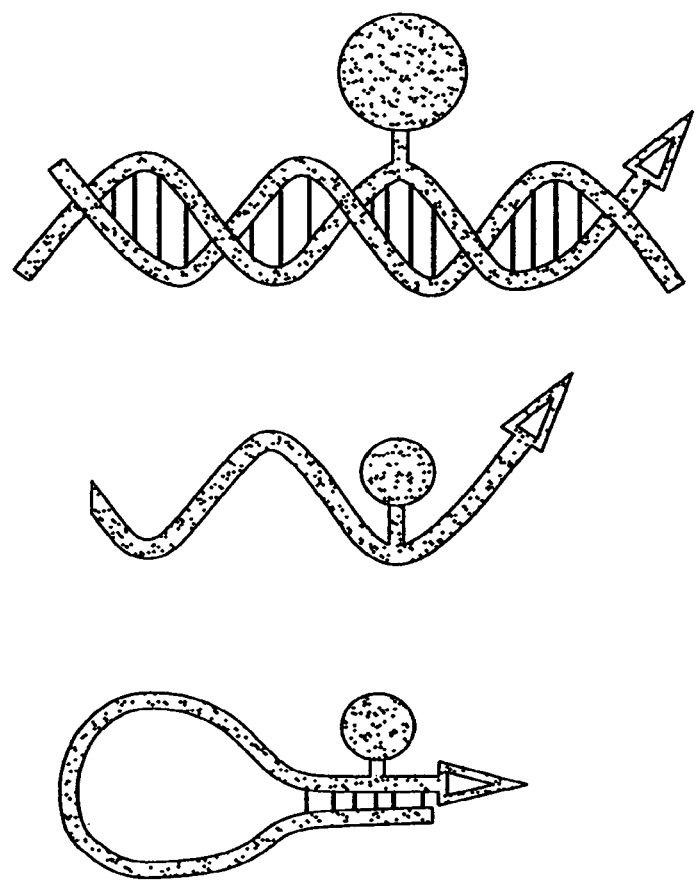
FIG. 38 is a schematic representation of a signal generation by fluorogenic primers. The oligonucleotide in blunt-end hairpin conformation emits the lowest fluorescent signal. The signal increases when the primer is linear, and reaches its maximum when the primer is incorporated into the double-stranded DNA.
Figure 39A:
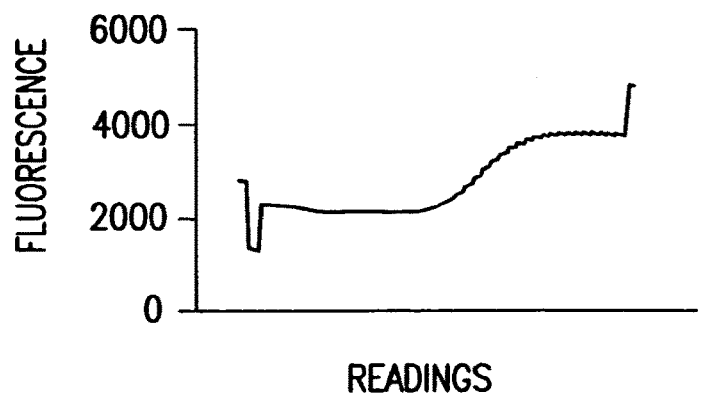
FIGS. 39A-B are line graphs of fluorescent intensity depicting fluorescence readings during real-time PCR using either a linear or hairpin fluorogenic primer. Fluorescence was measured at 25° C. before the PCR, during a preheating step at 94° C., at 55° C. during each cycle of PCR, and finally at 25° C. after the cycling. The fluorescence intensity during PCR using a FAM-labeled linear reverse primer is shown in FIG. 39A (see Example 31, primer set 1, Table 8). The fluorescence intensity during PCR using a FAM-labeled hairpin reverse primer is shown in FIG. 39B (see Example 31, primer set 2, Table 8). PCRs were performed on an ABI 7700 with $10^6$ copies of cloned IL-4 cDNA using similar conditions and with the same unlabeled forward primer.
Figure 39B:
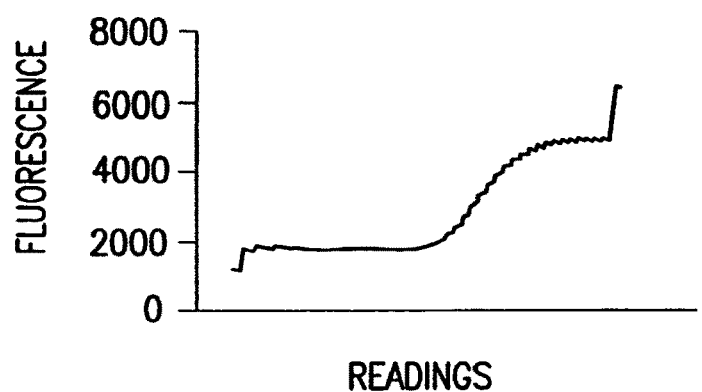
Figure 39C:
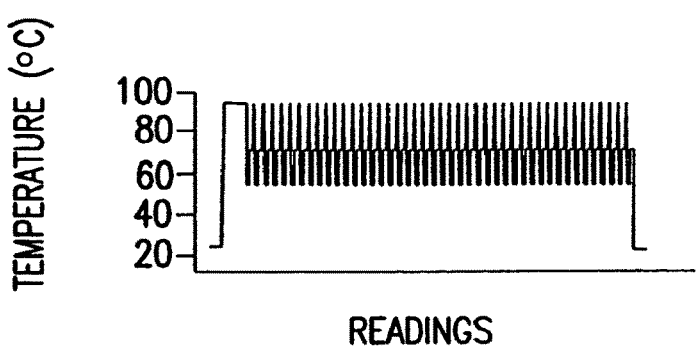
FIG. 39C is a plot of temperature versus detector readings.

A schematic diagram of PCR with the fluorogenic primers is presented in FIG. 38. The primer maintains a hairpin structure with a blunt-end that has a relatively low fluorescence at the temperature below Tm. When the hairpin melts, the fluorescence increases several fold, and reaches its maximum when the 3'-end of the primer is extended into the double-stranded PCR product. A hairpin primer generates a better signal during real-time PCR than a linear primer because it is more quenched when not extended (FIG. 39A-C). Two labeled reverse primers were prepared, one hairpin and one linear, with identical sequence-specific portions (primer sets 1 and 2, Table 8). They were used with the same forward unlabeled linear primer to amplify IL-4 cDNA. The fluorescence of the PCR mixture was measured during a 25° C. pre-reaction step, a 94° C. denaturation step, an annealing step (55° C.) of each PCR cycle and at 25° C. after completion of PCR using an ABI PRISM (FIG. 39A-C). The fluorescence of the linear primer at the 25° C. pre-incubation step is higher than at the 94° C. denaturing step because of the known effect of temperature and pH on fluorescence (Lakowicz, J. R., "Principles of fluorescence spectroscopy," Kluver Academic/Plenum Publishers, New York, $2^{nd}$ Ed., pp. 185-210 (1999)). During the PCR with the linear labeled primer, the fluorescence remains constant for the initial cycles of PCR creating a baseline, and then rises to a plateau with a gain of 2000 relative fluorescence units. The fluorescence at 25° C. after the PCR is 2000 units higher than before the PCR, for the linear primer. The hairpin primer is quenched 3-fold more than the linear primer at 25° C., so the resulting gain in fluorescence at end-point is greater than for the linear primer, and equal to 5700 relative fluorescence units. The enhanced gain of the hairpin primer is understandable because the hairpin conformation exists, to some degree, at 55° C. and therefore retains some quenching.

Figure 40:
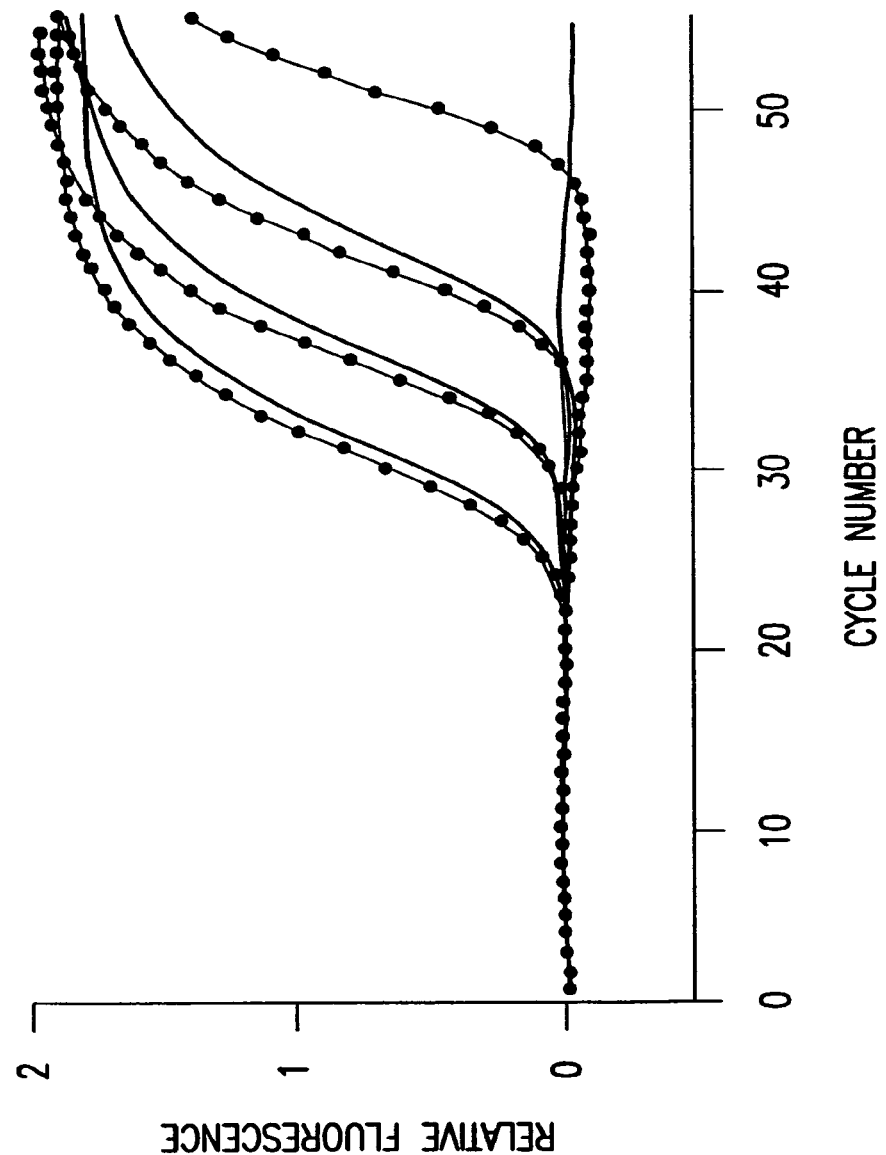
FIG. 40 is a line graph of relative fluorescence showing the effect of hairpin structure on PCR specificity and efficiency. Human RDS gene was amplified using either a linear (dotted line), or a hairpin (solid line) unlabeled reverse primer with the same fluorogenic linear forward primer (see Example 31, primer sets 3 and 4, Table 8). PCRs for both primer sets were performed using 100 ng, 2 ng, 0.08 ng and 0 ng of genomic DNA.

To study the effect that the hairpin primer has on PCR efficiency and specificity, the $C_T$s and the slopes of the amplification curves for the real-time PCRs performed with either a linear or hairpin primer were compared. The $C_T$s and the slopes of the amplification curves were comparable for the linear and hairpin primers, indicating that the hairpin structure did not adversely affect the PCR efficiency (FIGS. 39A-C and 40). Furthermore, the use of blunt-ended hairpin primers improves the specificity of PCR by reducing the formation of primer-dimer artifacts in the absence of target. Primer-dimer formation in separate reactions incorporating a linear labeled primer with an unlabeled counterpart primer that was either linear or hairpin were compared (FIG. 40; primer sets 3 and 4, Table 8). Reactions included 10-fold serial dilutions of genomic DNA and no-DNA controls. When both primers are linear, primer-dimers are amplified at the 45th cycle of PCR in the control with no added template. PCR containing a hairpin primer, conversely, does not result in primer-dimer amplification even after 55 cycles (FIG. 40). Agarose gel analysis confirmed the expected migration patterns of primer, primer-dimer and PCR product.

Example 32

Quantitative Real-Time PCR

Figure 41A:
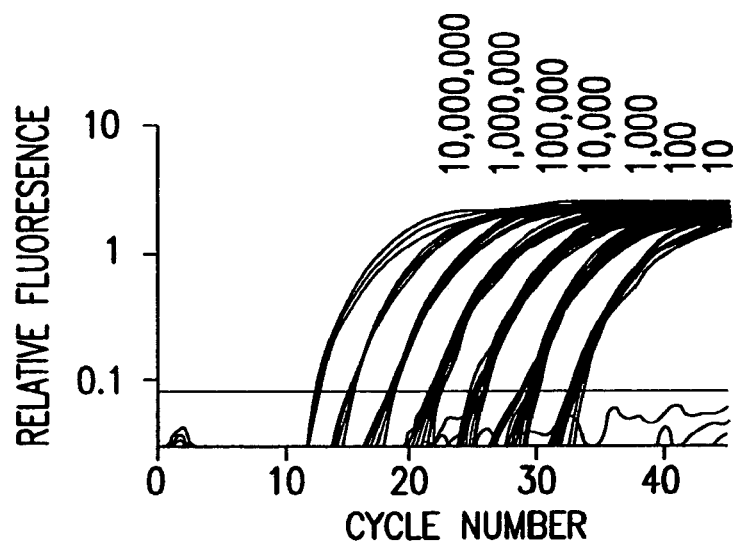
FIG. 41A is a line graph of relative fluorescence as a function of the number of cycles of amplification. Sensitivity, precision and dynamic range of fluorogenic real-time PCR is shown. Ten-fold serial dilutions of c-myc cDNA were amplified and detected using a FAM-labeled fluorogenic primer in two-step PCR on an ABI 7700 as described in Example 32 (see Example 31, primer set 5, Table 8).
Figure 41B:
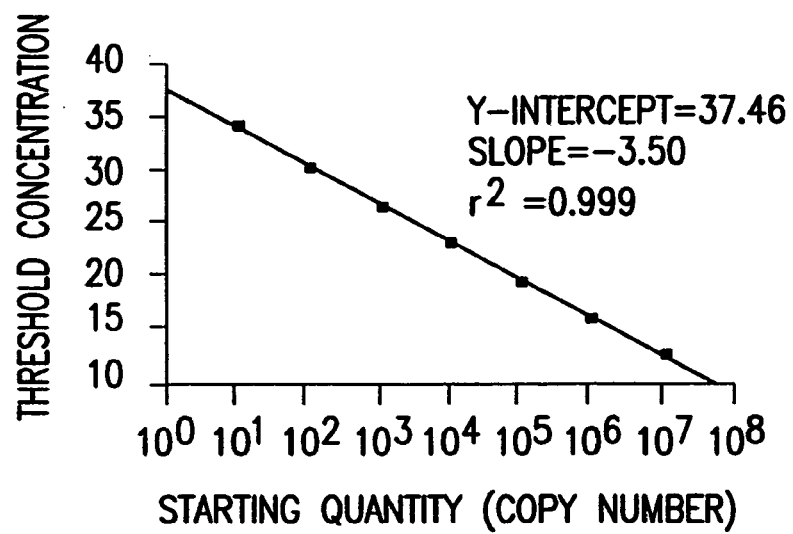
FIG. 41B is a graph depicting the initial cDNA concentrations verses threshold cycle ($C_T$), standard deviations are shown as error bars (12 replicates per dilution).

Samples with templates comprising a 10-fold, serial dilution of cloned, c-myc cDNA ranging from 10 to 10,000,000 copies are discriminated by two-step real time PCR (FIG. 41A; primer set 3, Table 8). A linear relationship ($r^2$=0.999) exists between the $C_T$ and starting copy numbers between 10 and 10,000,000 (standard curve, FIG. 41B). To demonstrate that the fluorogenic PCR may be used for various targets, similar fluorogenic PCRs were performed using ten-fold serial dilutions of IL-4 cloned cDNA (primer set 2, Table 8). Comparable results were obtained with a correlation coefficient of 0.992. Samples containing three-fold, serial dilutions (three replicate reactions per dilution) of cloned IL-4 cDNA ranging from 22 to 1,000,000 copies are discriminated by three-step, fluorogenic PCRs (primer set 2, Table 8). The correlation coefficient of $C_T$ verses copy number was 0.999.

Other fluorogenic PCRs were performed for amplicons of various sizes. FAM-labeled primers were designed for amplicons of c-myc with sizes 66, 562, 1107 base pairs and GAPDH with sizes 74, 570, 956 base pairs (Table 8). The fluorogenic PCRs (three-step cycling) were performed using cDNA from first-strand synthesis reactions (20 μl) using Hela total RNA (2.5 ng) as a template. PCRs were performed with 2, 0.2, 0.02 or 0 μl of these first strand reactions. For all primer sets, cDNA dilutions were determined with evenly spaced $C_T$s, which confirms that PCR efficiency is comparable for the amplicons of various sizes.

Example 33

Multiplex Quantitative PCR

Figure 42A:
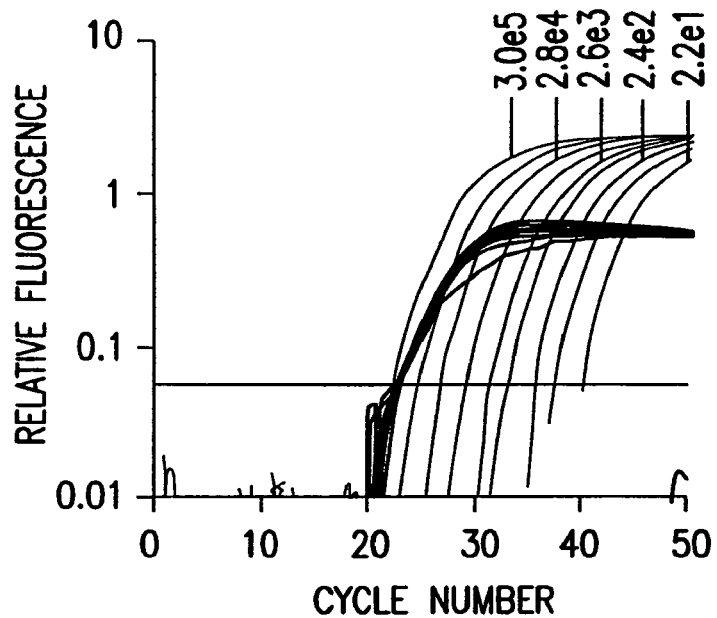
FIGS. 42A-B are line graphs of relative fluorescence as a function of the number of cycles of amplification performed which shows PCR comprising a 3-fold serial dilution of cloned cDNA as representation of multiplex fluorogenic PCR on ABI PRIZM 7700.
Figure 42B:
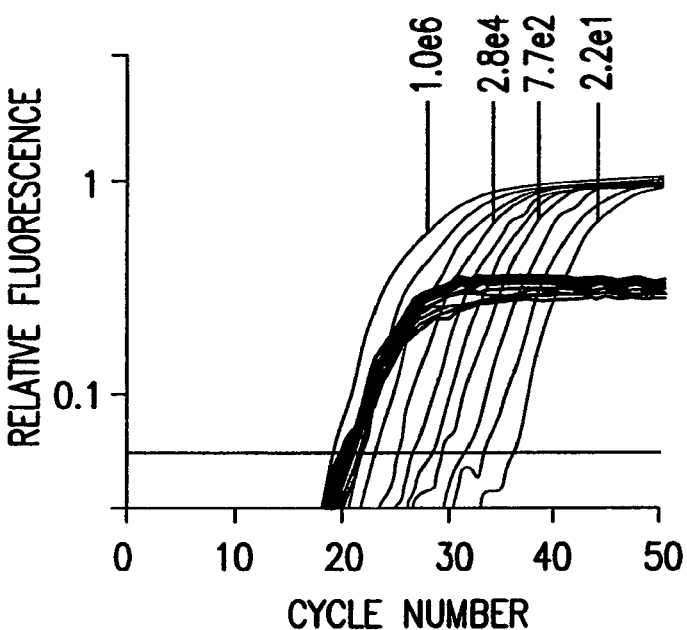
Figure 42C:
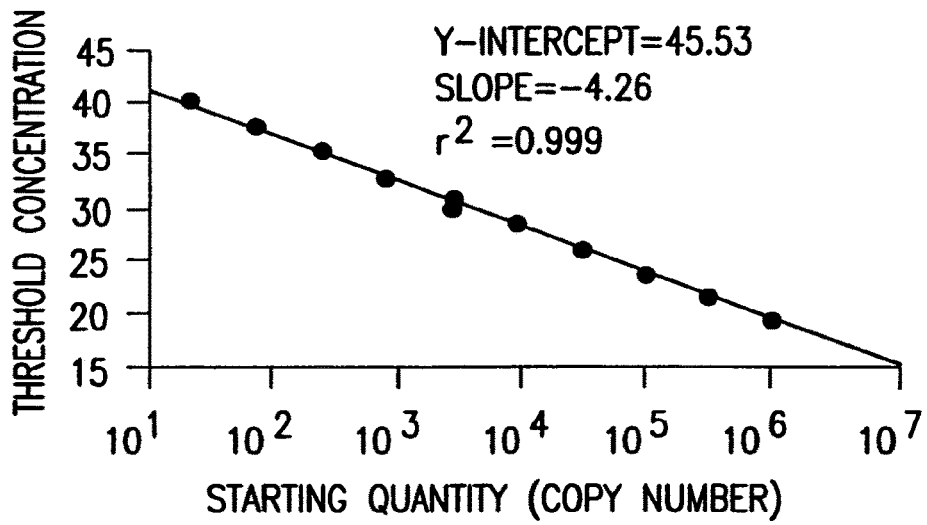
FIGS. 42C-D are corresponding plots of initial cDNA concentrations (two duplicate reactions per concentration) verses $C_T$.
Figure 42D:
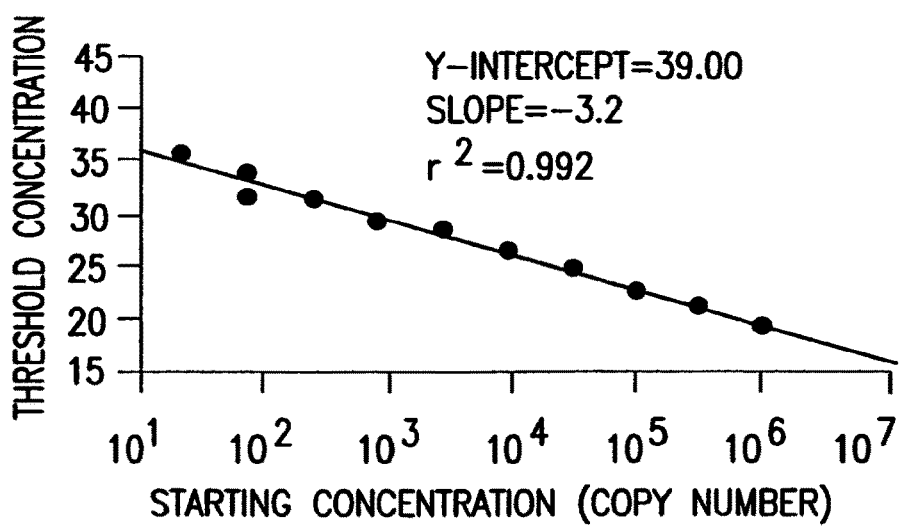

Quantitative, real-time, multiplex fluorogenic PCRs with two sets of gene-specific primers is useful because one primer set may be used to detect the amount of a gene that is variable and another for a gene that is relatively constant and used as a reference. Multiplex PCR using FAM-labeled primers for either c-myc or IL-4 and a JOE-labeled primers for the reference gene was used. Discrimination between 3-fold, serial dilutions of cloned IL-4 cDNA (primer set 2, Table 8) ranging from 22-300,000 copies, with each dilution containing 1,000,000 copies of cloned GAPDH cDNA was studied (primer set 12, Table 1; FIG. 42A). The correlation coefficient of $C_T$ verses IL-4 copy number was 0.999 for the best two out of three replicates. Thus, samples with unknown quantity of IL-4 may be determined by analyzing at what point the $C_T$ of a PCR with the unknown samples occurs on the standard curve. A similar set of PCRs using a cloned cDNA for c-myc (primer set 5, Table 8) as the variable gene and GAPDH as the constant gene was performed. The results in FIG. 42B showed that discrimination between dilutions of c-myc is similar to IL-4.

cDNAs other than GAPDH may be used as the reference gene. Three-fold serial dilutions of target concentration (IL-4) were discriminated by fluorogenic PCR when using either 1,000,000 copies of cloned cDNA β-actin (primer set 13, Table 8) or 18 S (primer set 14, Table 8) as the reference gene. Standard curve plots yield $r^2$ values of 0.995 and 0.998 for β-actin and 18S, respectively.

Figure 43A:
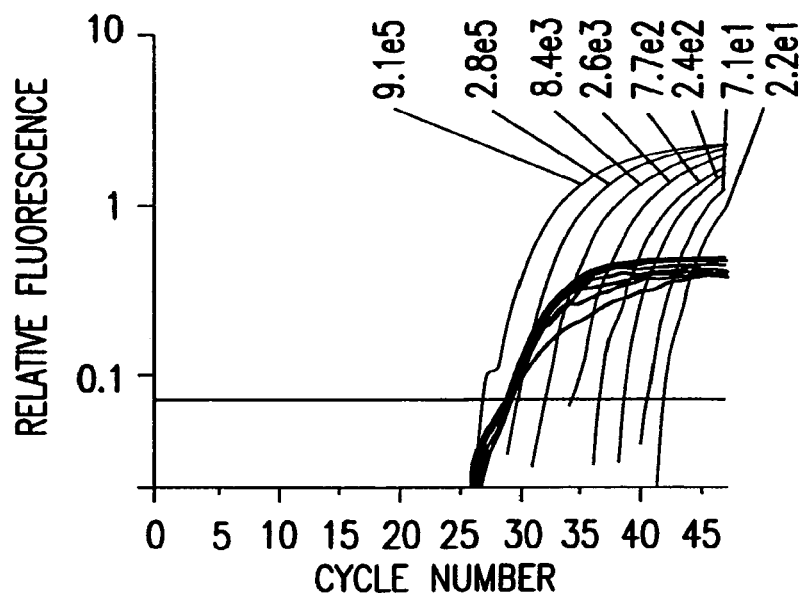
FIGS. 43A-B are line graphs showing multiplex real-time fluorogenic PCRs with a population of first-strand cDNAs from Hela cells. Three-step PCRs were performed with templates comprising a serial dilution of cloned IL-4 cDNA from 91,000 to 22 copies in the presence of a constant amount of cDNA generated from total Hela RNA. The variable IL-4 target was detected using a FAM-labeled hairpin primer (see Example 31, primer set 2, Table 8; gray lines) and the constant GAPDH target was detected with a JOE-labeled hairpin primer (see Example 31, primer set 12, Table 8; black lines).
Figure 43B:
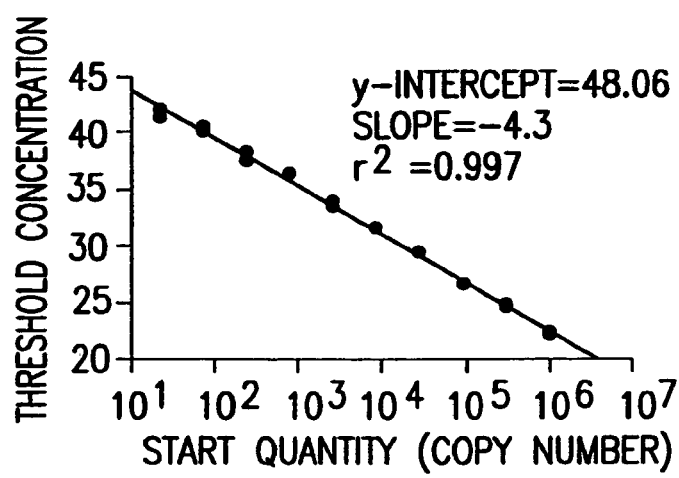

Furthermore, first-strand cDNA from Hela cell total RNA was used as a source of the reference gene in place of specific cloned cDNA. This was done to determine whether the PCRs would amplify their specific targets among a mixture of nonspecific cDNAs. For these experiments, the variable template was cloned IL-4 cDNA (3-fold dilutions) and the constant template was a fixed amount of first-strand cDNA from the reverse transcription of Hela total RNA (FIGS. 43A-B). Standard curves yield $r^2$ values of 0.997 for β-actin (primer set 13, Table 8), 0.996 for GAPDH (primer set 12, Table 8) and 0.999 for 18S (primer set 14, Table 8). The fluorogenic PCRs amplified only their appropriate target. Analysis of the PCR products by agarose gel electrophoresis revealed either insignificant or no non-specific PCR products or primer-dimers.

All the above results were obtained using the ABI 7700 system. Multiplex, fluorogenic PCR of variable amounts of cloned IL-4 mixed with a constant amount of cloned GAPDH on the BioRad i-Cycler IQ system was performed. The Biorad i-Cycler IQ system detected the cDNAs with similar sensitivity and dynamic range as the ABI 7700.

The results of quantitative PCR using fluorogenic primers may be analyzed by the comparative $C_T$ method. The comparative $C_T$ method is another commonly used method, besides the standard curve method, for quantifying an unknown amount of target cDNA in a sample (User Bulletin #2, ABI PRISM 7700 Sequence Detection System, P/N 4303859). This method of analysis does not require plotting a standard curve of $C_T$ verses starting copy number. Instead, the amount of target is calculated based on the difference between the $C_T$ of the target and an endogenous reference gene. A subset of RNA samples that were used in a published study where the comparative $C_T$ method was used in conjunction with the 5' nuclease assay to show that IL-4 expression is reduced in lymphocytes treated with aspirin (Cianferoni, A. et al., Blood 97:1742-1749 (2001)). The amount of IL-4 in these same samples were analyzed using fluorogenic, multiplex PCR by the comparative $C_T$ method. Total RNA (1 ng) from stimulated PBT samples that were treated, or untreated, with aspirin were reversed transcribed into cDNA and 2 μl of these reactions were used for real-time PCRs. One RT reaction was performed for each RNA sample and provided a template for three replicate PCRs. The three-step, real-time, multiplex PCR protocol was performed using a FAM-labeled primer for IL-4 and a JOE-labeled primer for GAPDH (primer sets 2 and 12, Table 8). The $C_T$s for the target gene (IL-4) and reference gene (GAPDH) were obtained using the ABI 7700. The level of IL-4 mRNA in an aspirin-treated PBTs sample was 33% lower that that found in the untreated PBTs sample, as calculated by the comparative $C_T$ method. This result is comparable with the 43% decrease in IL-4 expression after aspirin treatment that was reported in the previous study using TaqMan™ probes (Cianferoni, A. et al., Blood 97:1742-1749 (2001)).

Example 34

End-Point Detection of Allele-Specific PCR

Figure 44A:
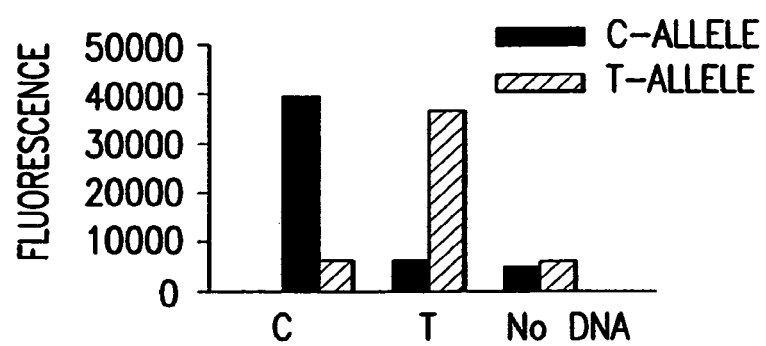
FIG. 44A is a bar graph showing fluorescence intensity of RDS polymorphs. Fluorescence was determined on a plat-ereader (Polarion, TECAN) with 490 nm exitation, 20 nm band width, 525 nm emission, 20 nm band width. Detection of the fluorescent PCR product at the end-point is shown. PCR products specific for C558/T558 polymorphism in RDS gene were generated using two different forward primers specific for C allele or T allele and common hairpin reverse primer labeled with FAM (primer set 15; Table 8). As described in Example 34, three-step PCRs were performed through 40 cycles.
Figure 44B:
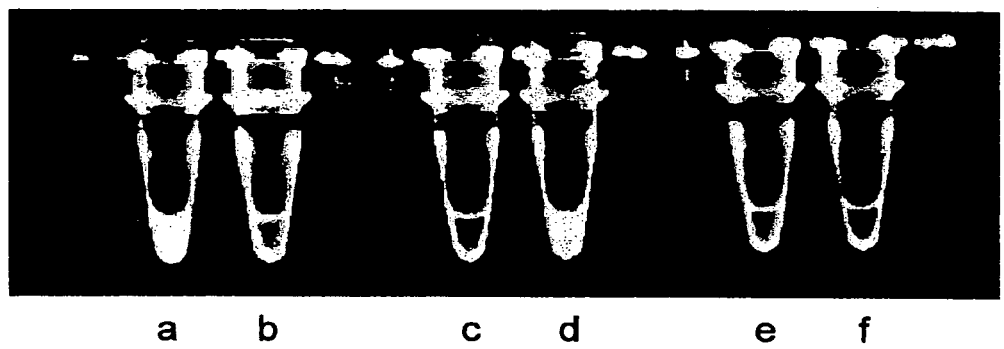
FIG. 44B is a photograph of the tubes that was taken on UV-transilluminator using Kodak imaging system equipped with the green filter (520 nm, 40 nm band width).

To demonstrate end-point detection capability, allele-specific PCRs were performed using human genomic DNA as a template. These PCRs detected the presence of a C/T polymorphism at position 558 of the RDS gene (Farrar, G. J. et al., Nucl. Acids Res. 19:6982 (1991)). Two unlabeled, allele-specific forward primers with C or T at the 3'-end, and a fluorogenic, reverse primer were designed to detect either the C or T polymorphism (primer set 15, Table 8). Discrimination of the alleles is based on the ability of DNA polymerase to extend 3' mismatches much less efficiently than correct matches (Petruska, J. et al., Proc. Natl. Acad. Sci. USA 85:6252-6256 (1988)). Two allele-specific PCRs were performed on each of two genomic DNA samples bearing different single-nucleotide polymorphisms (FIG. 44). Following PCR, the fluorescence was determined directly in the PCR tubes using either fluorescence plate-reader (Polarion, TECAN) or a UV-transilluminator. The results show that both alleles can be identified correctly with the appropriate primer and there is no signal increase in the absence of target.

Example 35

Quantitative RT-PCR for Studying Gene Expression

Real time one-step RT-PCR was accomplished using a primer pair where one primer (the fluorogenic primer) was labeled with a single fluorophore (FAM) on a T residue one base pair before to the 3'-end. No quencher is required. A tail of 5 nucleotides was added to the 5'-end of the fluorogenic primer to form a blunt-end hairpin when the primer is not incorporated into a PCR product. This design provides a low initial fluorescence of the primer that increases upon formation of the PCR product. The hairpin primer may be as efficient as linear primers and provide additional specificity to the PCR by preventing primer-dimers and mispriming. The fluorgenic primer and the unlabeled primer were designed by specialized software (see Example 21) that incorporates rules for identifying an efficient label site and also minimizes unspecific interactions during PCR. One step RT-PCR with HeLa total RNA as template was performed in real-time quantitation with a beta actin specific primer pair, designed as described above. The beta actin target was detected with precision in PCR using the FAM-labeled primer. Total RNA isolation was performed using Trizol reagent. One-step RT-PCR was performed by using a One Step Thermoscript qRT-PCR kit (Invitrogen Corporation, Catalog No.: 11731-015).

Figure 45:
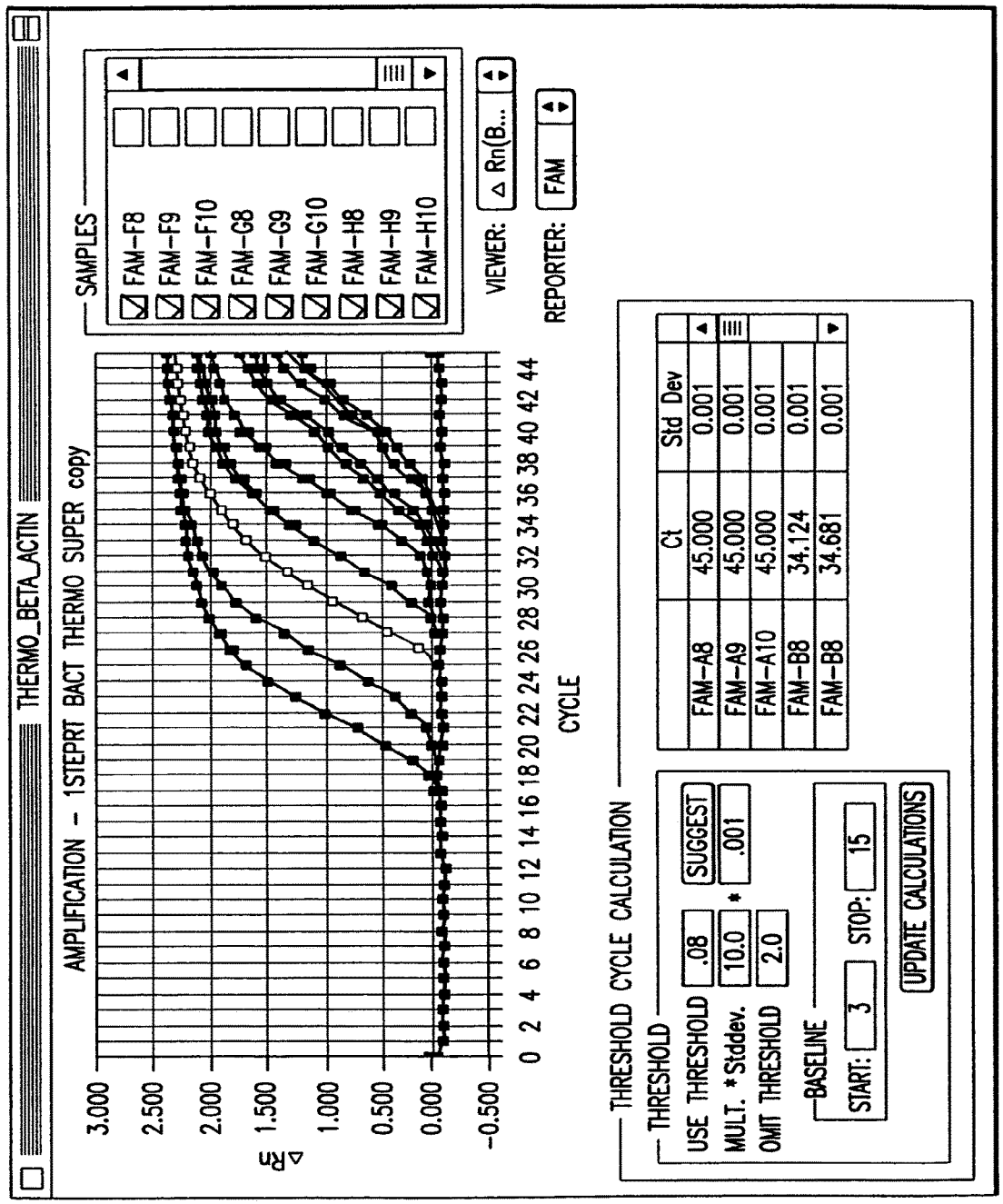
FIG. 45 is a line graph of fluorescence intensity as a function of number of cycles of amplification performed.
Figure 46:
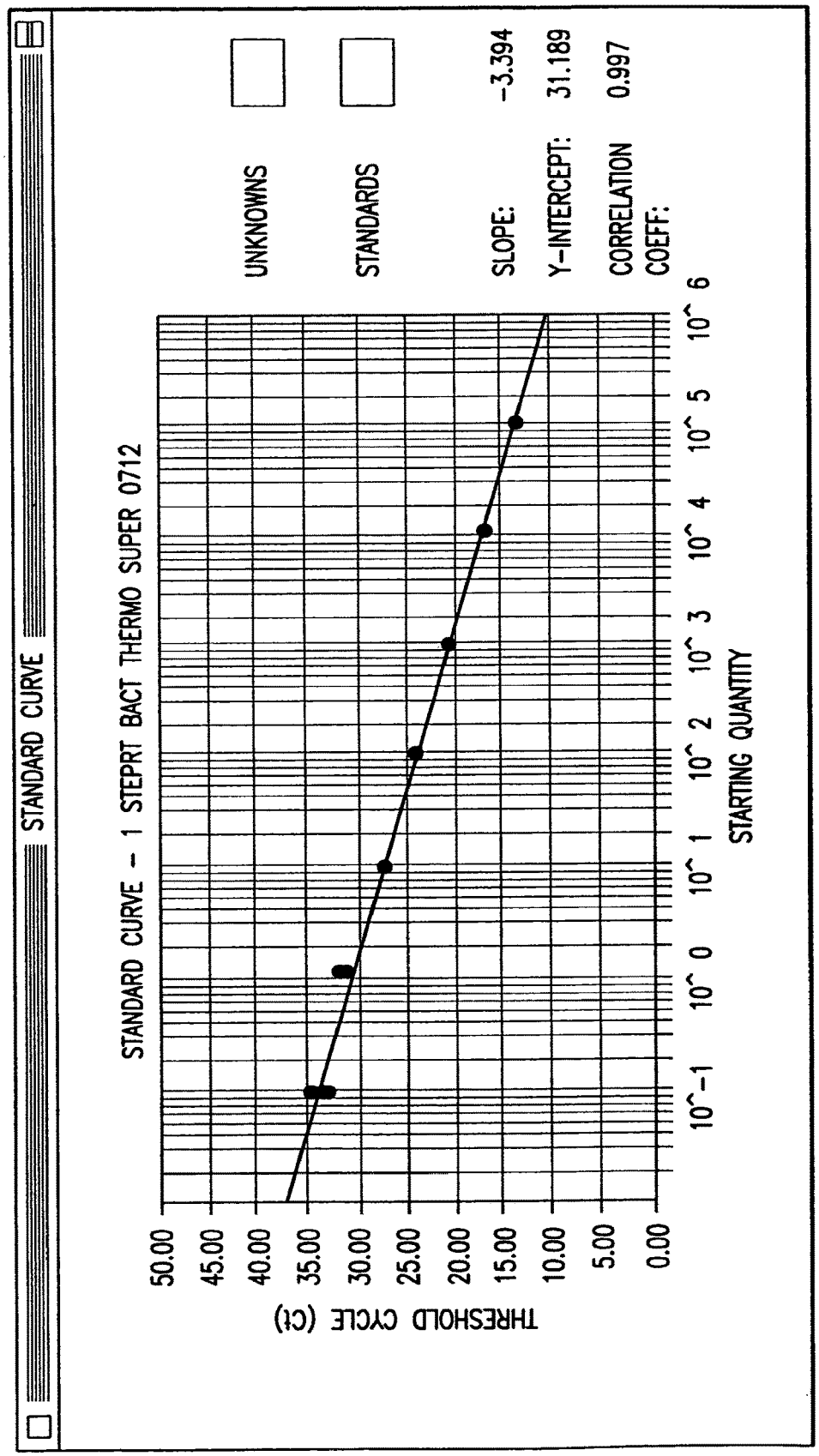
FIG. 46 is a standard curve plotting the number of cycles of amplification against the starting quantity of template DNA.

The beta-actin transcript was quantified in samples comprising 10-fold serial dilutions of HeLa cell total RNA ranging from 100 ng-0.1 pg in triplicates including no template controls also in triplicates. The one-step RT-PCR in real time was performed on an ABI PRISM 7700 instrument using 30 min at 50° C. (RT reaction) followed by 5 min at 95° C. and 45 cycles of 95° C. for 15 sec/60° C. for 45 sec (PCR reaction). Amplification plot is shown as FIG. 45 and initial RNA concentrations versus $C_T$ is shown as FIG. 46.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A composition comprising one or more target nucleic acid molecules and at least two different oligonucleotides, wherein said oligonucleotides are extendable by nucleic acid synthesis and wherein said oligonucleotides, when extended by nucleic acid synthesis, are incorporated into a double-stranded nucleic acid product on opposite strands, wherein said first oligonucleotide comprises a fluorescent moiety at or near its 3'-terminal nucleotide and said second oligonucleotide comprises a quenching moiety at or near its 3'-terminal nucleotide; and wherein said first oligonucleotide exhibits a detectable change upon incorporation into said double-stranded nucleic acid product.

2. The composition of claim 1, further comprising at least one component selected from the group consisting of one or more nucleotides, one or more DNA polymerases and one or more reverse transcriptases.

3. A method for amplifying a double-stranded nucleic acid molecule, comprising:
    providing a first and second primer, wherein said first primer is complementary to a portion of the first strand of said nucleic molecule and said second primer is complementary to a portion of the second strand of said nucleic acid molecule;
    hybridizing said first primer to said first strand and said second primer to said second strand in the presence of one or more polymerases, under conditions such that a third nucleic acid molecule complementary to all or a portion of said first strand and a fourth nucleic acid molecule complementary to all or a portion said second strand are synthesized; wherein said first and second primers are incorporated into said third and said fourth nucleic acid molecules, respectively;
    denaturing said first and third strand, and said second and fourth strands; and
    repeating the above steps one or more times, wherein said first primer comprises a fluorescent moiety at or near its 3'-terminal nucleotide and said second primer comprises a quencher moiety at or near its 3'-terminal nucleotide, wherein said fluorescent moiety exhibits a detectable change upon incorporation of said first primer into said third nucleic acid molecules.

4. The composition of claim 1, wherein said fluorescent moiety and said quencher moiety form a FRET pair.

5. The composition of claim 1, wherein said fluorescent moiety is selected from the group consisting of a fluorescein phosphoramidite (FAM) moiety, a 6-carboxyfluorescein succinimidyl ester (6-FAM, SE) moiety, a fluorescein-5-isothiocyanate (FITC) moiety, a 5-(6-)-carboxytetramethyl rhodamine (TAMRA) moiety, a succinimidyl ester moiety, and a 4,4-difluoro-5, 7-diphenyl-4-bora-3a,4a-diaza-s-indacene-3-propionic acid (BODIPY 530/550) moiety.

6. The composition of claim 1, wherein said target nucleic acid molecule is a cDNA molecule.

7. The method of claim 3, wherein said fluorescent moiety and said quencher moiety form a FRET pair.

8. The method of claim 3, wherein said fluorescent moiety is selected from the group consisting of a fluorescein phosphoramidite (FAM) moiety, a 6-carboxyfluorescein succinimidyl ester (6-FAM, SE) moiety, a fluorescein-5-isothiocyanate (FITC) moiety, a 5-(6-)-carboxytetramethyl rhodamine (TAMRA) moiety, a succinimidyl ester moiety, and a 4,4-difluoro-5, 7-diphenyl-4-bora-3a,4a-diaza-s-indacene-3-propionic acid (BODIPY 530/550) moiety.

9. The method of claim 3, wherein said double-stranded nucleic acid molecule is a DNA/RNA molecule.

10. The composition of claim 1, wherein said target nucleic acid is an RNA target.

11. The composition of claim 1, wherein said first and second oligonucleotides are linear.

12. The composition of claim 1, wherein said first and/or second oligonucleotides further comprise a specificity enhancing group.

13. The composition of claim 12, wherein said specificity enhancing group comprises a 2'-O-alkyl ribonucleotide.

14. The composition of claim 3, wherein said first and second primers are linear.

15. The composition of claim 3, wherein said first and/or second primers further comprise a specificity enhancing group.

16. The composition of claim 15, wherein said specificity enhancing group comprises a 2'-O-alkyl ribonucleotide.

* * * * *

SEQUENCE LISTING

```
<160> NUMBER OF SEQ ID NOS: 139

<210> SEQ ID NO 1
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)..(18)
<223> OTHER INFORMATION: Fluorescently labeled

<400> SEQUENCE: 1
ccttctcatg gtggctgtag aac                                              23

<210> SEQ ID NO 2
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: Fluorescently labeled

<400> SEQUENCE: 2
ccttctcatg gtggctgtag aac                                              23

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
ggtctacagc caccatgaga agg                                              23

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
ggggctgcga ctgtgctccg gca                                              23
```

```
<210> SEQ ID NO 5
<211> LENGTH: 23
<212> TYPE: DNA
<213> ORGANISM: Artificial Sequence
<220> FEATURE:
<223> OTHER INFORMATION: Primer

<400> SEQUENCE: 5
tgccggagca cagtcgcagc ccc                                              23

<210> SEQ ID NO 6
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: Fluorescently labeled

<400> SEQUENCE: 6
aataatagga tgaggcagga                                                  20

<210> SEQ ID NO 7
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: Labeled with BODIPY 530/550

<400> SEQUENCE: 7
aataatagga tgaggcagga                                                  20

<210> SEQ ID NO 8
<211> LENGTH: 20
<212> TYPE: DNA
<213> ORGANISM: Artificial Sequence
<220> FEATURE:
<223> OTHER INFORMATION: Primer

<400> SEQUENCE: 8
tcctgcctca tcctattatt                                                  20

<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
gagttgaccg taacagacat ctt                                              23

<210> SEQ ID NO 10
<211> LENGTH: 24
<212> TYPE: DNA
<213> ORGANISM: Artificial Sequence
<220> FEATURE:
<223> OTHER INFORMATION: Primer

<400> SEQUENCE: 10
```
ggcattgccg acaggatgta gaag                        24

<210> SEQ ID NO 11
<211> LENGTH: 18
<212> TYPE: DNA
<213> ORGANISM: Artificial Sequence
<220> FEATURE:
<223> OTHER INFORMATION: Primer

<400> SEQUENCE: 11
gggccggact cgtcatac                               18

<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12
ggttgtagag cactcagcac aatgaaga                    28

<210> SEQ ID NO 13
<211> LENGTH:
<212> TYPE:
<213> ORGANISM:

<400> SEQUENCE: 13

000

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
ccttctcatg gtggctgtag aac                         23

<210> SEQ ID NO 15
<211> LENGTH: 23
<212> TYPE: DNA
<213> ORGANISM: Artificial Sequence
<220> FEATURE:
<223> OTHER INFORMATION: Primer

<400> SEQUENCE: 15
ccttctcatg gtggctgtag aat                         23

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
gtgtccttct catggtggct gtag                        24

<210> SEQ ID NO 17
<211> LENGTH: 24
<212> TYPE: DNA
<213> ORGANISM: Artificial Sequence
<220> FEATURE:
<223> OTHER INFORMATION: Primer

<400> SEQUENCE: 17
gtgtccttct catggtggct gtat                                              24

<210> SEQ ID NO 18
<211> LENGTH:
<212> TYPE:
<213> ORGANISM:

<400> SEQUENCE: 18

000

<210> SEQ ID NO 19
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)..(18)
<223> OTHER INFORMATION: Fluorescently labeled

<400> SEQUENCE: 19
ccttctcatg gtggctgtag aat                                               23

<210> SEQ ID NO 20
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (22)..(22)
<223> OTHER INFORMATION: Fluorescently labeled

<400> SEQUENCE: 20
gtgtccttct catggtggct gtag                                              24

<210> SEQ ID NO 21
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (22)..(22)
<223> OTHER INFORMATION: Fluorescently labeled

<400> SEQUENCE: 21
gtgtccttct catggtggct gtat                                              24

<210> SEQ ID NO 22
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (23)..(23)
<223> OTHER INFORMATION: Labeled with fluoroscein

<400> SEQUENCE: 22
ctaccgggtg tctgtgtctc ggtag                                             25

```
<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
cgtacctggc tatctgtgtc                                                 20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
cgtacctggc tatctgtgtt                                                 20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
gacacctggc tatctgtgtc                                                 20

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
aacacacctg gctatctgtg tt                                              22

<210> SEQ ID NO 27
<211> LENGTH: 27
<212> TYPE: DNA
<213> ORGANISM: Artificial Sequence
<220> FEATURE:
<223> OTHER INFORMATION: Primer

<400> SEQUENCE: 27
ctacagtcct tctcatggtg gctgtag                                         27

<210> SEQ ID NO 28
<211> LENGTH: 25
<212> TYPE: DNA
<213> ORGANISM: Artificial Sequence
<220> FEATURE:
<223> OTHER INFORMATION: Primer

<400> SEQUENCE: 28
cttcctgaga gccgaactgt agtga                                           25

<210> SEQ ID NO 29
<211> LENGTH: 26
<212> TYPE: DNA
<213> ORGANISM: Artificial Sequence
<220> FEATURE:
<223> OTHER INFORMATION: Primer
```

```
<400> SEQUENCE: 29
acatgtattt gcatggaaaa caactc                                          26

<210> SEQ ID NO 30
<211> LENGTH: 31
<212> TYPE: DNA
<213> ORGANISM: Artificial Sequence
<220> FEATURE:
<223> OTHER INFORMATION: Primer

<400> SEQUENCE: 30
tcactacttc ctgagagccg aactgtagtg a                                    31

<210> SEQ ID NO 31
<211> LENGTH: 33
<212> TYPE: DNA
<213> ORGANISM: Artificial Sequence
<220> FEATURE:
<223> OTHER INFORMATION: Primer

<400> SEQUENCE: 31
gagttgtaca tgtatttgca tggaaaacaa ctc                                  33

<210> SEQ ID NO 32
<211> LENGTH: 24
<212> TYPE: DNA
<213> ORGANISM: Artificial Sequence
<220> FEATURE:
<223> OTHER INFORMATION: Primer

<400> SEQUENCE: 32
gctcagaatg atgtttccac cttc                                            24

<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33
aaatcatact agctcaccag caatg                                           25

<210> SEQ ID NO 34
<211> LENGTH: 30
<212> TYPE: DNA
<213> ORGANISM: Artificial Sequence
<220> FEATURE:
<223> OTHER INFORMATION: Primer

<400> SEQUENCE: 34
gaaggtgctc agaatgatgt ttccaccttc                                      30

<210> SEQ ID NO 35
<211> LENGTH: 31
<212> TYPE: DNA
<213> ORGANISM: Artificial Sequence
<220> FEATURE:
<223> OTHER INFORMATION: Primer

<400> SEQUENCE: 35
cattgcaaat catactagct caccagcaat g                                    31

<210> SEQ ID NO 36
```

```
<211> LENGTH: 22
<212> TYPE: DNA
<213> ORGANISM: Artificial Sequence
<220> FEATURE:
<223> OTHER INFORMATION: Primer

<400> SEQUENCE: 36
tggcagttga atgccaagta at                                              22

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
acagccactg tgcccaggtc                                                 20

<210> SEQ ID NO 38
<211> LENGTH: 28
<212> TYPE: DNA
<213> ORGANISM: Artificial Sequence
<220> FEATURE:
<223> OTHER INFORMATION: Primer

<400> SEQUENCE: 38
attacttggc agttgaatgc caagtaat                                        28

<210> SEQ ID NO 39
<211> LENGTH: 26
<212> TYPE: DNA
<213> ORGANISM: Artificial Sequence
<220> FEATURE:
<223> OTHER INFORMATION: Primer

<400> SEQUENCE: 39
gacctgacag ccactgtgcc caggtc                                          26

<210> SEQ ID NO 40
<211> LENGTH: 23
<212> TYPE: DNA
<213> ORGANISM: Artificial Sequence
<220> FEATURE:
<223> OTHER INFORMATION: Primer

<400> SEQUENCE: 40
atttcatggg ggaaacaaag atg                                             23

<210> SEQ ID NO 41
<211> LENGTH: 20
<212> TYPE: DNA
<213> ORGANISM: Artificial Sequence
<220> FEATURE:
<223> OTHER INFORMATION: Primer

<400> SEQUENCE: 41
atacctgcgc tcaccacagg                                                 20

<210> SEQ ID NO 42
<211> LENGTH: 30
<212> TYPE: DNA
<213> ORGANISM: Artificial Sequence
<220> FEATURE:
<223> OTHER INFORMATION: Primer

<400> SEQUENCE: 42
```

```
catctttatt tcatggggga aacaaagatg                                    30

<210> SEQ ID NO 43
<211> LENGTH: 26
<212> TYPE: DNA
<213> ORGANISM: Artificial Sequence
<220> FEATURE:
<223> OTHER INFORMATION: Primer

<400> SEQUENCE: 43
cctgtgatac ctgcgctcac cacagg                                        26

<210> SEQ ID NO 44
<211> LENGTH: 28
<212> TYPE: DNA
<213> ORGANISM: Artificial Sequence
<220> FEATURE:
<223> OTHER INFORMATION: Primer

<400> SEQUENCE: 44
caacataaga tcgccgtcct gtatgttg                                      28

<210> SEQ ID NO 45
<211> LENGTH: 27
<212> TYPE: DNA
<213> ORGANISM: Artificial Sequence
<220> FEATURE:
<223> OTHER INFORMATION: Primer

<400> SEQUENCE: 45
catcaaaagt tgaactggcc cttgatg                                       27

<210> SEQ ID NO 46
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (26)..(26)
<223> OTHER INFORMATION: Fluorescently labeled

<400> SEQUENCE: 46
caacataaga tcgccgtcct gtatgttg                                      28

<210> SEQ ID NO 47
<211> LENGTH: 30
<212> TYPE: DNA
<213> ORGANISM: Artificial Sequence
<220> FEATURE:
<223> OTHER INFORMATION: Primer

<400> SEQUENCE: 47
aacatacaaa gatcgccgtc ctgtatgttg                                    30

<210> SEQ ID NO 48
<211> LENGTH:
<212> TYPE:
<213> ORGANISM:

<400> SEQUENCE: 48

000

<210> SEQ ID NO 49
```

```
<211> LENGTH:
<212> TYPE:
<213> ORGANISM:

<400> SEQUENCE: 49

000

<210> SEQ ID NO 50
<211> LENGTH:
<212> TYPE:
<213> ORGANISM:

<400> SEQUENCE: 50

000

<210> SEQ ID NO 51
<211> LENGTH: 27
<212> TYPE: DNA
<213> ORGANISM: Artificial Sequence
<220> FEATURE:
<223> OTHER INFORMATION: Primer

<400> SEQUENCE: 51
atcaagaagt tgaactggcc cttgatg                                    27

<210> SEQ ID NO 52
<211> LENGTH: 28
<212> TYPE: DNA
<213> ORGANISM: Artificial Sequence
<220> FEATURE:
<223> OTHER INFORMATION: Primer

<400> SEQUENCE: 52
ctaaactgac ggtggaattt aagtttag                                   28

<210> SEQ ID NO 53
<211> LENGTH: 28
<212> TYPE: DNA
<213> ORGANISM: Artificial Sequence
<220> FEATURE:
<223> OTHER INFORMATION: Primer

<400> SEQUENCE: 53
gattctcttg ctccatgatt aaagaatc                                   28

<210> SEQ ID NO 54
<211> LENGTH: 29
<212> TYPE: DNA
<213> ORGANISM: Artificial Sequence
<220> FEATURE:
<223> OTHER INFORMATION: Primer

<400> SEQUENCE: 54
aaacttactg acggtggaat ttaagttta                                  29

<210> SEQ ID NO 55
<211> LENGTH: 28
<212> TYPE: DNA
<213> ORGANISM: Artificial Sequence
<220> FEATURE:
<223> OTHER INFORMATION: Primer

<400> SEQUENCE: 55
attcttcttg ctccatgatt aaagaatc                                   28
```

```
<210> SEQ ID NO 56
<211> LENGTH: 21
<212> TYPE: DNA
<213> ORGANISM: Artificial Sequence
<220> FEATURE:
<223> OTHER INFORMATION: Primer

<400> SEQUENCE: 56
tgaggccgcc atatctcctc a                                             21

<210> SEQ ID NO 57
<211> LENGTH: 21
<212> TYPE: DNA
<213> ORGANISM: Artificial Sequence
<220> FEATURE:
<223> OTHER INFORMATION: Primer

<400> SEQUENCE: 57
ggaggccgcc atatctcctc c                                             21

<210> SEQ ID NO 58
<211> LENGTH: 29
<212> TYPE: DNA
<213> ORGANISM: Artificial Sequence
<220> FEATURE:
<223> OTHER INFORMATION: Primer

<400> SEQUENCE: 58
gagataaaat aaaattcatg gtgtatctc                                     29

<210> SEQ ID NO 59
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (28)..(28)
<223> OTHER INFORMATION: Fluorescently labeled

<400> SEQUENCE: 59
gatcttcggc acccagcaca atgaagatc                                     29

<210> SEQ ID NO 60
<211> LENGTH: 31
<212> TYPE: DNA
<213> ORGANISM: Artificial Sequence
<220> FEATURE:
<223> OTHER INFORMATION: Primer

<400> SEQUENCE: 60
atgcttcaag tcatagtccg cctagaagca t                                  31

<210> SEQ ID NO 61
<211> LENGTH: 31
<212> TYPE: DNA
<213> ORGANISM: Artificial Sequence
<220> FEATURE:
<223> OTHER INFORMATION: Primer

<400> SEQUENCE: 61
aagatgtcga gttgaccgta acagacatct t                                  31

<210> SEQ ID NO 62
<211> LENGTH: 27
<212> TYPE: DNA
```

```
<213> ORGANISM: Artificial Sequence
<220> FEATURE:
<223> OTHER INFORMATION: Primer
<220> FEATURE:
<221> NAME/KEY: misc_feature
<222> LOCATION: (25)..(25)
<223> OTHER INFORMATION: Labeled with FAM

<400> SEQUENCE: 62
ctacagtcct tctcatggtg gctgtag                                       27

<210> SEQ ID NO 63
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (23)..(23)
<223> OTHER INFORMATION: Fluorescently labeled

<400> SEQUENCE: 63
ctaccgggtg tctgtgtctc ggtag                                         25

<210> SEQ ID NO 64
<211> LENGTH: 37
<212> TYPE: DNA
<213> ORGANISM: Artificial Sequence
<220> FEATURE:
<223> OTHER INFORMATION: Primer

<400> SEQUENCE: 64
gggtgtctgt gtctcggtag acctggctat ctgtgtc                            37

<210> SEQ ID NO 65
<211> LENGTH: 25
<212> TYPE: DNA
<213> ORGANISM: Artificial Sequence
<220> FEATURE:
<223> OTHER INFORMATION: Primer

<400> SEQUENCE: 65
ggtagtactt catgccgttc ttgag                                         25

<210> SEQ ID NO 66
<211> LENGTH: 37
<212> TYPE: DNA
<213> ORGANISM: Artificial Sequence
<220> FEATURE:
<223> OTHER INFORMATION: Primer

<400> SEQUENCE: 66
gggtgtctgt gtctcggtag acctggctat ctgtgtt                            37

<210> SEQ ID NO 67
<211> LENGTH: 25
<212> TYPE: DNA
<213> ORGANISM: Artificial Sequence
<220> FEATURE:
<223> OTHER INFORMATION: Primer

<400> SEQUENCE: 67
ctaccgggca tctgagtatc ggtag                                         25

<210> SEQ ID NO 68
<211> LENGTH: 25
```

```
<212> TYPE: DNA
<213> ORGANISM: Artificial Sequence
<220> FEATURE:
<223> OTHER INFORMATION: Primer

<400> SEQUENCE: 68
cgactgggca tctgagtatc agtcg                                              25

<210> SEQ ID NO 69
<211> LENGTH: 25
<212> TYPE: DNA
<213> ORGANISM: Artificial Sequence
<220> FEATURE:
<223> OTHER INFORMATION: Primer

<400> SEQUENCE: 69
gtaccggagg actgtgtttc ggtac                                              25

<210> SEQ ID NO 70
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (23)..(23)
<223> OTHER INFORMATION: Fluorescently labeled

<400> SEQUENCE: 70
caaccggagg actgtgtttc ggttg                                              25

<210> SEQ ID NO 71
<211> LENGTH:
<212> TYPE:
<213> ORGANISM:

<400> SEQUENCE: 71

000

<210> SEQ ID NO 72
<211> LENGTH: 23
<212> TYPE: DNA
<213> ORGANISM: Artificial Sequence
<220> FEATURE:
<223> OTHER INFORMATION: Primer

<400> SEQUENCE: 72
gaccggagga ctgtgtttcg gtc                                                23

<210> SEQ ID NO 73
<211> LENGTH: 23
<212> TYPE: DNA
<213> ORGANISM: Artificial Sequence
<220> FEATURE:
<223> OTHER INFORMATION: Primer

<400> SEQUENCE: 73
caccggagga ctgtgtttcg gtg                                                23

<210> SEQ ID NO 74
<211> LENGTH: 25
<212> TYPE: DNA
<213> ORGANISM: Artificial Sequence
<220> FEATURE:
<223> OTHER INFORMATION: Primer
```

<400> SEQUENCE: 74
ctaccgggtg tctgtgtctc ggtag                                         25

<210> SEQ ID NO 75
<211> LENGTH: 19
<212> TYPE: DNA
<213> ORGANISM: Artificial Sequence
<220> FEATURE:
<223> OTHER INFORMATION: Primer

<400> SEQUENCE: 75
gccggtgagc gtgggtcta                                                19

<210> SEQ ID NO 76
<211> LENGTH: 19
<212> TYPE: DNA
<213> ORGANISM: Artificial Sequence
<220> FEATURE:
<223> OTHER INFORMATION: Primer

<400> SEQUENCE: 76
gccggtgagc gtgggtctt                                                19

<210> SEQ ID NO 77
<211> LENGTH: 19
<212> TYPE: DNA
<213> ORGANISM: Artificial Sequence
<220> FEATURE:
<223> OTHER INFORMATION: Primer

<400> SEQUENCE: 77
gccggtgagc gtgggtctc                                                19

<210> SEQ ID NO 78
<211> LENGTH: 19
<212> TYPE: DNA
<213> ORGANISM: Artificial Sequence
<220> FEATURE:
<223> OTHER INFORMATION: Primer

<400> SEQUENCE: 78
gccggtgagc gtgggtctg                                                19

<210> SEQ ID NO 79
<211> LENGTH: 23
<212> TYPE: DNA
<213> ORGANISM: Artificial Sequence
<220> FEATURE:
<223> OTHER INFORMATION: Primer

<400> SEQUENCE: 79
ctctgctgaa gccagttacc ttc                                           23

<210> SEQ ID NO 80
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (19)..(19)
<223> OTHER INFORMATION: 2'-O-methyl ribonucleotide

<400> SEQUENCE: 80
gccggtgagc gtgggtcta                                                19

<210> SEQ ID NO 81
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (19)..(19)
<223> OTHER INFORMATION: 2'-O-methyl ribonucleotide

<400> SEQUENCE: 81
gccggtgagc gtgggtctt                    19

<210> SEQ ID NO 82
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (19)..(19)
<223> OTHER INFORMATION: 2'-O-methyl ribonucleotide

<400> SEQUENCE: 82
gccggtgagc gtgggtctc                    19

<210> SEQ ID NO 83
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (19)..(19)
<223> OTHER INFORMATION: 2'-O-methyl ribonucleotide

<400> SEQUENCE: 83
gccggtgagc gtgggtctg                    19

<210> SEQ ID NO 84
<211> LENGTH: 22
<212> TYPE: DNA
<213> ORGANISM: Artificial Sequence
<220> FEATURE:
<223> OTHER INFORMATION: Primer

<400> SEQUENCE: 84
atgcgccggt gagcgtgggt ct                22

<210> SEQ ID NO 85
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (23)..(23)
<223> OTHER INFORMATION: May be either T or U

<400> SEQUENCE: 85
atgcgccggt gagcgtgggt ctn               23

<210> SEQ ID NO 86

```
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (23)..(23)
<223> OTHER INFORMATION: 2'-O-methyl ribonucleotide

<400> SEQUENCE: 86
atgcgccggt gagcgtgggt ctg                                              23

<210> SEQ ID NO 87
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (23)..(23)
<223> OTHER INFORMATION: 2'-O-methyl ribonucleotide

<400> SEQUENCE: 87
atgcgccggt gagcgtgggt cta                                              23

<210> SEQ ID NO 88
<211> LENGTH: 22
<212> TYPE: DNA
<213> ORGANISM: Artificial Sequence
<220> FEATURE:
<223> OTHER INFORMATION: Primer

<400> SEQUENCE: 88
atgcaccgcc tccagattta tc                                               22

<210> SEQ ID NO 89
<211> LENGTH: 61
<212> TYPE: DNA
<213> ORGANISM: Artificial Sequence
<220> FEATURE:
<223> OTHER INFORMATION: Template Sequence for Oligo

<400> SEQUENCE: 89
cgaggcgctg ccgtcggtgc cgcagccggc cggtttctgc tacgccggta ggctaacgtt      60
a                                                                      61

<210> SEQ ID NO 90
<211> LENGTH: 59
<212> TYPE: DNA
<213> ORGANISM: Artificial Sequence
<220> FEATURE:
<223> OTHER INFORMATION: Template Sequence for Oligo

<400> SEQUENCE: 90
cgaggcgctg ccgtcggtgc cgcagccggc cggtttctgc tacgccggta ggctaacgt       59

<210> SEQ ID NO 91
<211> LENGTH: 32
<212> TYPE: DNA
<213> ORGANISM: Artificial Sequence
<220> FEATURE:
<223> OTHER INFORMATION: Primer

<400> SEQUENCE: 91
gctccgcgac ggcagccacg gcgtcggccg gc                                    32
```

<210> SEQ ID NO 92
<211> LENGTH: 32
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (32)..(32)
<223> OTHER INFORMATION: May be either T or U

<400> SEQUENCE: 92
gctccgcgac ggcagccacg gcgtcggccg gn            32

<210> SEQ ID NO 93
<211> LENGTH:
<212> TYPE:
<213> ORGANISM:

<400> SEQUENCE: 93

000

<210> SEQ ID NO 94
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (18)..(18)
<223> OTHER INFORMATION: Fluorescently labeled

<400> SEQUENCE: 94
ccttctcatg gtggctgtag            20

<210> SEQ ID NO 95
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (25)..(25)
<223> OTHER INFORMATION: Fluorescently labeled

<400> SEQUENCE: 95
ctacagtcct tctcatggtg gctgtag            27

<210> SEQ ID NO 96
<211> LENGTH:
<212> TYPE:
<213> ORGANISM:

<400> SEQUENCE: 96

000

<210> SEQ ID NO 97
<211> LENGTH: 23
<212> TYPE: DNA
<213> ORGANISM: Artificial Sequence
<220> FEATURE:
<223> OTHER INFORMATION: Primer

<400> SEQUENCE: 97
ccttctcatg gtgataataa tac                                          23

<210> SEQ ID NO 98
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: Fluorescently labeled

<400> SEQUENCE: 98
ccttctcatg gtggctgtag aac                                          23

<210> SEQ ID NO 99
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: Fluorescently labeled

<400> SEQUENCE: 99
ccttctcatg gtggctgtag aac                                          23

<210> SEQ ID NO 100
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: Fluorescently labeled

<400> SEQUENCE: 100
ccttctcatg gtggctgtag aac                                          23

<210> SEQ ID NO 101
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (12)..(12)
<223> OTHER INFORMATION: Fluorescently labeled

<400> SEQUENCE: 101
ccttctcatg gtggctgtag aac                                          23

<210> SEQ ID NO 102
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(16)
<223> OTHER INFORMATION: Fluorescently labeled

<400> SEQUENCE: 102
ccttctcatg gtggctgtag aac                    23

<210> SEQ ID NO 103
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(1)
<223> OTHER INFORMATION: Fluorescently labeled

<400> SEQUENCE: 103
ccttctcatg gtggctgtag                        20

<210> SEQ ID NO 104
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: Fluorescently labeled

<400> SEQUENCE: 104
ccttctcatg gtggctgtag                        20

<210> SEQ ID NO 105
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (13)..(13)
<223> OTHER INFORMATION: Fluorescently labeled

<400> SEQUENCE: 105
cctggttatc tgtgtc                            16

<210> SEQ ID NO 106
<211> LENGTH: 19
<212> TYPE: DNA
<213> ORGANISM: Artificial Sequence
<220> FEATURE:
<223> OTHER INFORMATION: Primer

<400> SEQUENCE: 106
ggtgtctgtg tctcggtag                         19

<210> SEQ ID NO 107
<211> LENGTH:
<212> TYPE:
<213> ORGANISM:

<400> SEQUENCE: 107

000

<210> SEQ ID NO 108
<211> LENGTH:
<212> TYPE:
<213> ORGANISM:

```
<400> SEQUENCE: 108

000

<210> SEQ ID NO 109
<211> LENGTH: 20
<212> TYPE: DNA
<213> ORGANISM: Artificial Sequence
<220> FEATURE:
<223> OTHER INFORMATION: Primer

<400> SEQUENCE: 109
gacgcgggga ggctattctg                                          20

<210> SEQ ID NO 110
<211> LENGTH: 29
<212> TYPE: DNA
<213> ORGANISM: Artificial Sequence
<220> FEATURE:
<223> OTHER INFORMATION: Primer

<400> SEQUENCE: 110
gactcgtaga aatacggctg caccgagtc                                29

<210> SEQ ID NO 111
<211> LENGTH: 21
<212> TYPE: DNA
<213> ORGANISM: Artificial Sequence
<220> FEATURE:
<223> OTHER INFORMATION: Primer

<400> SEQUENCE: 111
cacgaaactt tgcccatagc a                                        21

<210> SEQ ID NO 112
<211> LENGTH: 28
<212> TYPE: DNA
<213> ORGANISM: Artificial Sequence
<220> FEATURE:
<223> OTHER INFORMATION: Primer

<400> SEQUENCE: 112
cactggtcgg gtgttgtaag ttccagtg                                 28

<210> SEQ ID NO 113
<211> LENGTH: 24
<212> TYPE: DNA
<213> ORGANISM: Artificial Sequence
<220> FEATURE:
<223> OTHER INFORMATION: Primer

<400> SEQUENCE: 113
gatctcgtcc tgggaaggga gatc                                     24

<210> SEQ ID NO 114
<211> LENGTH: 19
<212> TYPE: DNA
<213> ORGANISM: Artificial Sequence
<220> FEATURE:
<223> OTHER INFORMATION: Primer

<400> SEQUENCE: 114
agggtgtgac cgcaacgta                                           19

<210> SEQ ID NO 115
<211> LENGTH:
```

```
<212> TYPE:
<213> ORGANISM:

<400> SEQUENCE: 115

000

<210> SEQ ID NO 116
<211> LENGTH: 23
<212> TYPE: DNA
<213> ORGANISM: Artificial Sequence
<220> FEATURE:
<223> OTHER INFORMATION: Primer

<400> SEQUENCE: 116
cagcggagtg gagggaggcg ctg                                              23

<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
agctgaacgg gaagctcact                                                  20

<210> SEQ ID NO 118
<211> LENGTH: 27
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (25)..(25)
<223> OTHER INFORMATION: Fluorescently labeled

<400> SEQUENCE: 118
caacgtaggt ccaccactga cacgttg                                          27

<210> SEQ ID NO 119
<211> LENGTH: 19
<212> TYPE: DNA
<213> ORGANISM: Artificial Sequence
<220> FEATURE:
<223> OTHER INFORMATION: Primer

<400> SEQUENCE: 119
gcaccgtcaa ggctgagaa                                                   19

<210> SEQ ID NO 120
<211> LENGTH:
<212> TYPE:
<213> ORGANISM:

<400> SEQUENCE: 120

000

<210> SEQ ID NO 121
<211> LENGTH:
<212> TYPE:
<213> ORGANISM:

<400> SEQUENCE: 121

000
```

<210> SEQ ID NO 122
<211> LENGTH: 30
<212> TYPE: DNA
<213> ORGANISM: Artificial Sequence
<220> FEATURE:
<223> OTHER INFORMATION: Primer

<400> SEQUENCE: 122
cacactggtg aggaggggag attcagtgtg                                    30

<210> SEQ ID NO 123
<211> LENGTH: 25
<212> TYPE: DNA
<213> ORGANISM: Artificial Sequence
<220> FEATURE:
<223> OTHER INFORMATION: Primer

<400> SEQUENCE: 123
cacgactggc gctgagtacg tcgtg                                         25

<210> SEQ ID NO 124
<211> LENGTH: 20
<212> TYPE: DNA
<213> ORGANISM: Artificial Sequence
<220> FEATURE:
<223> OTHER INFORMATION: Primer

<400> SEQUENCE: 124
atggcatgga ctgtggtcat                                               20

<210> SEQ ID NO 125
<211> LENGTH:
<212> TYPE:
<213> ORGANISM:

<400> SEQUENCE: 125

000

<210> SEQ ID NO 126
<211> LENGTH: 24
<212> TYPE: DNA
<213> ORGANISM: Artificial Sequence
<220> FEATURE:
<223> OTHER INFORMATION: Primer

<400> SEQUENCE: 126
aagtcatagt ccgcctagaa gcat                                          24

<210> SEQ ID NO 127
<211> LENGTH: 30
<212> TYPE: DNA
<213> ORGANISM: Artificial Sequence
<220> FEATURE:
<223> OTHER INFORMATION: Primer

<400> SEQUENCE: 127
gactcattgg ccctgtaatt ggaatgagtc                                    30

<210> SEQ ID NO 128
<211> LENGTH: 21
<212> TYPE: DNA
<213> ORGANISM: Artificial Sequence
<220> FEATURE:
<223> OTHER INFORMATION: Primer

<400> SEQUENCE: 128

```
ccaagatcca actacgagct t                                              21

<210> SEQ ID NO 129
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (16)..(16)
<223> OTHER INFORMATION: May be either C or T

<400> SEQUENCE: 129
cctggttatc tgtgtn                                                    16

<210> SEQ ID NO 130
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (23)..(23)
<223> OTHER INFORMATION: Labeled with FAM

<400> SEQUENCE: 130
ctaccgggtg tctgtgtctc ggtag                                          25

<210> SEQ ID NO 131
<211> LENGTH: 23
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(2)
<223> OTHER INFORMATION: May be any nucleotide

<400> SEQUENCE: 131
nnttctcatg gtggctgtag aac                                            23

<210> SEQ ID NO 132
<211> LENGTH: 24
<212> TYPE: DNA
<213> ORGANISM: Artificial Sequence
<220> FEATURE:
<223> OTHER INFORMATION: Primer

<400> SEQUENCE: 132
ccttctcatg gtggctgtag aact                                           24

<210> SEQ ID NO 133
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: Fluorescently labeled

<400> SEQUENCE: 133
gatggctctt gttctcggta g                                              21
```

```
<210> SEQ ID NO 134
<211> LENGTH: 21
<212> TYPE: DNA
<213> ORGANISM: Artificial Sequence
<220> FEATURE:
<223> OTHER INFORMATION: Primer

<400> SEQUENCE: 134
catccgagaa caagagccat c                                              21

<210> SEQ ID NO 135
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (19)..(19)
<223> OTHER INFORMATION: Fluorescently labeled

<400> SEQUENCE: 135
gatggctctt gttctcggta g                                              21

<210> SEQ ID NO 136
<211> LENGTH:
<212> TYPE:
<213> ORGANISM:

<400> SEQUENCE: 136

000

<210> SEQ ID NO 137
<211> LENGTH:
<212> TYPE:
<213> ORGANISM:

<400> SEQUENCE: 137

000

<210> SEQ ID NO 138
<211> LENGTH:
<212> TYPE:
<213> ORGANISM:

<400> SEQUENCE: 138

000

<210> SEQ ID NO 139
<211> LENGTH: 23
<212> TYPE: DNA
<213> ORGANISM: Artificial Sequence
<220> FEATURE:
<223> OTHER INFORMATION: Primer

<400> SEQUENCE: 139
taccaccgac ggaagacatc ttg                                            23
```